US011903959B2

(12) United States Patent
Painter et al.

(10) Patent No.: US 11,903,959 B2
(45) Date of Patent: *Feb. 20, 2024

(54) N4-HYDROXYCYTIDINE AND DERIVATIVES AND ANTI-VIRAL USES RELATED THERETO

(71) Applicant: EMORY UNIVERSITY, Atlanta, GA (US)

(72) Inventors: George R. Painter, Atlanta, GA (US); Gregory R. Bluemling, Decatur, GA (US); Michael G. Natchus, Alpharetta, GA (US); David Guthrie, Avondale Estates, GA (US)

(73) Assignee: Emory University, Atlanta, GA (US)

( * ) Notice: Subject to any disclaimer, the term of this patent is extended or adjusted under 35 U.S.C. 154(b) by 133 days.

This patent is subject to a terminal disclaimer.

(21) Appl. No.: 17/465,344

(22) Filed: Sep. 2, 2021

(65) Prior Publication Data

US 2022/0016153 A1 Jan. 20, 2022

Related U.S. Application Data

(63) Continuation of application No. 16/755,779, filed as application No. PCT/US2018/064503 on Dec. 7, 2018, now Pat. No. 11,331,331.

(60) Provisional application No. 62/760,434, filed on Nov. 13, 2018, provisional application No. 62/626,998, filed on Feb. 6, 2018, provisional application No. 62/595,907, filed on Dec. 7, 2017.

(51) Int. Cl.
*C07H 19/067* (2006.01)
*A61K 31/7068* (2006.01)
*A61P 31/12* (2006.01)

(52) U.S. Cl.
CPC .......... *A61K 31/7068* (2013.01); *A61P 31/12* (2018.01); *C07H 19/067* (2013.01)

(58) Field of Classification Search
None
See application file for complete search history.

(56) References Cited

U.S. PATENT DOCUMENTS

| | | | |
|---|---|---|---|
| 4,096,324 A | 6/1978 | Kelly et al. | |
| 5,349,947 A | 7/1994 | Newhouse et al. | |
| 5,691,319 A | 11/1997 | Kaneko | |
| 5,736,531 A | 4/1998 | von Borstel et al. | |
| 6,086,376 A | 7/2000 | Moussa et al. | |
| 6,274,563 B1 | 8/2001 | von Borstel et al. | |
| 6,369,086 B1 | 4/2002 | Davis et al. | |
| 6,369,087 B1 | 4/2002 | Whittle et al. | |
| 6,372,733 B1 | 4/2002 | Caldwell et al. | |
| 6,372,778 B1 | 4/2002 | Tung et al. | |
| 6,846,810 B2 | 1/2005 | Roche | |
| 7,439,344 B2 | 10/2008 | Sarma | |
| 7,718,790 B2 | 5/2010 | Stuyver et al. | |
| 7,893,037 B2 | 2/2011 | Roche | |
| 7,919,247 B2 | 4/2011 | Stuyver et al. | |
| 8,236,779 B2 | 8/2012 | Han et al. | |
| 8,686,045 B2 | 4/2014 | Longo et al. | |
| 9,073,960 B2 | 7/2015 | Beigelman et al. | |
| 9,211,300 B2 | 12/2015 | Mayes et al. | |
| 9,422,321 B2 | 8/2016 | Chang et al. | |
| 9,603,863 B2 | 3/2017 | Blatt et al. | |
| 9,603,864 B2 | 3/2017 | Blatt et al. | |
| 9,809,616 B2 | 11/2017 | Amblard et al. | |
| 9,862,743 B2 | 1/2018 | Beigelman et al. | |
| 9,877,990 B2 | 1/2018 | Krishnan et al. | |
| 10,052,342 B2 | 8/2018 | Blatt et al. | |
| 10,100,076 B2 | 10/2018 | Stuyver et al. | |
| 10,307,439 B2 | 6/2019 | Blatt et al. | |
| 10,370,401 B2 | 8/2019 | Beigelman et al. | |
| 10,464,965 B2 | 11/2019 | Beigelman et al. | |
| 10,874,638 B2 | 12/2020 | Zhi | |
| 10,874,683 B2 | 12/2020 | Painter et al. | |
| 11,331,331 B2 * | 5/2022 | Painter | C07H 19/067 |
| 2003/0008841 A1 | 1/2003 | Devos et al. | |
| 2003/0087873 A1 | 8/2003 | Stuyver et al. | |
| 2004/0121980 A1 | 6/2004 | Martin et al. | |
| 2004/0171860 A1 | 9/2004 | Zhao et al. | |
| 2005/0043268 A1 | 2/2005 | Loakes et al. | |
| 2006/0014709 A1 | 1/2006 | Ishibashi | |

(Continued)

FOREIGN PATENT DOCUMENTS

| | | |
|---|---|---|
| CA | 2426187 | 4/2002 |
| CA | 2743451 | 4/2002 |

(Continued)

OTHER PUBLICATIONS

Chen, Y.L., et al. "Inhibition of Dengue Virus by an ester prodrug of an adenosine analog," Antimicrobial Agents and Chemotherapy, 3255-3261, 2010.
Opposition in Indian application 202017019418, dated Dec. 1, 2021.
Opposition in Indian application 202017019418, dated Nov. 15, 2021.
Third party observations in Philippine application 12020550607, dated Oct. 11, 2021.

(Continued)

*Primary Examiner* — Traviss C McIntosh, III

(74) *Attorney, Agent, or Firm* — Meunier Carlin & Curfman LLC

(57) ABSTRACT

This disclosure relates to certain N4-hydroxycytidine derivatives, pharmaceutical compositions, and methods related thereto. In certain embodiments, the disclosure relates to the treatment or prophylaxis of viral infections, such as Eastern, Western, and Venezuelan Equine Encephalitis (EEE, WEE and VEE, respectively), Chikungunya fever (CHIK), Ebola, Influenza, RSV, and Zika virus infection with the disclosed compounds.

8 Claims, 16 Drawing Sheets

(56) References Cited

U.S. PATENT DOCUMENTS

| | | |
|---|---|---|
| 2007/0031824 A1 | 2/2007 | Stuyver et al. |
| 2007/0037773 A1 | 2/2007 | Sommadossi et al. |
| 2007/0160554 A1 | 7/2007 | Kempers et al. |
| 2007/0196824 A1 | 8/2007 | Stuyver et al. |
| 2008/0260826 A1 | 10/2008 | Birudaraj et al. |
| 2009/0105186 A1 | 4/2009 | Matthes et al. |
| 2009/0220950 A1 | 9/2009 | Stuyver et al. |
| 2010/0189772 A1 | 7/2010 | Vollmer et al. |
| 2010/0298256 A1 | 11/2010 | Dong et al. |
| 2011/0269707 A1 | 11/2011 | Stuyver et al. |
| 2014/0057863 A1 | 2/2014 | Stuyver et al. |
| 2014/0200277 A1 | 7/2014 | Longo et al. |
| 2014/0235566 A1 | 8/2014 | Amblard et al. |
| 2014/0273023 A1 | 9/2014 | Salamone et al. |
| 2014/0294769 A1 | 10/2014 | Mayes et al. |
| 2015/0011497 A1 | 1/2015 | Beigelman et al. |
| 2015/0105341 A1 | 4/2015 | Beigelman et al. |
| 2015/0366887 A1 | 12/2015 | Blatt et al. |
| 2015/0366888 A1 | 12/2015 | Blatt et al. |
| 2017/0143749 A1 | 5/2017 | Blatt et al. |
| 2017/0143751 A1 | 5/2017 | Blatt et al. |
| 2017/0253628 A1 | 9/2017 | Bougher, III et al. |
| 2018/0044369 A1 | 2/2018 | Beigelman et al. |
| 2018/0079774 A1 | 3/2018 | Beigelman et al. |
| 2019/0022116 A1 | 1/2019 | Painter et al. |
| 2019/0054108 A1 | 2/2019 | Blatt et al. |
| 2019/0083520 A1 | 3/2019 | Painter et al. |
| 2020/0276219 A1 | 9/2020 | Painter et al. |
| 2021/0060050 A1 | 3/2021 | Painter et al. |
| 2021/0252033 A1 | 8/2021 | Painter et al. |

FOREIGN PATENT DOCUMENTS

| | | |
|---|---|---|
| CA | 2449572 | 12/2002 |
| CA | 2889171 A1 | 5/2014 |
| CN | 101862345 | 10/2010 |
| CN | 104114568 | 10/2014 |
| CN | 105288635 | 2/2016 |
| CN | 107427529 A | 12/2017 |
| EP | 2615101 B1 | 7/2013 |
| GB | 1325798 A | 8/1973 |
| GB | 1386334 A | 3/1975 |
| GB | 1480120 A | 7/1977 |
| JP | 2006519169 A | 8/2006 |
| JP | 2010522705 A | 7/2010 |
| JP | 2013518076 A | 5/2013 |
| RU | 2322989 | 6/2005 |
| RU | 2264409 | 11/2005 |
| RU | 2327701 C2 | 6/2008 |
| WO | WO9015065 A1 | 12/1990 |
| WO | WO9209705 A1 | 6/1992 |
| WO | WO9310820 A1 | 6/1993 |
| WO | WO9403467 A2 | 2/1994 |
| WO | WO9424144 A2 | 10/1994 |
| WO | WO9507919 A1 | 3/1995 |
| WO | WO9507920 A1 | 3/1995 |
| WO | WO9626933 A1 | 9/1996 |
| WO | WO9817647 A1 | 4/1998 |
| WO | WO2002032920 A3 | 4/2002 |
| WO | 2002088159 | 11/2002 |
| WO | 2002100415 | 12/2002 |
| WO | WO2003090690 A3 | 11/2003 |
| WO | WO2003090691 A2 | 11/2003 |
| WO | WO2004005286 A2 | 1/2004 |
| WO | WO2004006843 A2 | 1/2004 |
| WO | WO2004031224 A2 | 4/2004 |
| WO | WO2004035576 A2 | 4/2004 |
| WO | WO2004035577 A2 | 4/2004 |
| WO | WO2004050613 A2 | 6/2004 |
| WO | WO2004064845 A1 | 8/2004 |
| WO | WO2004064846 A1 | 8/2004 |
| WO | WO2004096286 A2 | 11/2004 |
| WO | WO2004096287 A2 | 11/2004 |
| WO | WO2004096818 A2 | 11/2004 |
| WO | WO2004100960 A2 | 11/2004 |
| WO | WO2005002626 A2 | 1/2005 |
| WO | WO2005012324 A2 | 2/2005 |
| WO | WO2005028478 A1 | 3/2005 |
| WO | WO2005039552 A2 | 5/2005 |
| WO | WO2005042772 A1 | 5/2005 |
| WO | WO2005047898 A2 | 5/2005 |
| WO | WO2005063744 A2 | 7/2005 |
| WO | WO2005063751 A1 | 7/2005 |
| WO | WO2005064008 A1 | 7/2005 |
| WO | WO2005066189 A1 | 7/2005 |
| WO | WO2005070901 A2 | 8/2005 |
| WO | WO2005072748 A1 | 8/2005 |
| WO | WO2005117904 A2 | 12/2005 |
| WO | WO2006015261 A2 | 2/2006 |
| WO | WO2006017044 A2 | 2/2006 |
| WO | WO2006020276 A2 | 2/2006 |
| WO | WO2006033703 A1 | 3/2006 |
| WO | WO2006047661 A2 | 5/2006 |
| WO | WO2006069193 A2 | 6/2006 |
| WO | WO2006091905 A1 | 8/2006 |
| WO | WO2006110157 A2 | 10/2006 |
| WO | WO2006125048 A2 | 11/2006 |
| WO | WO2007009109 A2 | 1/2007 |
| WO | WO2007011658 A1 | 1/2007 |
| WO | WO2007014174 A2 | 2/2007 |
| WO | WO2007014352 A2 | 2/2007 |
| WO | WO2007022268 | 2/2007 |
| WO | WO2007079260 A1 | 7/2007 |
| WO | WO2007126812 A2 | 11/2007 |
| WO | WO2008003149 A2 | 1/2008 |
| WO | WO2008005519 A2 | 1/2008 |
| WO | WO2008005542 A2 | 1/2008 |
| WO | WO2008005555 A1 | 1/2008 |
| WO | WO2008009076 A2 | 1/2008 |
| WO | WO2008009077 A2 | 1/2008 |
| WO | WO2008009078 A2 | 1/2008 |
| WO | WO2008009079 A2 | 1/2008 |
| WO | WO2008010921 A2 | 1/2008 |
| WO | WO2008011116 A2 | 1/2008 |
| WO | WO2008011117 A2 | 1/2008 |
| WO | WO2008013834 A1 | 1/2008 |
| WO | WO2008016522 A2 | 2/2008 |
| WO | WO2008077649 A1 | 7/2008 |
| WO | WO2008077650 A1 | 7/2008 |
| WO | WO2008077651 A1 | 7/2008 |
| WO | WO2008100447 A2 | 8/2008 |
| WO | WO2008103949 A1 | 8/2008 |
| WO | WO2008133669 A2 | 11/2008 |
| WO | WO2009005674 A2 | 1/2009 |
| WO | WO2009005676 A2 | 1/2009 |
| WO | WO2009005677 A2 | 1/2009 |
| WO | WO2009005687 A1 | 1/2009 |
| WO | WO2009005690 A1 | 1/2009 |
| WO | WO2009005693 A1 | 1/2009 |
| WO | WO2009006199 A1 | 1/2009 |
| WO | WO2009006203 A1 | 1/2009 |
| WO | WO2009009001 A1 | 1/2009 |
| WO | 2009058800 | 5/2009 |
| WO | WO2009088719 A1 | 7/2009 |
| WO | WO2009105513 A2 | 8/2009 |
| WO | WO2009132123 A1 | 10/2009 |
| WO | WO2009132135 A1 | 10/2009 |
| WO | WO2009143011 A1 | 11/2009 |
| WO | WO2010002998 A1 | 1/2010 |
| WO | WO2010005986 A1 | 1/2010 |
| WO | WO2010011959 A1 | 1/2010 |
| WO | WO2010075127 A1 | 7/2010 |
| WO | WO2010077613 A1 | 7/2010 |
| WO | WO2010080389 A1 | 7/2010 |
| WO | WO2010093608 A1 | 8/2010 |
| WO | WO2010132601 A1 | 11/2010 |
| WO | WO2010135569 A1 | 11/2010 |
| WO | WO2010151472 A1 | 12/2010 |
| WO | WO2010151487 A1 | 12/2010 |
| WO | WO2010151488 A1 | 12/2010 |
| WO | WO2011005842 A1 | 1/2011 |
| WO | WO2011011303 A1 | 1/2011 |
| WO | WO2011031669 A1 | 3/2011 |
| WO | WO2011031965 A1 | 3/2011 |

(56) References Cited

FOREIGN PATENT DOCUMENTS

| | | |
|---|---|---|
| WO | WO2011035231 A1 | 3/2011 |
| WO | WO2011049825 A1 | 4/2011 |
| WO | WO2011079016 A1 | 6/2011 |
| WO | WO2011088303 A1 | 7/2011 |
| WO | WO2011088345 A1 | 7/2011 |
| WO | 2011092158 | 8/2011 |
| WO | WO2011106445 A1 | 9/2011 |
| WO | WO2011143105 A1 | 11/2011 |
| WO | WO2011143106 A1 | 11/2011 |
| WO | WO2011146817 A1 | 11/2011 |
| WO | WO2011150288 A1 | 12/2011 |
| WO | WO2011156416 A1 | 12/2011 |
| WO | WO2011156610 A2 | 12/2011 |
| WO | WO2011156757 A1 | 12/2011 |
| WO | WO2011163518 A1 | 12/2011 |
| WO | WO2012003497 A1 | 1/2012 |
| WO | WO2012003498 A1 | 1/2012 |
| WO | WO2012012465 A1 | 1/2012 |
| WO | WO2012012776 A1 | 1/2012 |
| WO | WO2012037038 A1 | 3/2012 |
| WO | WO2012039787 A1 | 3/2012 |
| WO | WO2012039791 A1 | 3/2012 |
| WO | WO2012068234 A2 | 5/2012 |
| WO | WO2012068535 A1 | 5/2012 |
| WO | WO2012078915 A1 | 6/2012 |
| WO | WO2012087596 A1 | 6/2012 |
| WO | WO2012088153 A1 | 6/2012 |
| WO | WO2012088156 A1 | 6/2012 |
| WO | WO2012088178 A1 | 6/2012 |
| WO | WO2012138669 A1 | 10/2012 |
| WO | WO2012138670 A1 | 10/2012 |
| WO | WO2012142523 A2 | 10/2012 |
| WO | WO2012145728 A1 | 10/2012 |
| WO | WO2012151165 A1 | 11/2012 |
| WO | WO2013006721 A1 | 1/2013 |
| WO | WO2013006722 A1 | 1/2013 |
| WO | WO2013006738 A1 | 1/2013 |
| WO | WO2013010112 A1 | 1/2013 |
| WO | WO2013025788 A1 | 2/2013 |
| WO | WO2013040492 A2 | 3/2013 |
| WO | WO2013066748 A1 | 5/2013 |
| WO | WO2013075029 A1 | 5/2013 |
| WO | WO2013082003 A1 | 6/2013 |
| WO | WO2013090840 A1 | 6/2013 |
| WO | WO2013090929 A1 | 6/2013 |
| WO | WO2013096512 A1 | 6/2013 |
| WO | WO2013096681 A1 | 6/2013 |
| WO | WO2013103724 A1 | 7/2013 |
| WO | WO2013103738 A1 | 7/2013 |
| WO | WO2013106732 A1 | 7/2013 |
| WO | WO2013115916 A1 | 8/2013 |
| WO | WO2013116720 A1 | 8/2013 |
| WO | WO2013116730 A1 | 8/2013 |
| WO | WO2013138236 A1 | 9/2013 |
| WO | WO2013142525 A1 | 9/2013 |
| WO | WO2013158776 A1 | 10/2013 |
| WO | WO2013159064 A1 | 10/2013 |
| WO | WO2013173488 A1 | 11/2013 |
| WO | WO2013173492 A1 | 11/2013 |
| WO | WO2013185090 A1 | 12/2013 |
| WO | WO2013185093 A1 | 12/2013 |
| WO | WO2013185103 A1 | 12/2013 |
| WO | WO2014008285 A1 | 1/2014 |
| WO | WO2014028343 A1 | 2/2014 |
| WO | WO2014055618 A1 | 4/2014 |
| WO | WO2014070771 A1 | 5/2014 |
| WO | WO2014070939 A1 | 5/2014 |
| WO | WO2014074620 A1 | 5/2014 |
| WO | 2014099941 | 6/2014 |
| WO | 2014100505 | 6/2014 |
| WO | WO2014100323 A1 | 6/2014 |
| WO | WO2014100500 A1 | 6/2014 |
| WO | WO2014110296 A1 | 7/2014 |
| WO | WO2014110297 A1 | 7/2014 |
| WO | WO2014110298 A1 | 7/2014 |
| WO | 2014124430 | 8/2014 |
| WO | WO2014134566 A2 | 9/2014 |
| WO | WO2014145095 A1 | 9/2014 |
| WO | WO2014169278 A1 | 10/2014 |
| WO | 2014186637 | 11/2014 |
| WO | 2014209979 | 12/2014 |
| WO | WO2014209979 A1 | 12/2014 |
| WO | WO2015023893 A1 | 2/2015 |
| WO | WO2015038596 A1 | 3/2015 |
| WO | 2015054465 | 4/2015 |
| WO | WO2015054465 A1 | 4/2015 |
| WO | WO2015069939 A1 | 5/2015 |
| WO | WO2015084741 A2 | 6/2015 |
| WO | WO2015099989 A1 | 7/2015 |
| WO | WO2015100144 A1 | 7/2015 |
| WO | WO2015108780 A1 | 7/2015 |
| WO | WO2015120057 A1 | 8/2015 |
| WO | WO2015130964 A1 | 9/2015 |
| WO | WO2015130966 A1 | 9/2015 |
| WO | WO2015179448 A1 | 11/2015 |
| WO | WO2015191526 A2 | 12/2015 |
| WO | WO2015191726 A1 | 12/2015 |
| WO | WO2015191743 A1 | 12/2015 |
| WO | WO2015191745 A1 | 12/2015 |
| WO | WO2015191752 A1 | 12/2015 |
| WO | WO2015191754 A2 | 12/2015 |
| WO | WO2015196137 A1 | 12/2015 |
| WO | WO2015200205 A1 | 12/2015 |
| WO | WO2015200219 A1 | 12/2015 |
| WO | WO2016007765 A1 | 1/2016 |
| WO | WO2016018697 A1 | 2/2016 |
| WO | WO2016028866 A1 | 2/2016 |
| WO | WO2016033243 A1 | 3/2016 |
| WO | WO2016036759 A1 | 3/2016 |
| WO | WO2016096116 A1 | 6/2016 |
| WO | WO2016105532 A1 | 6/2016 |
| WO | WO2016105534 A1 | 6/2016 |
| WO | WO2016105564 A1 | 6/2016 |
| WO | WO2016106050 A1 | 6/2016 |
| WO | WO2016106237 A1 | 6/2016 |
| WO | 2016134054 | 8/2016 |
| WO | WO2016141092 A1 | 9/2016 |
| WO | WO2016161382 A1 | 10/2016 |
| WO | WO2016168349 A1 | 10/2016 |
| WO | WO2016186967 A1 | 11/2016 |
| WO | WO2016205141 A1 | 12/2016 |
| WO | WO2017004012 A1 | 1/2017 |
| WO | WO2017004244 A1 | 1/2017 |
| WO | 2017040895 | 3/2017 |
| WO | 2017040896 | 3/2017 |
| WO | WO2017035230 A1 | 3/2017 |
| WO | WO2017048727 A1 | 3/2017 |
| WO | WO2017049060 A1 | 3/2017 |
| WO | WO2017059120 A1 | 4/2017 |
| WO | WO2017059224 A2 | 4/2017 |
| WO | WO2017083304 A1 | 5/2017 |
| WO | WO2017106346 A2 | 6/2017 |
| WO | WO2017106556 A1 | 6/2017 |
| WO | WO2017156380 A1 | 9/2017 |
| WO | WO2017165489 A1 | 9/2017 |
| WO | WO2017184668 A1 | 10/2017 |
| WO | WO2017184670 A2 | 10/2017 |
| WO | WO2017205078 A1 | 11/2017 |
| WO | WO2017205115 A1 | 11/2017 |
| WO | 2017223020 | 12/2017 |
| WO | WO2017223268 A1 | 12/2017 |
| WO | 2019113462 | 6/2019 |
| WO | WO2019173602 A1 | 9/2019 |

OTHER PUBLICATIONS

Third party observations in Eurasian Application 202091005, dated Nov. 8, 2021.

Fujan, Li., et al., "Prodrugs of nucleoside analogs for improved oral absorption and tissue targeting," J. Pharm. Sci. 97(3):1109-1134, 2008.

Zhang, et al. "Current prodrug strategies for improving oral absorption of nucleoside analogs," Asian J. Pharm. Sci. 9:65-74, 2014.

(56) References Cited

OTHER PUBLICATIONS

Felczak, K., et al. "5-substituted N4-hydroxy-2'-deoxycytidines and their 5'-monophosphates: synthesis, conformation, interaction with tumor thymidylate synthase, and in vitro antitumor activity," J. Med. Chem. 43:4647-4656, 2000.

Third Party Observation in Eurasian Application No. 202091005, dated Dec. 3, 2021.

Mehellou, Youcef, Hardeep S. Rattan, and Jan Balzarini. "The ProTide Prodrug Technology: From the Concept to the Clinic: Miniperspective." Journal of medicinal chemistry 61.6 (2017): 2211-2226.

Dawadi, Surendra, et al. "Synthesis and pharmacological evaluation of nucleoside prodrugs designed to target siderophore biosynthesis in Mycobacterium tuberculosis." Bioorganic & medicinal chemistry 24.6 (2016): 1314-1321.

Office Action issued for Chinese Application No. 201880073278.8, dated Oct. 15, 2021.

Office Action and Search Report issued for Brazilian Application No. BR112017013858-1 dated Sep. 16, 2021.

Brown et al. Mechanism of the Mutagenic Action of Hydroxylamine, Journal of Molecular Biology, vol. 11, n. 4, Apr. 1, 1965, p. 663-671.

Mertes, M. P., and J. Smrt. "Nucleic acid components and their analogues. CXV. Synthesis of N 4-hydroxy-6-azacytidine 5'-phosphate and 5'-diphosphate." Collection of Czechoslovak Chemical Communications 33.10 (1968): 3304-3312.

International Search Report and Written Opinion for International Application No. PCT/US2018/064503, dated Feb. 7, 2019.

Translation of Office Action issued for Brazilian Application No. BR122021012627-5, dated Nov. 1, 2021.

Translation of Objections of Third Party Observations in connection to Eurasian Application No. EA202091005, dated Dec. 6, 2021.

Extended European Search Report issued for Application No. 21178364.2, dated Nov. 30, 2021.

Office Action issued for U.S. Appl. No. 16/921,359, dated Dec. 24, 2021.

Office Action issued for U.S. Appl. No. 16/921,359, dated Mar. 21, 2022.

Verrault, Daniel, et al. "Evaluation of inhaled cidofovir as postexposure prophylactic in an aerosol rabbitpox model." Antiviral Research 93.1 (2012): 204-208.

Barnard et al. "Inhibition of severe acute respiratory syndrome-associated coronavirus (SARSCoV) by calpain inhibitors and Beta-D-N4 hydroxycytidine." Antiviral Chemistry & Chemotherapy (2004), vol. 15, pp. 15-22.

Office Action issued for Israeli Application No. 279663, dated Jul. 14, 2021.

Office Action issued for Chinese Application No. 201580076718.1, dated Jul. 28, 2021.

Office Action issued for Japanese Application No. 2017-534192, dated Aug. 17, 2021.

Office Action issued for Russian Application No. 2020116571, dated Aug. 27, 2021.

Kummerer, Klaus. "Pharmaceuticals in the environment." Annual review of environment and resources 35 (2010):57-75.

Examination report issued for Philippine Application No. 1-2020-550607, dated Sep. 7, 2021.

Office Action issued for Philippine Application No. 2020550607, dated Dec. 14, 2021.

Office Action issued for Eurasian Application No. 202091005, dated Dec. 24, 2021.

Translation of the Official Notification issued for Eurasian Application No. 202091005, dated Dec. 17, 2021.

Rautio, Prodrugs and Targeted Delivery: Towards Better ADME Properties, 2011, 6 pages.

Kim, Dae-Kee, et al. "Synthesis and evaluation of 2-amino-6-fluoro-9-(2-hydroxyethoxymethyl) purine esters as potential prodrugs of acyclovir." Bioorganic & medicinal chemistry 6.12 (1998): 2525-2530.

Khimicheskiy entsiklopedicheskiy slovar (Chemical Encyclopedic Dictionary), edited by I.L. Knunyants, M.:Sovetskaya entsilopediya, 1983, p. 23.

LL. Fizer, M. Fizer, Organicheskaya khimiya (Organic Chemistry), M.: Khimiya, 1966, p. 445.

Coats, Steven J., et al. "Chutes and ladders in hepatitis C nucleoside drug development." Antiviral research 102 (2014): 119-147.

Iglesias, Luis E., et al. "Biocatalytic approaches applied to the synthesis of nucleoside prodrugs." Biotechnology advances 33.5 (2015): 412-434.

Rautio, Jarkko, et al. "Prodrugs: design and clinical applications." Nature reviews Drug discovery 7.3 (2008): 255-270.

Cho, Seung-Ju, et al. "Ibulocydine is a novel prodrug Cdk inhibitor that effectively induces apoptosis in hepatocellular carcinoma cells." Journal of Biological Chemistry 286.22 (2011): 19662-19671.

Agrawal, Vijay K., Ruchi Sharma, and P. V. Khadikar. "QSAR study on antiviral activity of ester prodrugs of 6-methoxypurine arabinosides." (2002). NISCAIR-CSIR, India, 1163-1166.

Brandl, Michael, et al. "Physicochemical properties of the nucleoside prodrug R1626 leading to high oral bioavailability." Drug development and industrial pharmacy 34.7 (2008): 683-691.

Nilsson, Magnus, et al. "Discovery of 4'-azido-2'-deoxy-2'-C-methyl cytidine and prodrugs thereof: A potent inhibitor of Hepatitis C virus replication." Bioorganic & medicinal chemistry letters 22.9 (2012): 3265-3268.

Jonckers, Tim HM, et al. "2'-Deoxy-2'-spirocyclopropylcytidine revisited: a new and selective inhibitor of the hepatitis C virus NS5B polymerase." Journal of medicinal chemistry 53.22 (2010): 8150-8160.

Kim, Dae-Kee, et al. "Synthesis and evaluation of 2-amino-6-fluoro-9-(4-hydroxy-3-hydroxymethylbut-1-yl) purine mono-and diesters as potential prodrugs of penciclovir." Bioorganic & medicinal chemistry 7.3 (1999): 565-570.

Roy, Chad J., et al. "Pathogenesis of aerosolized Eastern Equine Encephalitis virus infection in guinea pigs." Virology journal 6.1 (2009): 170.

Stuyver, Lieven J., et al. "Ribonucleoside analogue that blocks replication of bovine viral diarrhea and hepatitis C viruses in culture." Antimicrobial agents and chemotherapy 47.1 (2003): 244-254.

Costantini, Verónica P., et al. "Antiviral activity of nucleoside analogues against norovirus." Antiviral therapy 17.6 (2012): 981-991.

Purohit, Meena K., et al. "Novel cytidine-based orotidine-5'-monophosphate decarboxylase inhibitors with an unusual twist." Journal of medicinal chemistry 55.22 (2012): 9988-9997.

Ivanov, Maksim A., et al. "New N 4-hydroxycytidine derivatives: synthesis and antiviral activity." Collection of Czechoslovak Chemical Communications 71.7 (2006): 1099-1106.

Fox, Jack J., et al. "Thiation of Nucleosides. II. Synthesis of 5-Methyl-2'-deoxycytidine and Related Pyrimidine Nucleosides1." Journal of the American Chemical Society 81.1 (1959): 178-187.

Lam, Angela M., et al. "PSI-7851, a pronucleotide of β-D-2'-deoxy-2'-fluoro-2'-C-methyluridine monophosphate, is a potent and pangenotype inhibitor of hepatitis C virus replication." Antimicrobial agents and chemotherapy 54.8 (2010): 3187-3196.

Partial European Search Report issued for European Patent Application No. 15874145.4, dated Aug. 15, 2018.

Supplementary European Search Report issued for European Patent Application No. 15874145.4, dated Jan. 1, 2019.

Communication Pursuant to Article 94(3) EPC, Report issued for European Patent Application No. 15874145.4, dated May 6, 2020.

Bonnac et al., "Structure Activity Relationships and Design of Viral Mutagens and Application to Lethal Mutagenesis" J. Med Chem 2013, 56, 9403-9414.

Reynard et. al., "Identification of a New Ribonucleoside Inhibitor of Ebola Virus Replication" Viruses 2015, 6233-6240.

International Search Report for PCT/US2015/066144, dated Feb. 26, 2016.

Pubchem-'458' Date Created: Oct. 26, 2006 (Oct. 26, 2006) Date Accessed: Feb. 9, 2016 (Feb. 9, 2016); p. 3, compound.

Pubchem-'284' Date Created: Mar. 26, 2005 (Mar. 26, 2005) Date Accessed: Feb. 9, 2016 (Feb. 9, 2016); p. 3, compound.

(56) References Cited

OTHER PUBLICATIONS

First Examination Report dated Feb. 25, 2020 for Australian Application No. 2015370004.
Translation of Office Action dated Nov. 12, 2019 for Japanese Application No. 2017-534192.
First Exam Report dated Dec. 20, 2019 for Indian Application No. 201717025098.
Falco, Elvira A., Elizabeth Pappas, and George H. Hitchings. "1, 2, 4-Triazine analogs of the natural pyrimidines." Journal of the American Chemical Society 78.9 (1956): 1938-1941.
Vujjini, Satish Kumar, et al. "An improved and scalable process for the synthesis of 5-azacytidine: An antineoplastic drug." Organic Process Research & Development 17.2 (2013): 303-306.
Barnard DL, et al. RW. 2004. "Inhibition of severe acute respiratory syndrome-associated coronavirus (SARSCoV) by calpain inhibitors and β-D-N4-hydroxycytidine" Antivir Chem Chemother 15:15-22. https://doi.org/10.1177/095632020401500102.
Urakova N, et al. 2017 "β-D-N4-Hydroxycytidine is a potent anti-alphavirus compound that induces a high level of mutations in the viral genome" J Virol 92:e01965-17. https://doi.org/10.1128/JVI.01965-17.
Ehteshami, Maryam, et al. "Characterization of β-d-N4-hydroxycytidine as a novel inhibitor of chikungunya virus." Antimicrobial agents and chemotherapy 61.4 (2017): e02395-16. https://doi.org/10.1128/AAC.02395-16.
Yoon J-J, et al., 2018. "Orally efficacious broadspectrum ribonucleoside analog inhibitor of influenza and respiratory syncytial viruses. Antimicrob Agents Chemother 62:1427". https://doi.org/10.1128/AAC.00766-18.
Reynard O, et al., 2015. Identification of a new ribonucleoside inhibitor of Ebola virus replication. Viruses 7:6233-6240. https://doi.org/10.3390/v7122934.
Suzuki, T.; Moriyama, K.; Otsuka, C.; Loakes, D.; Negishi, K., Template properties of mutagenic cytosine analogs in reverse transcription. Nucleic Acids Res. 2006, 34 (22), 6438-6449.
Pyrc, K.; Bosch, B. J.; Berkhout, B.; Jebbink, M. F.; Dijkman, R.; Rottier, P.; van der Hoek, L., Inhibition of human coronavirus NL63 infection at early stages of the replication cycle. Antimicrob. Agents Chemother. 2006, 50 (6), 2000-2008.
Barnard, D. L.; Day, C. W.; Bailey, K.; Heiner, M.; Montgomery, R.; Lauridsen, L.; Chan, P. K. S.; Sidwell, R. W., Evaluation of immunomodulators, interferons and known in vitro SARS-CoV inhibitors for inhibition of SARS-CoV replication in BALB/c mice. Antiviral Chem. Chemother. 2006, 17 (5), 275-284.
Hollecker, L.; Choo, H.; Chong, Y.; Chu, C. K.; Lostia, S.; McBrayer, T. R.; Stuyver, L. J.; Mason, J. C.; Du, J.; Rachakonda, S.; Shi, J.; Schinazi, R. F.; Watanabe, K. A., Synthesis of β-enantiomers of N4-hydroxy-3'-deoxypyrimidine nucleosides and their evaluation against bovine viral diarrhoea virus and hepatitis C virus in cell culture. Antiviral Chem. Chemother. 2004, 15 (1), 43-55.
Hernandez-Santiago, B. I.; Beltran, T.; Stuyver, L.; Chu, C. K.; Schinazi, R. F., Metabolism of the anti-hepatitis C virus nucleoside β-D-N4-hydroxycytidine in different liver cells. Antimicrob. Agents Chemother. 2004, 48 (12), 4636-4642.
Sledziewska-Gojska, E.; Grzesiuk, E.; Plachta, A.; Janion, C., Mutagenesis of *Escherichia coli*: a method for determining mutagenic specificity by analysis of tRNA suppressors. Mutagenesis 1992, 7 (1), 41-6.
Shugar, D.; Kierdaszuk, B., New light on tautomerism of purines and pyrimidines and its biological and genetic implications. J. Biosci. 1985, 8 (3-4), 657-68.
Janion, C., Some problems of mutagenesis induced by base analogues. Acta Biochim Pol 1984, 31 (1), 183-92.
Janion, C., On the different response of *Salmonella typhimurium* hisG46 and TA1530 to the mutagenic action of base analogs. Acta Biochim. Pol. 1979, 26 (1-2), 171-7.
Popowska, E.; Janion, C., The N4-hydroxycytidine reduction system in toluenized cells of *Salmonella typhimurium*. Acta Biochim. Pol. 1977, 24 (3), 197-205.
Simukova, N. A.; Yakovlev, D. Y.; Budovskii, E. I., Mechanism of the mutagenic action of hydroxylamine. IX. The uv-induced cleavage of the nitrogen-oxygen bond in N4-hydroxy- and N4-methoxycytidine and N6-methoxyadenosine. Nucleic Acids Res. 1975, 2 (12), 2269-78.
Popowska, E.; Janion, C., Metabolism of N4-hydroxycytidine, a mutagen for *Salmonella typhimurium*. Nucleic Acids Res. 1975, 2 (7), 1143-51.
Trimble, R. B.; Maley, F., Metabolism of 4-N-hydroxycytidine in *Escherichia coli*. J. Bacteriol. 1971, 108 (1), 145-53.
Bebenek, K.; Janion, C., Ability of base analogs to induce the SOS response: effect of a dam mutation and mismatch repair system. MGG, Mol. Gen. Genet. 1985, 201 (3), 519-24.
Borodavkin, A. V.; Chekhov, V. O.; Dolin, Y. S.; Morozov, Y. V.; Savin, F. A.; Budowskii, E. I.; Yakovlev, D. Y., Absorption UV spectroscopy and electronic structure of ionic and tautomeric forms of hydroxy and methoxy derivatives of cytosine and adenine, and of some 5-substituted analogs of pyrimidines. Int. J. Quantum Chem. 1980, 17 (4), 803-11.
Brown, D. M.; Schell, P., Nucleotides. XLVIII. The reaction of hydroxylamine with cytosine and related compounds. J. Chem. Soc. 1965, (Jan.), 208-15.
Budovskii, E. I.; Postnova, T. I., Mechanism of the mutagenic action of hydroxylamine. X. Certain specificities in the mutagenesis of N-hydroxy and N-methoxy analogs of cytosine and adenine derivatives. Mutat. Res. 1976, 37 (1), 11-17.
Chekhov, V. O.; Budovskii, E. I.; Morozov, Y. V.; Savin, F. A.; Yakovlev, D. Y., UV spectroscopy of fixed amino and imino forms of cytidine and its N4-hydroxy and N4-methoxy derivatives. Biofizika 1979, 24 (4), 772-3. English Abstract Only.
Chekhov, V. O.; Savin, F. A.; Morozov, Y. V.; Budovskii, E. I.; Yakovlev, D. Y., Electron structure of some hydroxy and methoxy derivatives of cytosine and adenine. Biofizika 1979, 24 (4), 773-4. English Abstract only.
Chung, K. C.; Hayatsu, H., The reaction of hydroxylamine with 4-thiouridine. Yongnam Taehakkyo Chonyonmul Hwahak Yonguso Yongu Pogo 1976, 3, 31-6. English Abstract Only.
De Serres, F. J.; Brockman, H. E., Comparison of the spectra of genetic damage in N4-hydroxycytidine-induced ad-3 mutations between nucleotide excision repair-proficient and -deficient heterokaryons of Neurospora crassa. Mutat. Res., Fundam. Mol. Mech. Mutagen. 1993, 285 (2), 145-63.
Fraenkel-Conrat, H.; Singer, B., Chemical basis for the mutagenicity of hydroxylamine and methoxyamine. Biochim. Biophys. Acta, Nucleic Acids Protein Synth. 1972, 262 (3), 264-8.
Iida, S.; Chung, K. C.; Hayatsu, H., Reaction of hydroxylamine with 4-thiouridine. Biochim. Biophys. Acta, Nucleic Acids Protein Synth. 1973, 308 (2), 198-204.
Janion, C., The efficiency and extent of mutagenic activity of some new mutagens of the base-analog type. Mutat. Res., Genet. Toxicol. Test. 1978, 56 (3), 225-34.
Janion, C.; Bebenek, K.; Plewako, S., Are *Escherichia coli* dam—as compared to dam+ hypermutable by base analogs? Acta Biochim. Pol. 1987, 34 (2), 183-93.
Janion, C.; Glickman, B. W., N4-Hydroxycytidine: a mutagen specific for AT to GC transitions. Mutat. Res. 1980, 72 (1), 43-7.
Janion, C.; Kajtaniak, E., Mutagenesis induced in amber P22 phages by base analogs. Mutat. Res. 1979, 62 (1), 191-5.
Janion, C.; Popowska, E., The reduction of N4-hydroxycytidine to cytidine by *Salmonella typhimurium* cells. Nucleic Acids Res., Spec. Publ. 1975, (III Symp. on Chemistry of Nucleic Acids Components, Liblice Castle, Czechoslovakia, Oct. 8-12, 1975), S159-S163.
Janion, C.; Shugar, D., Mechanism of hydroxylamine mutagenesis: complexing properties of copolymers of hydroxycytidylic acid with cytidylic or uridylic acids. Acta Biochim. Pol. 1969, 16 (2), 219-32.
Krompholz, et al., "The Mitochondrial Amidoxime Reducing Component (mARC) is Involved in Detoxification of N-Hydroxylated Base Analogues." Chem. Res. Toxicol. 2012, 25 (11), 2443-2450.
Levin, D. E.; Ames, B. N., Classifying mutagens as to their specificity in causing the six possible transitions and transversions: a simple analysis using the *Salmonella* mutagenicity assay. Environ. Mutagen. 1986, 8 (1), 9-28.

(56) References Cited

OTHER PUBLICATIONS

Morozov, Y. V.; Savin, F. A.; Chekhov, V. O.; Budovskii, E. I.; Yakovlev, D. Y., Photochemistry of N6-methoxyadenosine and of N4-hydroxycytidine and its methyl derivatives. I: Spectroscopic and quantum chemical investigation of ionic and tautomeric forms: syn-anti isomerization. J. Photochem. 1982, 20 (3), 229-52.

Popowska, E.; Janion, C., N4-Hydroxycytidine. New mutagen of a base analog type. Biochem. Biophys. Res. Commun. 1974, 56 (2), 459-66.

Poslovina, A. S.; Vasyunina, E. A.; Andreeva, I. S.; Salganik, R. I. In Effect of adenine and cytosine on the mutagenic effect of hydroxylamine and study of the mutagenic activity of the products of their modification by hydroxylamine, "Nauka": 1976; pp. 142-145. English Abstract Only.

Poslovina, A. S.; Vasyunina, E. A.; Andreeva, I. S.; Salganik, R. I., Mutagenic effect of N4-HYDR oxycytidine, the product of cytidine modification by hydroxylamine, in *Escherichia coli* B. Genetika 1973, 9 (5), 76-81. English Abstract Only.

Poslovina, A. S.; Vasyunina, E. A.; Andreeva, I. S. In Mutagenic action of cytidine and adenosine derivatives modified by hydroxylamine, Akad. Nauk SSSR, Sib. Otd., Inst. Tsitol. Genet.: 1974; pp. 7-8. English Abstract Only.

Salganik, R. I.; Vasyunina, E. A.; Poslovina, A. S.; Andreeva, I. S., Mutagenic action of N4-hydroxycytidine on *Escherichia coli* B cyt. Mutat. Res. 1973, 20 (1), 1-5.

Sidwell, R.W., D.F. Smee, and D.L. Barnard 2006. Development of antiviral drugs against avian (H5N1) influenza virus. In: J.P. Wong (Ed.), Recent Developments on the Avian Influenza (H5N1) Crisis. Transworld Research Network, Kerala, India pp. 63-83.

Singer, B., The effect of base modification on fidelity in transcription. Jerusalem Symp. Quantum Chem. Biochem. 1980, 13 (Carcinog.: Fundam. Mech. Environ. Eff.), 91-102.

Singer, B.; Spengler, S., Ambiguity and transcriptional errors as a result of modification of exocyclic amino groups of cytidine, guanosine, and adenosine. Biochemistry 1981, 20 (5), 1127-32.

Sledziewska, E.; Janion, C., Mutagenic specificity of N4-hydroxycytidine. Mutat. Res. 1980, 70 (1), 11-16.

Sledziewska-Gojska, E.; Janion, C., Do DNA repair systems affect N4-hydroxycytidine-induced mutagenesis? Acta Biochim. Pol. 1983, 30 (2), 149-57.

Sledziewska-Gojska, E.; Janion, C., Effect of proofreading and dam-instructed mismatch repair systems on N4-hydroxycytidine-induced mutagenesis. MGG, Mol. Gen. Genet. 1982, 186 (3), 411-18.

Smrt, J., Homopolymers of N4-hydroxy- and N4-methoxycytidylic acid and their interaction with polyadenylic acid. Collect. Czech. Chem. Commun. 1970, 35 (8), 2314-23.

Yakovlev, D. Y.; Simukova, N. A.; Budovskii, E. I.; Chekhov, V. O.; Savin, F. A.; Morozov, Y. V., Photochemistry of N6-methoxyadenosine and of N4-hydroxycytidine and its methyl derivatives. II: Photoinduced rupture of the nitrogen-oxygen bond. J. Photochem. 1982, 20 (3), 253-68.

Examination report No. 1 issued for Australian Application No. 2018378832, dated May 7, 2020.

Examination report No. 2 issued for Australian Application No. 2018378832, dated May 12, 2020.

International Preliminary Report on Patentability issued for Application No. PCT/US2018/064503, dated Jun. 18, 2020.

Office Action issued for Eurasian Application No. 202091005, dated Jun. 26, 2020. English Translation included.

Office Action issued for Canadian Application No. 3,082,191, dated Jun. 29, 2020.

Office Action issued for Korean Application No. 10-2020-7014737, dated Jun. 29, 2020. English Translation included.

Office Action issued for British Application No. 2008628.6, dated Jul. 10, 2020.

Notice of Intention to grant Office Action issued from IPO issued in British Application No. 2008628.6, dated Nov. 23, 2020.

Office Action issued for Russian Application No. 2020116571, dated Nov. 2, 2020 and English Translation included.

Notice of Allowance issued for Japanese Application No. 2020544817, dated Oct. 27, 2020.

English Translation of Office Action issued for Israeli Application No. 274155, dated Oct. 23, 2020.

Office Action issued for Indian Application No. 202017019418, dated Oct. 19, 2020 and English Translation.

Office Action issued in Canadian Application No. 3,082,191 dated Nov. 12, 2020.

English translation of Search Report issued in Chinese Application No. 2018800732788 dated Dec. 25, 2020.

English translation of First Office Action issued in Chinese Application No. 2018800732788 dated Dec. 25, 2020.

Agostini, Maria L., et al. "Small-molecule antiviral β-d-N4-hydroxycytidine inhibits a proofreading-intact coronavirus with a high genetic barrier to resistance." Journal of virology 93.24 (2019).

Beigel, John H., et al. "Advances in respiratory virus therapeutics—A meeting report from the 6th isirv Antiviral Group conference." Antiviral research 167 (2019): 45-67.

Cheng, Vincent CC, et al. "Severe acute respiratory syndrome coronavirus as an agent of emerging and reemerging infection." Clinical microbiology reviews 20.4 (2007): 660-694.

Cinatl Jr, Jindrich, et al. "Development of antiviral therapy for severe acute respiratory syndrome." Antiviral research 66.2-3 (2005): 81-97.

Day, Craig W., et al. "A new mouse-adapted strain of SARS-CoV as a lethal model for evaluating antiviral agents in vitro and in vivo." Virology 395.2 (2009): 210-222.

De Clercq, Erik. "Recent highlights in the development of new antiviral drugs." Current opinion in microbiology 8.5 (2005): 552-560.

De Clercq, Erik. "Status presens of antiviral drugs and strategies: Part II: RNA Viruses (Except Retroviruses)." Advances in antiviral drug design 5 (2007): 59-112.

De Clercq, E. "Viruses and viral diseases." Comprehensive Medicinal Chemistry II (2007): 7.10:253-293.

Dollinger, M. A., Burchenal, J. H., Kreis, W., and Fox, J. J. Analogs of 1-f3-D-Arabinofuranosylcytosine. Studies on Mechanisms of Action in Burkitt's Cell Culture and Mouse Leukemia and in Vitro Deamination Studies. Biochem. Pharmacol., 16: 689-706, 1967.

Dooley, Andrea J., et al. "From genome to drug lead: identification of a small-molecule inhibitor of the SARS virus." Bioorganic & medicinal chemistry letters 16.4 (2006): 830-833.

Gaurav, Anand, and Mayasah Al-Nema. "Polymerases of coronaviruses: structure, function, and inhibitors." Viral Polymerases. Academic Press, 2019. 271-300.

Haagmans, Bart L., and Albert DME Osterhaus. "Coronaviruses and their therapy." Antiviral research 71.2-3 (2006): 397-403.

Hampton, Tracy, "New Flu Antiviral Candidate May Thwart Drug Resistance" JAMA Jan. 7, 2020 vol. 323, No. 1, 17.

Kliger, Yossef, Erez Y. Levanon, and Doron Gerber. "From genome to antivirals: SARS as a test tube." Drug discovery today 10.5 (2005): 345-352.

Kumaki, Yohichi, et al. "Inhibition of adenovirus serotype 14 infection by octadecyloxyethyl esters of (S)-[(3-hydroxy-2-phosphonomethoxy)propyl]-nucleosides in vitro." Antiviral research 158 (2018): 122-126.

Law, Siukan, Albert Wingnang Leung, and Chuanshan Xu. "Severe acute respiratory syndrome (SARS) and coronavirus disease-2019 (COVID-19): From causes to preventions in Hong Kong." International Journal of Infectious Diseases 94 (2020): 156-163. doi: https://doi.org/10.1016/j.ijid.2020.03.059.

Matthes, E., and H. Bünger. "Cellular Pharmacology of the Anti-Hepatitis B Virus Agent β-1-2', 3'-Didehydro-2', 3'-Dideoxy-N4-Hydroxycytidine: Relevance for Activation in HepG2 Cells." Antimicrobial agents and chemotherapy 54.1 (2010): 341-345.

Memish, Ziad A., et al. "Middle East respiratory syndrome." The Lancet 395.10229 (2020): 1063-1077.

Nichols, W. Garrett, Angela J. Peck Campbell, and Michael Boeckh. "Respiratory viruses other than influenza virus: impact and therapeutic advances." Clinical microbiology reviews 21.2 (2008): 274-290.

(56) References Cited

OTHER PUBLICATIONS

Oxford, John S., et al. "New antiviral drugs, vaccines and classic public health interventions against SARS coronavirus." Antiviral Chemistry and Chemotherapy 16.1 (2005): 13-21.
Painter, George R., et al. "The prophylactic and therapeutic activity of a broadly active ribonucleoside analog in a murine model of intranasal Venezuelan equine encephalitis virus infection." Antiviral research 171 (2019): 104597.
Pruijssers, Andrea J., and Mark R. Denison. "Nucleoside analogues for the treatment of coronavirus infections." Current opinion in virology 35 (2019): 57-62.
Rothan, Hussin A., and Siddappa N. Byrareddy. "The epidemiology and pathogenesis of coronavirus disease (COVID-19) outbreak." Journal of autoimmunity 109 (2020): 102433.
Sheahan, Timothy P., et al. "An orally bioavailable broad-spectrum antiviral inhibits SARS-CoV-2 in human airway epithelial cell cultures and multiple coronaviruses in mice." Science translational medicine 12.541 (2020), eabb5883.
Shigeta, Shiro, and Toshihiro Yamase. "Current status of anti-SARS agents." Antiviral Chemistry and Chemotherapy 16.1 (2005): 23-31.
Subissi, Lorenzo, et al. "SARS-CoV ORF1b-encoded nonstructural proteins 12-16: replicative enzymes as antiviral targets." Antiviral research 101 (2014): 122-130.
Tong, Tommy R. "Therapies for coronaviruses. Part 2: Inhibitors of intracellular life cycle." Expert opinion on therapeutic patents 19.4 (2009): 415-431.
Tong, Tommy R. "Drug targets in severe acute respiratory syndrome (SARS) virus and other coronavirus infections." Infectious Disorders-Drug Targets (Formerly Current Drug Targets-Infectious Disorders) 9.2 (2009): 223-245.
Toots, Mart, et al. "Characterization of orally efficacious influenza drug with high resistance barrier in ferrets and human airway epithelia." Science translational medicine 11.515 (2019).
Toots, Mart, et al. "Quantitative efficacy paradigms of the influenza clinical drug candidate EIDD-2801 in the ferret model." Translational Research 218 (2020): 16-28.
Toots, Mart, and Richard K. Plemper. "Next-generation direct-acting influenza therapeutics." Translational Research (2020).
Van Der Hoek, Lia, Krzysztof Pyrc, and Ben Berkhout. "Human coronavirus NL63, a new respiratory virus." FEMS microbiology reviews 30.5 (2006): 760-773.
Van der Hoek, Lia. "Human coronaviruses: what do they cause ?." Antiviral therapy 12.4 Pt B (2007): 651-658.
Van der Hoek, L., et al. "Inhibition of HCoV-NL63 infection at early stages of the replication cycle." Journal of Clinical Virology 36 (2006): S35.
Weiss, Susan R., and Sonia Navas-Martin. "Coronavirus pathogenesis and the emerging pathogen severe acute respiratory syndrome coronavirus." Microbiology and molecular biology reviews 69.4 (2005): 635-664.
Wu, Yu-Shan, et al. "Antiviral drug discovery against SARS-CoV." Current medicinal chemistry 13.17 (2006): 2003-2020.
Zhang, Xue Wu, Yee Leng Yap, and Ralf M. Altmeyer. "Generation of predictive pharmacophore model for SARS-coronavirus main proteinase." European journal of medicinal chemistry 40.1 (2005): 57-62.
Zhuang, Min, et al. "Procyanidins and butanol extract of Cinnamomi Cortex inhibit SARS-CoV infection." Antiviral research 82.1 (2009): 73-81.
Second Examination Report dated Feb. 5, 2021 for Australian Application No. 2015370004.
Third Examination Report dated Feb. 24, 2021 for Australian Application No. 2018378832.
Translation of Office Action dated Oct. 20, 2020 for Japanese Application No. 2017-534192.
Office Action and Search Report issued for Brazilian Application No. BR112017013858-1 dated Oct. 8, 2020. English Translation included.
Office Action issued for Chinese Application No. 201580076718.1, dated Aug. 24, 2020. English Translation included.
Office Action issued for Chinese Application No. 201580076718.1, dated Feb. 8, 2021. English Translation included.
Office Action issued for Chinese Application No. 201580076718.1, dated Aug. 15, 2019. English Translation included.
Pre-Grant Opposition issued for Indian Application No. 201717025098, dated Mar. 22, 2021.
Search and Examination Report issued for Application No. GB2020498.8, dated Mar. 23, 2021.
Pre-Grant Opposition issued for Indian Application No. 201717025098, dated Apr. 1, 2021, 172 pages.
Office Action and search report issued in Russian Application No. 2020116571, dated Apr. 1, 2021, and English Language translation.
Office Action issued in Philippine Application No. 1-2020-550607, dated Apr. 27, 2021.
Office Action and search report issued in Eurasian Application No. 202091005, dated Apr. 8, 2021, and English Language translation.
Pre-grant opposition issued in Indian Application No. 202017019418, dated Apr. 29, 2021 (253 pages).
Pre-Grant Opposition for Indian Application No. 201717025098, dated Mar. 10, 2021.
Communication Pursuant to Rule 114(2) EPC, issued for Application No. 18886104.1, dated Jun. 30, 2021.
Communication Pursuant to Rule 114(2) EPC, issued for Application No. 18886104.1, dated Jun. 17, 2021.
Written Opinion issue for Singaporean Application No. 11202004403Q, dated Jun. 18, 2021.
Office Action issued for Eurasian Application No. 201791460, dated Jun. 23, 2021.
Extended European Search Report issued for European Application No. 18886104.1, dated Jul. 29, 2021, 8 pages.
English translation of Brazilian Office Action issued in BR112020010581-3, dated Jan. 13, 2023.
English translation of Brazilian Office Action issued in BR122021012627-5, dated Jan. 10, 2023.
English translation of Japanese Office Action issued in JP 2021-106296 dated Jan. 11, 2023.
English summary of Korean Office Action issued in Korean Application No. 10-2017-7020692, dated Oct. 31, 2022.
English translation of Brazilian Office Action issued in BR122021015700-6, dated Feb. 7, 2023.
Written Opinion issued in Singapore application No. 11202004403Q, dated Nov. 15, 2022.
Office Action issued in Canadian application No. 2972259, dated Feb. 20, 2023.
English translation of Mexican Office Action issued in MX/a/2020/005392, dated Dec. 16, 2022.
English translation of Japanese Office Action issued in JP 204082 dated Dec. 20, 2022.
English translation of Brazilian Office Action issued in BR112017013858-1, dated Dec. 20, 2022.
Third Party Observation in Philippine Application No. 2020550607, dated Jan. 31, 2022.
Office Action issued for Russian Application No. 2020116571, dated Jan. 25, 2022.
Michael J Sofia; "Nucleotide prodrugs for HCV therapy" Antiviral Chemistry & Chemotherapy 2011; 22:23-49.
Office Action issued for Japanese Application No. 2020 195927, dated Jul. 6, 2022.
Larsen C. S. et al., Textbook of Drug Design and Discovery, Chartper 14, 2002, p. 460-514.
Camille G.Wermuth et al., The Practice of Medicinal Chemistry (Third edition), 2008, Chapter 36 pp. 721-746.
Third Party Observation on Philippine application 12020550607 dated Feb. 3, 2022.
Office Action issued for Eurasian Application No. 202091005, dated Mar. 28, 2022.
Translation of Third Party Observation for Eurasian Application No. 202091005, dated Apr. 20, 2022.
Office Action issued for Canadian Application No. 2,972,259, dated Apr. 4, 2022.
Office Action issued for Eurasian Application No. 201791460/28, dated Mar. 28, 2022.

(56) References Cited

OTHER PUBLICATIONS

Examination Report issued for Australian Application No. 2021203840, dated Aug. 19, 2022.
Office Action issued for Brazilian Application No. BR112020010581-3, dated Jul. 12, 2022.
Office Action issued for Brazilian Application No. BR122021012627-5, dated Jul. 12, 2022.
Office Action issued for Brazilian Application No. BR122022008466-4, dated Jul. 12, 2022.
Office Action issued for Brazilian Application No. BR12202208542-3, dated Jul. 12, 2022.
Official Action issued for Russian Application No. 2020116571/04, dated Sep. 23, 2022.
H. Musther et al. Animal versus human oral drug bioavailability: Do they correlate? European Journal of Pharmaceutical Sciences, 2014, 57(100), 280-291.
English translation of Third Party Obesrvation—Complementary Subsidy to the Technical Examination issued for Brazilian Patent Application No. BR122021012627-5, dated Oct. 6, 2022.
Notice of Allowance issued for U.S. Appl. No. 16/921,359, dated Sep. 28, 2022.
Official Action issued for Korean Application No. 10-2022-0077077, dated Oct. 14, 2022.
Decision to Grant issued for Japanese Patent Application No. 2020-195927, dated Oct. 19, 2022.
Ehteshami, Nucleotide Substrate Specificity of Anti Hepatitis C Virus Nucleoside Analogs for Human Mitochondrial RNA Polymerase Antimicrobial agents and chemotherapy vol. 61 Issue 8 pp. e00492-17.
Foster, A.B., et al., "Deuterium Isotope Effects in the Metabolism of Drugs and Xenobiotics: Implications for Drug Design", Advances in Drug Research, 1985, vol. 14, pp. 1-40.
Haraguchi et al., Ring Opening of 4', 5'-Epoxynucleosides: A Novel Stereoselective Entry to 4'-C-Branched Nucleosides, Org. Lett., vol. 5, No. 9, 1399-1402.
Henderson et al., Lithium 2,2,2-Trifluoroethoxide, Encyclopedia of Reagents for Organic Synthesis, 1-3, 2009.
Ivanov et al., Synthesis and Biological Properties of Pyrimidine 4'-Fluoronucleosides and 4'-Fluorouridine 5'-OTriphosphate, Russian Journal of Bioorganic Chemistry vol. 36, No. 4, 2010, pp. 488-496.
Nowak et al., Selective Removal of the 2'- and 3'-O-Acyl Groups from 2',3',5'-Tri-Oacylribonucleoside Derivatives with Lithium Trifluoroethoxide, J. Org. Chem. 2006, 71, 3077-3081.
PUBCHEM database, prior reported chemical structures, created before Jul. 12, 2017.
Shimada et al., Nucleophilic substitution approach to 4'-substituted thymidines by employing 4'-benzenesulfonyl leaving group, Tetrahedronm vol. 65, Jun. 3, 2009, pp. 6008-6016.
Singh et al., Manipulation of enzyme regioselectivity by solvent engineering: Enzymatic synthesis of 5'-Oacylribonucleosides. Tetrahedron Letters.
Sun et al., Synthesis, transport and pharmacokinetics of 5'-amino acid ester prodrugs of 1-beta-D-arabinofuranosylcytosine, Molecular Pharmaceutics, vol. 6, No. 1, 315-325, 2009.
Ueda et al., Synthesis and Reaction of Pyrimidine Nucleosides, Chemistry of Nucleosides and Nucleotides, 1988, pp. 1-112.
Belikov V.G. "Pharmaceutical Chemistry", textbook , 2007, M, "MEDpress—inform", 624 pages, p. 27-29.
Information of national phases of the application PCT/US2018/064503 from the WIPO website (PATENTSCOPE).
First Examination Report dated Aug. 19, 2022, for Australian Application No. 2021203840.
First Examination Report for Australian Application No. 2021068666 dated Apr. 17, 2023.
Examination Report dated Jun. 30, 2023, for Australian Application No. 2021203840.
Office Action issued for Brazilian Application No. BR112017013858-1 dated Nov. 25, 2022.
Office Action issued in Brazilian Application No. BR112020010581-3, dated Sep. 16, 2021.
Office Action issued for Brazilian Application No. BR112020010581-3, dated Feb. 1, 2022.
Office Action issued for Brazilian Application No. BR122021012627-5, dated Mar. 8, 2022.
Office Action issued for Brazilian Application No. BR122022008466-4 dated Apr. 11, 2023.
Office Action issued for Brazilian Application No. BR12202208542-3 dated Mar. 2, 2023.
Office Action issued for Chinese Application No. 201880073278.8 dated Jun. 8, 2021.
Reexamination Notice issued for Chinese Application No. 201580076718.1 dated May 24, 2023.
Office Action issued for Eurasian Application No. 202091005, dated Mar. 16, 2022.
Office Action issued for Eurasian Application No. 202091005, dated Apr. 21, 2022.
Office Action issued in Eurasian Application No. 202091005 dated Nov. 25, 2022.
English translation of Office Action issued for Eurasian Application No. 202091005 dated Apr. 25, 2023.
Office Action issued for Eurasian Application No. 201791460/28 dated Aug. 18, 2020.
Office Action issued for Eurasian Application No. 201791460/28 dated Jan. 25, 2023.
Communication issued in EP Application No. 21178364.2, dated Apr. 4, 2023.
Office Action issued for Japanese Application No. 2017-534192, dated Apr. 25, 2023.
Re-Examination report issued for JP2021-017354, dated Mar. 8, 2022.
Pre-Grant Opposition issued in IN 202017019418, dated Oct. 8, 2021.
Pre-Grant Opposition issued in IN 201717025098, dated Mar. 10, 2021.
Pre-Grant Opposition issued in IN 201717025098, dated Apr. 7, 2021.
Pre-Grant Opposition issued in IN 201717025098, dated Jun. 23, 2021.
Pre-Grant Opposition issued in IN 201717025098, dated Sep. 6, 2021.
Office Action issued in Indian Application No. 201717025098 dated Feb. 16, 2023.
Office Action for Israeli Application No. 252997 dated Aug. 15, 2019.
Office Action for Israeli Application No. 279663 dated Feb. 16, 2022.
Office Action for Israeli Application No. 296496 dated Mar. 22, 2023.
English summary of Korean Application No. 10-2017-7020692 dated Feb. 15, 2023.
English summary of Korean Application No. 10-2017-7020692 dated May 30, 2023.
English translation of Office Action for Korean Application No. 10-2021-7012910 dated Jul. 3, 2023.
English translation of Korean Notice of Preliminary Rejection issued KR 10-2021-7012910 dated Dec. 22, 2022.
Office Action for Russian Application No. 2020116571 dated Jan. 25, 2022.
Office Action for Russian Application No. 2020116571 dated May 19, 2023.
Office Action Issued for Singaporean Application No. 11201705069Y, dated Mar. 22, 2021.
Office Action Issued for Singaporean Application No. 10202105371Y, dated Jul. 5, 2023.
Search Report Issued for Singaporean Application No. 10202105371Y, dated Jul. 5, 2023.
International Search Report and Written Opinion issued for Application No. PCT/US2021/016984 dated Jun. 28, 2021.
International Search Report and Written Opinion for International Application No. PCT/US2019/021168 dated Jul. 8, 2019, 12 pages.
International Preliminary Report on Patentability issued for Application No. PCT/US2019/021168, dated Sep. 17, 2020.
Office Action dated Sep. 3, 2020, in U.S. Appl. No. 16/755,779.

(56) References Cited

OTHER PUBLICATIONS

Office Action dated Jan. 6, 2021, in U.S. Appl. No. 16/755,779.
Notice of Allowance issued for U.S. Appl. No. 16/755,779, dated Apr. 28, 2021.
Office Action issued in Philippine Application No. 1-2020-550607, dated Jan. 31, 2022.
Third Party Observation in Philippine Application No. 2020550607, dated Feb. 3, 2022.
Office Action for Philippines Application No. 1-2022-550371 dated Oct. 7, 2022.
English translation of Indonesian Application No. P00202003494 mailed Jun. 30, 2022.
English summary of Substantive Examination for Application No. 520412305 OA dated Feb. 25, 2022.
Office Action for Saudi Arabian Application No. 522432673 dated May 22, 2023.
Office Action with English translation for Georgian Application No. 202116034 dated 5/10/223.
English translation of Office Action for Mongolian Application No. 10-2022-00681 dated Jan. 3, 2023.
Office Action for Vietnamese Application No. 1-2022-01444 dated Sep. 13, 2022.
Examination Report for Pakistan Application No. 115/2021 dated Mar. 1, 2022.
Office Action for Korean Application No. 10-2021-7012910 dated Jul. 3, 2023.
Office Action and Search Report for Malaysian Application No. PI2022001117 dated Jun. 21, 2023.
Office Action for Russian Application No. 20201165701 dated May 19, 2023.
English translation of Office Action for Iranian Application No. 140150140003003647, dated Jul. 12, 2023.
Office Action for Sri Lankan Application No. 22215, dated Jul. 20, 2023.
Extended European Search Report issued in EP 21750787.0, dated Aug. 2, 2023.
Sheahan et al: "An orally bioavailable broad-spectrum antiviral inhibits SARS-CoV-2 and multiple endemic, epidemic and bat coronavirus", bioRxiv, Mar. 20, 2020.
Sheahan et al: "An orally bioavailable broad-spectrum antiviral inhibits SARS-CoV-2 in human airway epithelial cell cultures and multiple coronaviruses in mice", Sci. Transl. Med, Apr. 29, 2020 p. eabb5883.
Al-Horani et al: "Potential Anti-SARS-CoV-2 Therapeutics That Target the Post-Entry Stages of the Viral Life Cycle: A Comprehensive Review", Viruses, vol. 12, No. 10, Sep. 26, 2020.
Painter Wendy P. et al: "Human Safety, Tolerability, and Pharmacokinetics of a Novel Broad-Spectrum Oral Antiviral Compound, Molnupiravir, with Activity Against SARS-CoV-2", medRxiv, Dec. 14, 2020.
Painter Wendy P. et al: "Human Safety, Tolerability, and Pharmacokinetics of Molnupiravir, a Novel Broad-Spectrum Oral Antiviral Agent with Activity against SARS-CoV-2", Antimicrobial Agents and Chemotherapy, vol. 65, No. 5, Apr. 19, 2021.
Wahl Angela et al: "SARS-CoV-2 infection is effectively treated and prevented by EIDD-2801", Nature, vol. 591, No. 7850, Feb. 9, 2021.
Imran Mohd. et al: "Discovery, Development, and Patent Trends on Molnupiravir: A Prospective Oral Treatment for COVID-19", Molecules, vol. 26, No. 19, Sep. 24, 2021.
Notice of Acceptance issued in Australian Application No. 2021203840, dated Aug. 15, 2023.
English translation of Office Action for Chilean Application No. 2022-423, dated Aug. 3, 2023.
English translation of Office Action for Indonesian Application No. P00202211381, dated Aug. 23, 2023.
English Translation of Office Action issued for MX/a/2020/005392 dated Sep. 2, 2022.
English translation of Office Action issued in Ukrainian application No. a202203239, dated Sep. 27, 2023.
English translation of Japanese Notice of Allowance issued in JP2017-534192, dated Oct. 10, 2023.
English translation of Eurasian Office Action issued in Application No. 202291843, dated Oct. 11, 2023.
English translation of Decision to Grant issued in KR 10-2021-7012910, dated Oct. 12, 2023.
English summary of office action issued in Saudi Arabian Application No. 520412305, dated Oct. 19, 2023.
English summary of office action issued in Saudi Arabian Application No. 522432673, dated Oct. 19, 2023.
Substantive Examination Report issued in Philippines Application No. 1/2020/550607, dated Nov. 13, 2023.
English translation of Office Action issued in Indonesia Application No. P00202201460, dated Oct. 20, 2023.
Office Action issued in Canadian Application No. 297259, dated Dec. 8, 2023.

* cited by examiner

Therapeutic EIDD 2801 with SARS-CoV challenge: Lung Hemhorrage

FIG. 21

SARS MA15 Virus lung Titer with EIDD 2801 Treatment

FIG. 22

N4-HYDROXYCYTIDINE AND DERIVATIVES AND ANTI-VIRAL USES RELATED THERETO

ACKNOWLEDGEMENT OF GOVERNMENT SUPPORT

This invention was made with government support under grant nos. HDTRA1-13-C-0072 and HDTRA1-15-C-0075 awarded by the Department of Defense and grant nos. HHSN272201500008C and 75N93019C00058 awarded by National Institutes of Health. The government has certain rights in the invention.

FIELD

This disclosure relates to N4-hydroxycytidine nucleoside and derivatives, as well as compositions and methods related thereto. In certain embodiments, the disclosure relates to the treatment or prophylaxis of viral infections, in particular, Eastern, Western, and Venezuelan Equine Encephalitis (EEE, WEE and VEE, respectively), Chikungunya fever (CHIK), Ebola, Influenza, RSV, and Zika virus infections.

BACKGROUND

The causative agents for Eastern, Western, and Venezuelan Equine Encephalitis (EEE, WEE and VEE, respectively) and Chikungunya fever (CHIK) are vector-borne viruses (family *Togaviridae*, genus *Alphavirus*) that can be transmitted to humans through mosquito bites. The equine encephalitis viruses are CDC Category B pathogens, and the CHIK virus is Category C. There is considerable concern about the use of virulent strains of VEE virus, delivered via aerosol, as a bioweapon against warfighters. Animal studies have demonstrated that infection with VEE virus by aerosol exposure rapidly leads to a massive infection of the brain, with high mortality and morbidity. See Roy et al., Pathogenesis of aerosolized Eastern equine encephalitis virus infection in guinea pigs. *Virol J*, 2009, 6:170.

Stuyver et al., report β-D-N(4)-hydroxycytidine (NHC) was found to have antipestivirus and antihepacivirus activities. *Antimicrob Agents Chemother*, 2003, 47(1):244-54. Constantini et al. report evaluations on the efficacy of 2'-C—MeC, 2'-F-2'-C—MeC, and NHC on Norwalk virus. See also Purohit et al., *J Med Chem*, 2012, 55(22):9988-9997; Ivanov et al., Collection of Czechoslovak Chem Commun, 2006, 71(7):1099-1106; and Fox et al., JACS, 1959, 81:178-87.

What are needed are new compounds and treatments for viral infections. The compounds and methods disclosed herein addressed these needs.

SUMMARY

This disclosure relates to certain N4-hydroxycytidine and derivatives, combinations, pharmaceutical compositions, and methods related thereto. In certain embodiments, the disclosure relates to a compound having Formula I, Formula A or a pharmaceutically acceptable salt, derivative, or prodrug thereof, as defined herein.

In certain embodiments, the disclosure contemplates derivatives of compounds disclosed herein, such as those containing one or more, the same or different, substituents.

In certain embodiments, the disclosure contemplates pharmaceutical compositions comprising a pharmaceutically acceptable excipient and a compound disclosed herein. In certain embodiments, the pharmaceutical composition is in the form of a tablet, capsule, pill, or aqueous buffer, such as a saline or phosphate buffer.

In certain embodiments, the disclosed pharmaceutical compositions can comprise a compound disclosed herein and a propellant. In certain embodiments, the propellant is an aerosolizing propellant such as compressed air, ethanol, nitrogen, carbon dioxide, nitrous oxide, hydrofluoroalkanes (HFAs), 1,1,1,2,-tetrafluoroethane, 1,1,1,2,3,3,3-heptafluoropropane or combinations thereof.

In certain embodiments, the disclosure contemplates a pressurized or unpressurized container comprising a compound or pharmaceutical composition as described herein. In certain embodiments, the container is a manual pump spray, inhaler, meter-dosed inhaler, dry powder inhaler, nebulizer, vibrating mesh nebulizer, jet nebulizer, or ultrasonic wave nebulizer.

In certain embodiments, the disclosure relates to methods of increasing bioavailability for treating or preventing a viral infection comprising administering an effective amount of a compound or pharmaceutical composition disclosed herein to a subject in need thereof.

In certain embodiments, the disclosure relates to methods of treating or preventing a viral infection comprising administering an effective amount of a compound or pharmaceutical composition disclosed herein to a subject in need thereof. In certain embodiments, the viral infection is a Zika virus infection. In other embodiments, the viral infection is Eastern, Western, and Venezuelan Equine Encephalitis (EEE, WEE and VEE, respectively), Chikungunya fever (CHIK), Ebola, Influenza, or RSV.

In certain embodiments, the compound or pharmaceutical composition is administered orally, intravenously, or through the lungs, i.e., pulmonary administration.

In certain embodiments, the disclosure relates to the use of a compound as described herein in the production of a medicament for the treatment or prevention of a viral infection, such as Eastern, Western, and Venezuelan Equine Encephalitis (EEE, WEE and VEE, respectively), Chikungunya fever (CHIK), Ebola, Influenza, RSV, or Zika virus infection.

In certain embodiments, the disclosure relates to method of making compounds disclosed herein by mixing starting materials and reagents disclosed herein under conditions such that the compounds are formed.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIG. 21 shows the effect of EIDD-2801 time of treatment on lung hemorrhage scores of SARS infected mice.

FIG. 22 shows the effect of EIDD-2801 time of treatment on lung viral titers of SARS infected mice.

DETAILED DESCRIPTION

Figure 1:
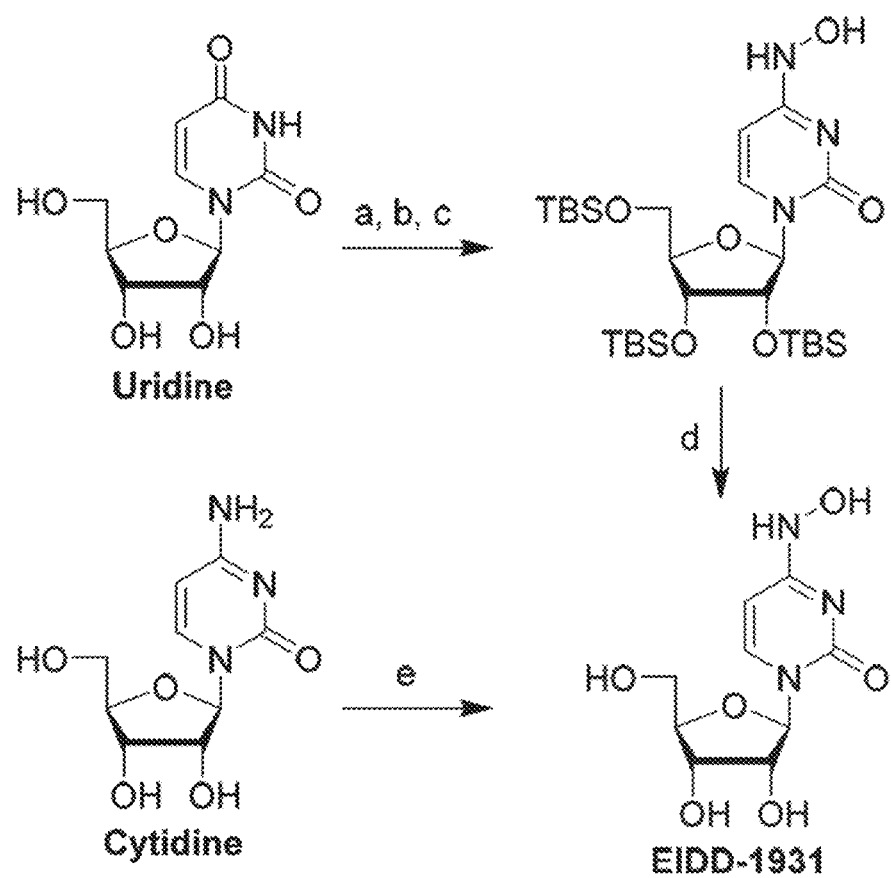
FIG. 1 is a scheme illustrating the preparation of β-D-N-hydroxycytidine. The steps of the synthesis are a.) TBSC1, DMAP, DIPEA, DCM; b.) (2,4,6-iPr)PhSO$_2$Cl, DIPEA, DMAP, DCM; c.) NH$_2$OH—HCl, DIPEA, DCM; d.) F-source; and e.) aq NH$_2$OH, AcOH, 50° C.
Figure 2:
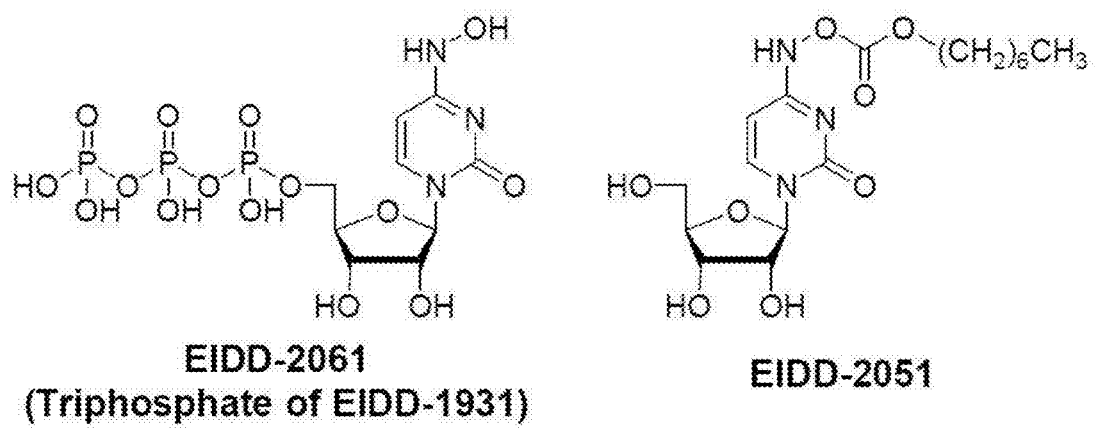
FIG. 2 illustrates certain exemplary compounds.
Figure 3:
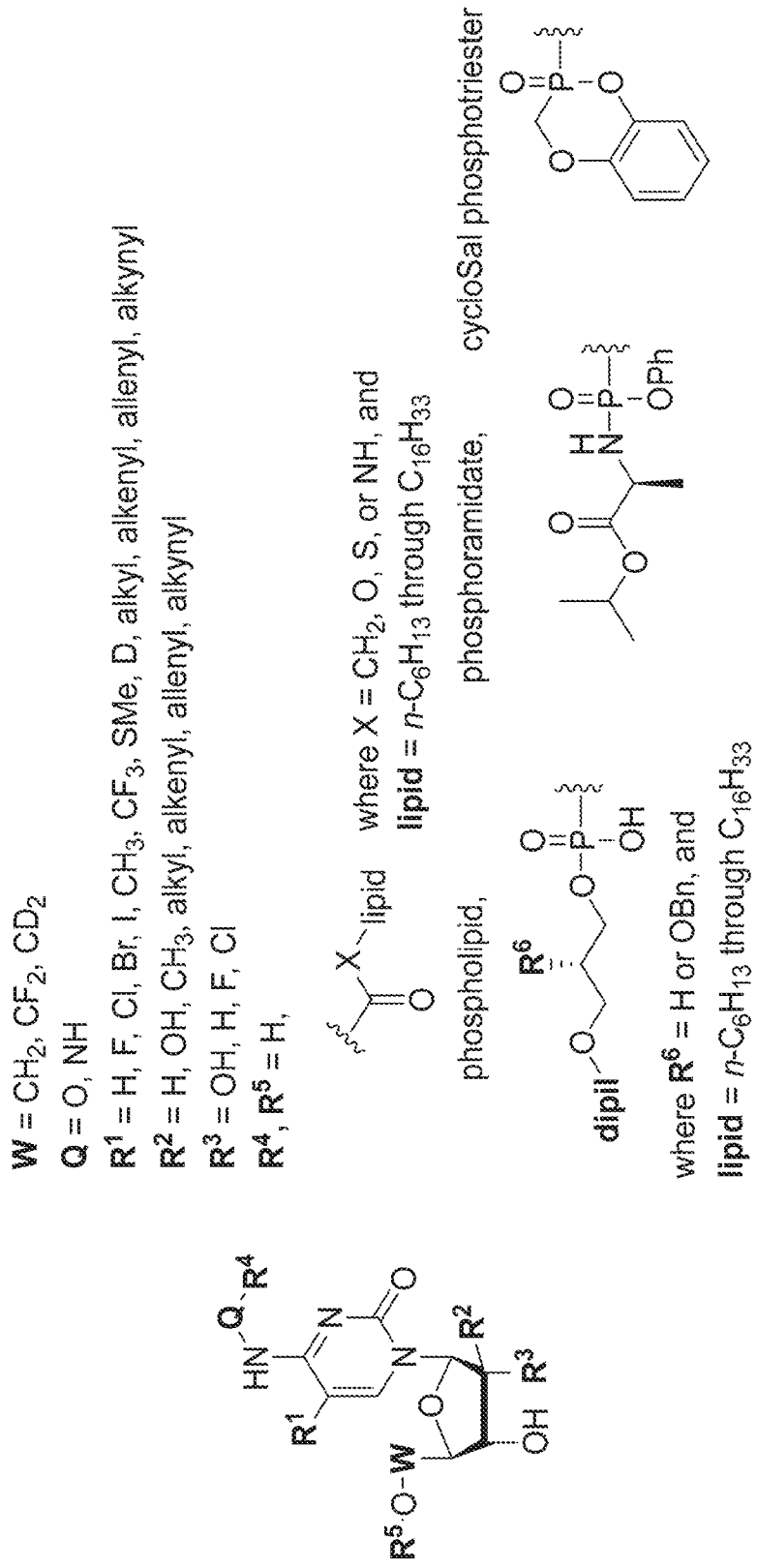
FIG. 3 illustrates certain exemplary compounds.
Figure 4:
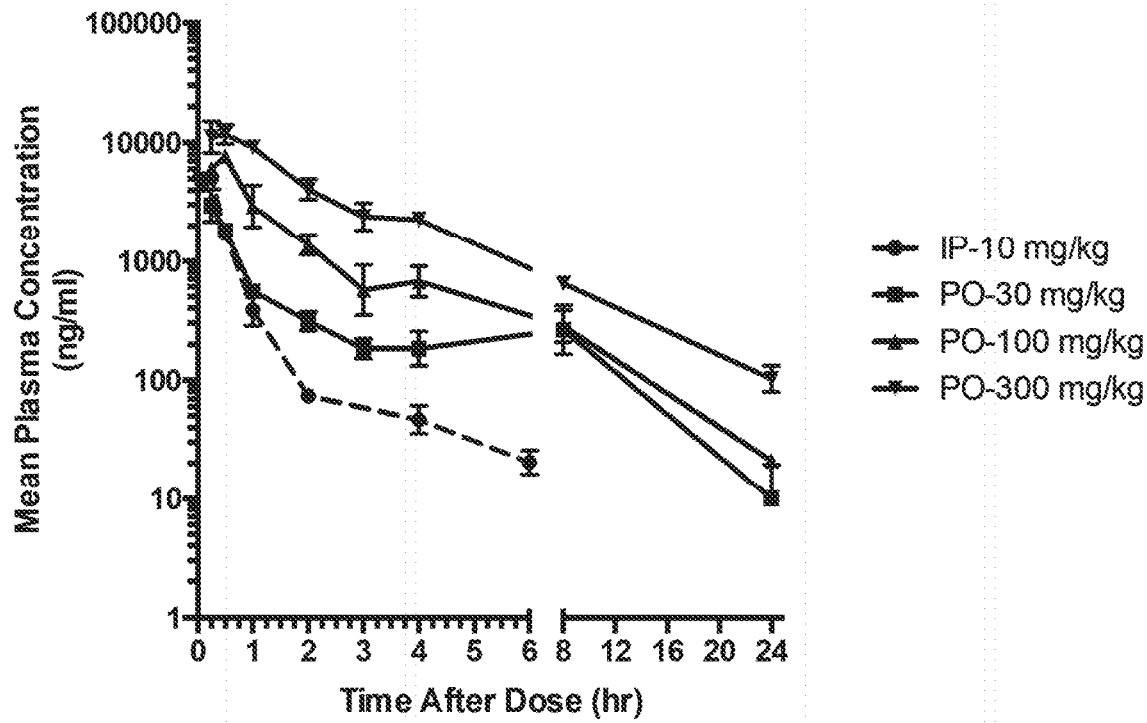
FIG. 4 shows mean plasma concentrations and pharmacokinetic parameters from mice treated with an exemplary compound.
Figure 5:
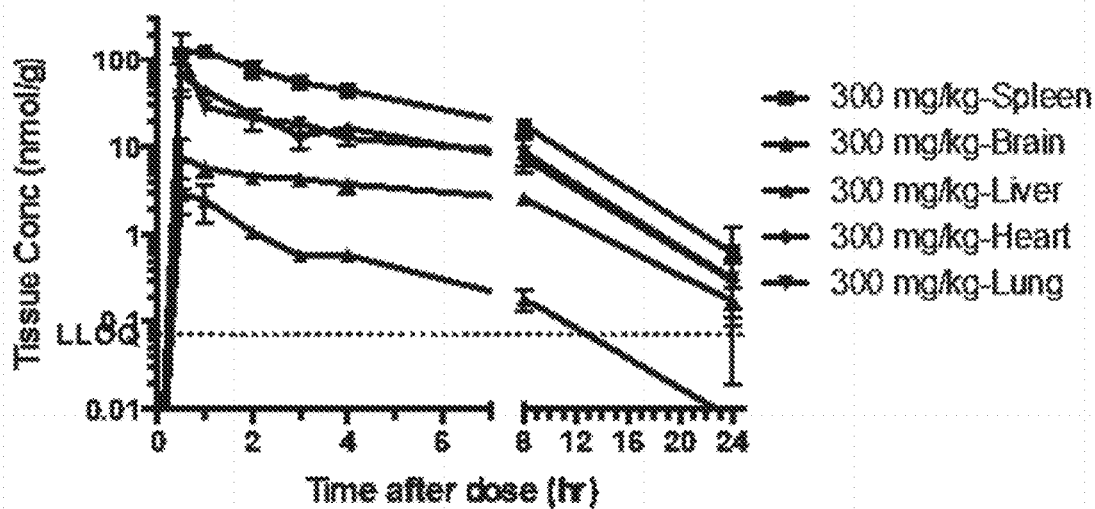
FIG. 5 shows nucleoside accumulation in mouse organs in mice treated with an exemplary compound.
Figure 6:
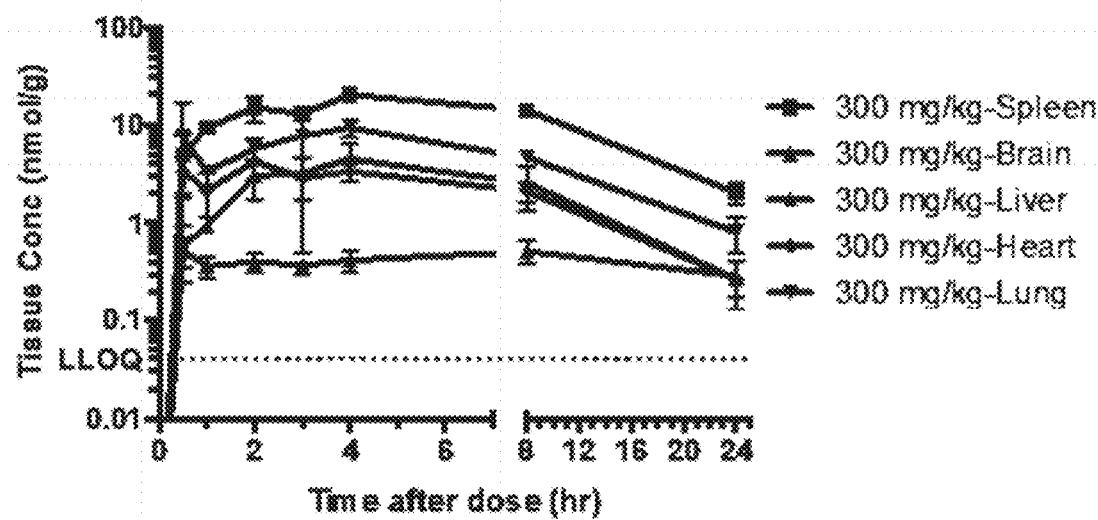
FIG. 6 shows triphosphate accumulation in mouse organs in mice treated with an exemplary compound.
Figure 7:
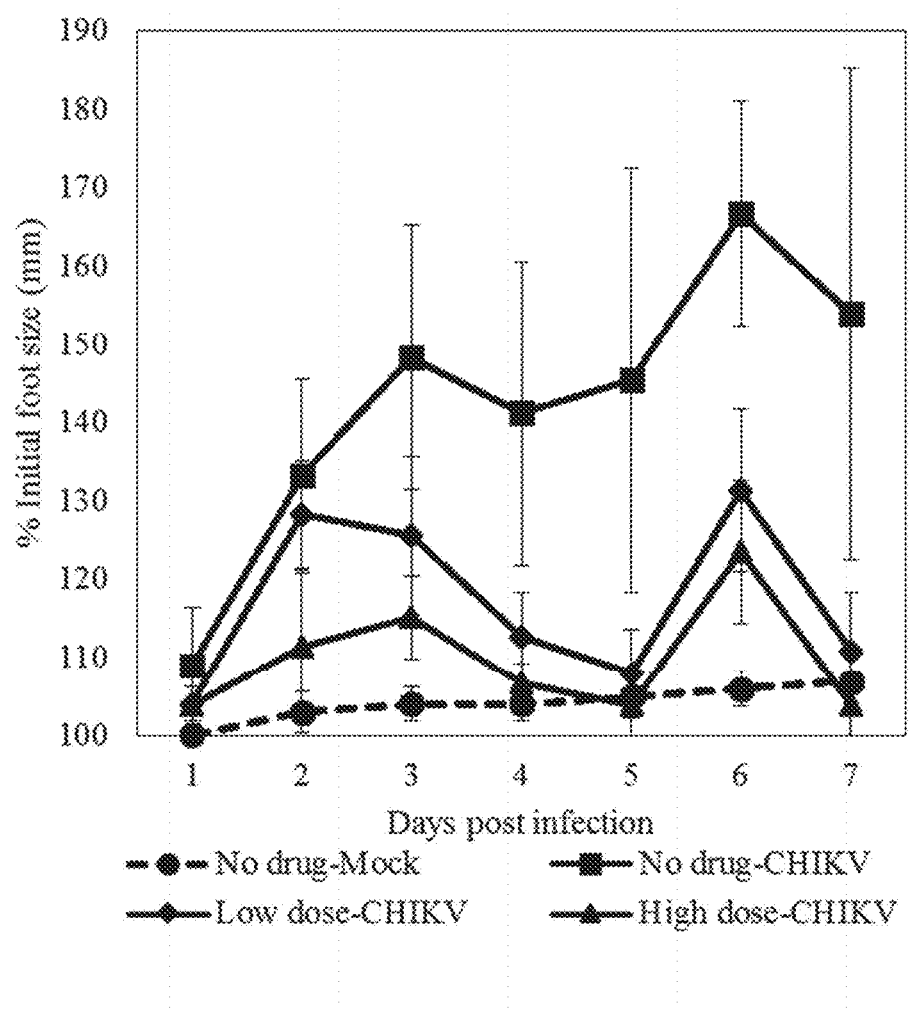
FIG. 7 shows reduction in footpad swelling in CHIKV-challenged mice treated with an exemplary compound.
Figure 8:
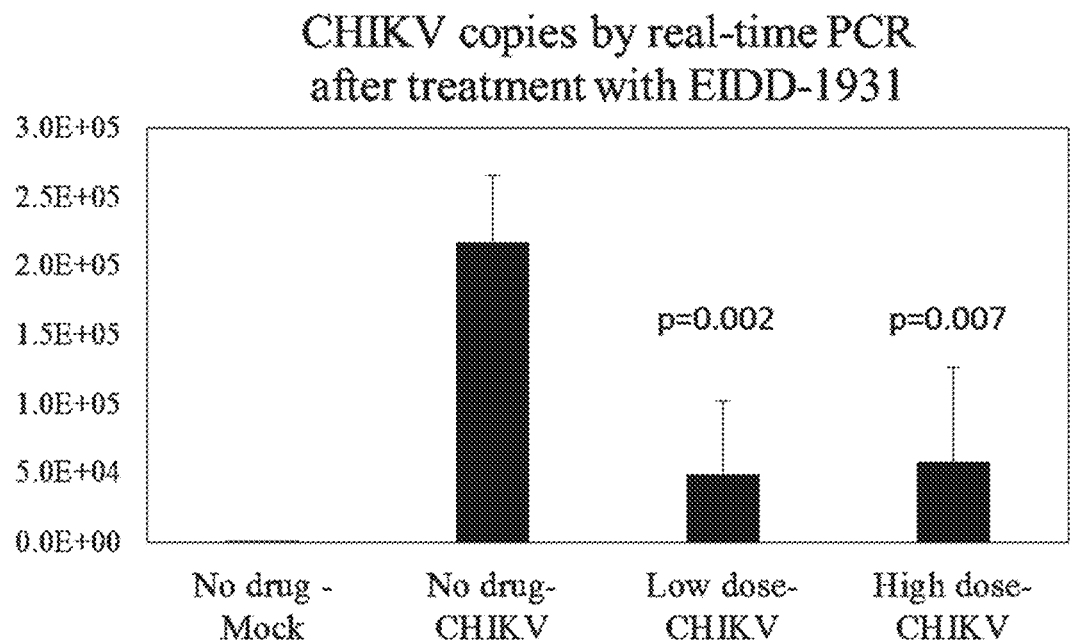
FIG. 8 shows reduction of CHIKV-RNA copies by PCR in CHIKV-challenged mice treated with an exemplary compound.
Figure 9:
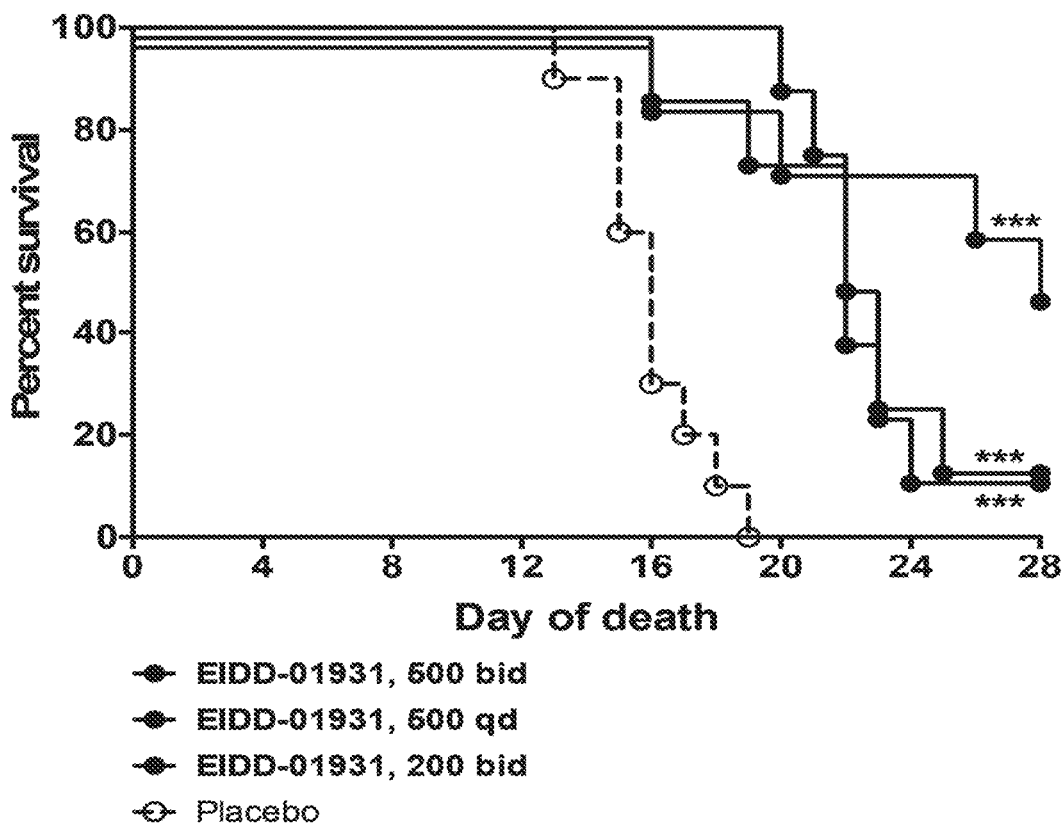
FIG. 9 shows the survival of ZIKV-challenged mice treated with an exemplary compound for 7 days.
Figure 10:
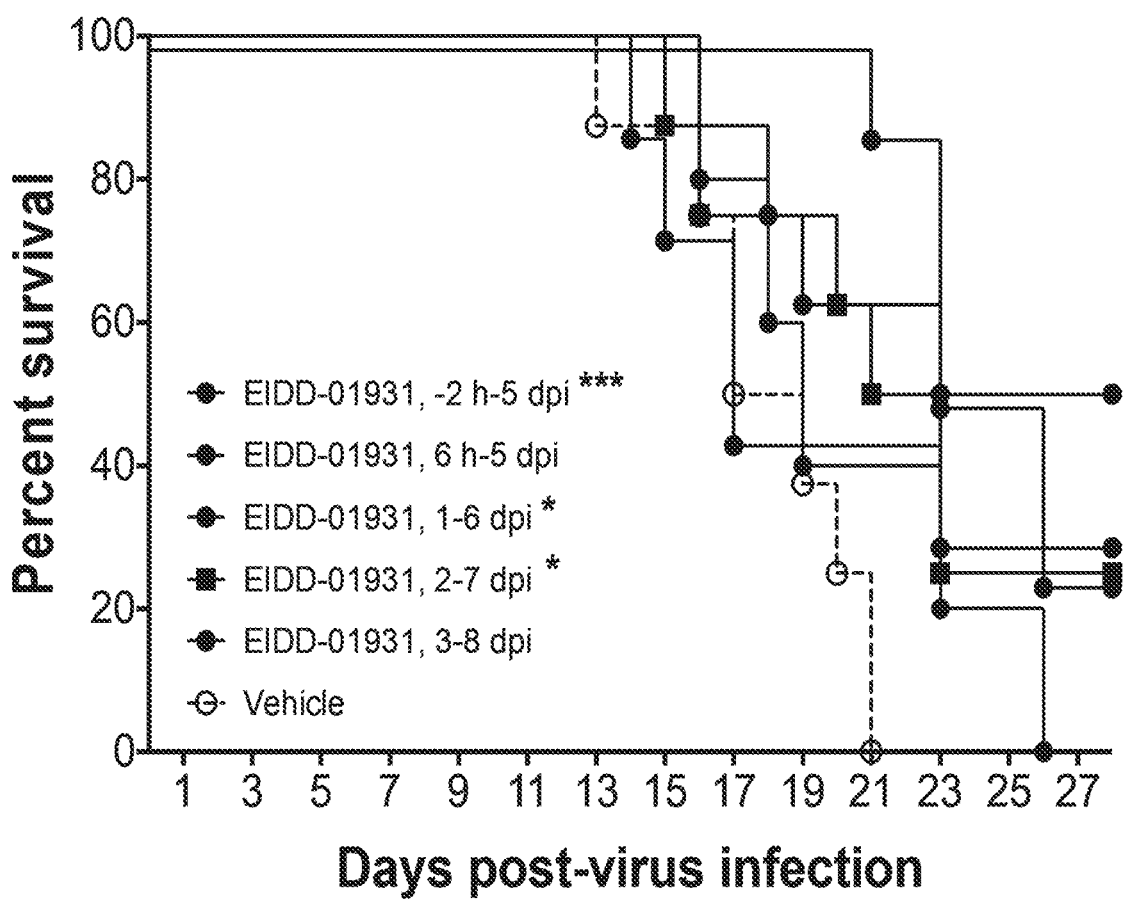
FIG. 10 shows the survival of ZIKV-challenged mice treated with an exemplary compound for 7 days, with varying treatment initiation times post-infection.
Figure 11:
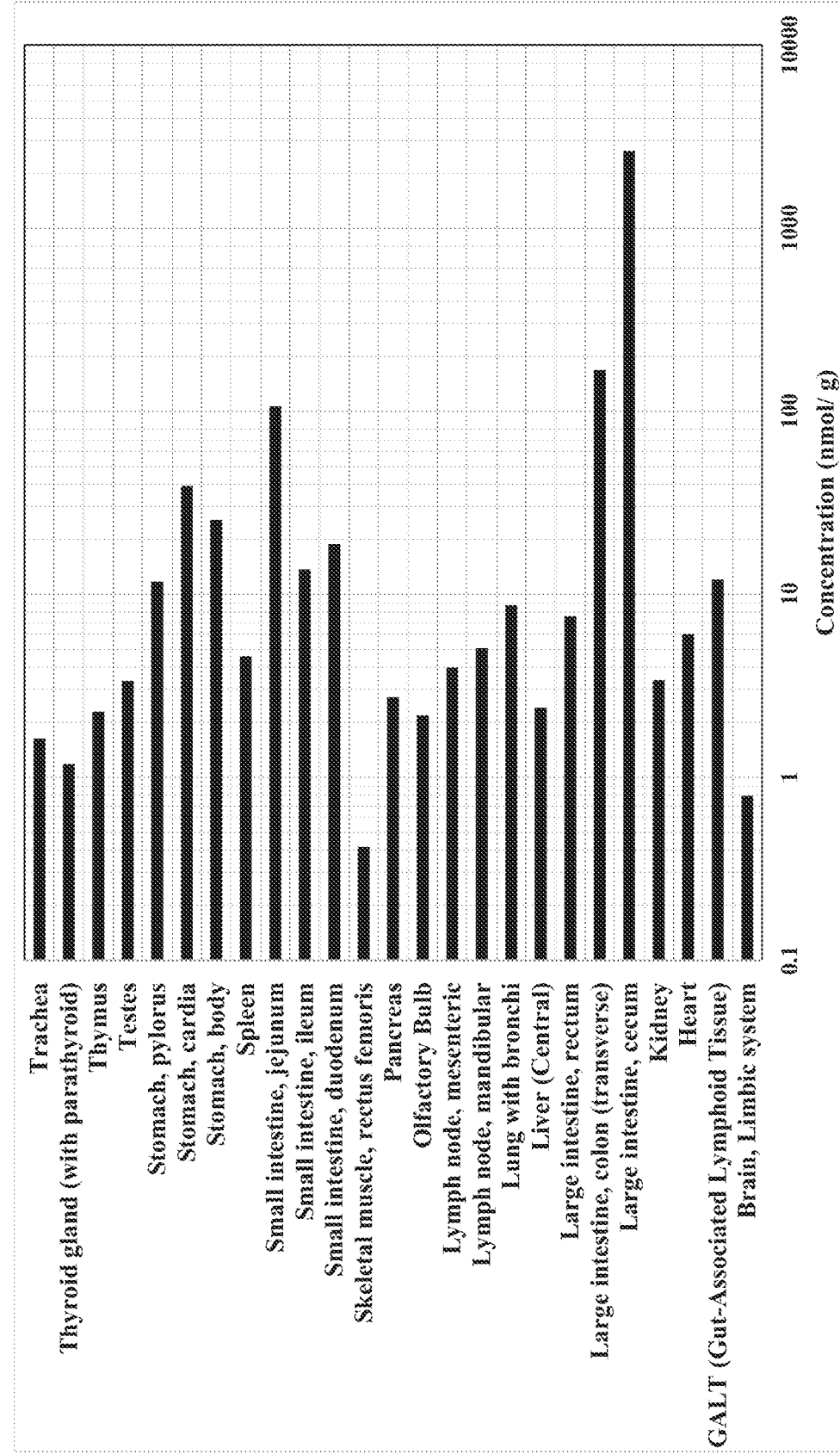
FIG. 11 shows the N4-hydroxycytidine nucleoside tissue concentrations from a cynomolgus macaque orally administered EIDD-1931 (100 mg/kg).
Figure 12:
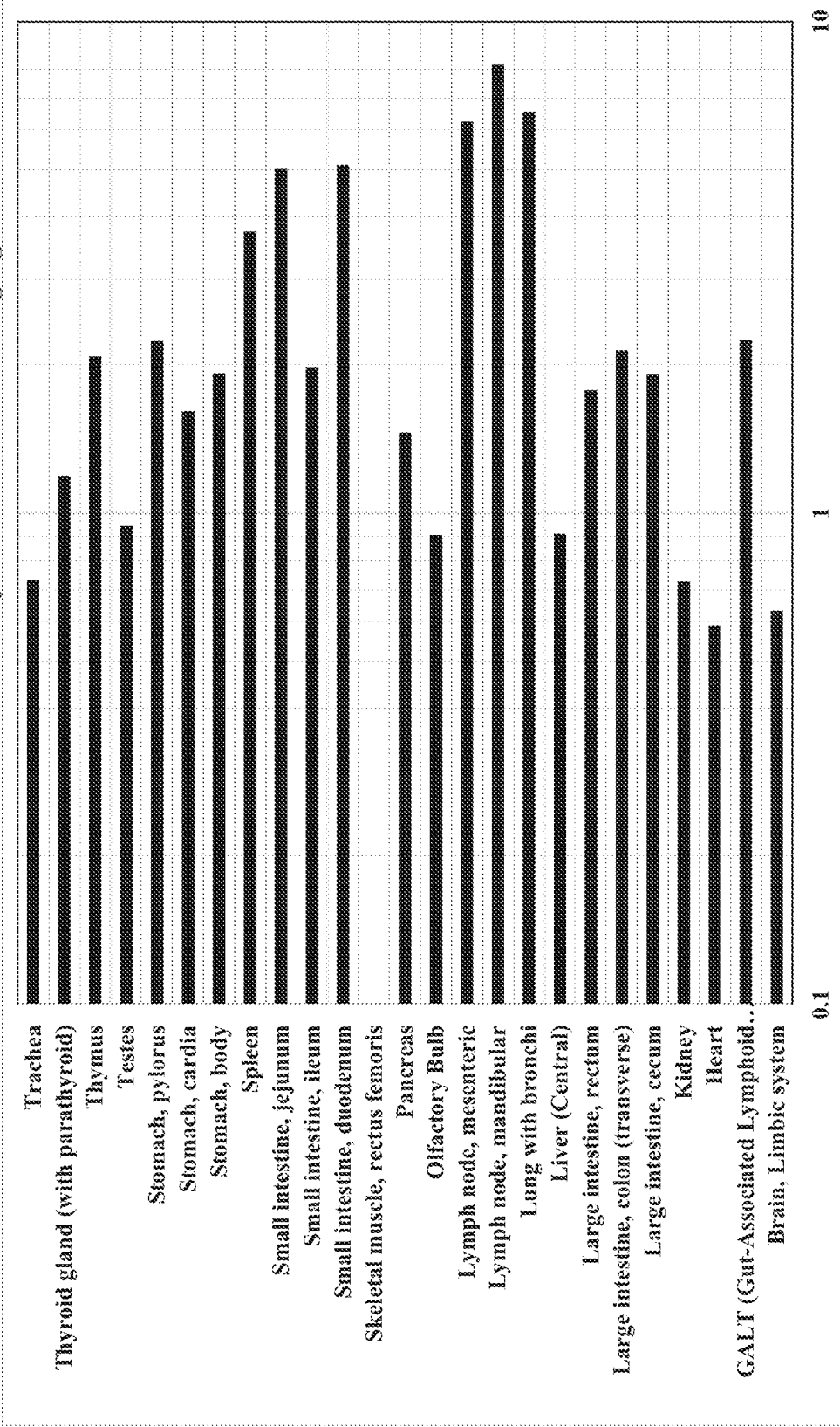
FIG. 12 shows the N4-hydroxycytidine nucleoside tissue concentrations from a cynomolgus macaque intravenously administered EIDD-1931 (10 mg/kg).
Figure 13:
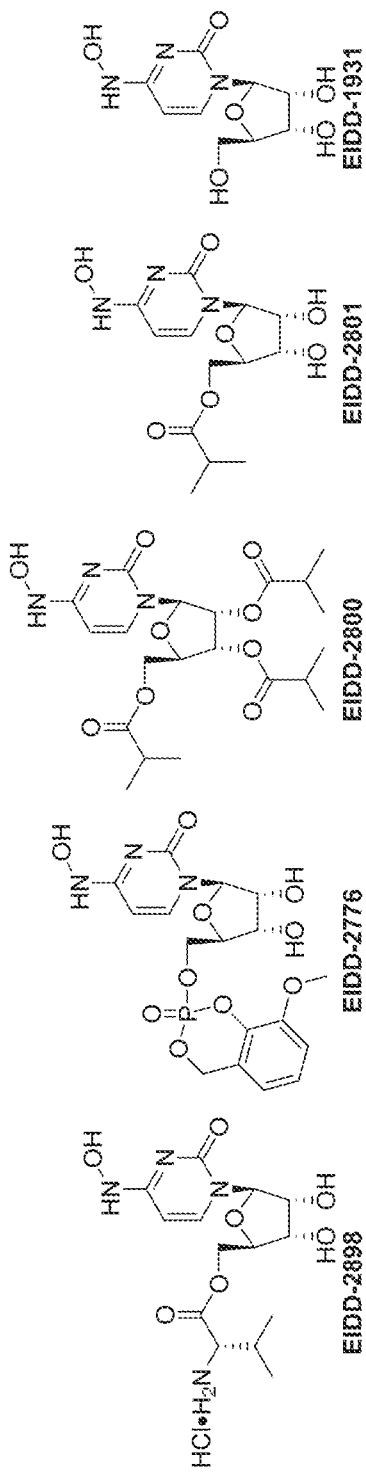
FIG. 13 shows the structure of compounds orally administered to cynomolgus macaques.
Figure 14:
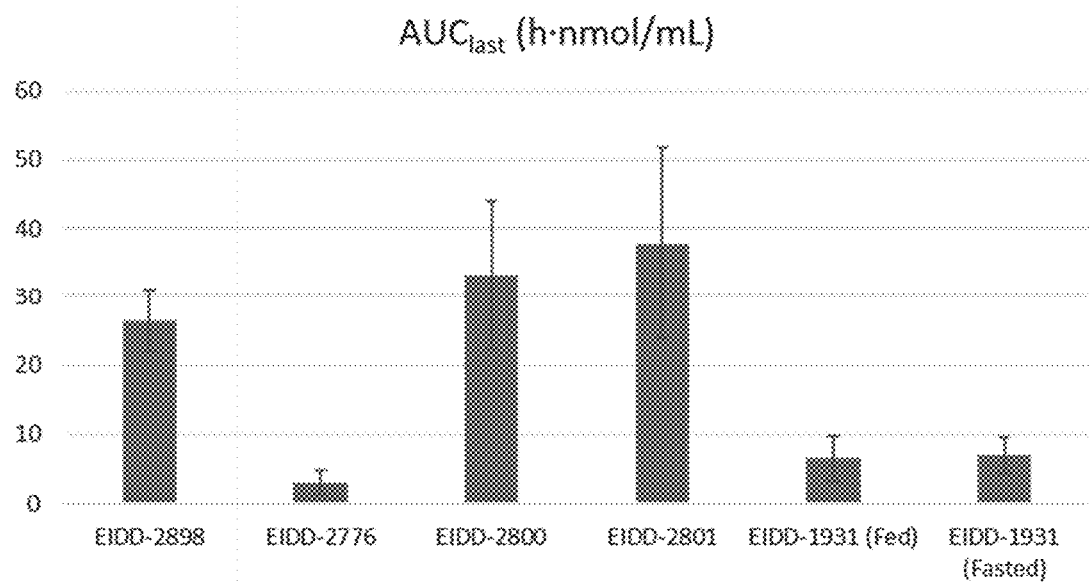
FIG. 14 shows the mean N4-hydroxycytidine nucleoside plasma concentrations from cynomolgus macaques orally administered with an ester derivative.
Figure 15:
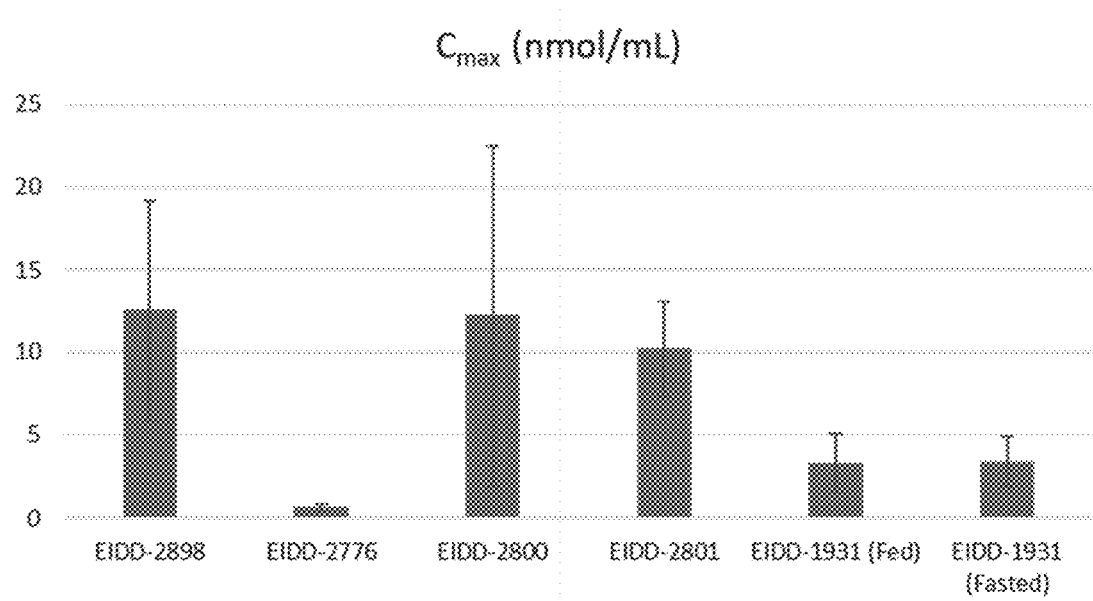
FIG. 15 shows the mean maximum concentration of N4-hydroxycytidine nucleoside in plasma from cynomolgus macaques orally administered with an ester derivative.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features, which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

In certain embodiments, a pharmaceutical agent, which may be in the form of a salt or prodrug, is administered in methods disclosed herein that is specified by a weight. This refers to the weight of the recited compound. If in the form of a salt or prodrug, then the weight is the molar equivalent of the corresponding salt or prodrug.

It must be noted that, as used in the specification and the appended claims, the singular forms "a," "an," and "the" include plural referents unless the context clearly dictates otherwise.

"Subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent can be administered prior to, together with, or after the additional treatment, or a combination thereof.

As used herein, "alkyl" means a straight or branched chain saturated hydrocarbon moieties such as those containing from 1 to 10 carbon atoms. A "higher alkyl" refers to saturated hydrocarbon having 11 or more carbon atoms. A "$C_6$-$C_{16}$" refers to an alkyl containing 6 to 16 carbon atoms. Likewise a "$C_6$-$C_{22}$" refers to an alkyl containing 6 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like.

As used herein, the term "alkenyl" refers to unsaturated, straight or branched hydrocarbon moieties containing a double bond. Unless otherwise specified, $C_2$-$C_{24}$ (e.g., $C_2$-$C_{22}$, $C_2$-$C_{20}$, $C_2$-$C_{18}$, $C_2$-$C_{16}$, $C_2$-$C_{14}$, $C_2$-$C_{12}$, $C_2$-$C_{10}$, $C_2$-$C_8$, $C_2$-$C_6$, or $C_2$-$C_4$) alkenyl groups are intended. Alkenyl groups may contain more than one unsaturated bond. Examples include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. The term "vinyl" refers to a group having the structure —CH=$CH_2$; 1-propenyl refers to a group with the structure —CH=CH—$CH_3$; and 2-propenyl refers to a group with the structure —$CH_2$—CH=$CH_2$. Asymmetric structures such as ($Z^1Z^2$)C=C($Z^3Z^4$) are intended to include both the E and Z isomers. This can be presumed in structural formulae herein wherein an asymmetric alkene is present, or it can be explicitly indicated by the bond symbol C=C.

As used herein, the term "alkynyl" represents straight or branched hydrocarbon moieties containing a triple bond. Unless otherwise specified, $C_2$-$C_{24}$ (e.g., $C_2$-$C_{24}$, $C_2$-$C_{20}$, $C_2$-$C_{18}$, $C_2$-$C_{16}$, $C_2$-$C_{14}$, $C_2$-$C_{12}$, $C_2$-$C_{10}$, $C_2$-$C_8$, $C_2$-$C_6$, or $C_2$-$C_4$) alkynyl groups are intended. Alkynyl groups may contain more than one unsaturated bond. Examples include $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or "heterocarbocyclyl" groups are carbocycles which contain from 1 to 4 heteroatoms independently selected from nitrogen, oxygen and sulfur which can be saturated or unsaturated (but not aromatic), monocyclic or polycyclic, and wherein the nitrogen and sulfur heteroatoms can be optionally oxidized, and the nitrogen heteroatom can be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems can, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems can be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—$CH_3$).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, propoxy, n-butoxy, s-butoxy, t-butoxy.

"Alkylamino" refers an alkyl group as defined above with the indicated number of carbon atoms attached through an amino bridge. An example of an alkylamino is methylamino, (i.e., —NH—$CH_3$).

"Alkanoyl" refers to an alkyl as defined above with the indicated number of carbon atoms attached through a carbonyl bride (i.e., —(C=O)alkyl).

"Alkylsulfonyl" refers to an alkyl as defined above with the indicated number of carbon atoms attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfamoyl" refers to an alkyl as defined above with the indicated number of carbon atoms attached through a sulfamoyl bridge (i.e., —NHS(=O)$_2$alkyl), and an "Arylsulfamoyl" refers to an alkyl attached through a sulfamoyl bridge (i.e., —NHS(=O)$_2$aryl).

"Alkylsulfinyl" refers to an alkyl as defined above with the indicated number of carbon atoms attached through a sulfinyl bridge (i.e. —S(=O)alkyl).

The terms "cycloalkyl" and "cycloalkenyl" refer to mono-, bi-, or tri homocyclic ring groups of 3 to 15 carbon atoms which are, respectively, fully saturated and partially unsaturated. The term "cycloalkenyl" includes bi- and tricyclic ring systems that are not aromatic as a whole, but contain aromatic portions (e.g., fluorene, tetrahydronapthalene, dihydroindene, and the like). The rings of multi-ring cycloalkyl groups can be either fused, bridged and/or joined through one or more spiro unions. The terms "substituted cycloalkyl" and "substituted cycloalkenyl" refer, respectively, to cycloalkyl and cycloalkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The terms "halogen" and "halo" refer to fluorine, chlorine, bromine, and iodine.

The term "substituted" refers to a molecule wherein at least one hydrogen atom is replaced with a substituent. When substituted, one or more of the groups are "substituents." The molecule can be multiply substituted. In the case of an oxo substituent ("=O"), two hydrogen atoms are replaced. Example substituents within this context can include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context can be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution with an additional group is optional and therefore it is possible for the designated atom to be unsubstituted. Thus, by use of the term "optionally substituted" the disclosure includes examples where the group is substituted and examples where it is not.

Examples of prodrugs that can be used to improve bioavailability include esters, optionally substituted esters, branched esters, optionally substituted branched esters, carbonates, optionally substituted carbonates, carbamates, optionally substituted carbamates, thioesters, optionally substituted thioesters, branched thioesters, optionally substituted branched thioesters, thiocarbonates, optionally substituted thiocarbonates, S-thiocarbonate, optionally substituted S-thiocarbonate, dithiocarbonates, optionally substituted dithiocarbonates, thiocarbamates, optionally substituted thiocarbamates, oxymethoxycarbonyl, optionally substituted oxymethoxycarbonyl, oxymethoxythiocarbonyl, optionally substituted oxymethoxythiocarbonyl, oxymethylcarbonyl, optionally substituted oxymethylcarbonyl, oxymethylthiocarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, sulfenyl, optionally substituted sulfenyl, imidate, optionally substituted imidate, hydrazonate, optionally substituted hydrazonate, oximyl, optionally substituted oximyl, imidinyl, optionally substituted imidinyl, imidyl, optionally substituted imidyl, aminal, optionally substituted aminal, hemiaminal, optionally substituted hemiaminal, acetal, optionally substituted acetal, hemiacetal, optionally substituted hemiacetal, carbonimidate, optionally substituted carbonimidate, thiocarbonimidate, optionally substituted thiocarbonimidate, carbonimidyl, optionally substituted carbonimidyl, carbamimidate, optionally substituted carbamimidate, carbamimidyl, optionally substituted carbamimidyl, thioacetal, optionally substituted thioacetal, S-acyl-2-thioethyl, optionally substituted S-acyl-2-thioethyl, bis-(acyloxybenzyl)esters, optionally substituted bis-(acyloxybenzyl)esters, (acyloxybenzyl) esters, optionally substituted (acyloxybenzyl)esters, and BAB-esters.

Compounds

In certain embodiments, the disclosure relates to a compound of Formula I,

Formula I

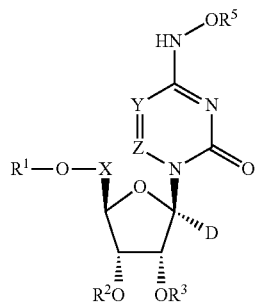

or a pharmaceutical or physiological salt thereof, wherein
X is $CH_2$, $CHCH_3$, $C(CH_3)_2$, CHF, $CF_2$, or $CD_2$;
Y is N or CR';
Z is N or CR";
R' is hydrogen, deuterium, halogen, hydroxyl, amino, thiol, alkyl, alkenyl, alkynyl, aryl, heteroaryl, carbocyclyl, heterocarbocyclyl, cycloalkyl, heterocyclyl, or carbonyl, wherein R' is optionally substituted with one or more, the same or different, $R^{10}$;
R" is hydrogen, deuterium, halogen, hydroxyl, amino, thiol, alkyl, alkenyl, alkynyl, aryl, heteroaryl, carbocyclyl, heterocarbocyclyl, cycloalkyl, heterocyclyl, hydroxyl, thiol, or carbonyl, wherein R' is optionally substituted with one or more, the same or different, $R^{10}$;
$R^1$, $R^2$, $R^3$, and $R^5$ are each independently selected from H,

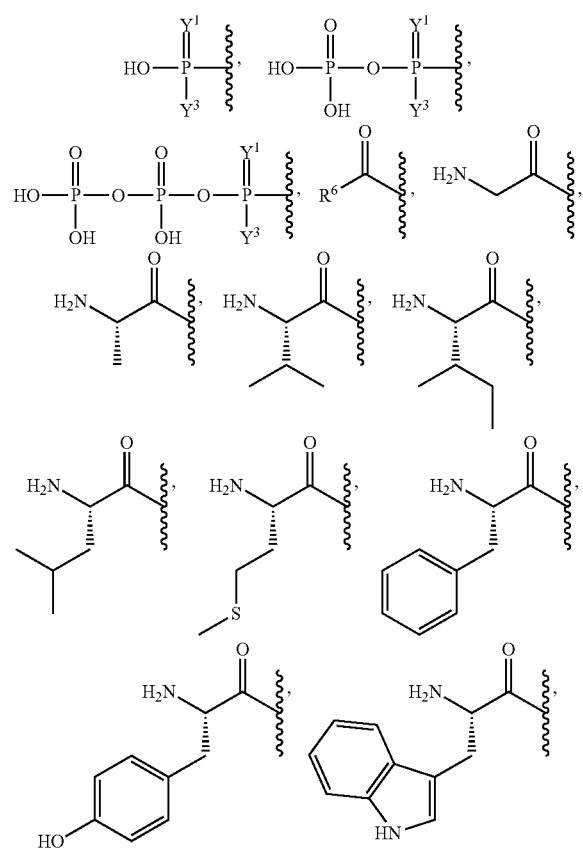

-continued

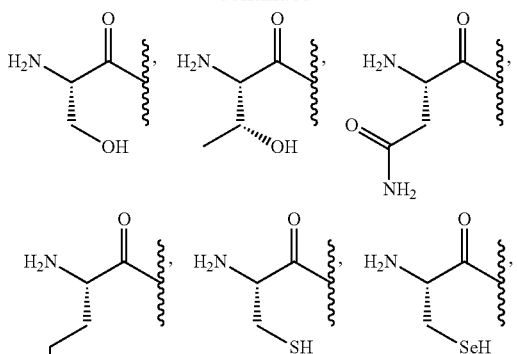

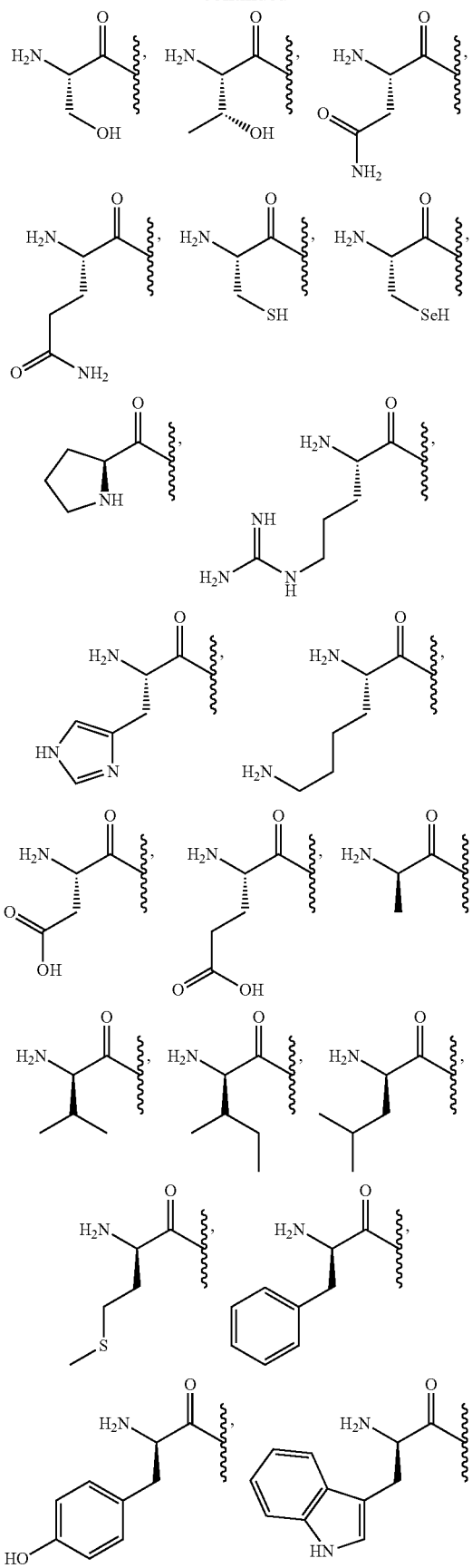

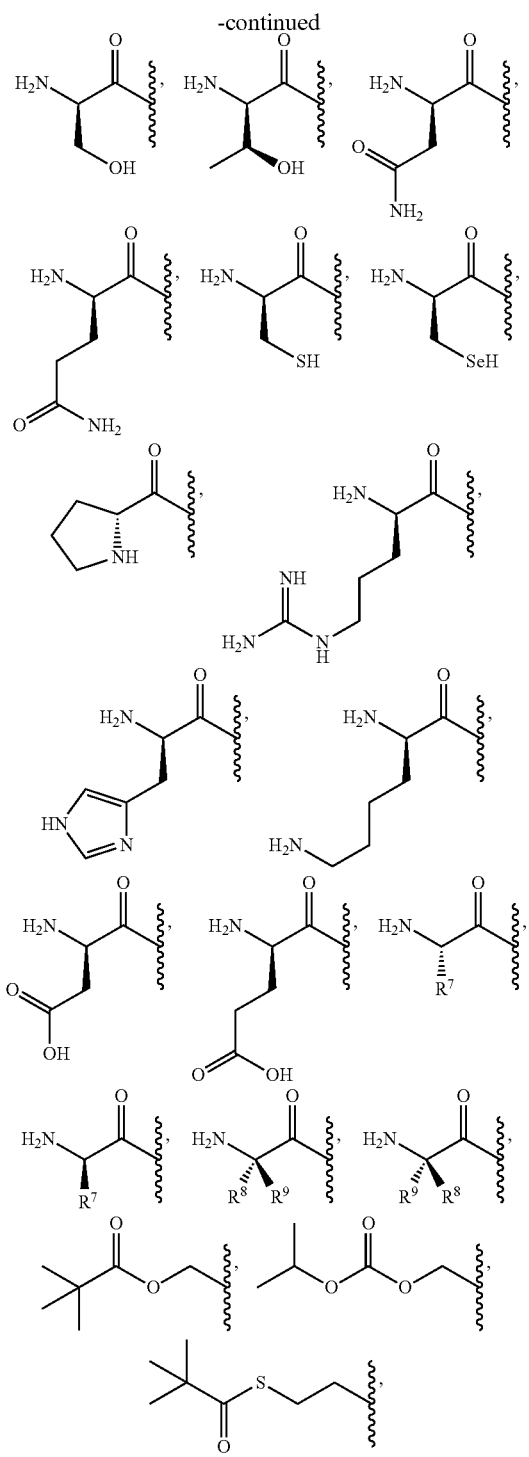

optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^1$, $R^2$, $R^3$, and $R^5$ are optionally substituted with one or more, the same or different, $R^{10}$;

$Y^1$ is O or S;

$Y^3$ is OH or $BH_3^-M^+$;

$R^6$ is hydrogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;

$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;

$R^7$, $R^8$, and $R^9$ can form a ring with the α-carbon they are attached to and the amino group attached to the α-carbon;

$R^8$ and $R^9$ can form a ring with the α-carbon which they are attached;

$R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;

$R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In certain embodiments, the lipid is a fatty alcohol, fatty amine, or fatty thiol derived from essential and/or non-essential fatty acids.

In certain embodiments, the lipid is an unsaturated, polyunsaturated, omega unsaturated, or omega polyunsaturated fatty alcohol, fatty amine, or fatty thiol derived from essential and/or non-essential fatty acids.

In certain embodiments, the lipid is a fatty alcohol, fatty amine, or fatty thiol derived from essential and non-essential fatty acids that have one or more of its carbon units substituted with an oxygen, nitrogen, or sulfur.

In certain embodiments, the lipid is an unsaturated, polyunsaturated, omega unsaturated, or omega polyunsaturated fatty alcohol, fatty amine, or fatty thiol derived from essential and/or non-essential fatty acids that have one or more of its carbon units substituted with an oxygen, nitrogen, or sulfur.

In certain embodiments, the lipid is a fatty alcohol, fatty amine, or fatty thiol derived from essential and/or non-essential fatty acids that is optionally substituted.

In certain embodiments, the lipid is an unsaturated, polyunsaturated, omega unsaturated, or omega polyunsaturated fatty alcohol, fatty amine, or fatty thiol derived from essential and/or non-essential fatty acids that is optionally substituted.

In certain embodiments, the lipid is a fatty alcohol, fatty amine, or fatty thiol derived from essential and/or non-essential fatty acids that have one or more of its carbon units substituted with an oxygen, nitrogen, or sulfur that is optionally substituted.

In certain embodiments, the lipid is an unsaturated, polyunsaturated, omega unsaturated, or omega polyunsaturated fatty alcohol, fatty amine, or fatty thiol derived from essential and/or non-essential fatty acids that have one or more of its carbon units substituted with an oxygen, nitrogen, or sulfur that is also optionally substituted.

In certain embodiments, the lipid is hexadecyloxypropyl.

In certain embodiments, the lipid is 2-aminohexadecyloxypropyl.

In certain embodiments, the lipid is 2-aminoarachidyl.

In certain embodiments, the lipid is 2-benzyloxyhexadecyloxypropyl.

In certain embodiments, the lipid is lauryl, myristyl, palmityl, stearyl, arachidyl, behenyl, or lignoceryl.

In certain embodiments, the lipid is a sphingolipid of the formula:

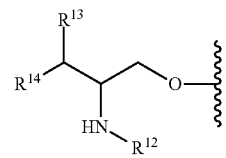

wherein,
$R^{12}$ of the sphingolipid is hydrogen, alkyl, C(=O)$R^{16}$, C(=O)O$R^{16}$, or C(=O)NH$R^{16}$;
$R^{13}$ of the sphingolipid is hydrogen, fluoro, O$R^{16}$, OC(=O)$R^{16}$, OC(=O)O$R^{16}$, or OC(=O)NH$R^{16}$;
$R^{14}$ of the sphingolipid is a saturated or unsaturated alkyl chain of greater than 6 and less than 22 carbons optionally substituted with one or more halogen or hydroxy or a structure of the following formula:

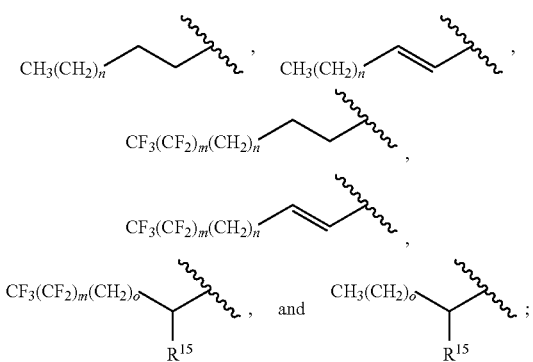

wherein n is 8 to 14 or less than or equal to 8 to less than or equal to 14, o is 9 to 15 or less than or equal to 9 to less than or equal to 15, the total or m and n is 8 to 14 or less than or equal to 8 to less than or equal to 14, the total of m and o is 9 to 15 or less than or equal to 9 to less than or equal to 15; or

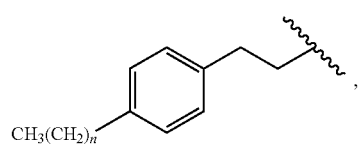

-continued

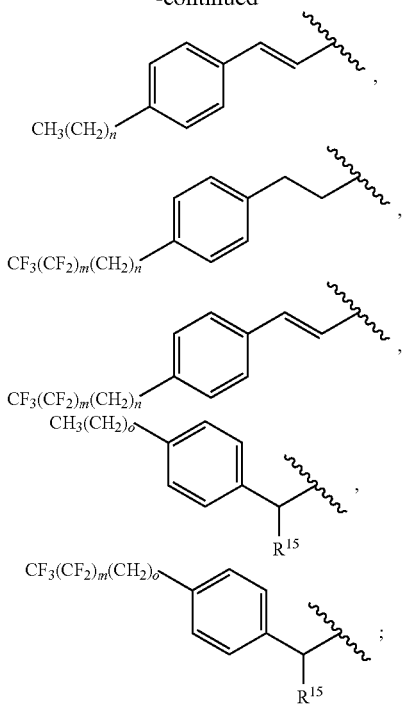

wherein n is 4 to 10 or less than or equal to 4 to less than or equal to 10, o is 5 to 11 or less than or equal to 5 to less than or equal to 11, the total of m and n is 4 to 10 or less than or equal to 4 to less than or equal to 10, and the total of m and o is 5 to 11 or less than or equal to 5 to less than or equal to 11; or

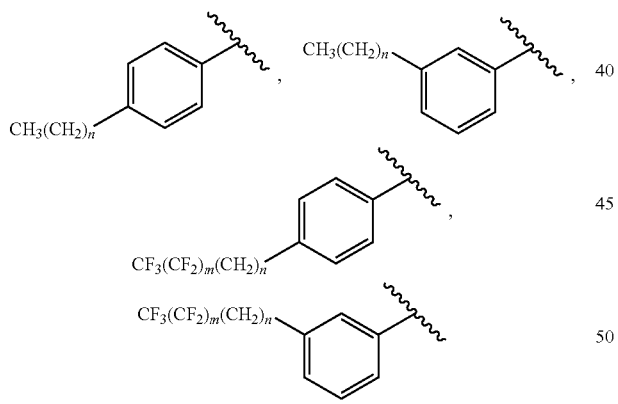

wherein n is 6 to 12 or n is less than or equal to 6 to less than or equal to 12, the total of m and n is 6 to 12 or n is less than or equal to 6 to less than or equal to 12;

$R^{15}$ of the sphingolipid is $OR^{16}$, $OC(=O)R^{16}$, $OC(=O)OR^{16}$, or $OC(=O)NHR^{16}$;

$R^{16}$ of the sphingolipid is hydrogen, cyano, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, cycloalkoxy, cycloalkenoxy, alkylamino, (alkyl)$_2$amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, or lipid; wherein $R^{16}$ is optionally substituted with one or more, the same or different $R^{17}$; and $R^{17}$ of the sphingolipid is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl.

In certain embodiments, $R^{12}$ of the sphingolipid is H, methyl, ethyl, propyl, n-butyl, isopropyl, 2-butyl, 1-ethylpropyl,1-propylbutyl, cyclopropyl, cyclobutyl, cyclopentyl, cyclohexyl, benzyl, or phenyl.

In certain embodiments, the sphingolipid is a sphingolipid of the formula:

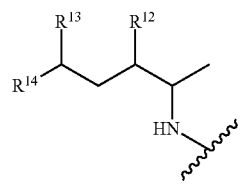

wherein,
$R^{12}$ of the sphingolipid is hydrogen, hydroxy, fluoro, $OR^{16}$, $OC(=O)R^{16}$, $OC(=O)OR^{16}$, or $OC(=O)NHR^{16}$;

$R^{13}$ of the sphingolipid is hydrogen, hydroxy, fluoro, $OR^{16}$, $OC(=O)R^{16}$, $OC(=O)OR^{16}$, or $OC(=O)NHR^{16}$;

$R^{14}$ of the sphingolipid is a saturated or unsaturated alkyl chain of greater than 6 and less than 22 carbons optionally substituted with one or more halogens or a structure of the following formula:

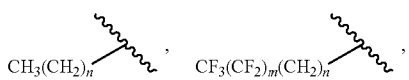

wherein n is 8 to 14 or less than or equal to 8 to less than or equal to 14, the total or m and n is 8 to 14 or less than or equal to 8 to less than or equal to 14;

$R^{16}$ of the sphingolipid is hydrogen, cyano, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, or lipid; wherein $R^{16}$ is optionally substituted with one or more, the same or different $R^{17}$; and $R^{17}$ of the sphingolipid is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, esteryl, formyl, carboxy, carbamoyl, amido, or acyl.

In certain embodiments, $R^{16}$ of the sphingolipid is H, methyl, ethyl, propyl, n-butyl, isopropyl, 2-butyl, 1-ethylpropyl,1-propylbutyl, cyclopropyl, cyclobutyl, cyclopentyl, cyclohexyl, or benzyl.

Suitable sphingolipids include, but are not limited to, sphingosine, ceramide, or sphingomyelin, or 2-aminoalkyl optionally substituted with one or more substituents.

Other suitable sphingolipids include, but are not limited to, 2-aminooctadecane-3,5-diol; (2S,3 S,5S)-2-aminooctadecane-3,5-diol; (2S,3R,5 S)-2-aminooctadecane-3,5-diol; 2-(methylamino)octadecane-3,5-diol; (2S,3R,5S)-2-(methylamino)octadecane-3,5-diol; 2-(dimethylamino)octadecane-3,5-diol; (2R,3S,5S)-2-(dimethylamino)octadecane-3,5-diol; 1-(pyrrolidin-2-yl)hexadecane-1,3-diol; (1S,3 S)-1-((S)-pyrrolidin-2-yl)hexadecane-1,3-diol; 2-amino-11,11-difluorooctadecane-3,5-diol; (2S,3 S,5S)-2-amino-11,11-difluorooctadecane-3,5-diol; 11,11-difluoro-2-(methylamino)octadecane-3,5-diol; (2S,3 S,5 S)-11,11-difluoro-2-(methylamino)octadecane-3,5-diol; N-((2S,3S,5S)-3,5-dihydroxyoctadecan-2-yl)acetamide; N-((2S,3S,5S)-3,5-dihydroxyoctadecan-2-yl)palmitamide; 1-(1-aminocyclopropyl)hexadecane-1,3-diol; (1S,3R)-1-(1-aminocyclopropyl)hexadecane-1,3-diol; (1S,3 S)-1-(1-aminocyclopropyl)hexadecane-1,3-diol; 2-amino-2-methyloctadecane-3,5-diol; (3 S,5S)-2-amino-2-methyloctadecane-3,5-diol; (3 S,5R)-2-amino-2-methyloctadecane-3,5-diol; (3 S,5 S)-2-methyl-2-(methylamino)octadecane-3,5-diol; 2-amino-5-hydroxy-2-methyloctadecan-3-one; (Z)-2-amino-5-hydroxy-2-methyloctadecan-3-one oxime; (2S,3R,5R)-2-amino-6,6-difluorooctadecane-3,5-diol; (2S,3 S,5R)-2-amino-6,6-difluorooctadecane-3,5-diol; (2S,3 S,5S)-2-amino-6,6-difluorooctadecane-3,5-diol; (2S,3R,5S)-2-amino-6,6-difluorooctadecane-3,5-diol; and (2S,3S,5S)-2-amino-18,18,18-trifluorooctadecane-3,5-diol, which can be optionally substituted with one or more substituents.

In exemplified embodiments of Formula I, $R^1$ is hydrogen,

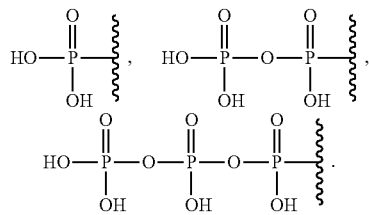

In exemplified embodiments of Formula I, R' is methyl, fluoro, hydroxymethyl, fluoromethyl, difluoromethyl, trifluoromethyl, trideuteromethyl, thiomethyl, carboxylic acid, formyl, vinyl, or ethynyl.

In exemplified embodiments of Formula I, R" is methyl, fluoro, hydroxymethyl, fluoromethyl, difluoromethyl, trifluoromethyl, trideuteromethyl, thiomethyl, carboxylic acid, formyl, vinyl, or ethynyl.

In exemplified embodiments of Formula I, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula I, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula I, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula I, $R^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula II,

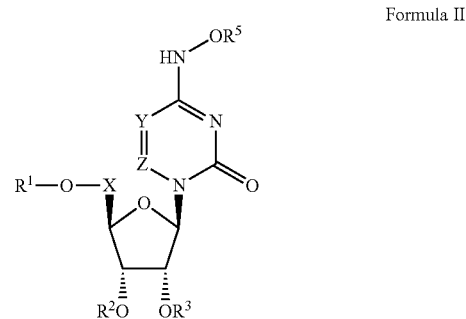

Formula II or a pharmaceutical or physiological salt thereof, wherein
X is $CH_2$, $CHCH_3$, $C(CH_3)_2$, CHF, $CF_2$, or $CD_2$;
Y is N or CR';
Z is N or CR";
R' is deuterium, halogen, hydroxyl, amino, thiol, alkyl, alkenyl, alkynyl, aryl, heteroaryl, carbocyclyl, heterocarbocyclyl, cycloalkyl, heterocyclyl, or carbonyl, wherein R' is optionally substituted with one or more, the same or different, $R^{10}$;
R" is hydrogen, deuterium, halogen, hydroxyl, amino, thiol, alkyl, alkenyl, alkynyl, aryl, heteroaryl, carbocyclyl, heterocarbocyclyl, cycloalkyl, heterocyclyl, hydroxyl, thiol, or carbonyl, wherein R' is optionally substituted with one or more, the same or different, $R^{10}$;
$R^1$, $R^2$, $R^3$, and $R^5$ are each independently selected from H,

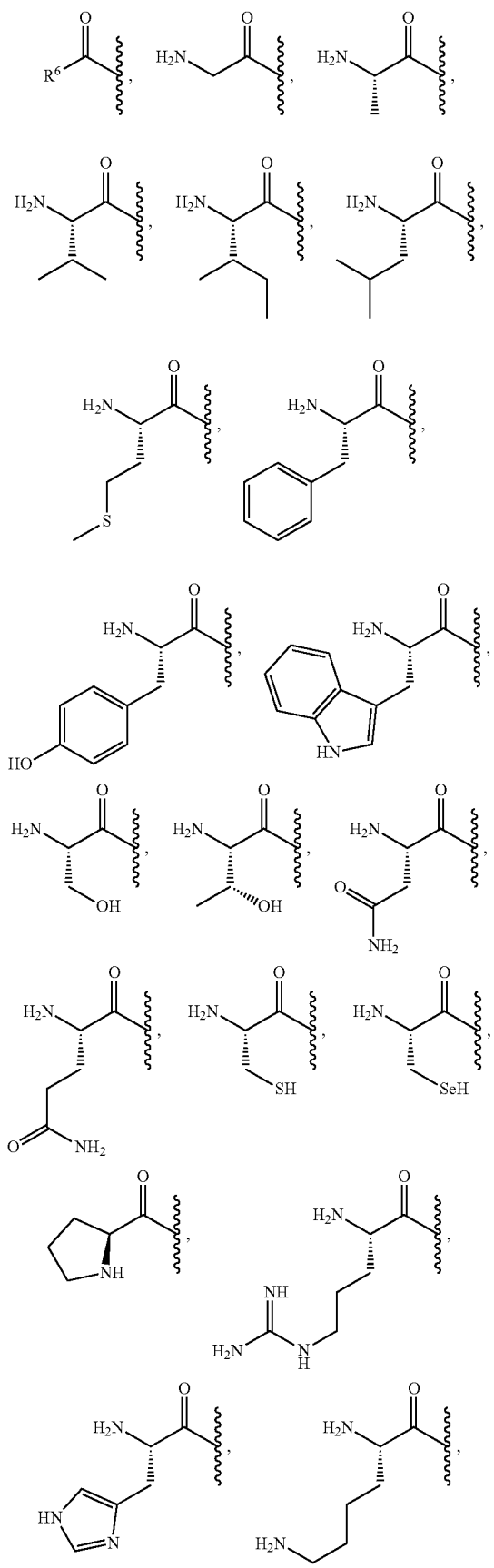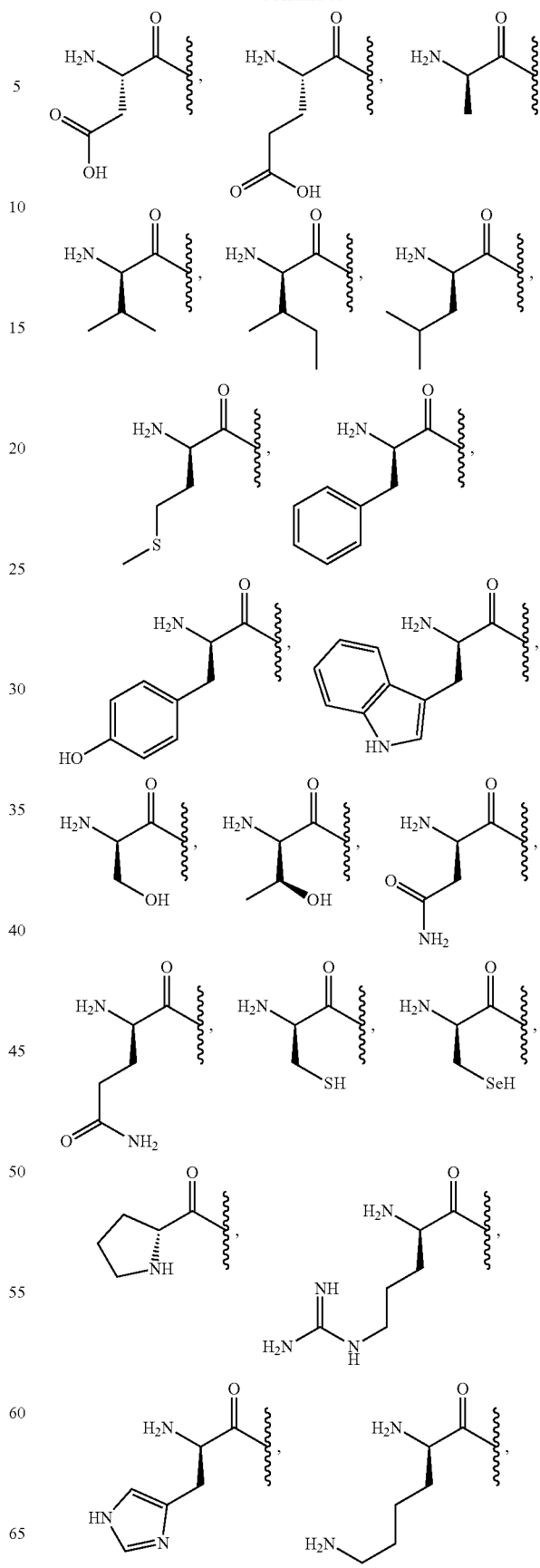

-continued

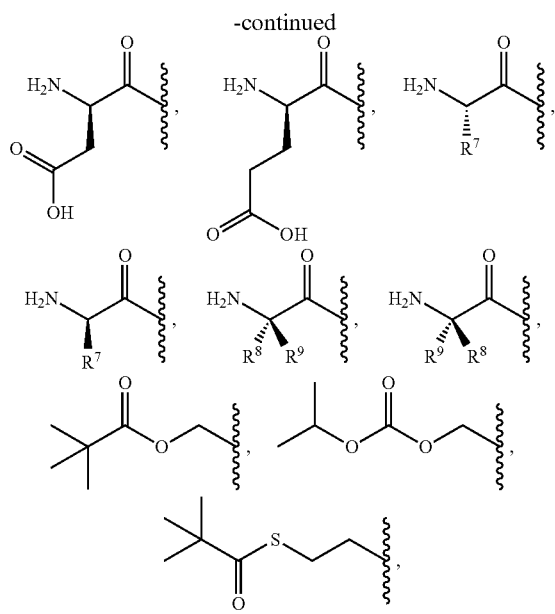

optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^1$, $R^2$, $R^3$, and $R^5$ are optionally substituted with one or more, the same or different, $R^{10}$;
with the proviso that $R^1$, $R^2$, $R^3$, and $R^5$ are not all H;
$R^6$ is hydrogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;
$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;
$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;
$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;
$R^7$, $R^8$, and $R^9$ can form a ring with the α-carbon they are attached to and the amino group attached to the α-carbon;
$R^8$ and $R^9$ can form a ring with the α-carbon which they are attached;
$R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;
$R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula II, R' is methyl, fluoro, hydroxymethyl, fluoromethyl, difluoromethyl, trifluoromethyl, trideuteromethyl, thiomethyl, carboxylic acid, formyl, vinyl, or ethynyl.

In exemplified embodiments of Formula II, R" is methyl, fluoro, hydroxymethyl, fluoromethyl, difluoromethyl, trifluoromethyl, trideuteromethyl, thiomethyl, carboxylic acid, formyl, vinyl, or ethynyl.

In exemplified embodiments of Formula II, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula II, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula II, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula II, $R^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula III,

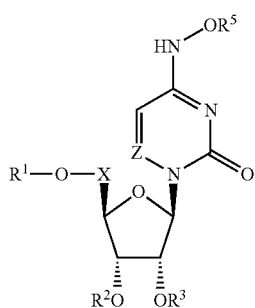

Formula III or a pharmaceutical or physiological salt thereof, wherein
X is $CH_2$, $CHCH_3$, $C(CH_3)_2$, CHF, $CF_2$, or $CD_2$;
Z is N or CR";
R" is deuterium, halogen, hydroxyl, amino, thiol, alkyl, alkenyl, alkynyl, aryl, heteroaryl, carbocyclyl, heterocarbocyclyl, cycloalkyl, heterocyclyl, hydroxyl, thiol, or carbonyl, wherein R' is optionally substituted with one or more, the same or different, $R^{10}$;

$R^1$, $R^2$, $R^3$, and $R^5$ are each independently selected from H,

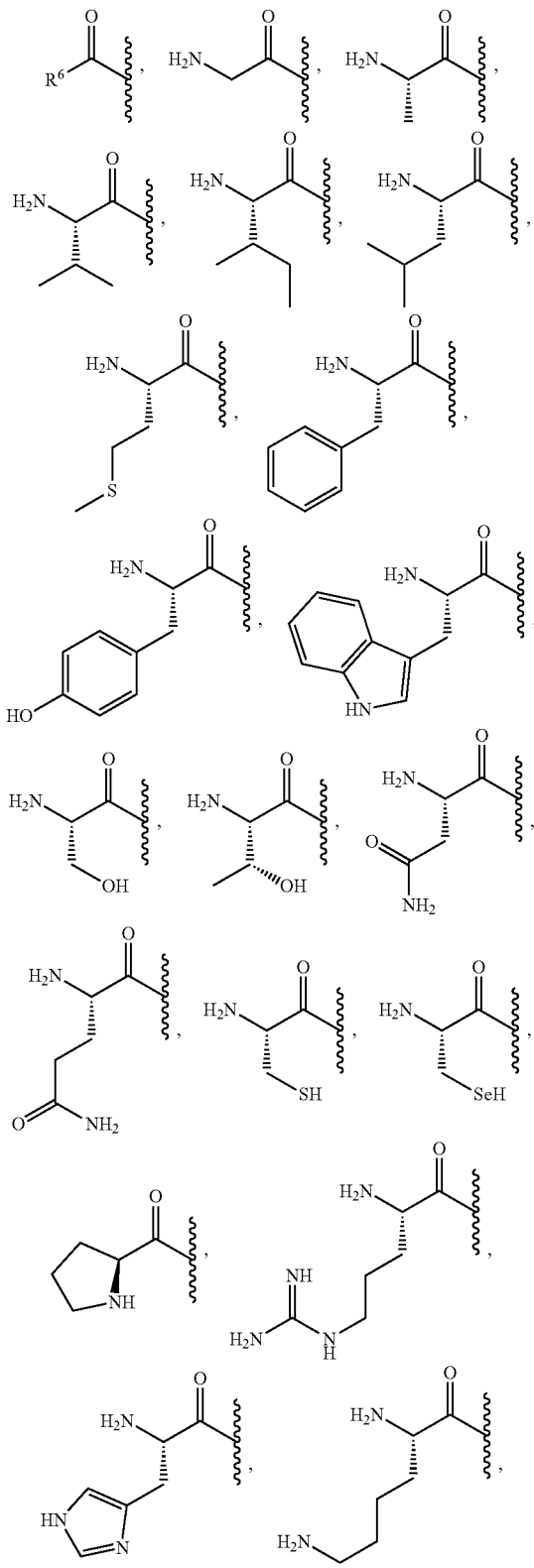

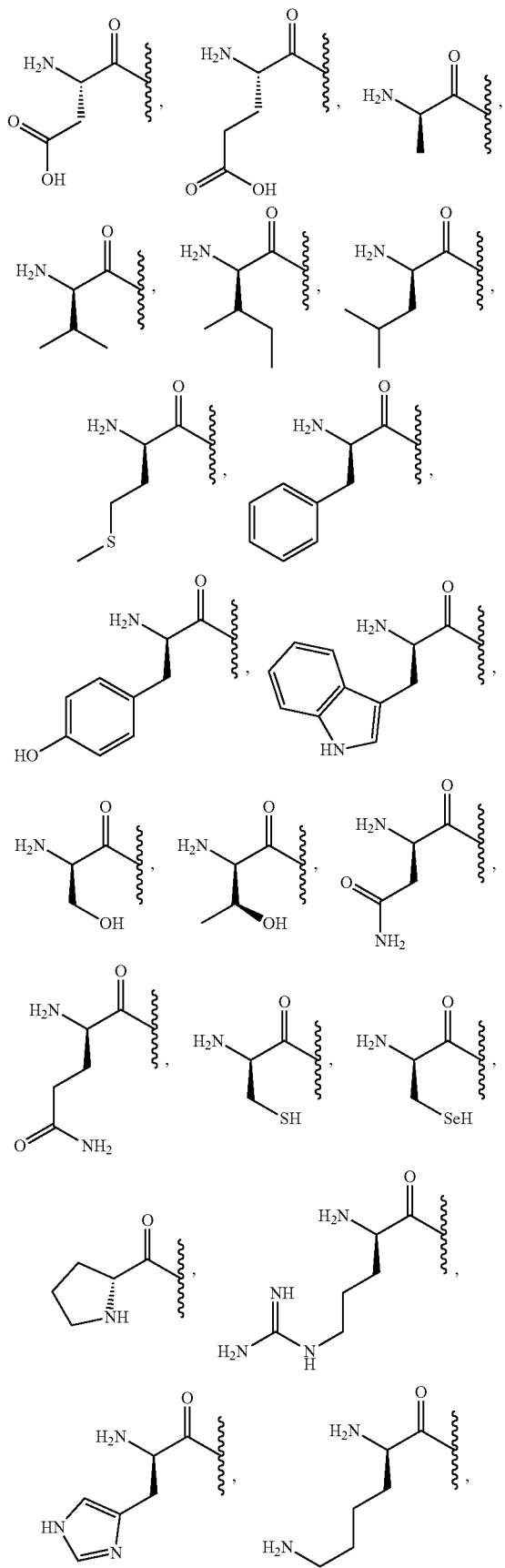
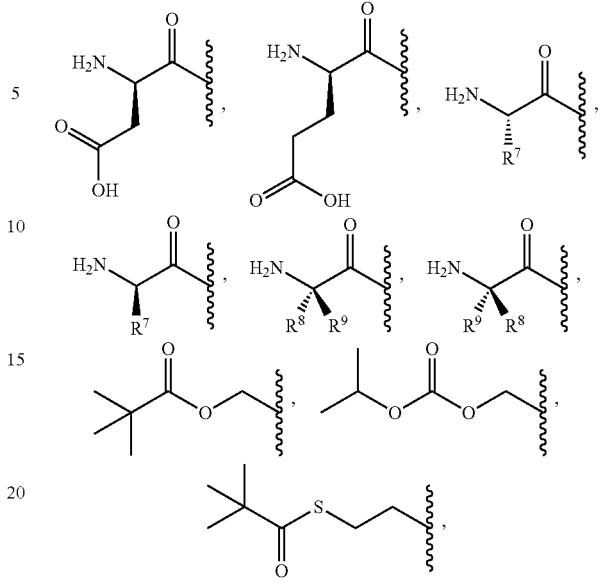

optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^1$, $R^2$, $R^3$, and $R^5$ are optionally substituted with one or more, the same or different, $R^{10}$;
with the proviso that $R^1$, $R^2$, $R^3$, and $R^5$ are not all H;
$R^6$ is hydrogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, $(alkyl)_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;
$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;

$R^7$, $R^8$, and $R^9$ can form a ring with the α-carbon they are attached to and the amino group attached to the α-carbon;

$R^8$ and $R^9$ can form a ring with the α-carbon which they are attached;

$R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;

$R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula III, R" is methyl, fluoro, hydroxymethyl, fluoromethyl, difluoromethyl, trifluoromethyl, trideuteromethyl, thiomethyl, carboxylic acid, formyl, vinyl, or ethynyl.

In exemplified embodiments of Formula III, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, and N,N-dipropylamino.

In exemplified embodiments of Formula III, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula III, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula III, $R^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula IV,

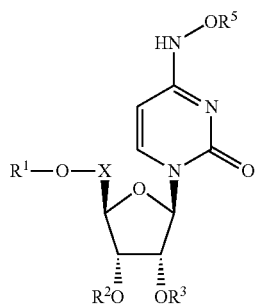

Formula IV or a pharmaceutical or physiological salt thereof, wherein

X is $CHCH_3$, $C(CH_3)_2$, CHF, $CF_2$, or $CD_2$;

$R^1$, $R^2$, $R^3$, and $R^5$ are each independently selected from H,

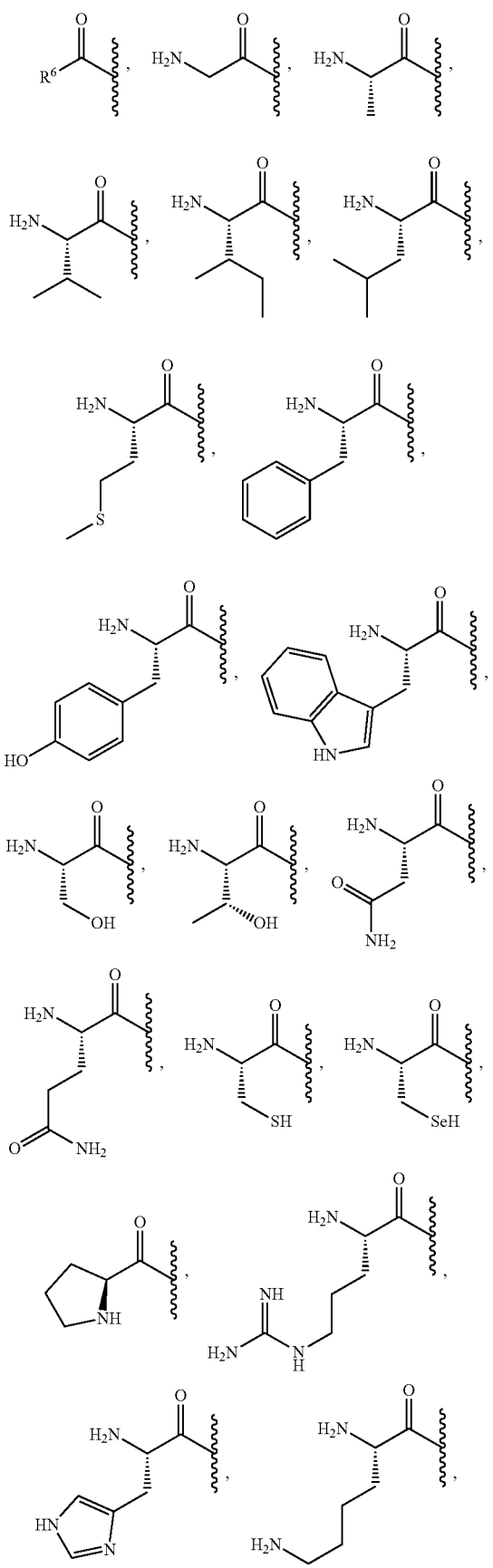
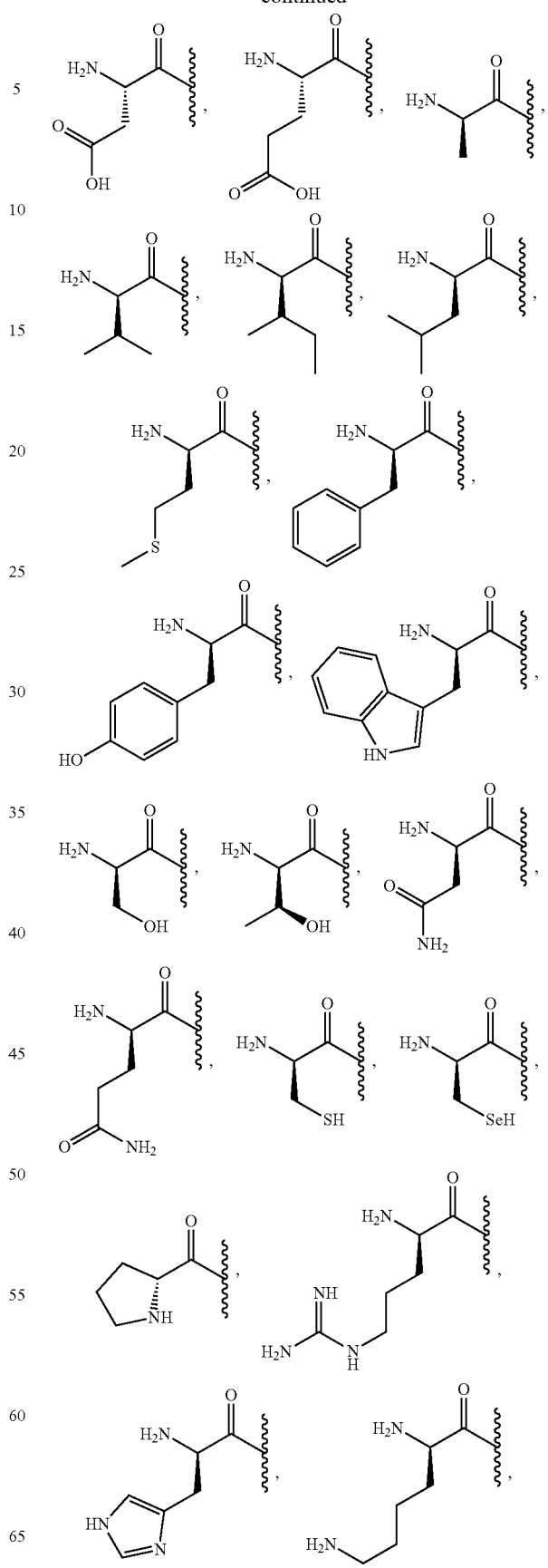

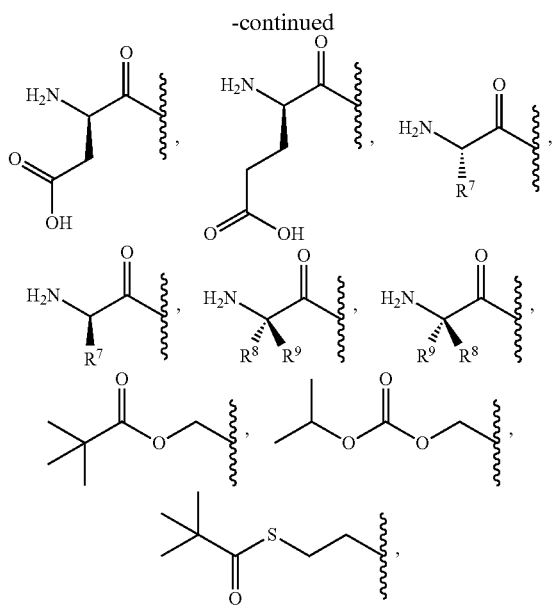

optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^1$, $R^2$, $R^3$, and $R^5$ are optionally substituted with one or more, the same or different, $R^{10}$;

with the proviso that $R^1$, $R^2$, $R^3$, and $R^5$ are not all H;

$R^6$ is hydrogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;

$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;

$R^7$, $R^8$, and $R^9$ can form a ring with the α-carbon they are attached to and the amino group attached to the α-carbon;

$R^8$ and $R^9$ can form a ring with the α-carbon which they are attached;

$R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;

$R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula IV, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula IV, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula IV, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula IV, $R^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula V,

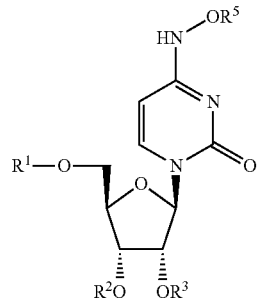

Formula V or a pharmaceutical or physiological salt thereof, wherein
$R^1$, $R^2$, $R^3$, and $R^5$ are each independently selected from the following:

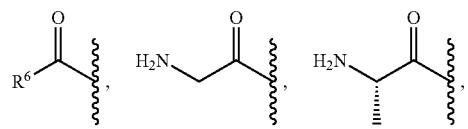

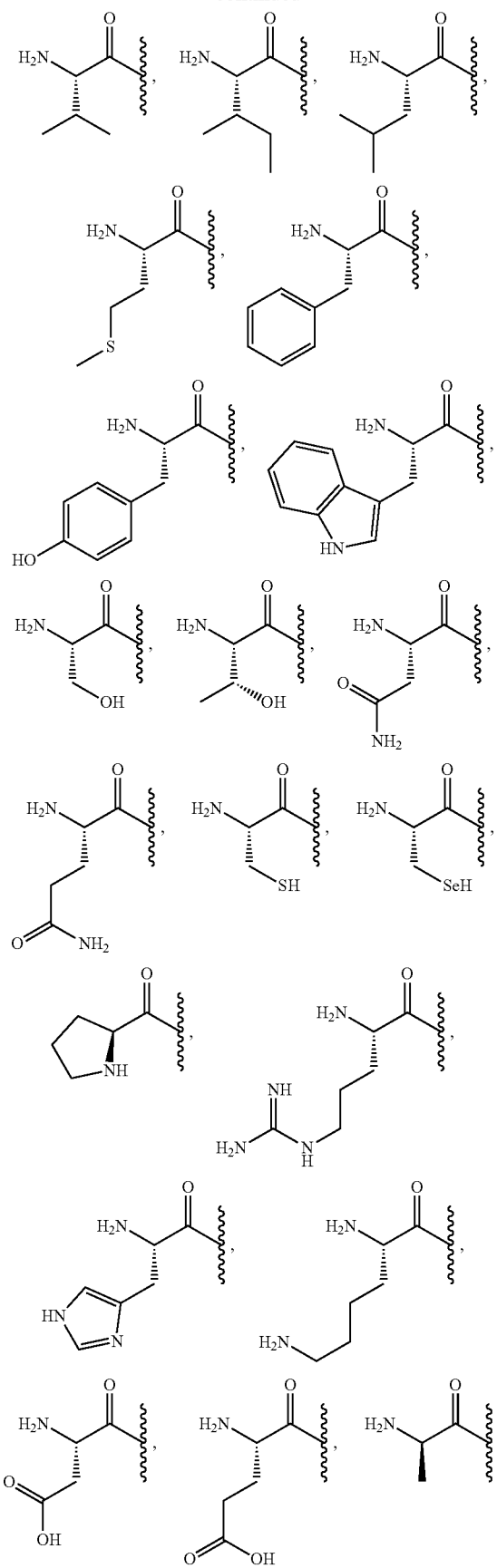

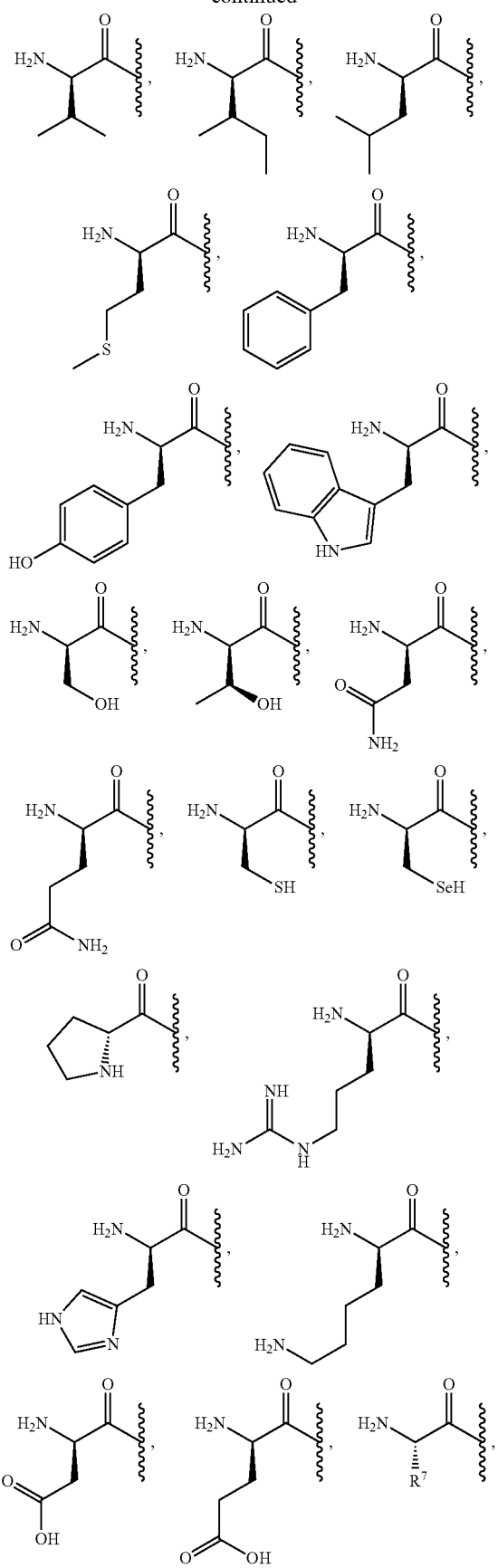

optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^1$, $R^2$, $R^3$, and $R^5$ are optionally substituted with one or more, the same or different, $R^{10}$;

$R^6$ is hydrogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;

$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;

$R^7$, $R^8$, and $R^9$ can form a ring with the α-carbon they are attached to and the amino group attached to the α-carbon;

$R^8$ and $R^9$ can form a ring with the α-carbon which they are attached;

$R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;

$R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula V, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula V, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula V, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula V, $R^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula VI,

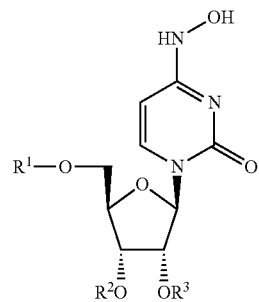

Formula VI or a pharmaceutical or physiological salt thereof, wherein
$R^1$, $R^2$, and $R^3$ are each independently selected from the following:

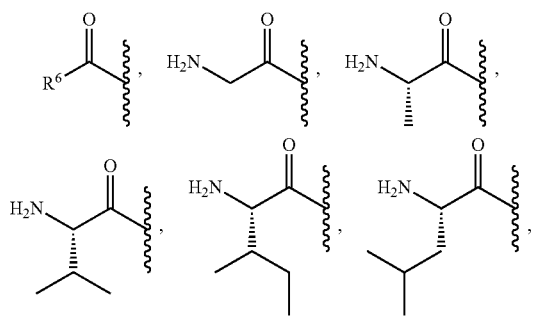

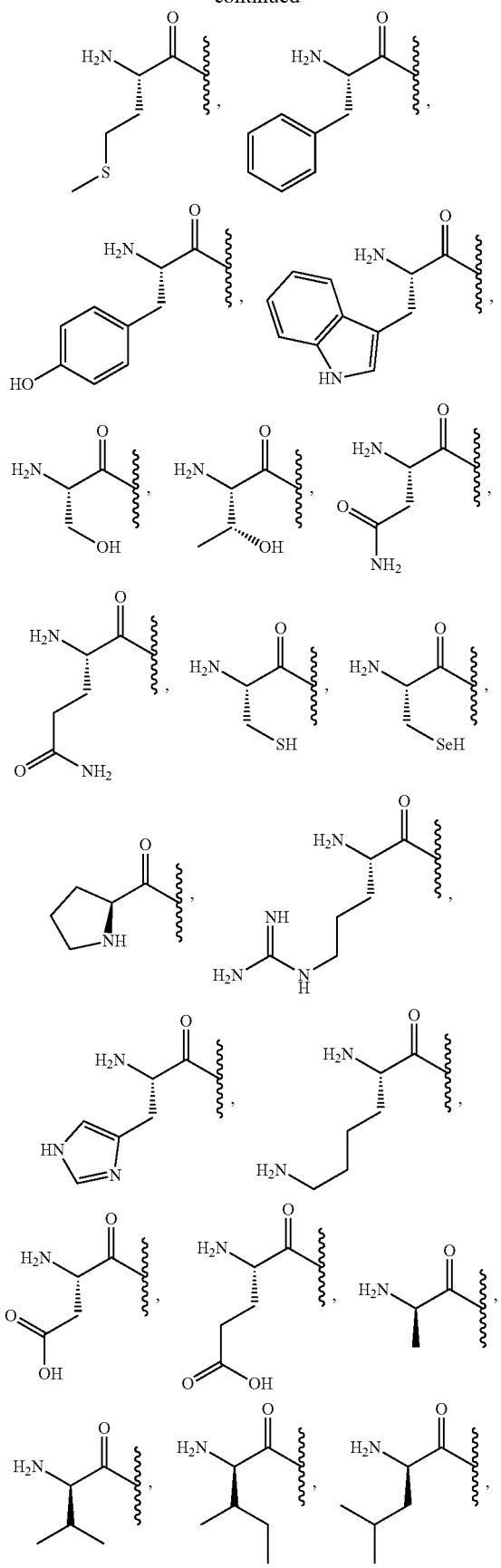
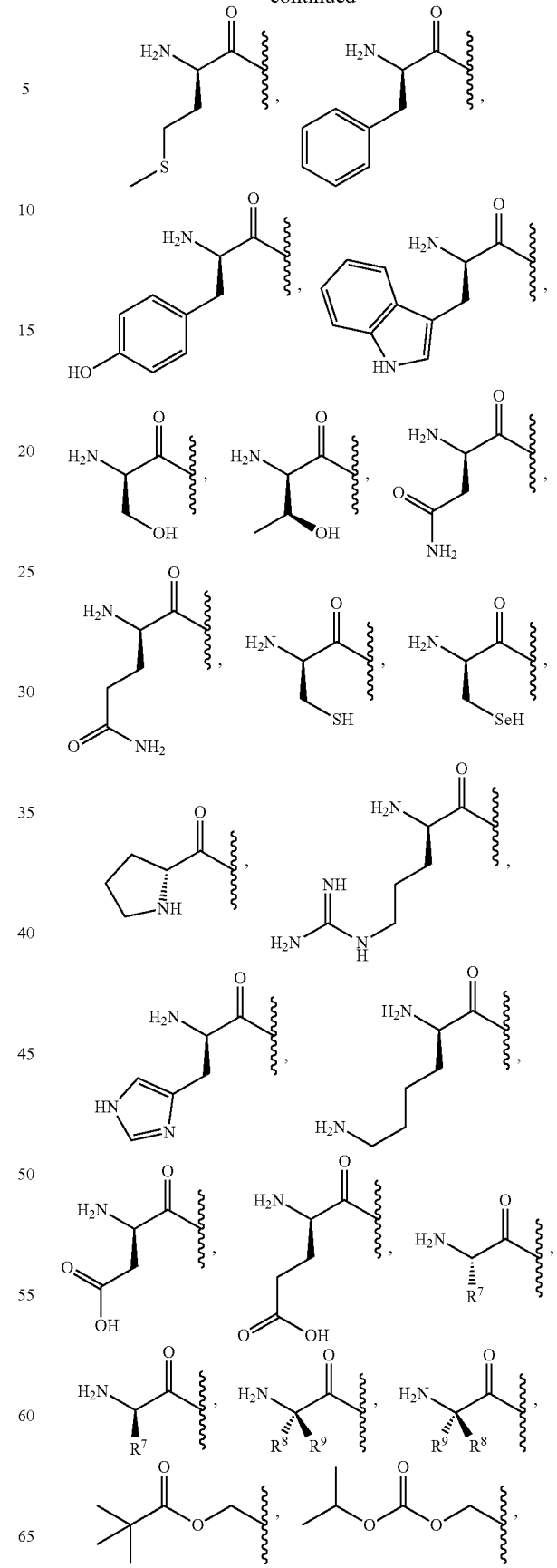

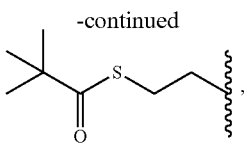

optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^1$, $R^2$, and $R^3$ are optionally substituted with one or more, the same or different, $R^{10}$;

$R^6$ is hydrogen, alkyl, alkenyl, alkynyl, carbocyclyl, heterocarbocyclyl, optionally substituted phenyl, optionally substituted aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;

$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;

$R^7$, $R^8$, and $R^9$ can form a ring with the α-carbon they are attached to and the amino group attached to the α-carbon;

$R^8$ and $R^9$ can form a ring with the α-carbon which they are attached;

$R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;

$R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula VI, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, and N,N-dipropylamino.

In exemplified embodiments of Formula VI, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula VI, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula VI, $R^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula VIa-f,

Formula VIa
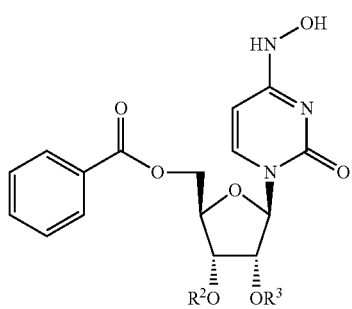

Formula VIb
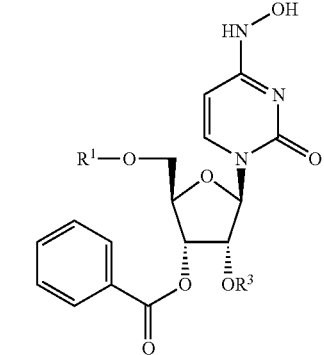

Formula VIc
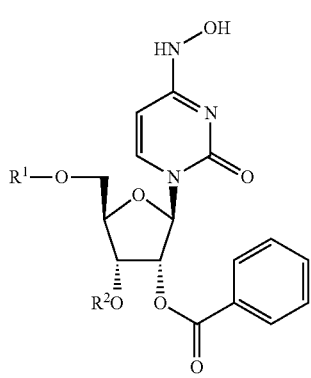

Formula VId
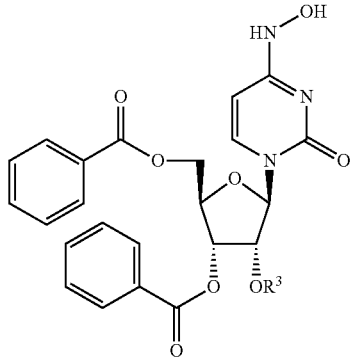

Formula VIe
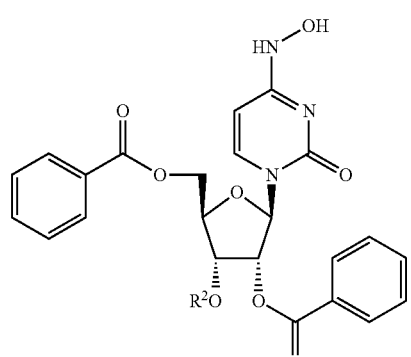

Formula VIf
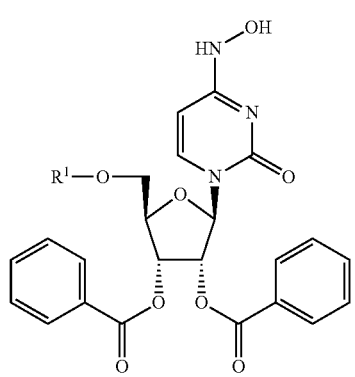

or a pharmaceutical or physiological salt thereof, wherein $R^1$, $R^2$, and $R^3$ are each independently selected from the following:

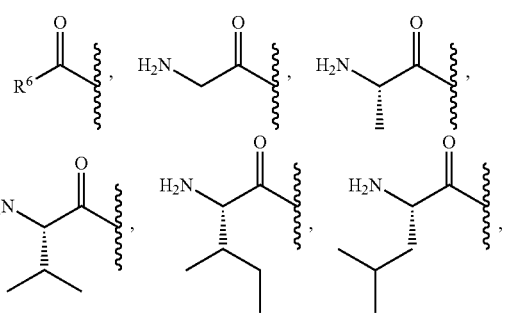

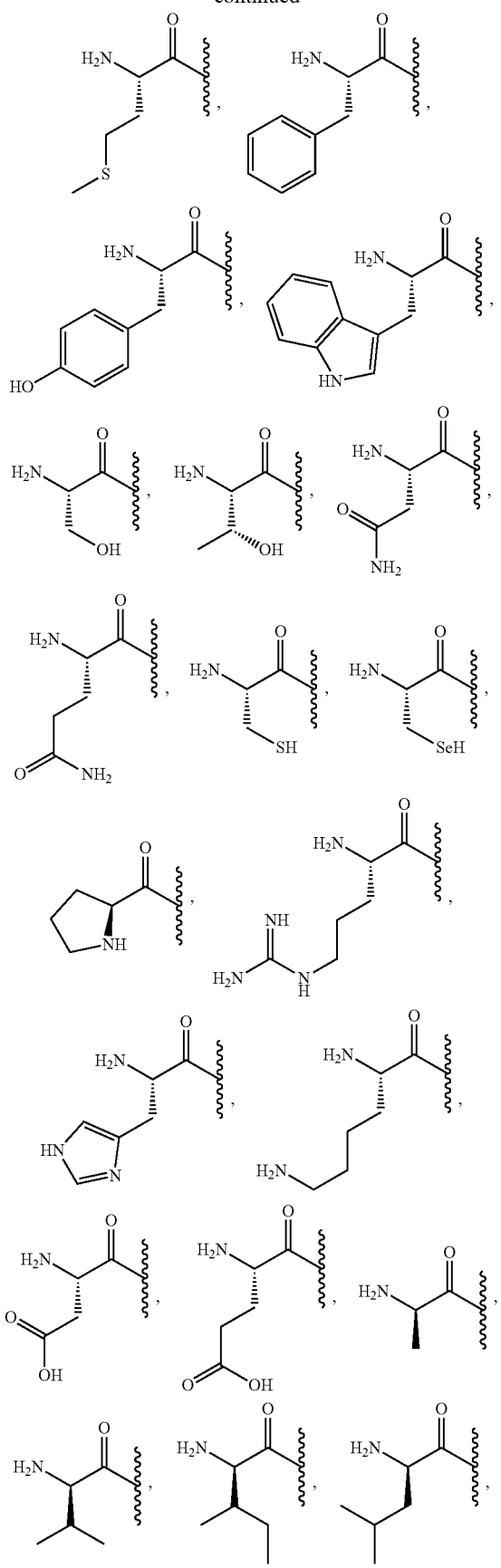
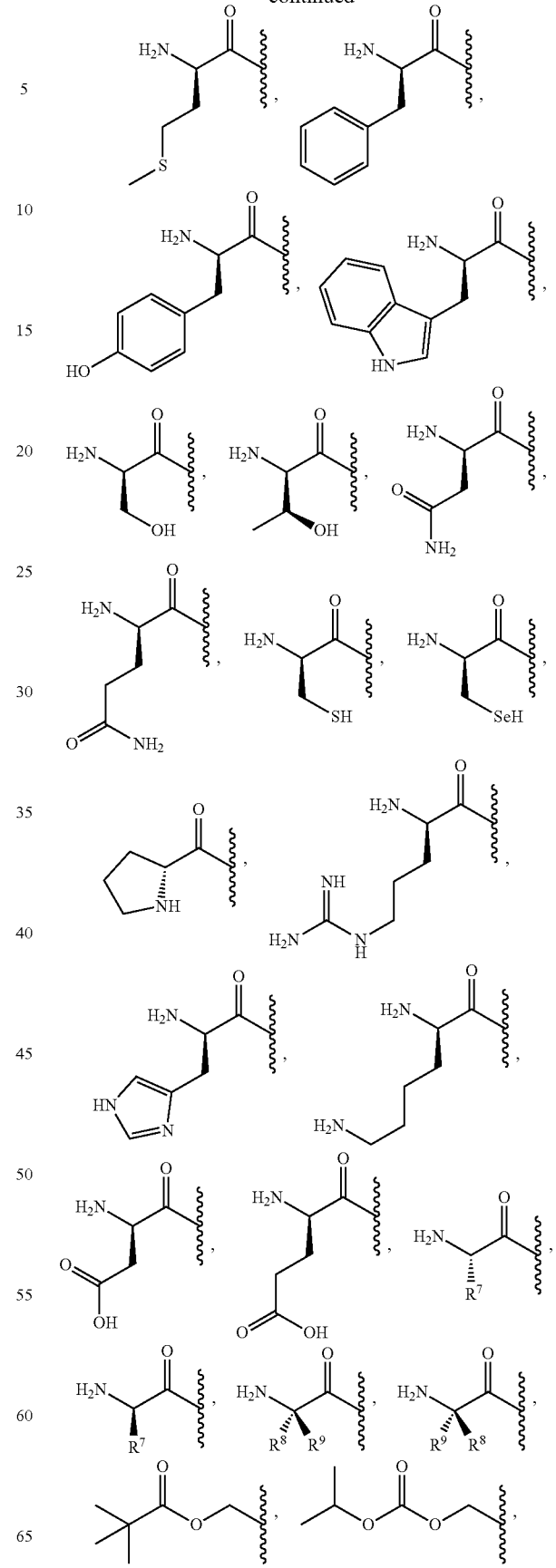

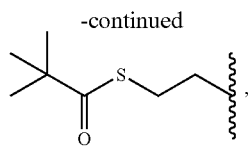

optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^1$, $R^2$, and $R^3$ are optionally substituted with one or more, the same or different, $R^{10}$;

- $R^6$ is hydrogen, alkyl, alkenyl, alkynyl, carbocyclyl, heterocarbocyclyl, optionally substituted phenyl, optionally substituted aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;
- $R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;
- $R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;
- $R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;
- $R^7$, $R^8$, and $R^9$ can form a ring with the α-carbon they are attached to and the amino group attached to the α-carbon;
- $R^8$ and $R^9$ can form a ring with the α-carbon which they are attached;
- $R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;
- $R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula VIa-f, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, and N,N-dipropylamino.

In exemplified embodiments of Formula VIa-f, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula VIa-f, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula VIa-f, $R^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula VII,

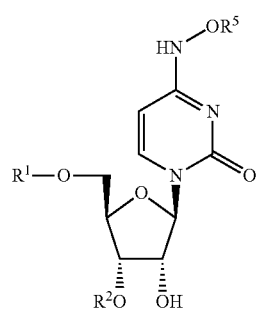

Formula VII or a pharmaceutical or physiological salt thereof, wherein
$R^1$, $R^2$, and $R^5$ are each independently selected from the following:

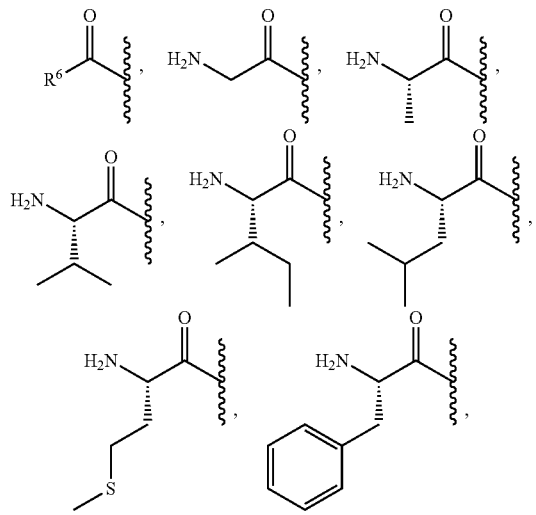

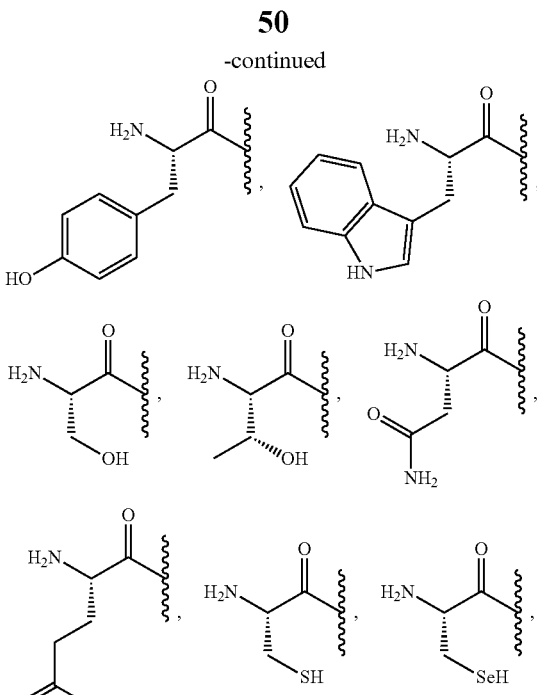

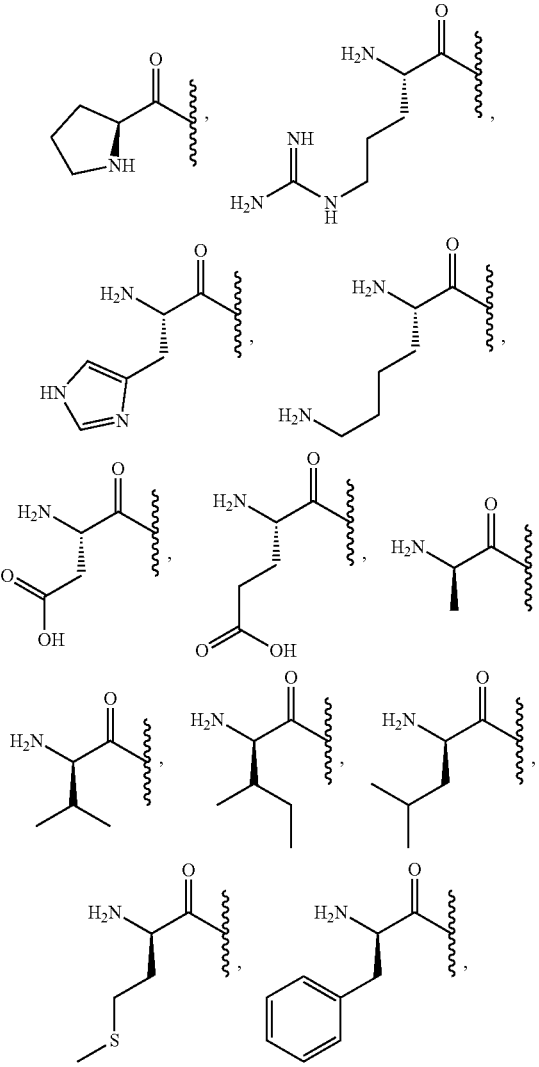

-continued

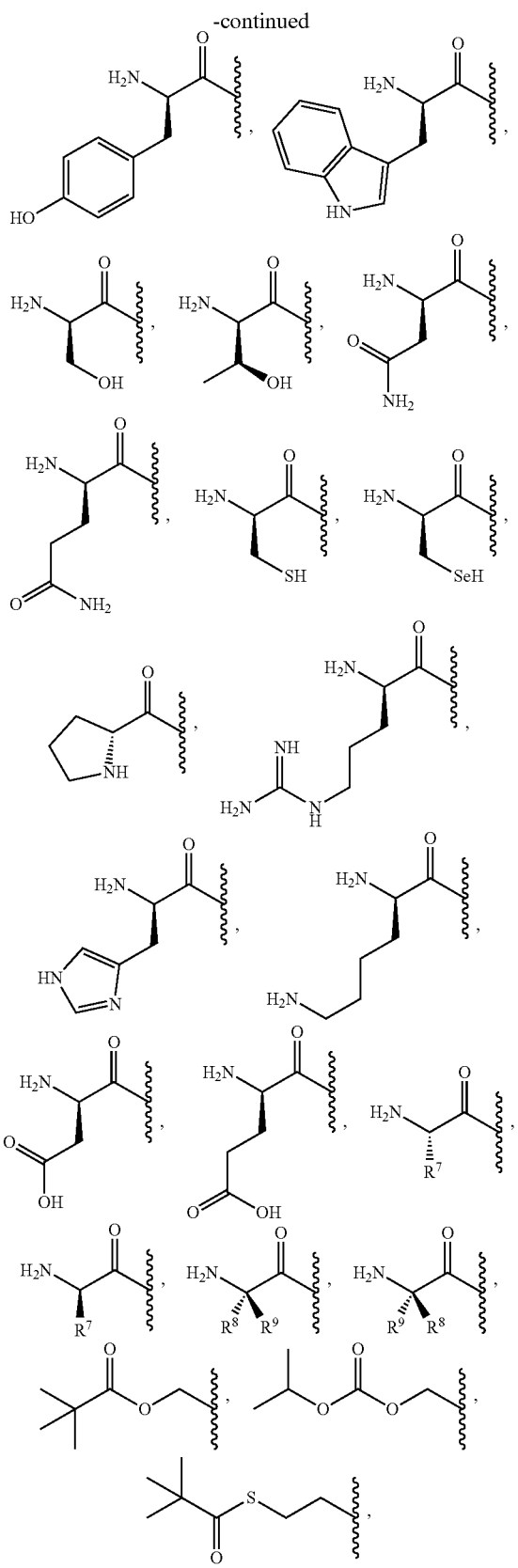

optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^1$, $R^2$, and $R^5$ are optionally substituted with one or more, the same or different, $R^{10}$;

$R^6$ is hydrogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, $(alkyl)_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;

$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, $(alkyl)_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, $(alkyl)_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein R$^9$ is optionally substituted with one or more, the same or different, R$^{10}$;

R$^7$, R$^8$, and R$^9$ can form a ring with the α-carbon they are attached to and the amino group attached to the α-carbon;

R$^8$ and R$^9$ can form a ring with the α-carbon which they are attached;

R$^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein R$^{10}$ is optionally substituted with one or more, the same or different, R$^{11}$;

R$^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula VII, R$^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, and N,N-dipropylamino.

In exemplified embodiments of Formula VII, R$^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula VII, R$^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula VII, R$^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula VIII,

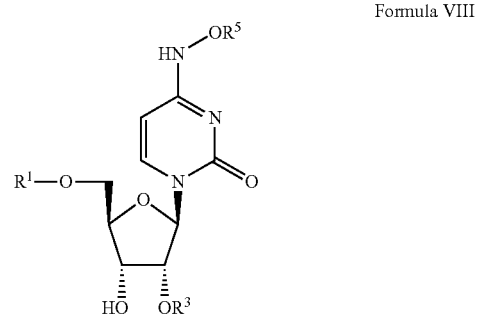

Formula VIII or a pharmaceutical or physiological salt thereof, wherein
R$^1$, R$^3$, and R$^5$ are each independently selected from the following:

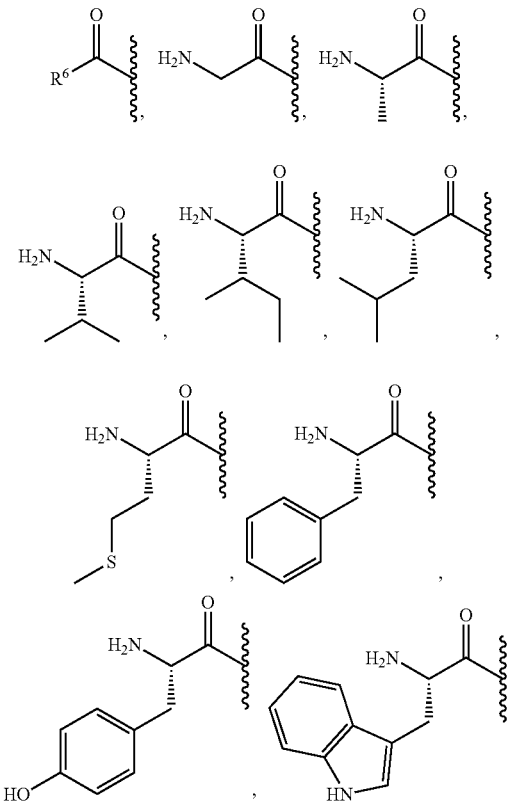

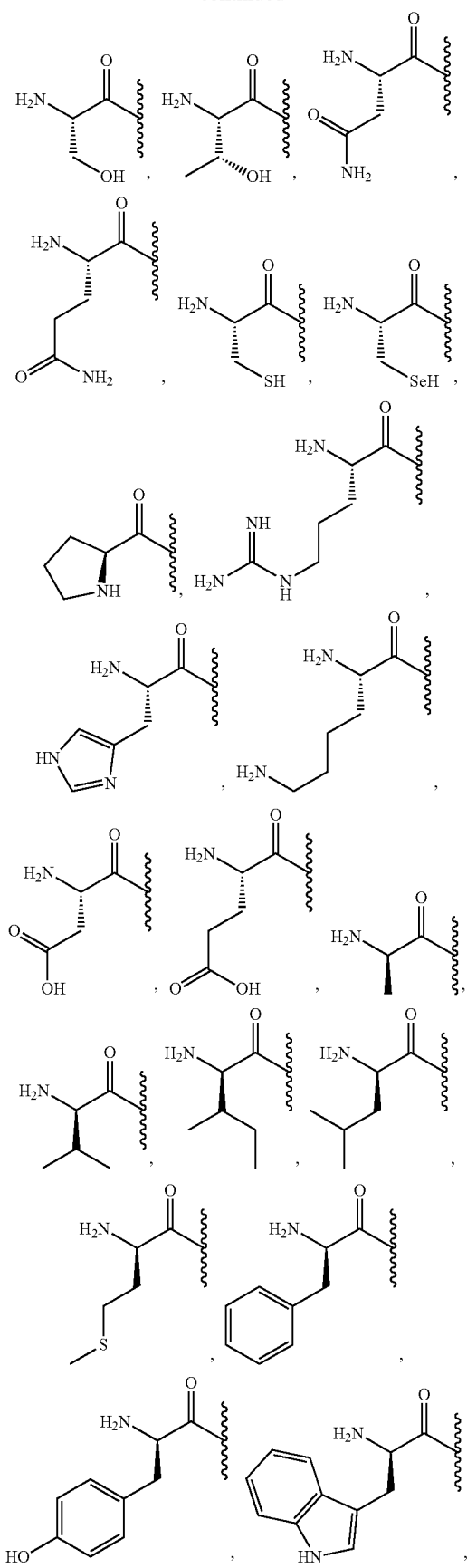
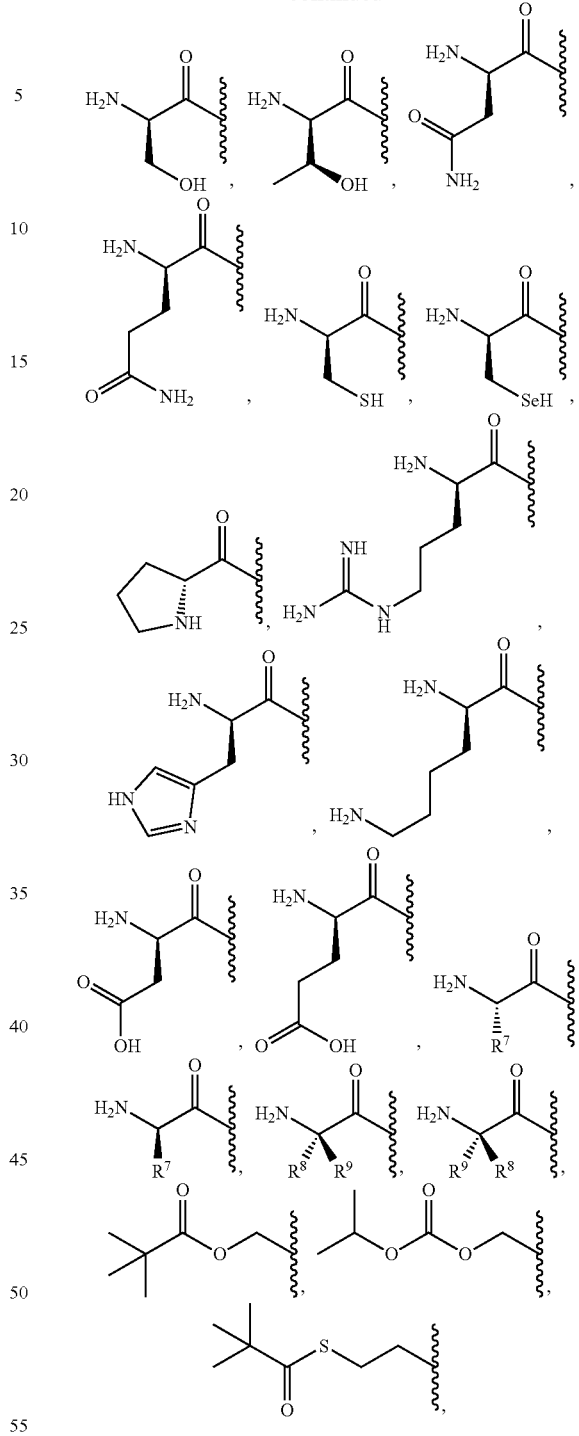

optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^1$, $R^3$, and $R^5$ are optionally substituted with one or more, the same or different, $R^{10}$;

$R^6$ is hydrogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, $(alkyl)_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;

$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, $(alkyl)_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, $(alkyl)_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, $(alkyl)_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;

$R^7$, $R^8$, and $R^9$ can form a ring with the α-carbon they are attached to and the amino group attached to the α-carbon;

$R^8$ and $R^9$ can form a ring with the α-carbon which they are attached;

$R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, $(alkyl)_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;

$R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, $(alkyl)_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula VIII, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, and N,N-dipropylamino.

In exemplified embodiments of Formula VIII, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula VIII, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula VIII, $R^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.
In certain embodiments, the disclosure relates to a compound of Formula IX,
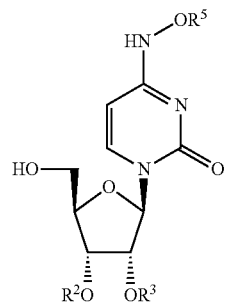
Formula IX
or a pharmaceutical or physiological salt thereof, wherein
$R^2$, $R^3$, and $R^5$ are each independently selected from the following:
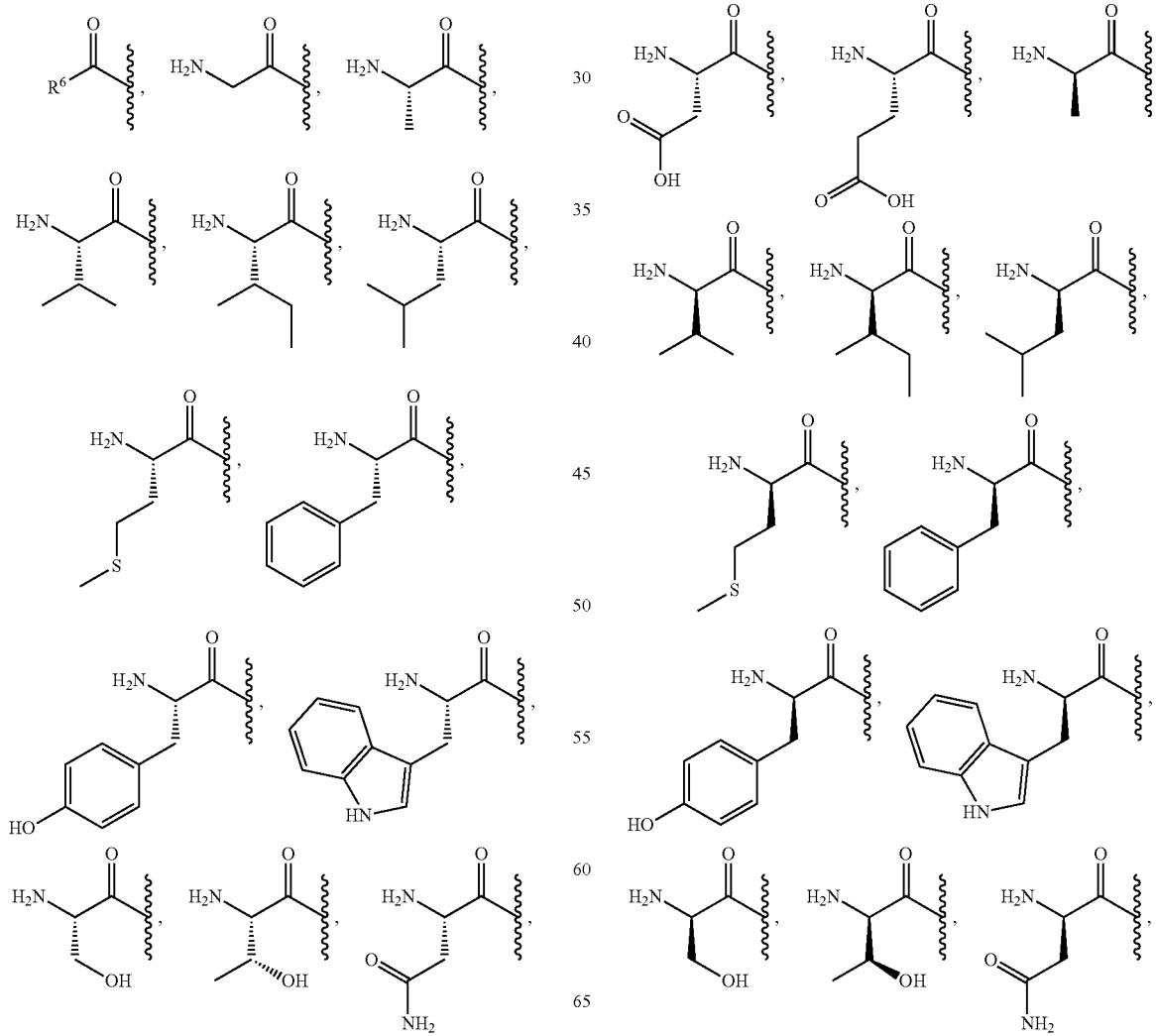
-continued

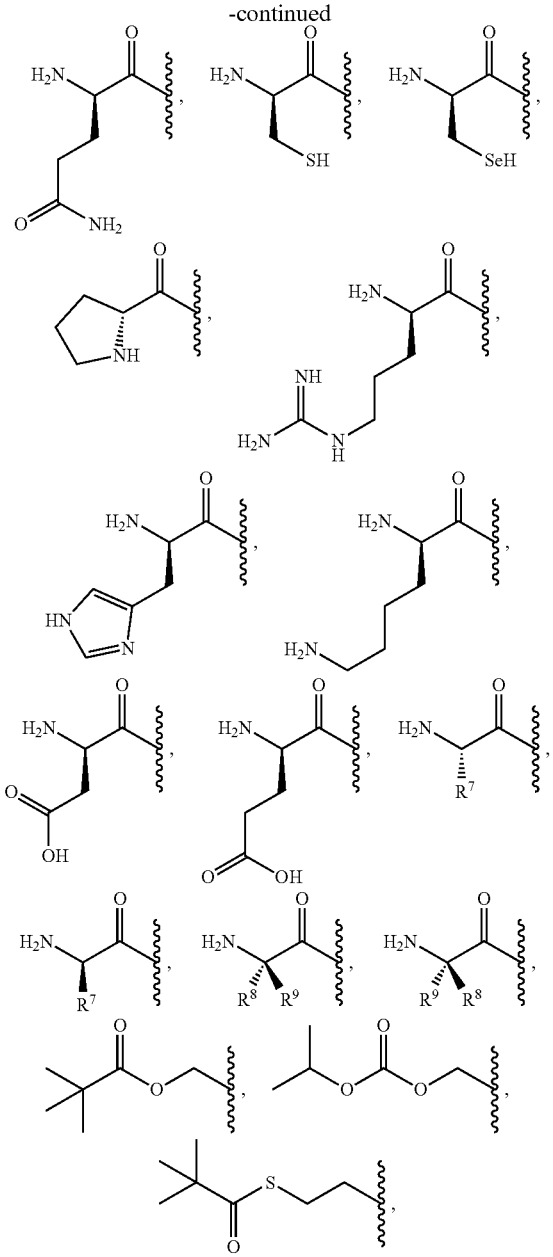

optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^2$, $R^3$, and $R^5$ are optionally substituted with one or more, the same or different, $R^{10}$;

$R^6$ is hydrogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;

$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;

R⁷, R⁸, and R⁹ can form a ring with the α-carbon they are attached to and the amino group attached to the α-carbon;

R⁸ and R⁹ can form a ring with the α-carbon which they are attached;

R¹⁰ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)₂ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein R¹⁰ is optionally substituted with one or more, the same or different, R¹¹;

R¹¹ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)₂ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula IX, R⁶ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, and N,N-dipropylamino.

In exemplified embodiments of Formula IX, R⁷ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula IX, R⁸ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula IX, R⁹ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula X,

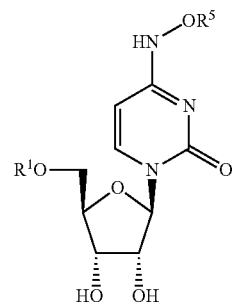

Formula X or a pharmaceutical or physiological salt thereof, wherein
R¹ and R⁵ are each independently selected from the following:

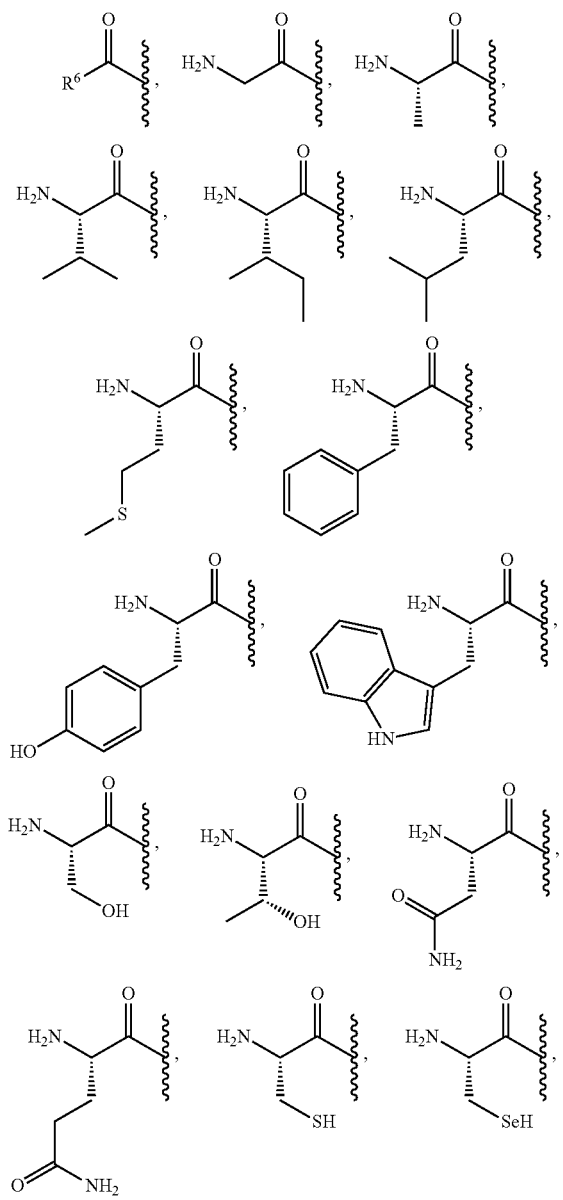

-continued

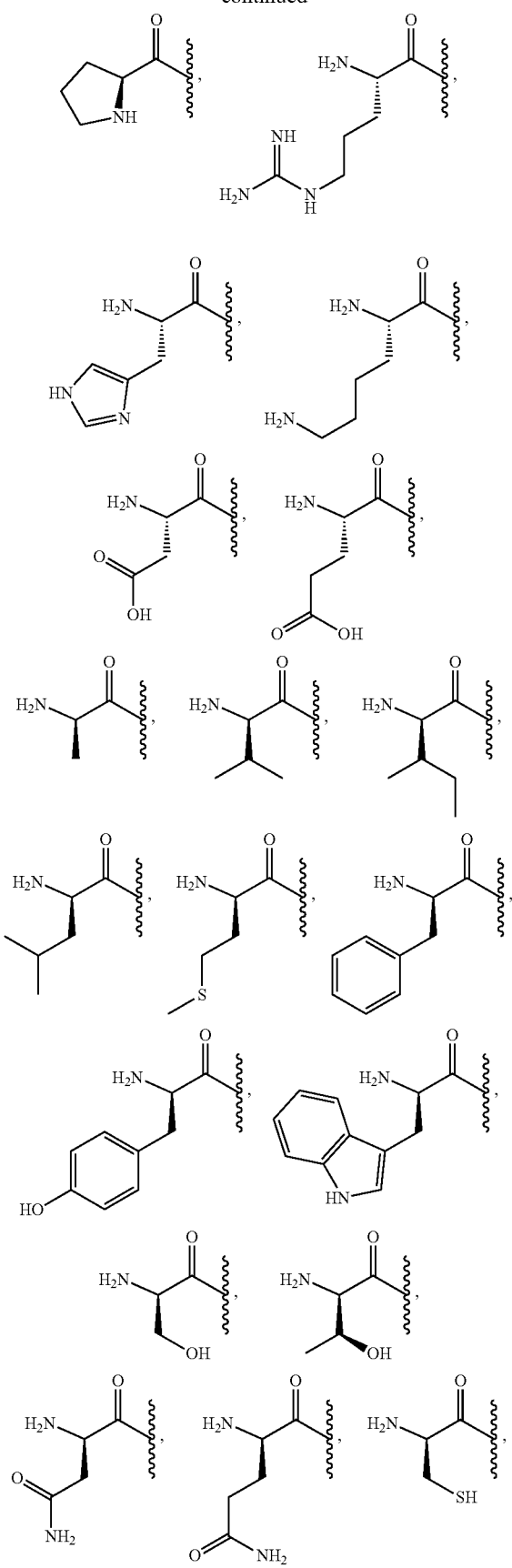

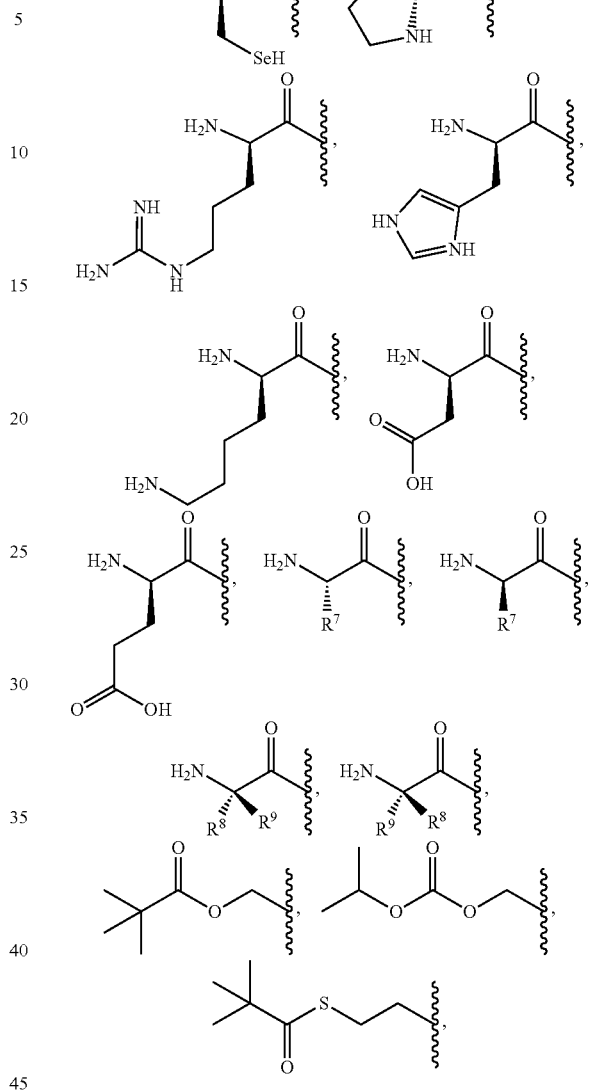

optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^1$ and $R^5$ are optionally substituted with one or more, the same or different, $R^{10}$;

$R^6$ is hydrogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;

$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;

$R^7$, $R^8$, and $R^9$ can form a ring with the α-carbon they are attached to and the amino group attached to the α-carbon;

$R^8$ and $R^9$ can form a ring with the α-carbon which they are attached;

$R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;

$R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula X, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, and N,N-dipropylamino.

In exemplified embodiments of Formula X, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula X, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula X, $R^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula XI.

Formula XI
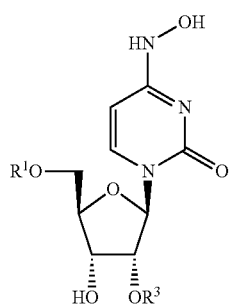
or a pharmaceutical or physiological salt thereof, wherein R[1] and R[3] are each independently selected from the following:
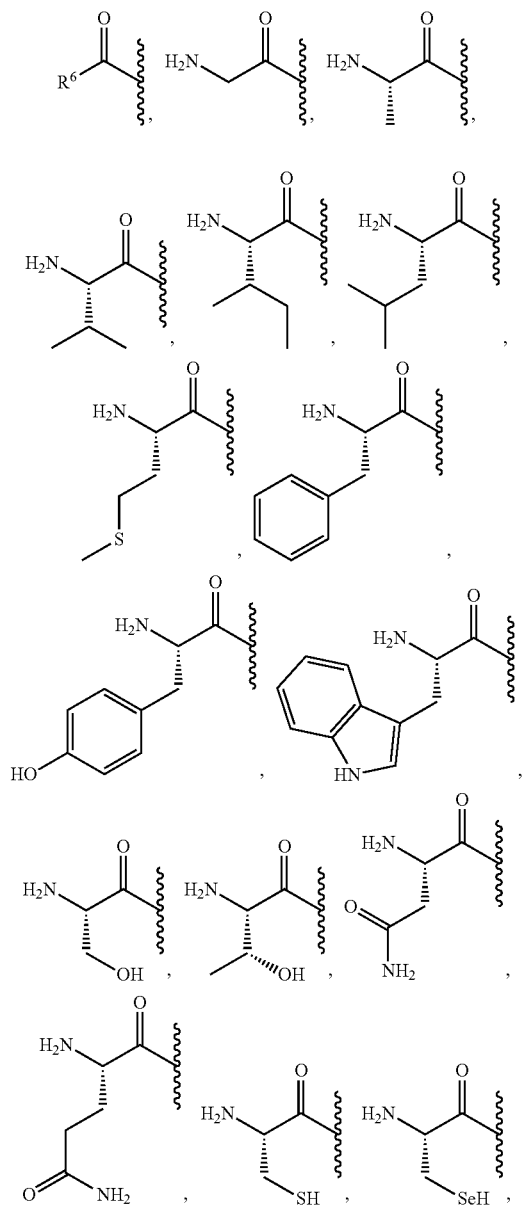
-continued
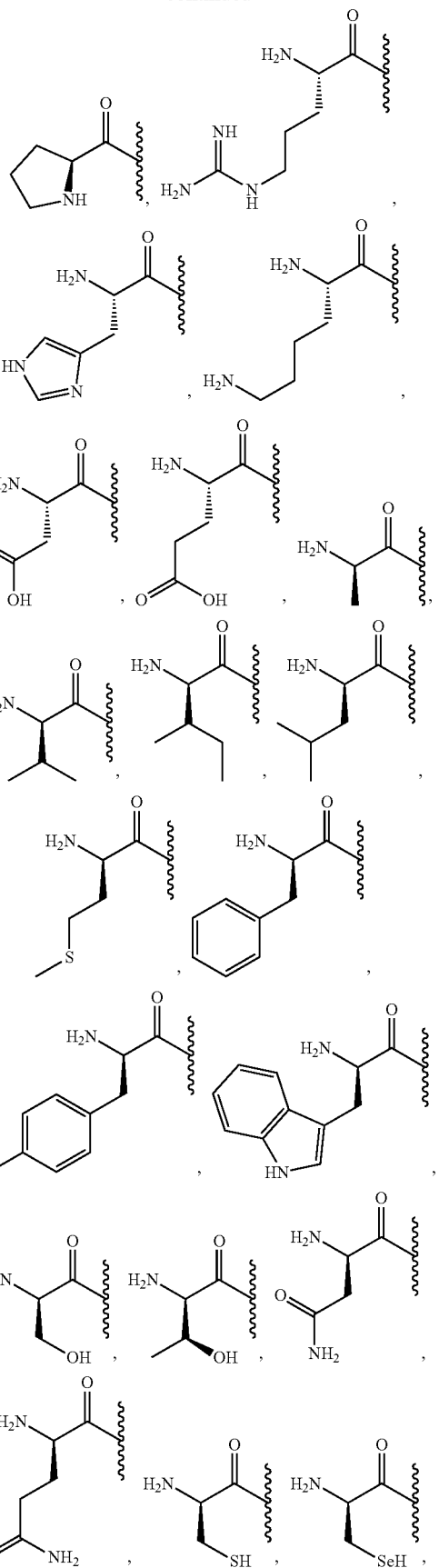

-continued

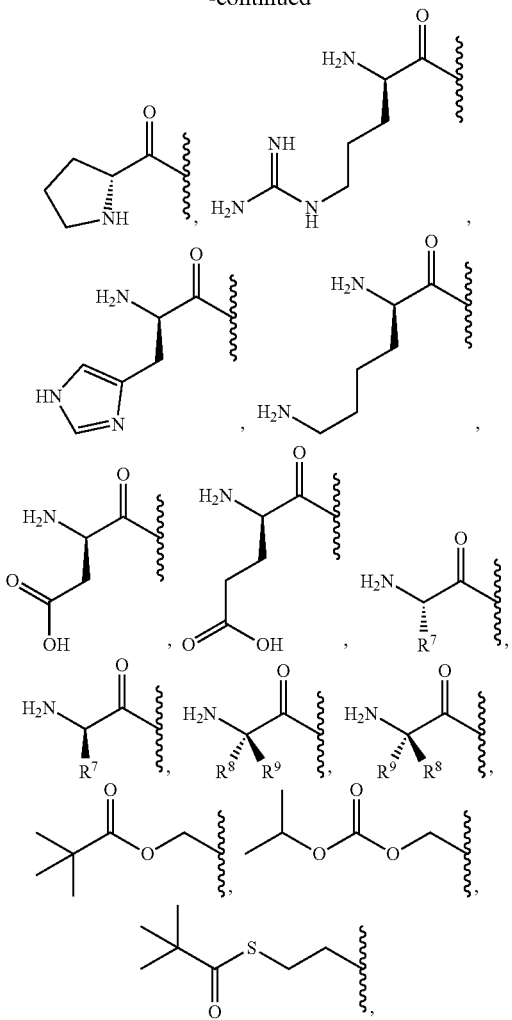

optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^1$ and $R^3$ are optionally substituted with one or more, the same or different, $R^{10}$;

$R^6$ is hydrogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;

$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;

$R^7$, $R^8$, and $R^9$ can form a ring with the α-carbon they are attached to and the amino group attached to the α-carbon;

$R^8$ and $R^9$ can form a ring with the α-carbon which they are attached;

$R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;

$R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula XI, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, and N,N-dipropylamino.

In exemplified embodiments of Formula XI, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XI, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XI, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula XII,

Formula XII

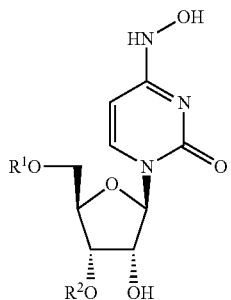

or a pharmaceutical or physiological salt thereof, wherein $R^1$ and $R^2$ are each independently selected from the following:

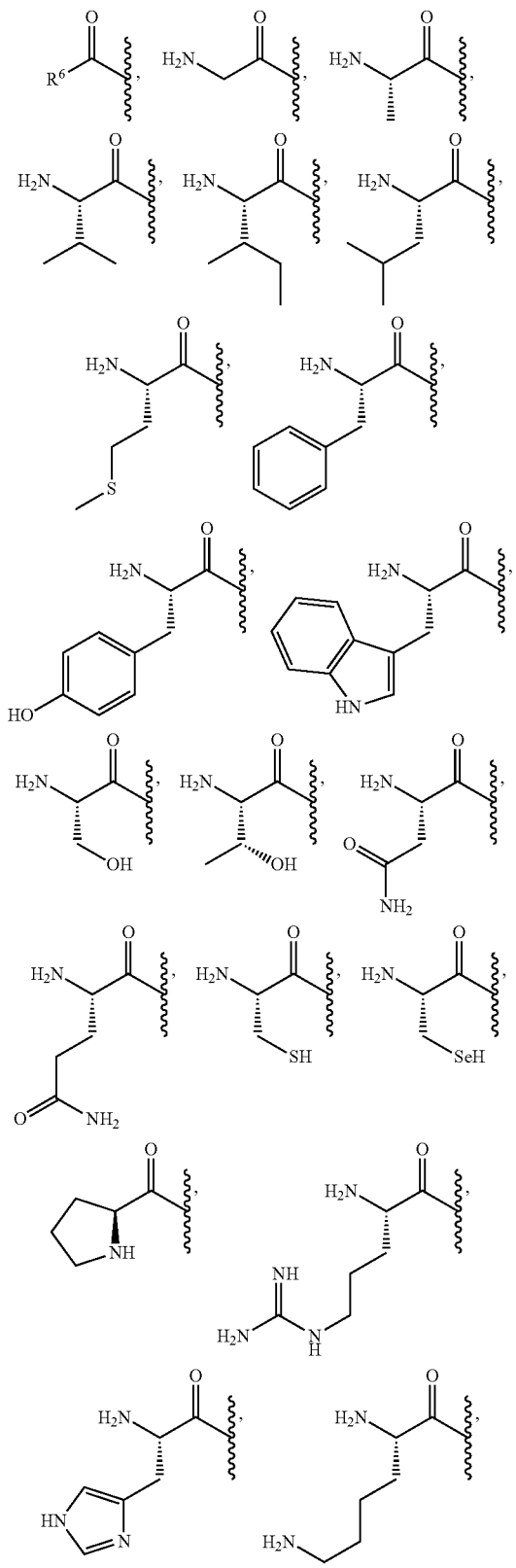

-continued

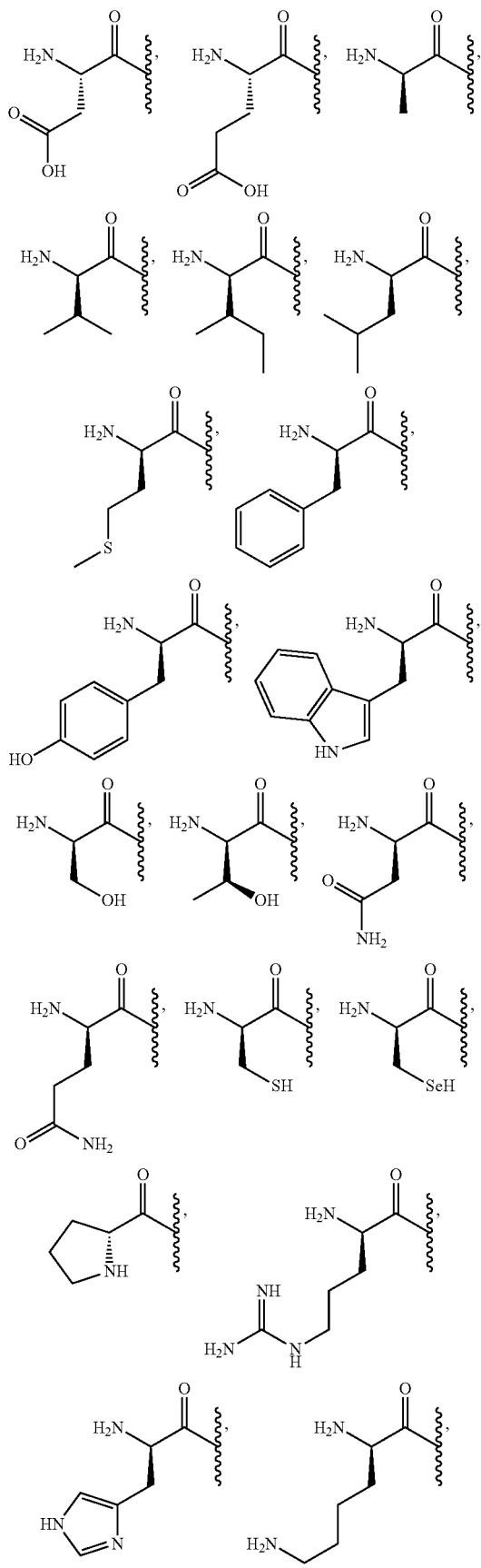

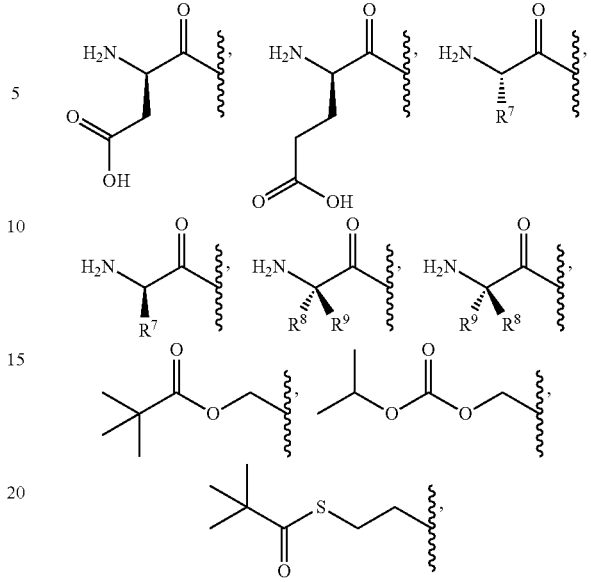

optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^1$ and $R^2$ are optionally substituted with one or more, the same or different, $R^{10}$;

$R^6$ is hydrogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;

$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;

$R^7$, $R^8$, and $R^9$ can form a ring with the α-carbon they are attached to and the amino group attached to the α-carbon;

$R^8$ and $R^9$ can form a ring with the α-carbon which they are attached;

$R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;

$R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula XII, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, and N,N-dipropylamino.

In exemplified embodiments of Formula XII, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XII, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XII, $R^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula XIII,

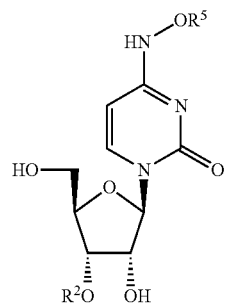

Formula XIII or a pharmaceutical or physiological salt thereof, wherein $R^2$ and $R^5$ are each independently selected from the following:

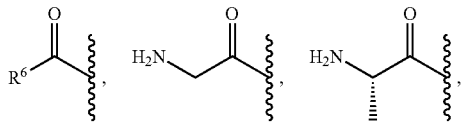

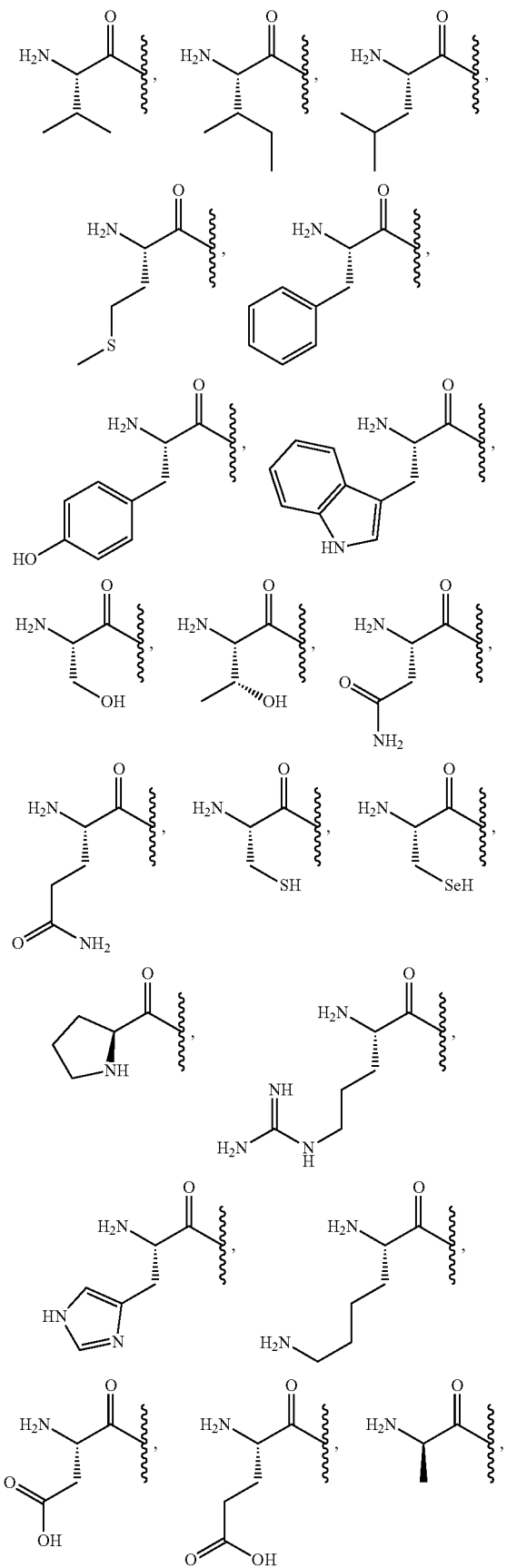
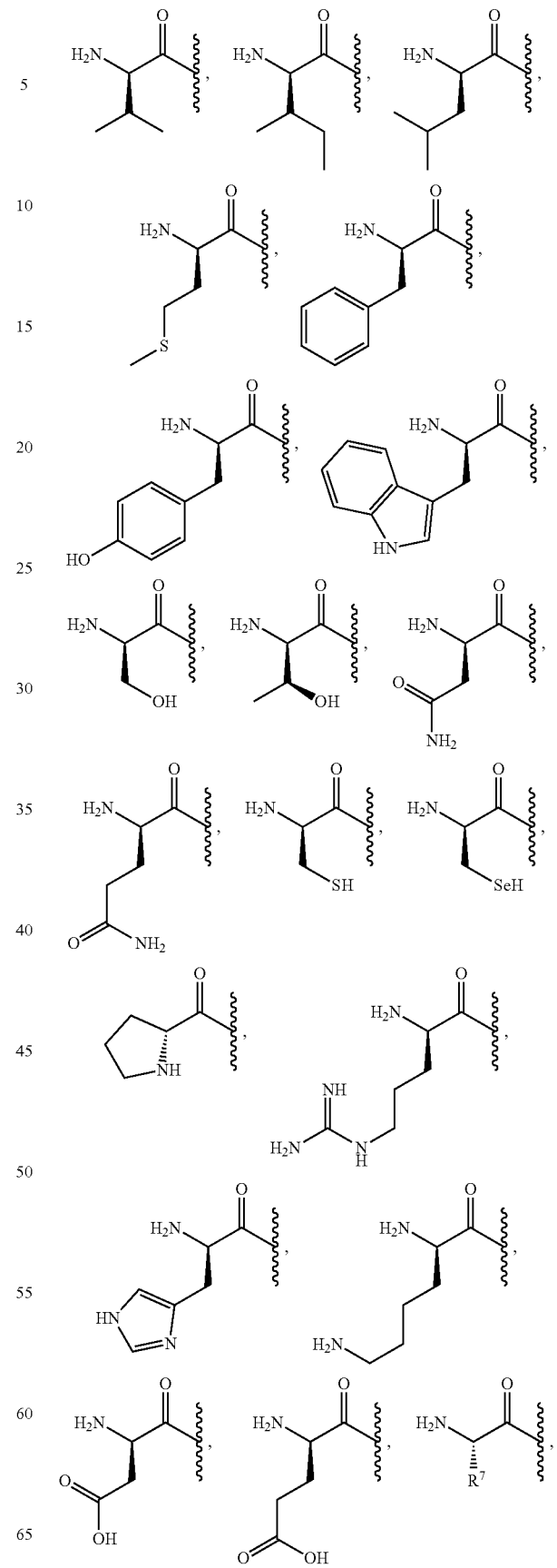

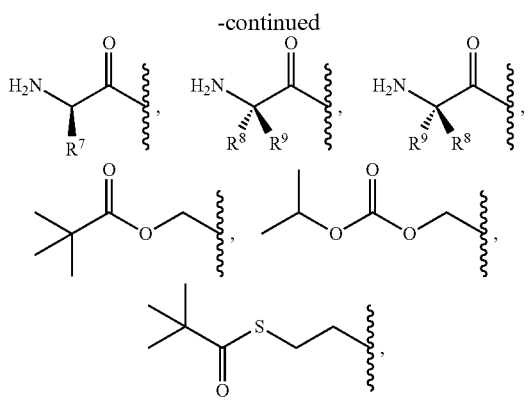

optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^2$ and $R^5$ are optionally substituted with one or more, the same or different, $R^{10}$;

$R^6$ is hydrogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;

$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;

$R^7$, $R^8$, and $R^9$ can form a ring with the α-carbon they are attached to and the amino group attached to the α-carbon;

$R^8$ and $R^9$ can form a ring with the α-carbon which they are attached;

$R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;

$R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula XIII, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, and N,N-dipropylamino.

In exemplified embodiments of Formula XIII, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XIII, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XIII, $R^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula XIV,

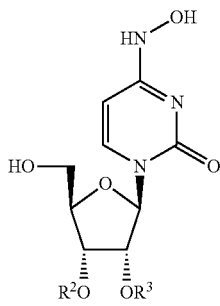

Formula XIV or a pharmaceutical or physiological salt thereof, wherein $R^2$ and $R^3$ are each independently selected from the following:

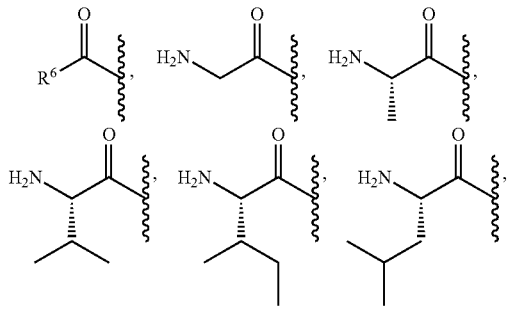

-continued

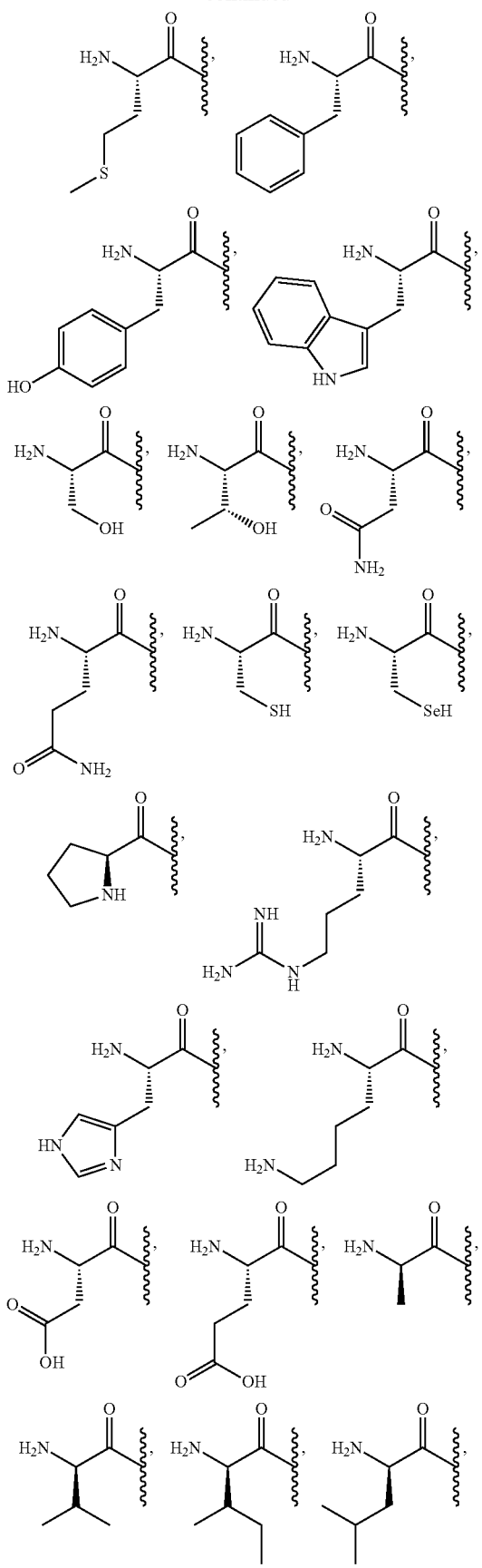

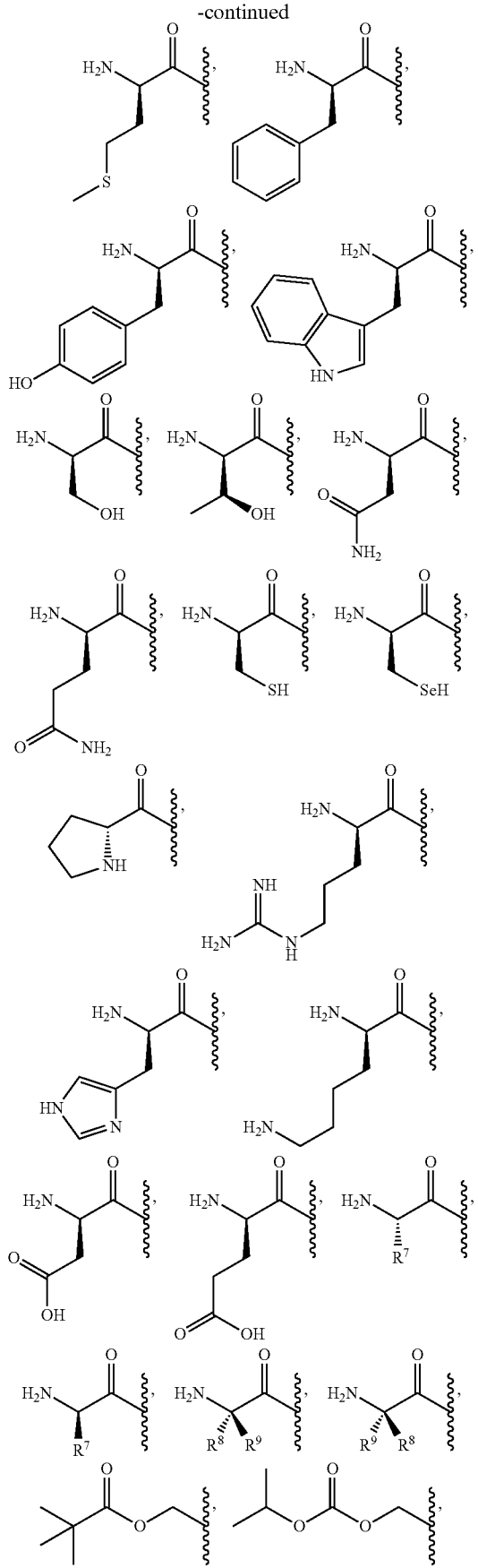

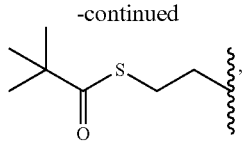

optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^2$ and $R^3$ are optionally substituted with one or more, the same or different, $R^{10}$;

$R^6$ is hydrogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;

$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, $(alkyl)_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;

$R^7$, $R^8$, and $R^9$ can form a ring with the α-carbon they are attached to and the amino group attached to the α-carbon;

$R^8$ and $R^9$ can form a ring with the α-carbon which they are attached;

$R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, $(alkyl)_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;

$R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, $(alkyl)_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula XIV, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, and N,N-dipropylamino.

In exemplified embodiments of Formula XIV, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XIV, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XIV, $R^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula XV,

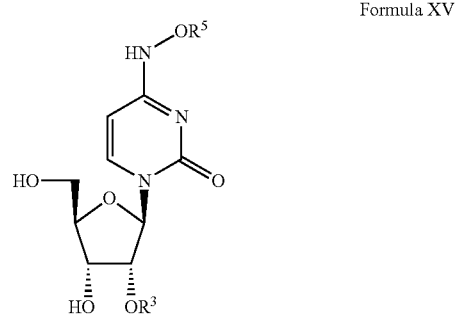

Formula XV or a pharmaceutical or physiological salt thereof, wherein $R^3$ and $R^5$ are each independently selected from the following:

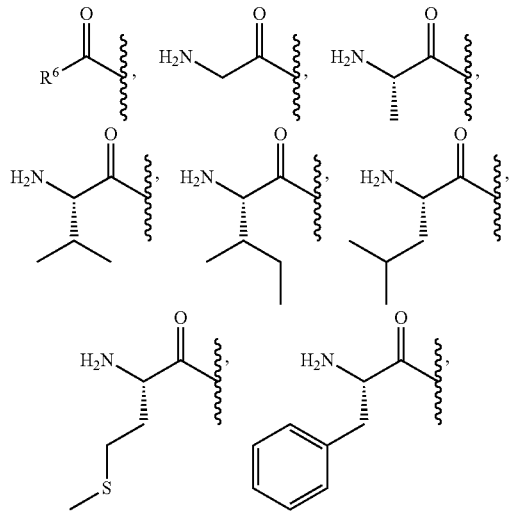

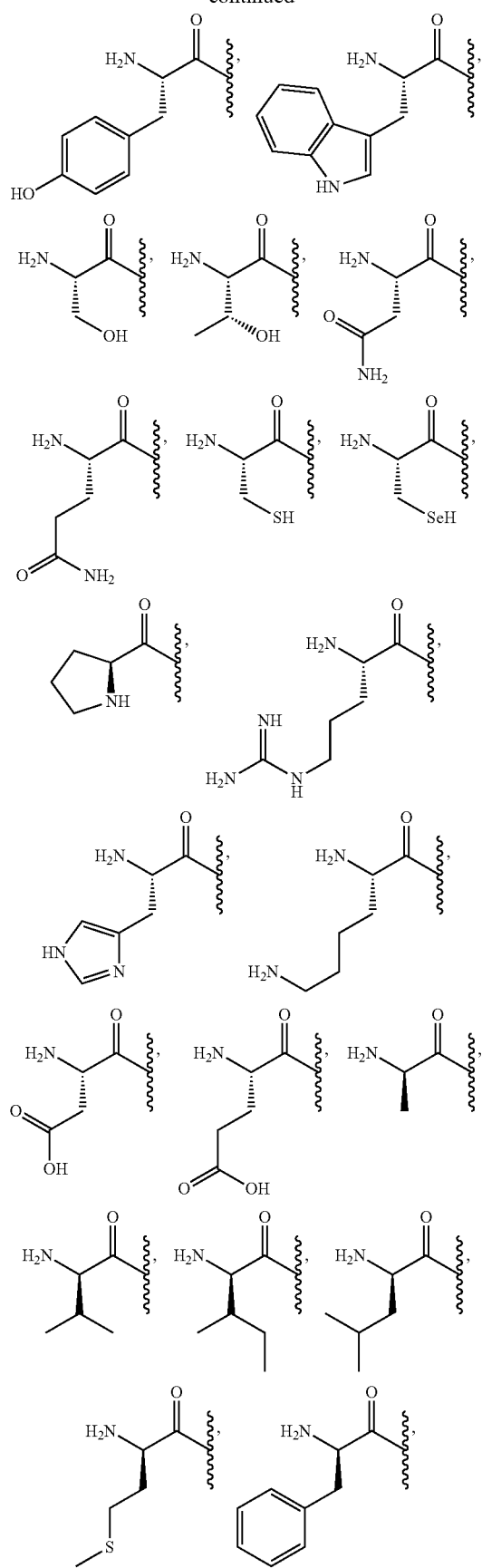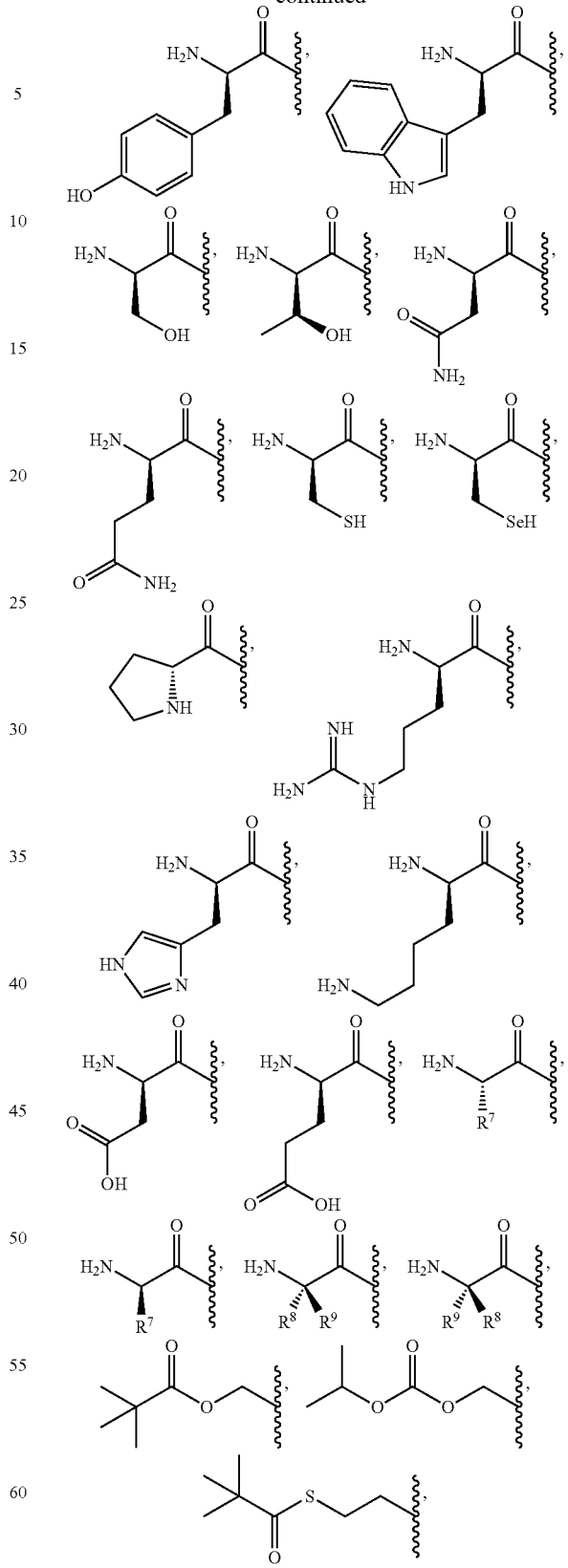
optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^3$ and $R^5$ are optionally substituted with one or more, the same or different, $R^{10}$;

$R^6$ is hydrogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;

$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;

$R^7$, $R^8$, and $R^9$ can form a ring with the α-carbon they are attached to and the amino group attached to the α-carbon;

$R^8$ and $R^9$ can form a ring with the α-carbon which they are attached;

$R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;

$R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula XV, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, and N,N-dipropylamino.

In exemplified embodiments of Formula XV, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XV, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XV, $R^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula XVI,

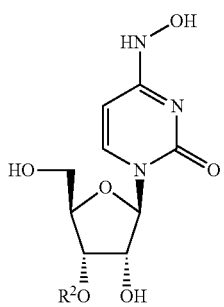

Formula XVI or a pharmaceutical or physiological salt thereof, wherein
$R^2$ is selected from the following:

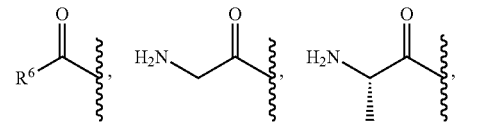

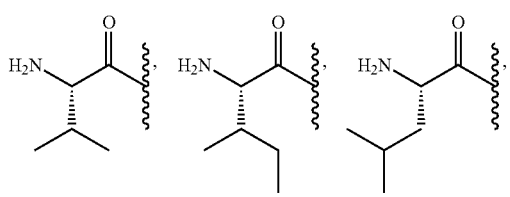

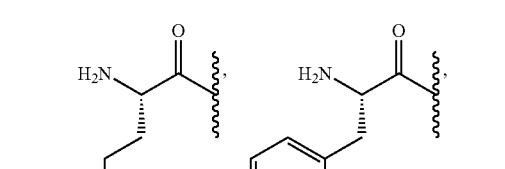

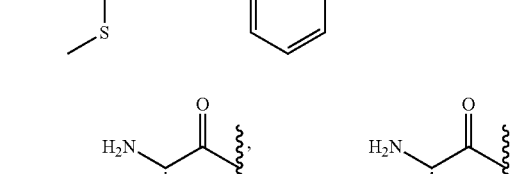

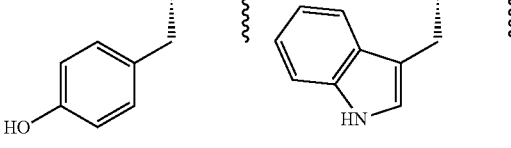

-continued

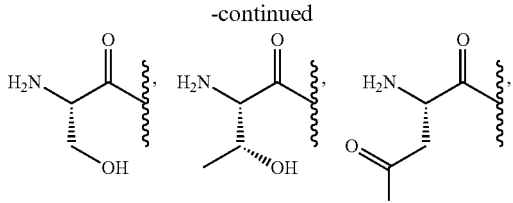

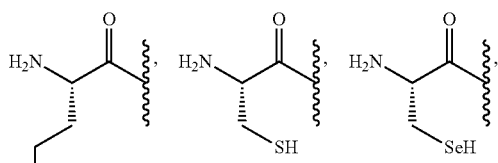

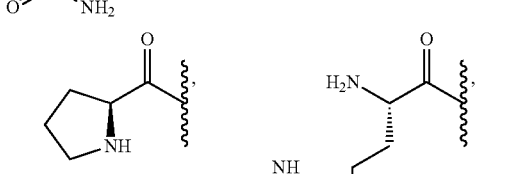

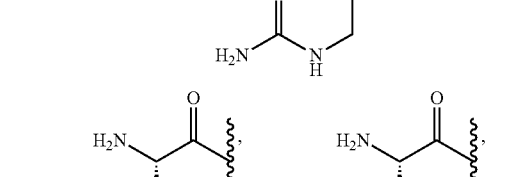

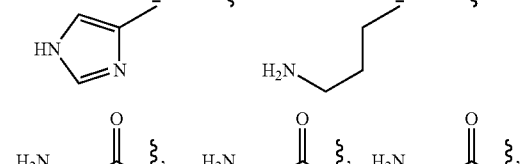

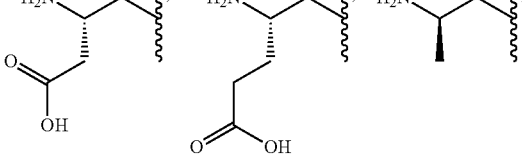

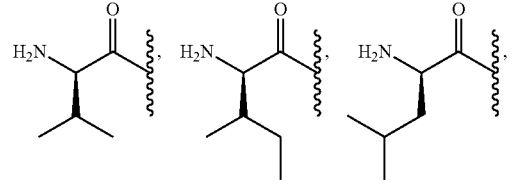

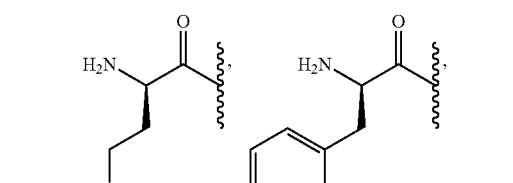

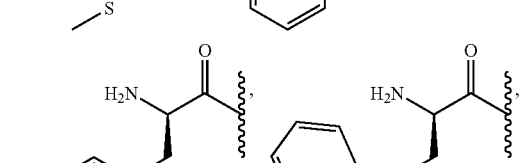

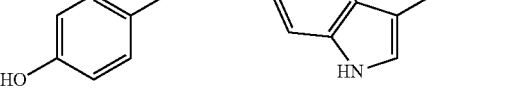

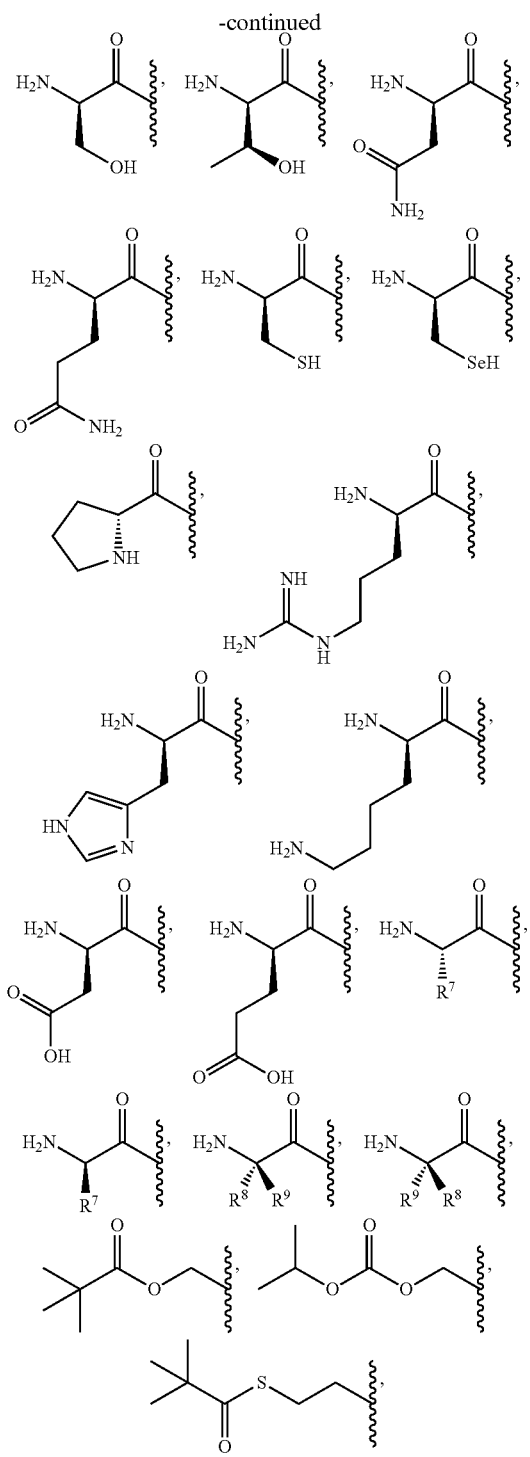

optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^2$ are optionally substituted with one or more, the same or different, $R^{10}$;

$R^6$ is hydrogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;

$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;

$R^7$, $R^8$, and $R^9$ can form a ring with the α-carbon they are attached to and the amino group attached to the α-carbon;

$R^8$ and $R^9$ can form a ring with the α-carbon which they are attached;

$R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, $(alkyl)_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;

$R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, $(alkyl)_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula XVI, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, and N,N-dipropylamino.

In exemplified embodiments of Formula XVI, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XVI, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XVI, $R^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula XVII,

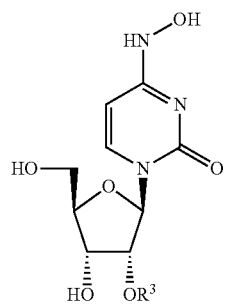

Formula XVII or a pharmaceutical or physiological salt thereof, wherein $R^3$ is selected from the following:

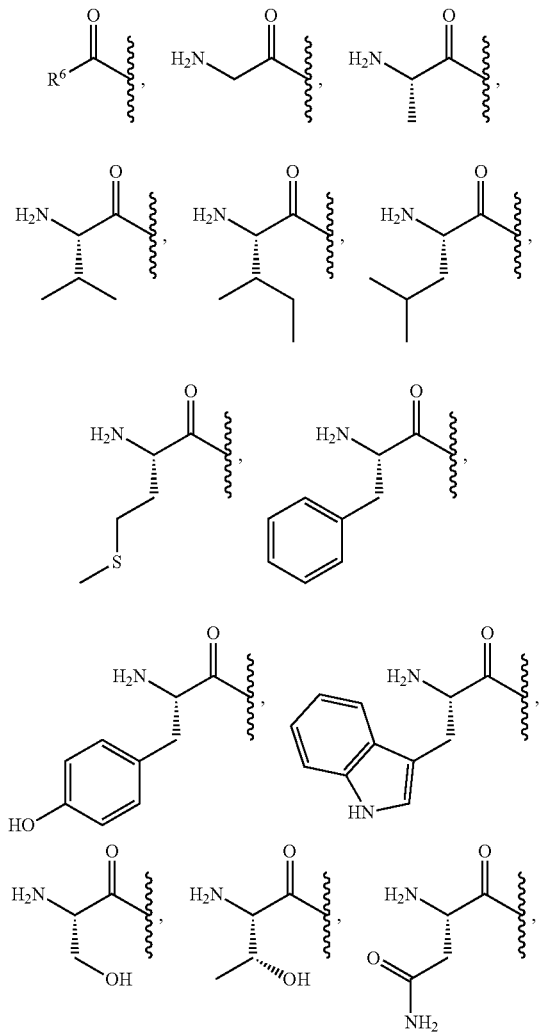

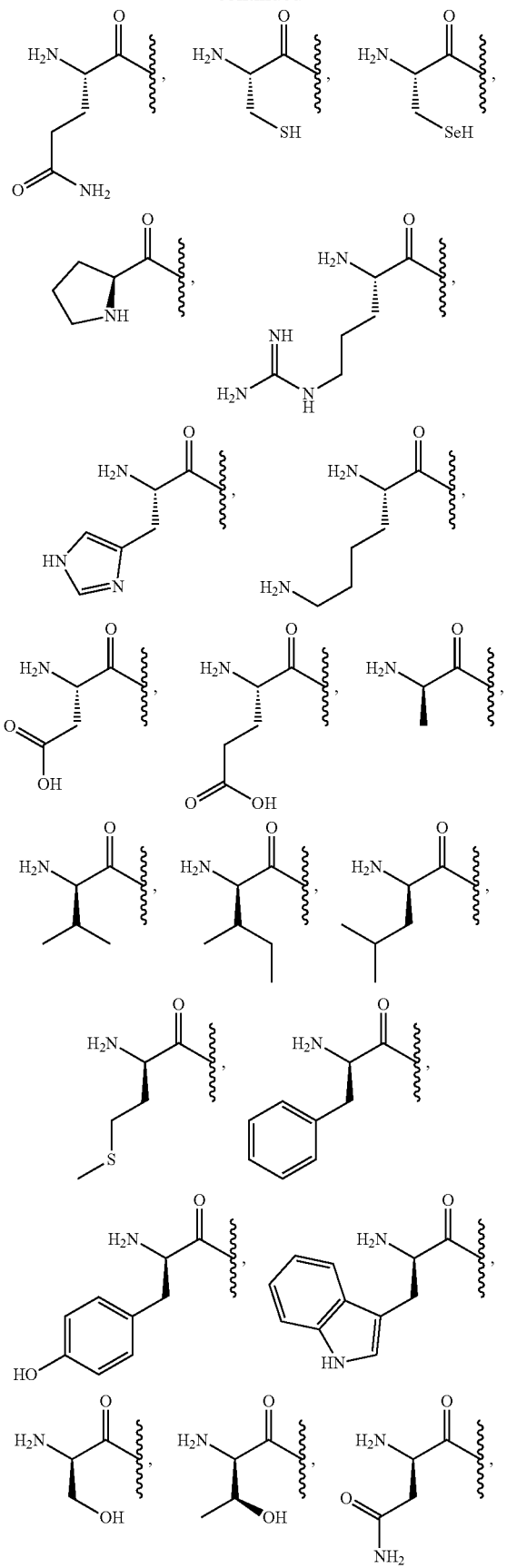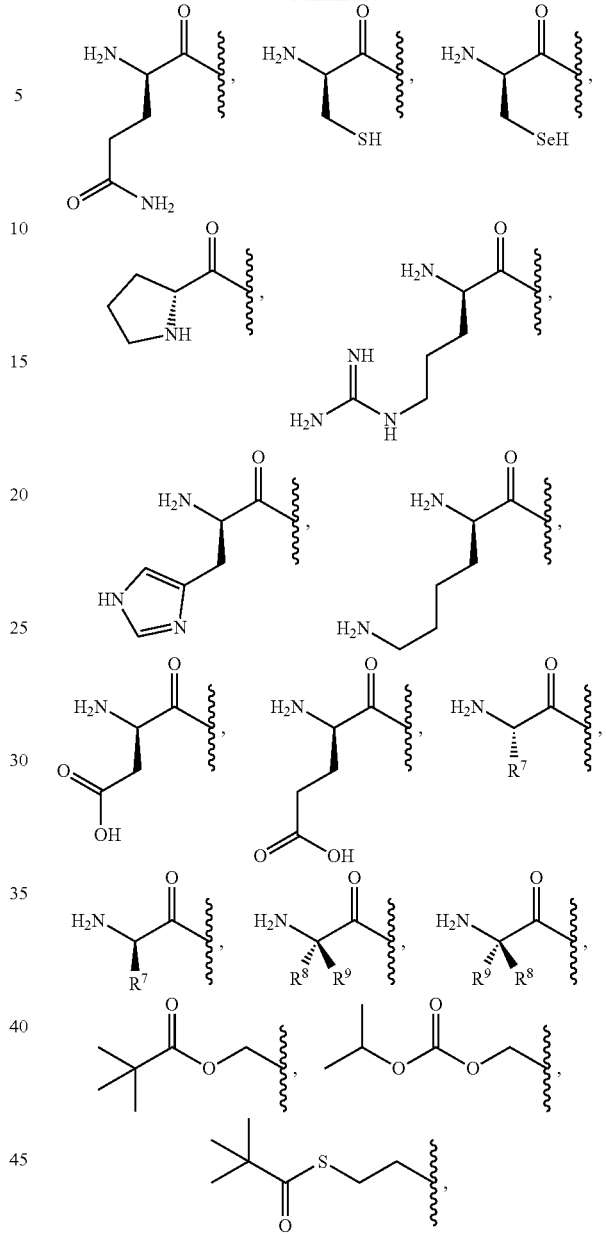

optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^3$ are optionally substituted with one or more, the same or different, $R^{10}$;

$R^6$ is hydrogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;

$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;

$R^7$, $R^8$, and $R^9$ can form a ring with the α-carbon they are attached to and the amino group attached to the α-carbon;

$R^8$ and $R^9$ can form a ring with the α-carbon which they are attached;

$R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;

$R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula XVII, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, and N,N-dipropylamino.

In exemplified embodiments of Formula XVII, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XVII, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula I, $R^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula XVIII,

Formula XVIII
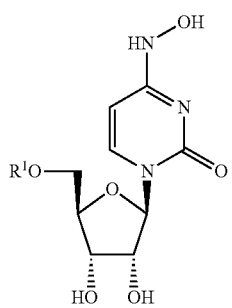
or a pharmaceutical or physiological salt thereof, wherein R[1] is selected from the following:
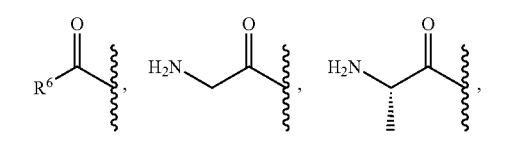
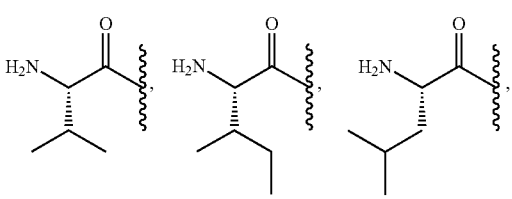
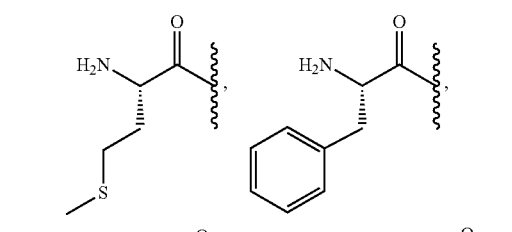
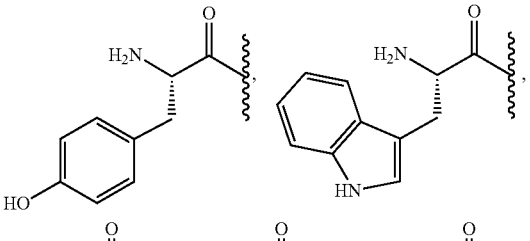
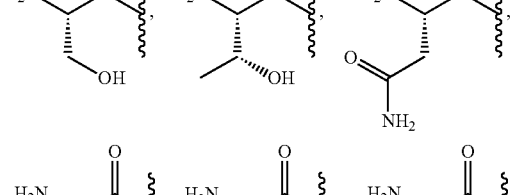
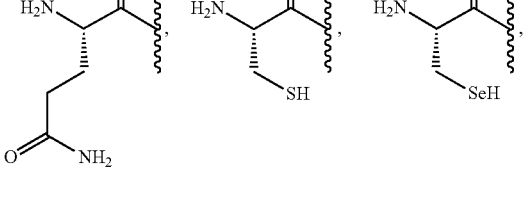
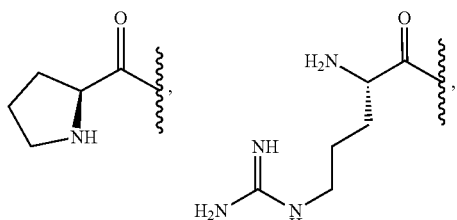
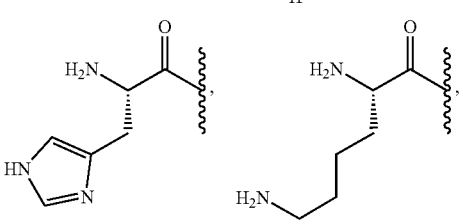
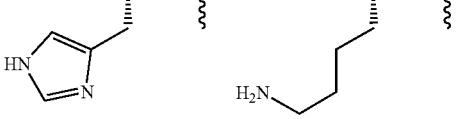
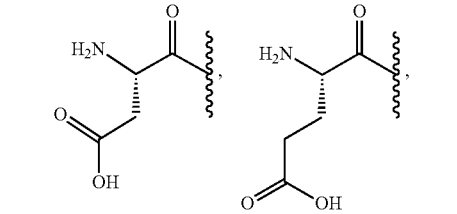
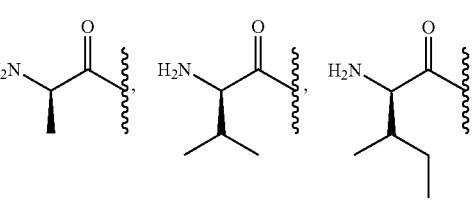
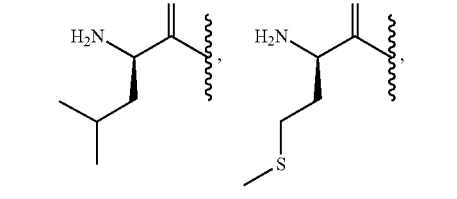
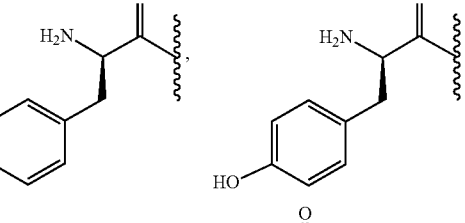
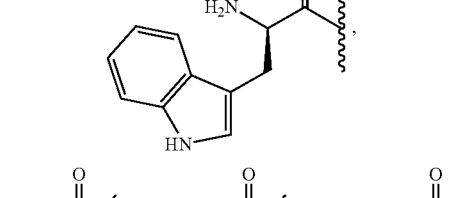
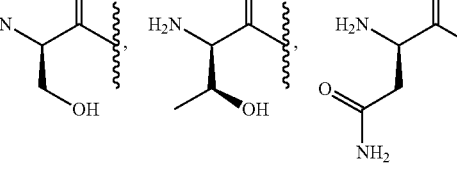

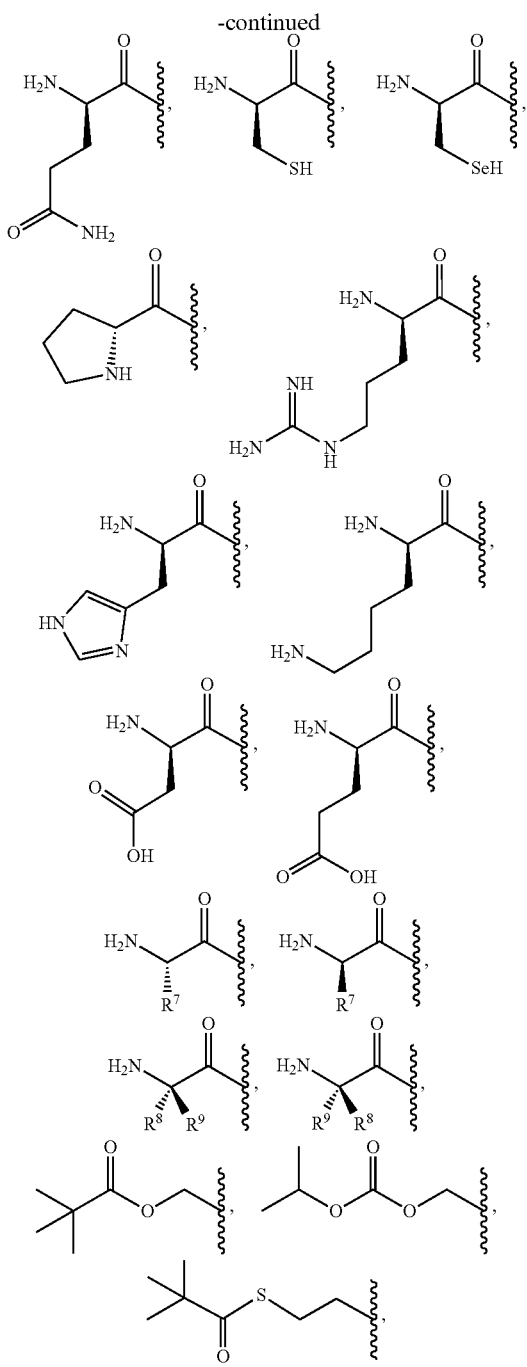

optionally substituted branched esters, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^1$ are optionally substituted with one or more, the same or different, $R^{10}$;

$R^6$ is hydrogen, $C_1$-$C_7$ n-alkyl, $C_9$-$C_{22}$ n-alkyl, optionally substituted $C_8$ n-alkyl, branched alkyl, alkenyl, alkynyl, carbocyclyl, heterocarbocyclyl, aryl, heteroaryl, heterocyclyl, cycloalkyl, cycloalkenyl, —O($C_1$-$C_6$ n-alkyl), —O($C_8$-$C_{21}$ n-alkyl), optionally substituted —O($C_7$ n-alkyl), —O(branched alkyl) carbocycloxy, heterocarbocycloxy, aryloxy, heteroaryloxy, heterocycloxy, cycloalkoxy, cycloalkenoxy, —NH($C_1$-$C_6$ n-alkyl), —NH($C_8$-$C_{21}$ n-alkyl), optionally substituted —NH($C_7$ n-alkyl), —NH(branched alkyl) (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;

$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;

$R^7$, $R^8$, and $R^9$ can form a ring with the α-carbon they are attached to and the amino group attached to the α-carbon;

$R^8$ and $R^9$ can form a ring with the α-carbon which they are attached;

$R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;

$R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula XVIII, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, and N,N-dipropylamino.

In exemplified embodiments of Formula XVIII, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XVIII, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XVIII, $R^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula XIX

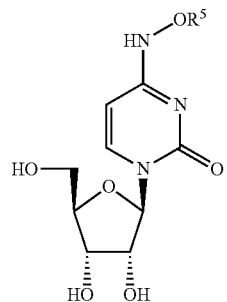

Formula XIX or a pharmaceutical or physiological salt thereof, wherein $R^5$ is selected from the following:

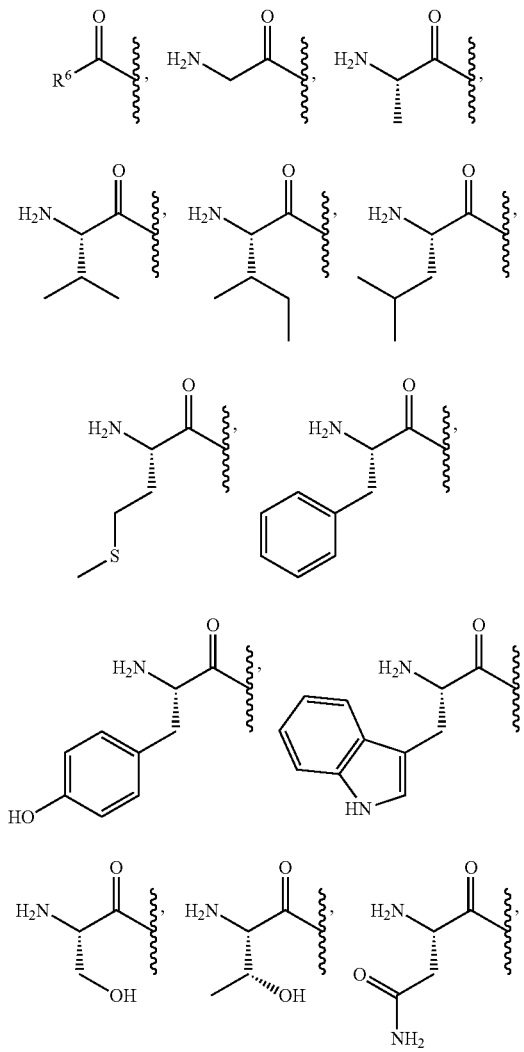

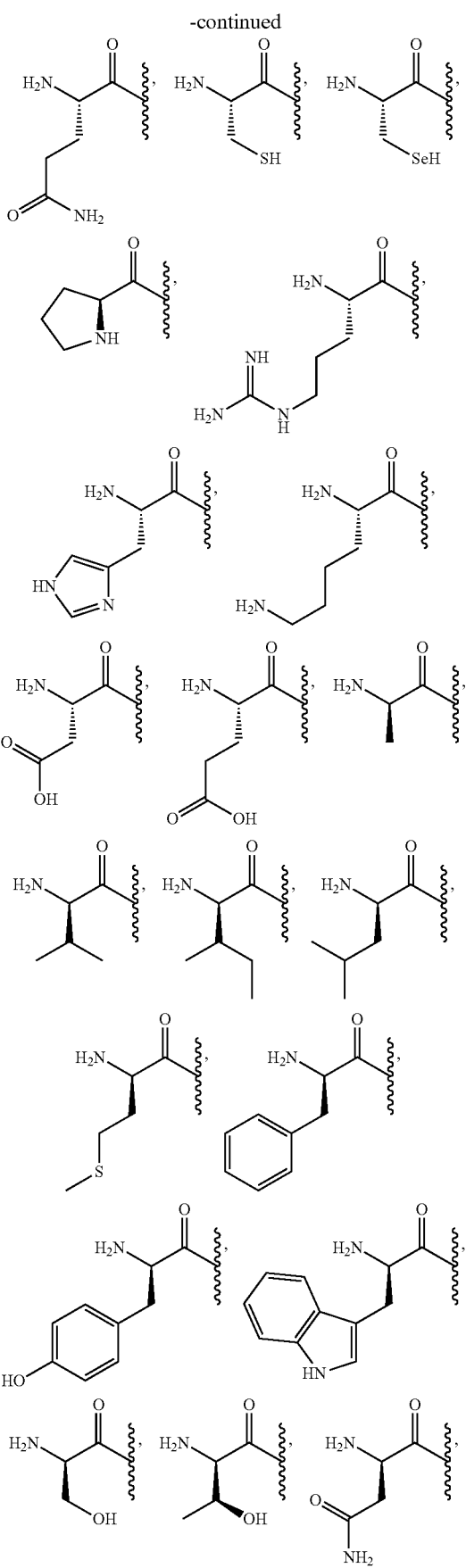
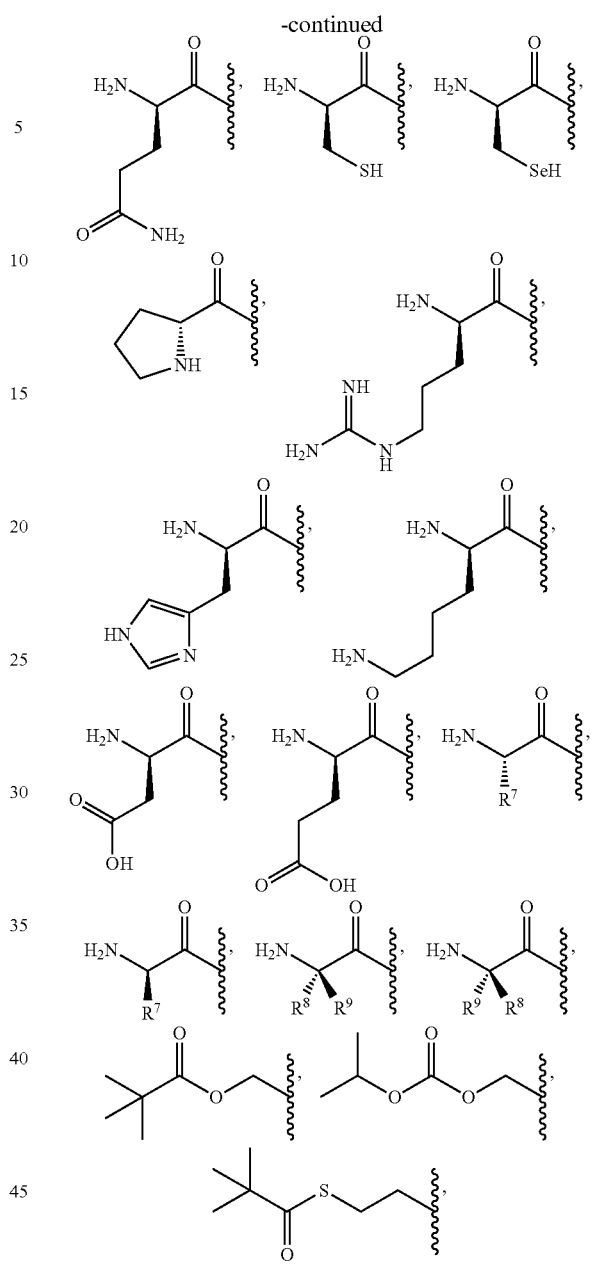

optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^5$ are optionally substituted with one or more, the same or different, $R^{10}$;

$R^6$ is hydrogen, $C_2$-$C_7$ n-alkyl, optionally substituted $C_8$ n-alkyl, $C_9$-$C_{22}$ n-alkyl, alkenyl, alkynyl, carbocyclyl, heterocarbocyclyl, aryl, heteroaryl, heterocyclyl, $C_3$-$C_9$ cycloalkyl, $C_{11}$-$C_{22}$ cycloalkyl, optionally substituted $C_{10}$ cycloalkyl, cycloalkenyl, —O($C_1$-$C_6$ n-alkyl), —O(optionally substituted $C_7$ n-alkyl), —O($C_8$-$C_{21}$ n-alkyl), —O(branched alkyl), carbocycloxy, heterocarbocycloxy, aryloxy, heteroaryloxy, heterocycloxy, cycloalkoxy, cycloalkenoxy, —N($C_2$-$C_{21}$ n-alkyl)$_2$, —N(optionally substituted $C_1$ alkyl)$_2$, —NH(optionally substituted $C_1$ alkyl), —NH($C_2$-$C_6$ n-alkyl), —NH(optionally substituted $C_7$ n-alkyl), —NH($C_8$-$C_{15}$ n-alkyl), —NH(optionally substituted $C_{16}$ n-alkyl), —NH($C_{17}$ n-alkyl), —NH(optionally substituted $C_8$ n-alkyl), —NH($C_{19}$-$C_{21}$ n-alkyl), —NH(branched alkyl), —N(branched alkyl)$_2$, carbocyclamino, heterocarbocyclamino, optionally substituted arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;

$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;

$R^7$, $R^8$, and $R^9$ can form a ring with the α-carbon they are attached to and the amino group attached to the α-carbon;

$R^8$ and $R^9$ can form a ring with the α-carbon which they are attached;

$R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;

$R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula XIX, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, and N,N-dipropylamino.

In exemplified embodiments of Formula XIX, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XIX, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XIX, $R^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, the disclosure relates to a compound of Formula XX,

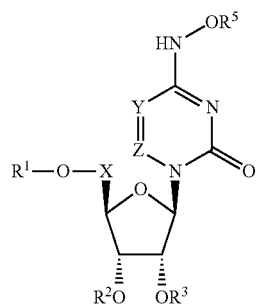

Formula XX or a pharmaceutical or physiological salt thereof, wherein
X is $CH_2$, $CHCH_3$, $C(CH_3)_2$, CHF, $CF_2$, or $CD_2$;
Y is N or CR';
Z is N or CR";
R' is hydrogen, deuterium, halogen, hydroxyl, amino, thiol, alkyl, alkenyl, alkynyl, aryl, heteroaryl, carbocyclyl, heterocarbocyclyl, cycloalkyl, heterocyclyl, or carbonyl, wherein R' is optionally substituted with one or more, the same or different, $R^{10}$;
R" is hydrogen, deuterium, halogen, hydroxyl, amino, thiol, alkyl, alkenyl, alkynyl, aryl, heteroaryl, carbocyclyl, heterocarbocyclyl, cycloalkyl, heterocyclyl, hydroxyl, thiol, or carbonyl, wherein R' is optionally substituted with one or more, the same or different, $R^{10}$;
$R^1$, $R^2$, $R^3$, and $R^5$ are each independently selected from H,

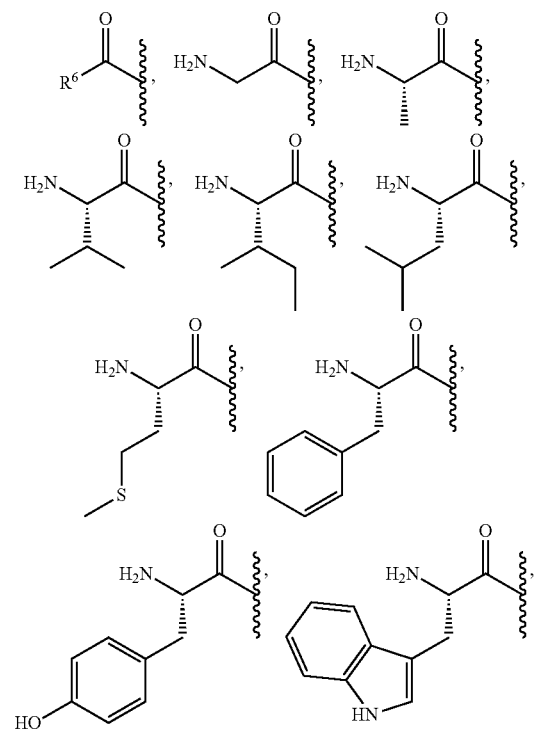

-continued

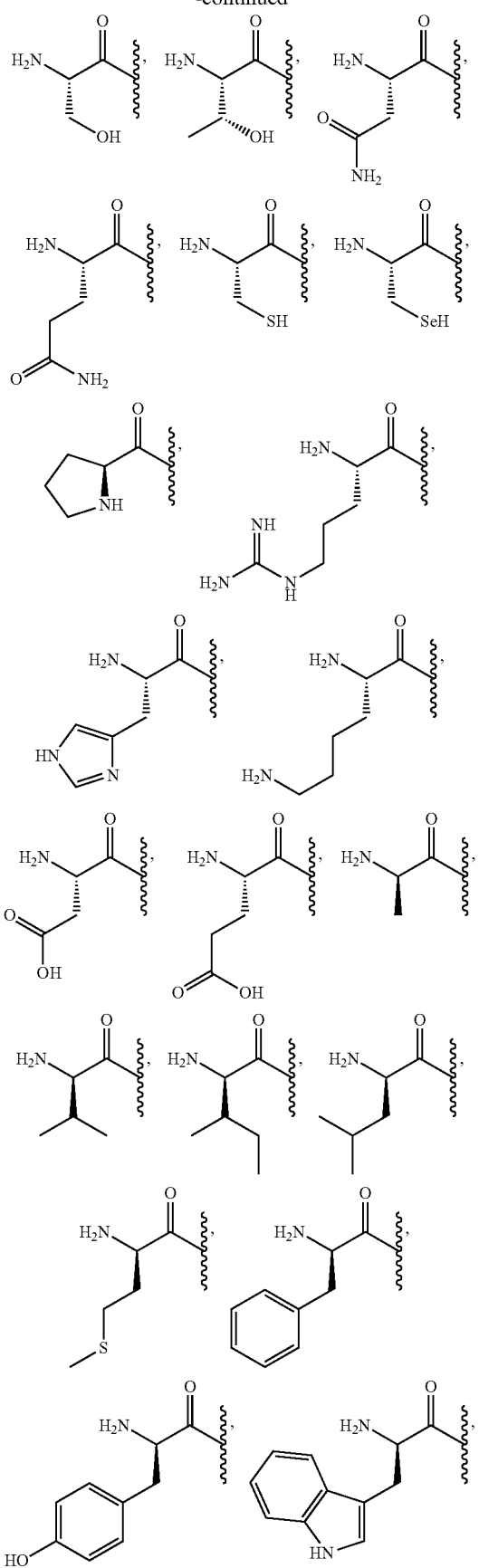

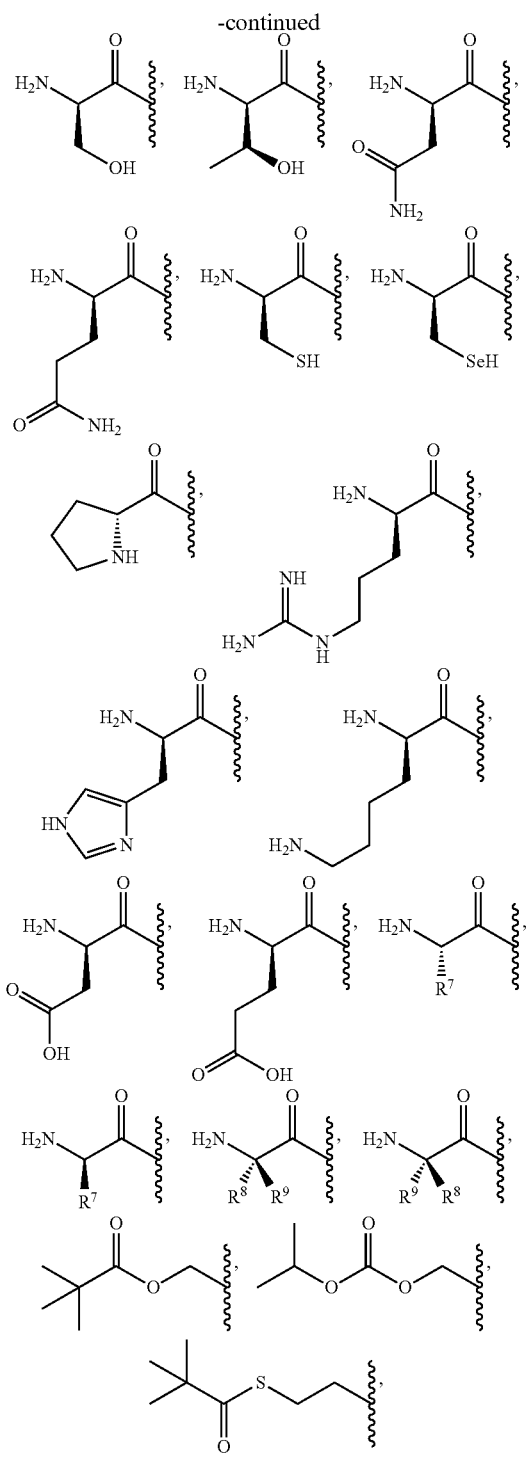

optionally substituted esters, optionally substituted branched esters, optionally substituted carbonates, optionally substituted carbamates, optionally substituted thioesters, optionally substituted branched thioesters, optionally substituted thiocarbonates, optionally substituted S-thiocarbonate, optionally substituted dithiocarbonates, optionally substituted thiocarbamates, optionally substituted oxymethoxycarbonyl, optionally substituted oxymethoxythiocarbonyl, optionally substituted oxymethylcarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, optionally substituted sulfenyl, optionally substituted imidate, optionally substituted hydrazonate, optionally substituted oximyl, optionally substituted imidinyl, optionally substituted imidyl, optionally substituted aminal, optionally substituted hemiaminal, optionally substituted acetal, optionally substituted hemiacetal, optionally substituted carbonimidate, optionally substituted thiocarbonimidate, optionally substituted carbonimidyl, optionally substituted carbamimidate, optionally substituted carbamimidyl, optionally substituted thioacetal, optionally substituted S-acyl-2-thioethyl, optionally substituted bis-(acyloxybenzyl)esters, optionally substituted (acyloxybenzyl)esters, and BAB-esters, wherein $R^1$, $R^2$, $R^3$ and $R^5$ are optionally substituted with one or more, the same or different, $R^{10}$;

With the provision that $R^1$, $R^2$, $R^3$ and $R^5$ are not all H;

$R^6$ is hydrogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, cyano, or lipid, wherein $R^6$ is optionally substituted with one or more, the same or different, $R^{10}$;

$R^7$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^7$ is optionally substituted with one or more, the same or different, $R^{10}$;

$R^8$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^8$ is optionally substituted with one or more, the same or different, $R^{10}$;

$R^9$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^9$ is optionally substituted with one or more, the same or different, $R^{10}$;

$R^7$, $R^8$, and $R^9$ can form a ring with the α-carbon they are attached to and the amino group attached to the α-carbon;

$R^8$ and $R^9$ can form a ring with the α-carbon which they are attached;

$R^{10}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl, wherein $R^{10}$ is optionally substituted with one or more, the same or different, $R^{11}$;

$R^{11}$ is deuterium, hydroxy, azido, thiol, amino, cyano, halogen, alkyl, alkenyl, alkynyl, carbocyclyl, heterocarbocyclyl, aryl, heteroaryl, heterocyclyl, cycloalkyl, cycloalkenyl, alkoxy, carbocycloxy, heterocarbocycloxy, aryloxy, heteroaryloxy, heterocycloxy, cycloalkoxy, cycloalkenoxy, alkylamino, (alkyl)$_2$ amino, carbocyclamino, heterocarbocyclamino, arylamino, heteroarylamino, heterocyclamino, cycloalkamino, cycloalkenamino, alkylthio, carbocyclylthio, heterocarbocyclylthio, arylthio, heteroarylthio, heterocyclylthio, cycloalkylthio, cycloalkenylthio, allenyl, sulfinyl, sulfamoyl, sulfonyl, lipid, nitro, or carbonyl; and Lipid is a $C_{11}$-$C_{22}$ higher alkyl, $C_{11}$-$C_{22}$ higher alkoxy, polyethylene glycol, or aryl substituted with an alkyl group, or a lipid as described herein.

In exemplified embodiments of Formula XX, $R^6$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, and N,N-dipropylamino.

In exemplified embodiments of Formula XX, $R^7$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XX, $R^8$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In exemplified embodiments of Formula XX, $R^9$ is methyl, ethyl, propyl, isopropyl, butyl, s-butyl, t-butyl, pentyl, s-pentyl, t-pentyl, neopentyl, 3-pentyl, hexyl, t-hexyl, 4-septyl, cyclopropyl, cyclobutyl, cyclopentyl, cyclohexyl, phenyl 2,6-dimethylphenyl, isopropoxide, tert-butoxide, N-propylamino, N-isopropylamino, N-tert-butylamino, N,N-dimethylamino, N,N-diethylamino, or N,N-dipropylamino.

In certain embodiments, a compound of Formula XX is not one of the following structures:

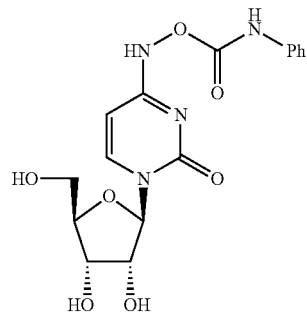

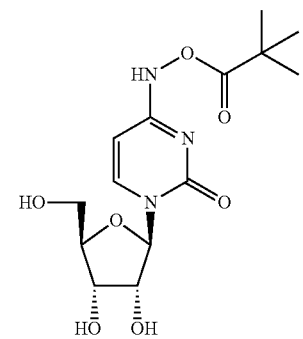

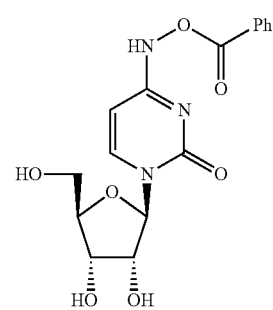

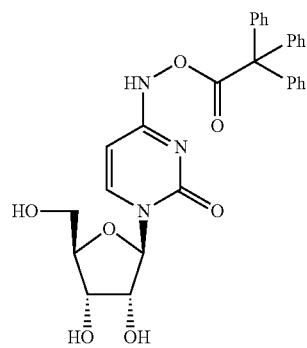

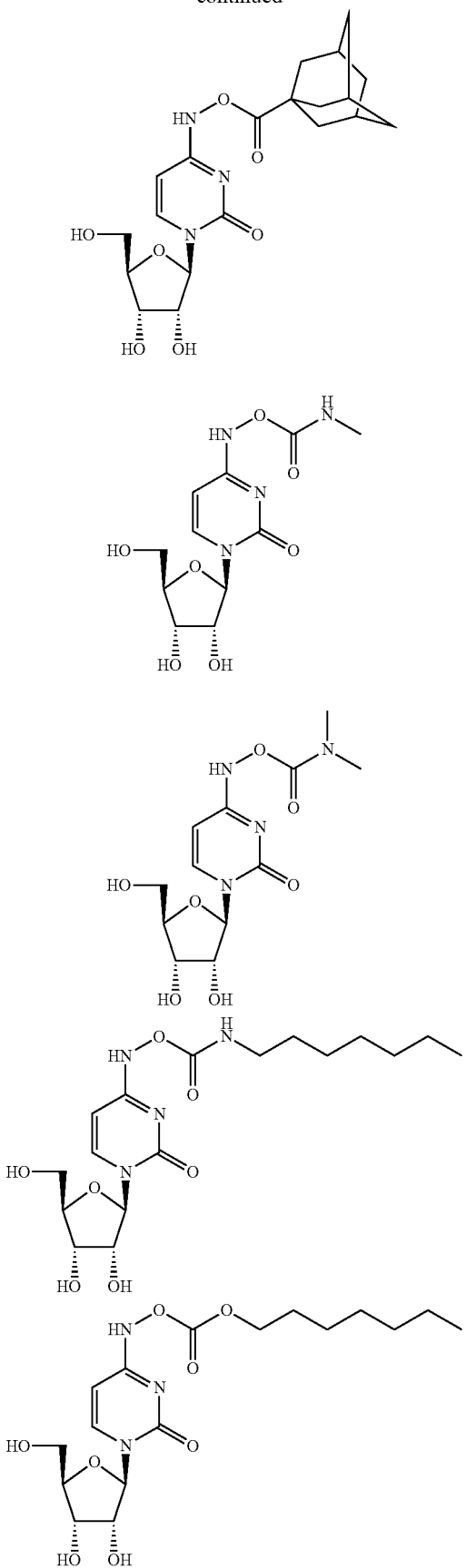
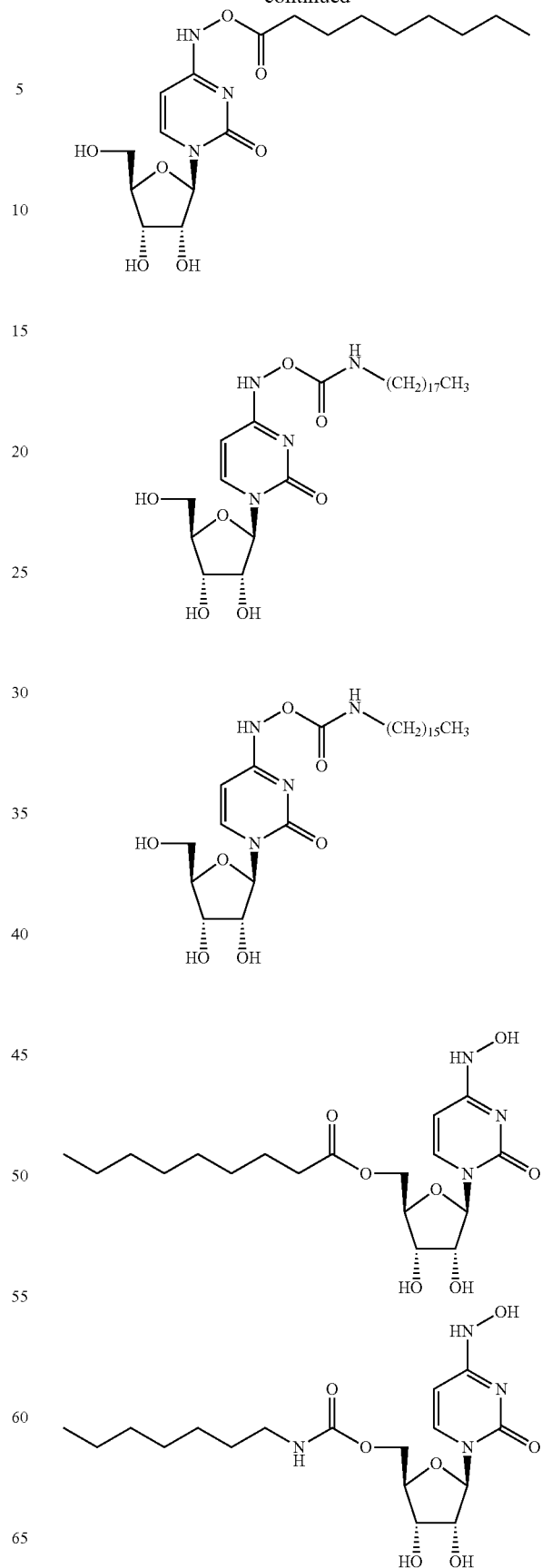

| 121 -continued | 122 -continued |
|---|---|
| 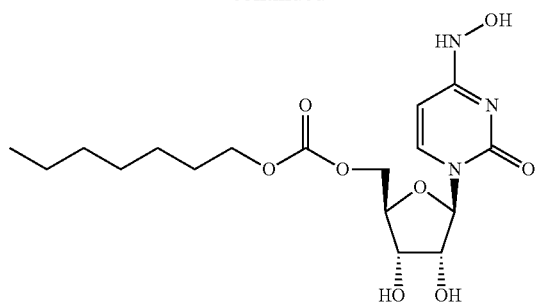 | 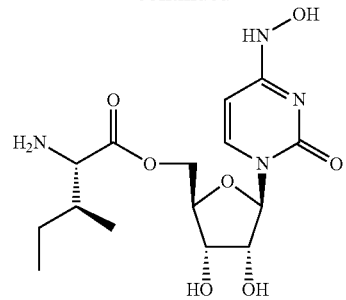 |
| 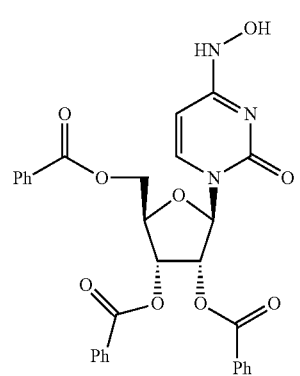 | 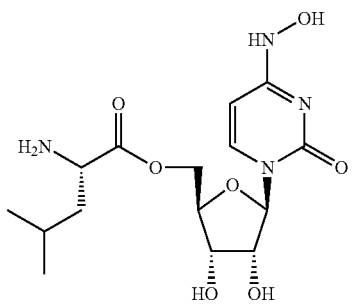 |
| 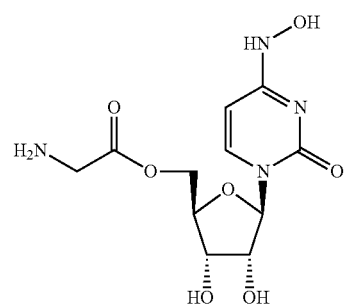 | 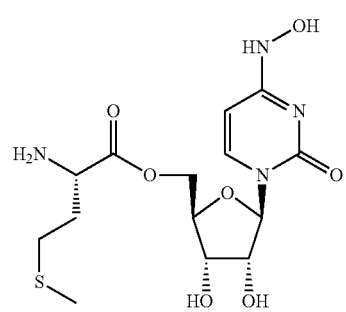 |
| 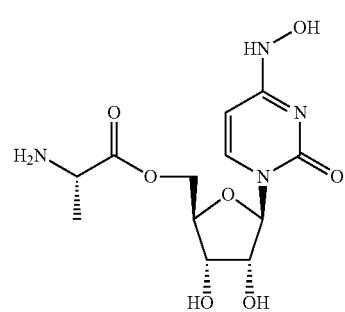 | 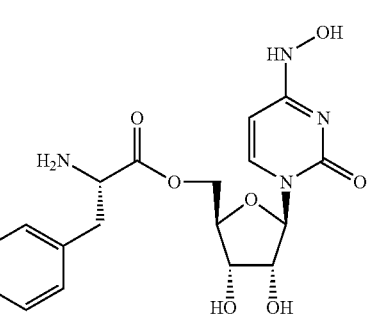 |
| 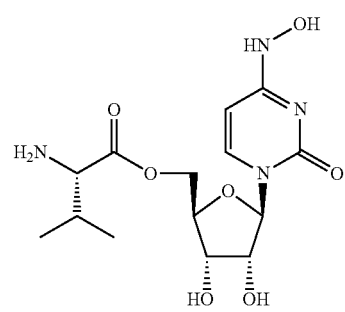 | 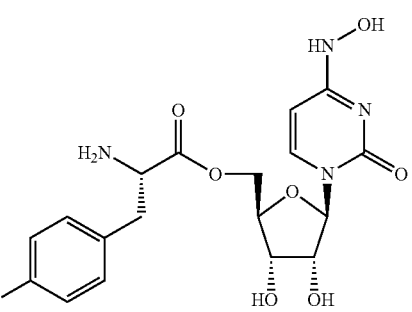 |

123
-continued
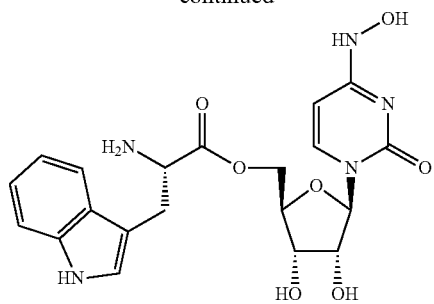
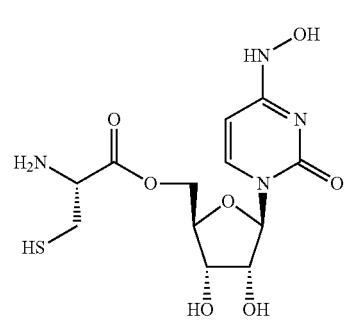
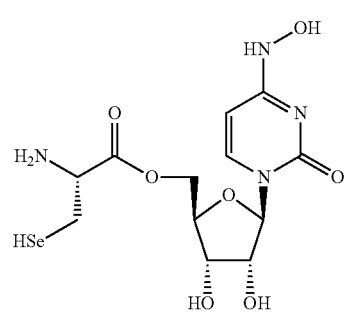
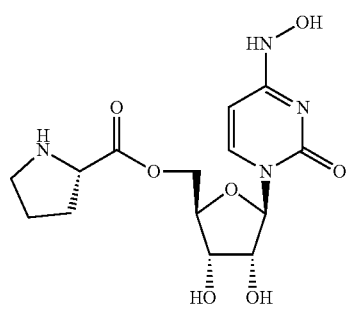
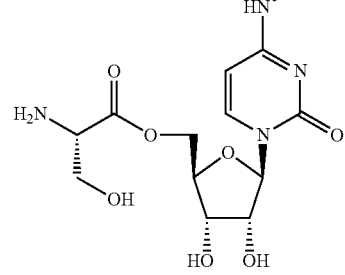
124
-continued
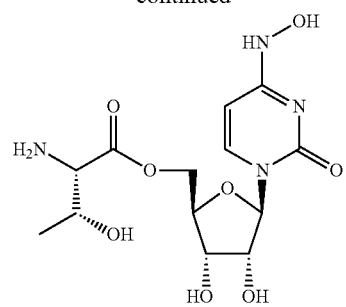
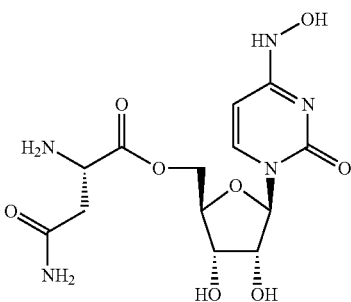
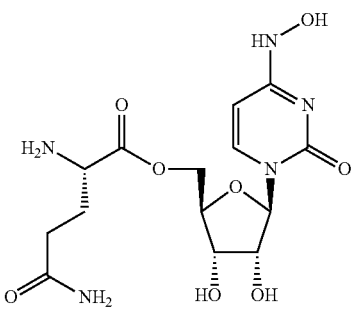
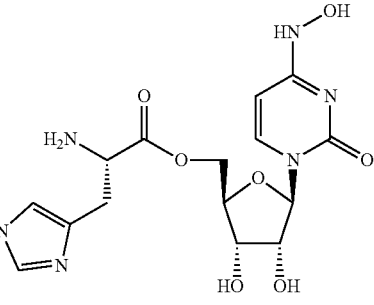
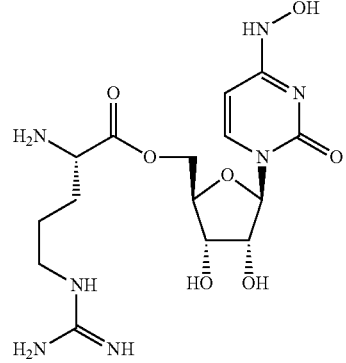

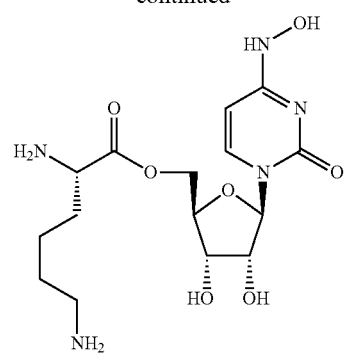
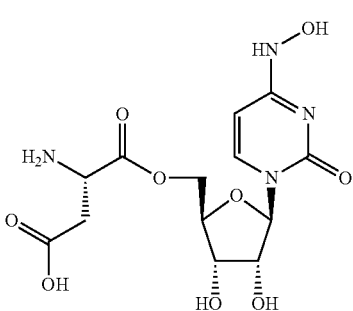
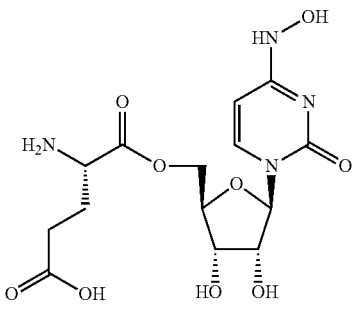
In exemplary embodiments, the compound is selected from:
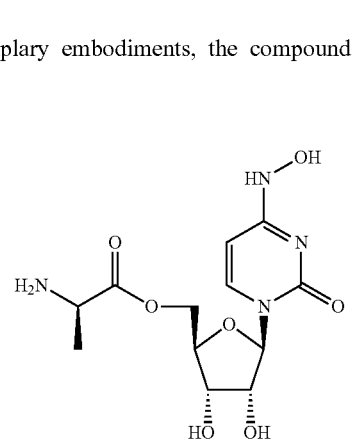
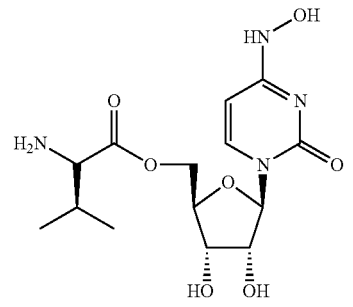
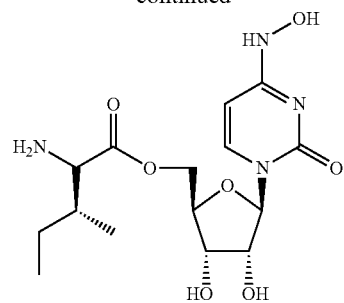
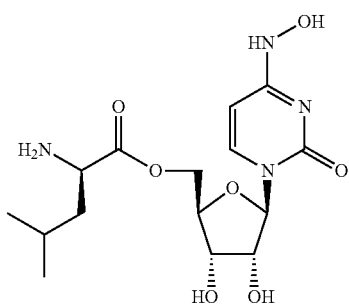
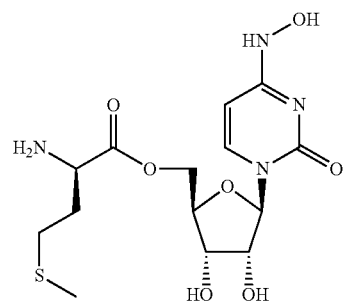
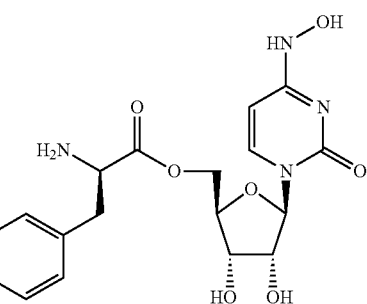
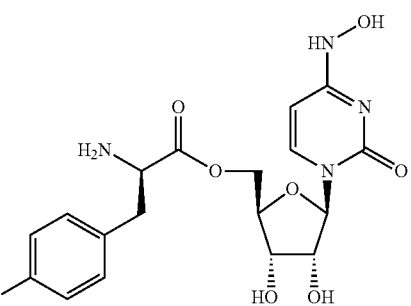

127
-continued
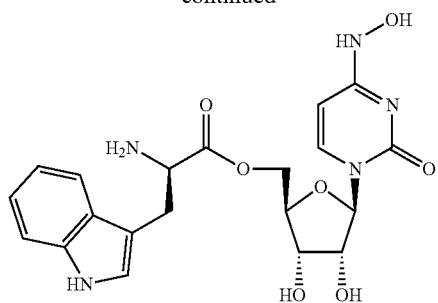
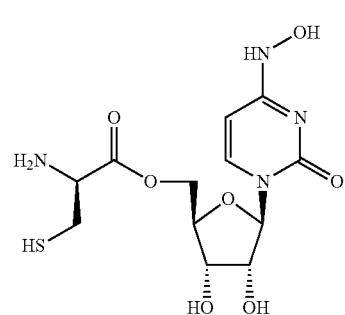
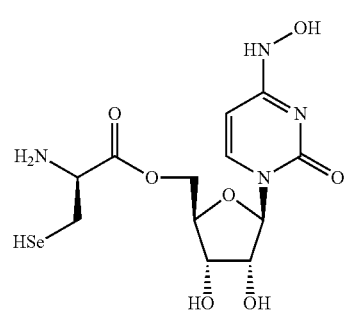
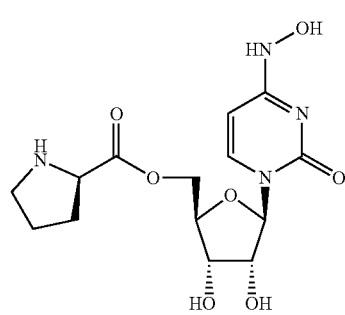
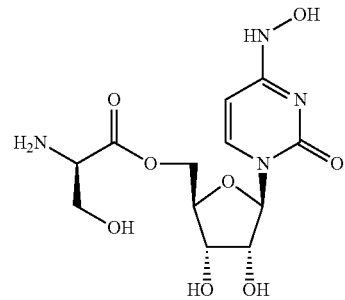
128
-continued
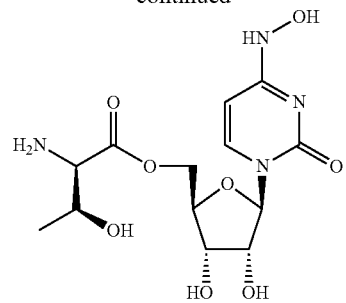
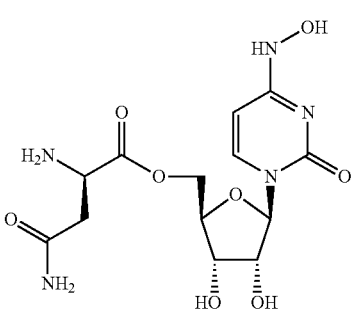
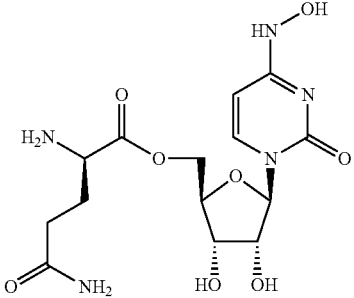
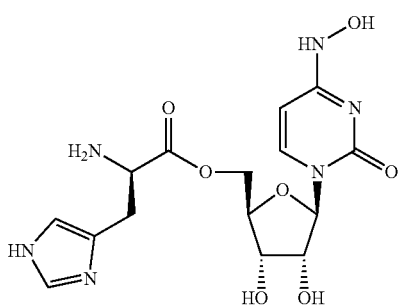
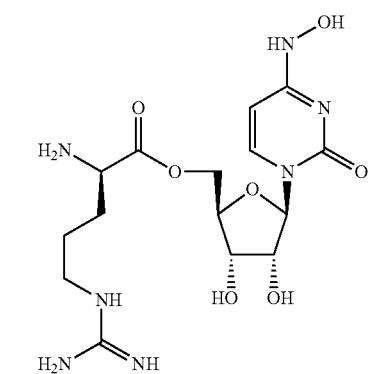

-continued
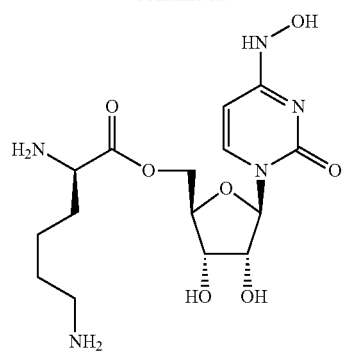
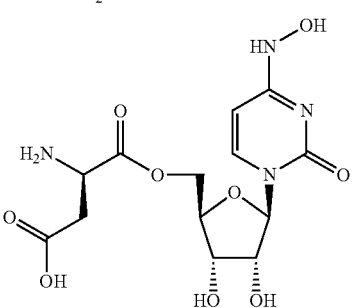
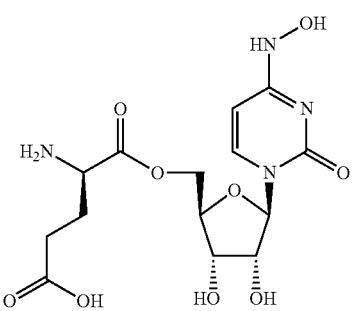
In exemplary embodiments, the compound is selected from:
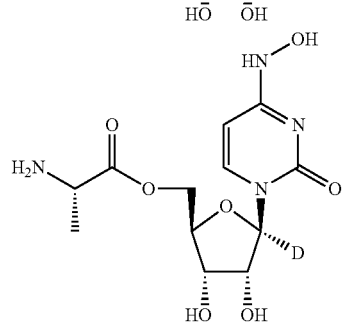
-continued
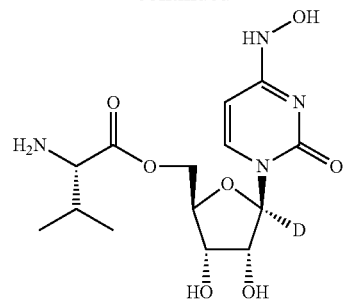
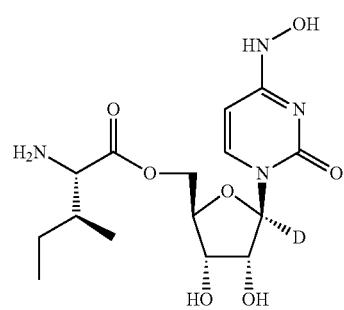
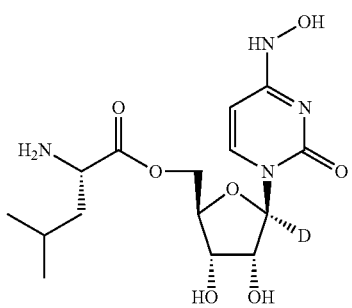
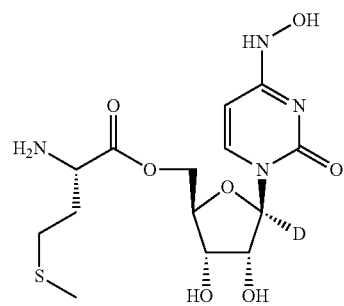
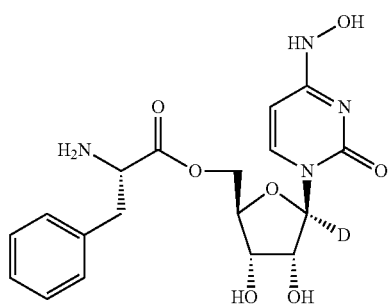

131
-continued
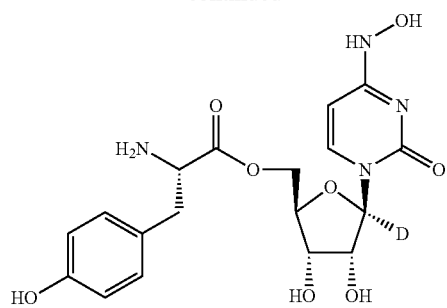
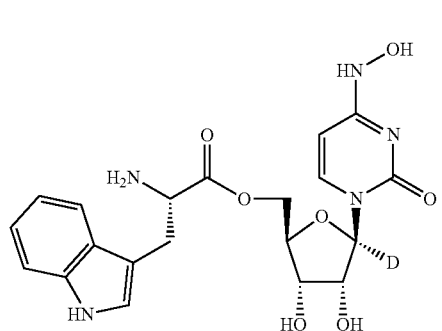
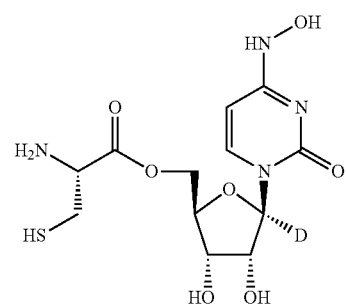
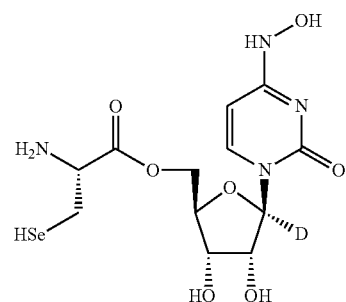
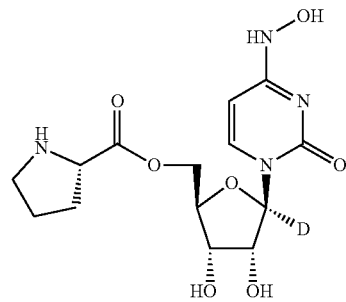
132
-continued
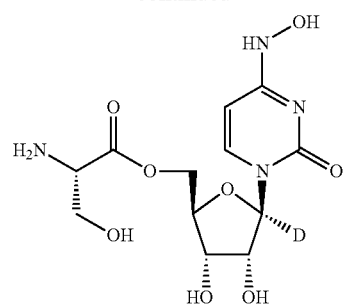
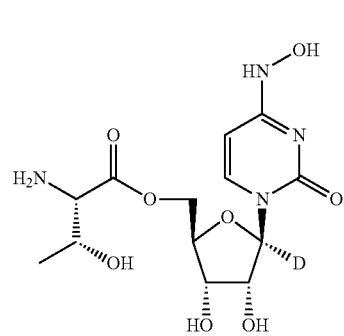
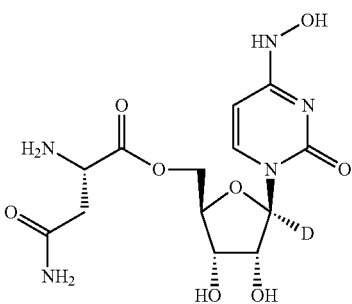
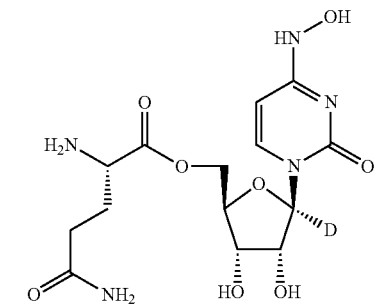
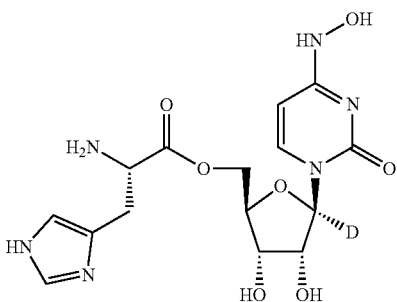

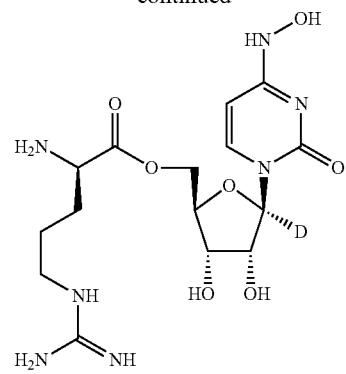
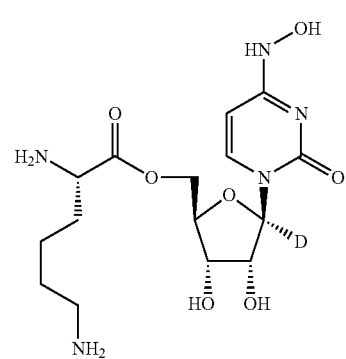
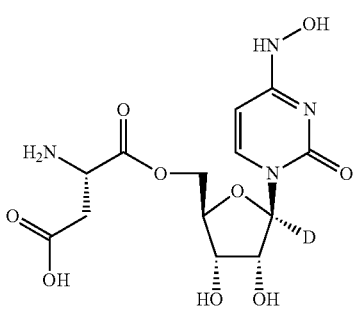
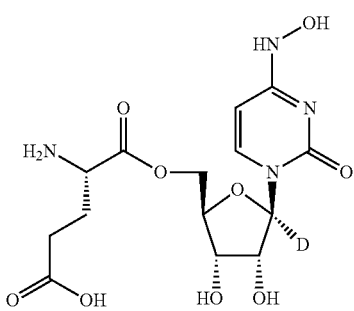 [SMILES: [2H][C@@]1(n2ccc(NO)nc2=O)O[C@H](COC(=O)[C@@H](N)CCC(=O)O)[C@@H](O)[C@H]1O]
In exemplary embodiments, the compound is selected from:
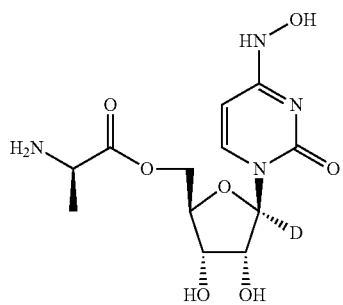
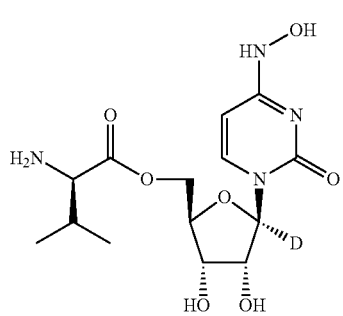
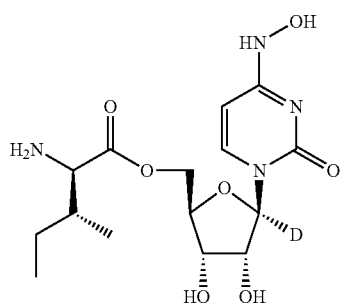
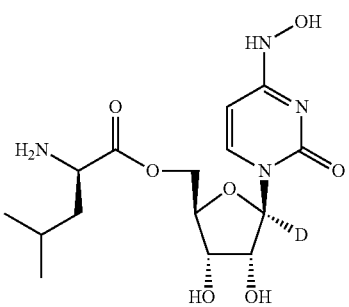
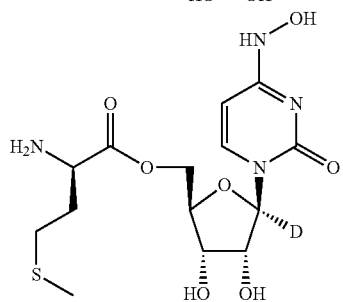

135
-continued
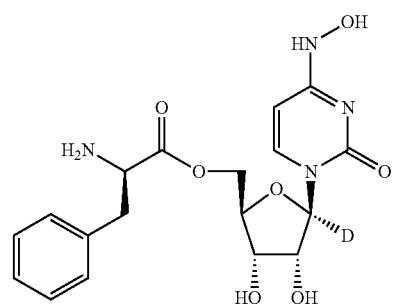
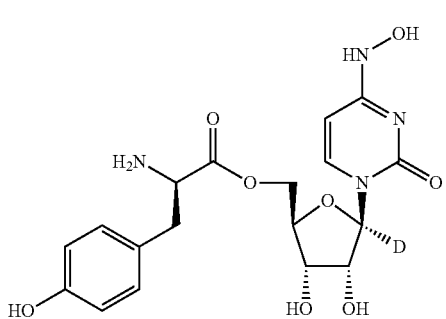
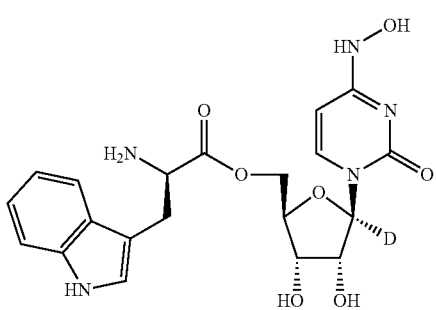
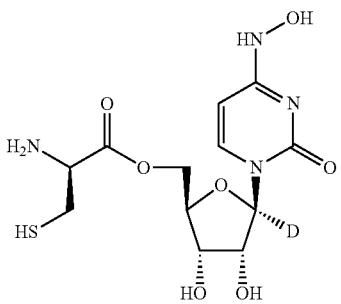
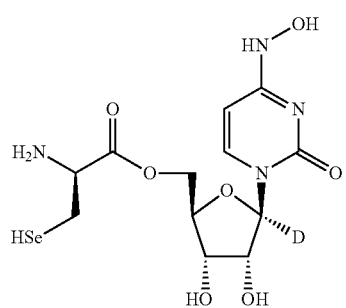
136
-continued
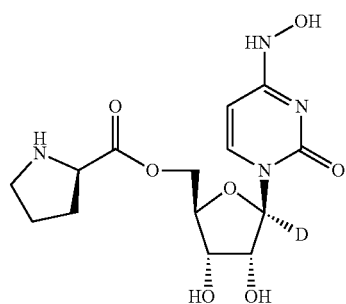
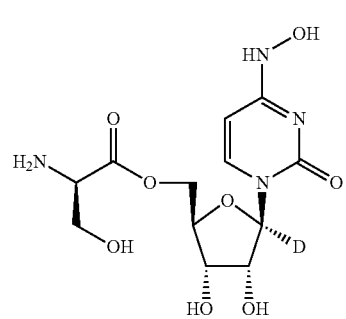
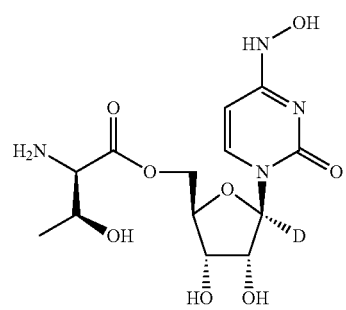
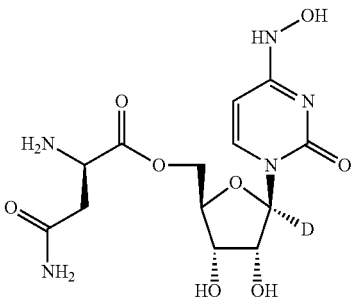
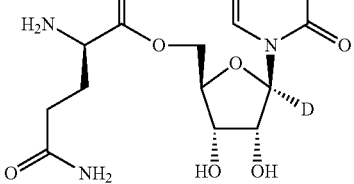

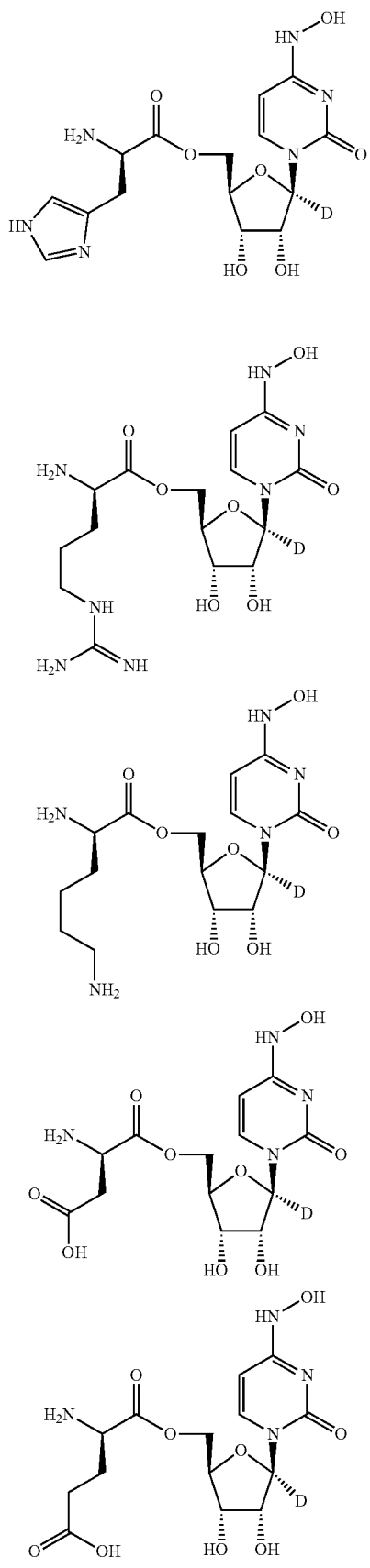
In exemplary embodiments, the compound is selected from:
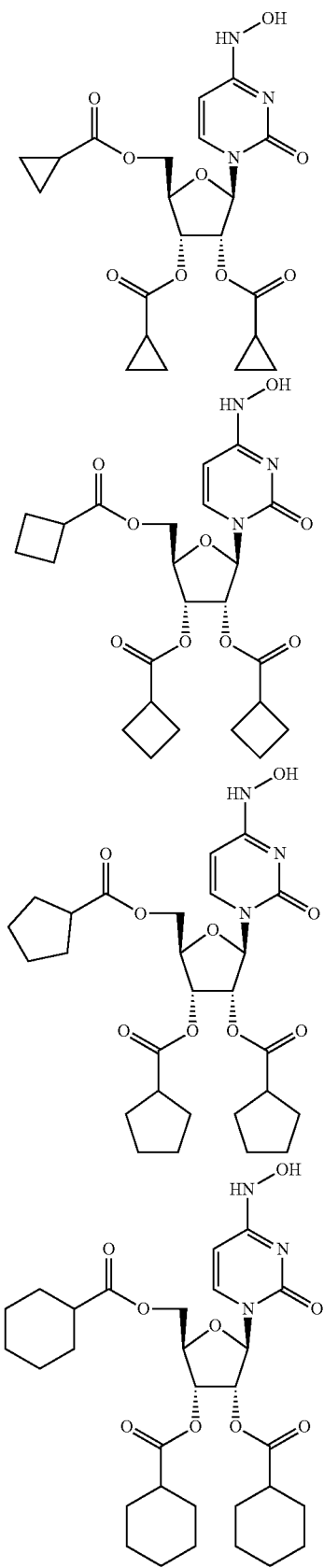

139
-continued
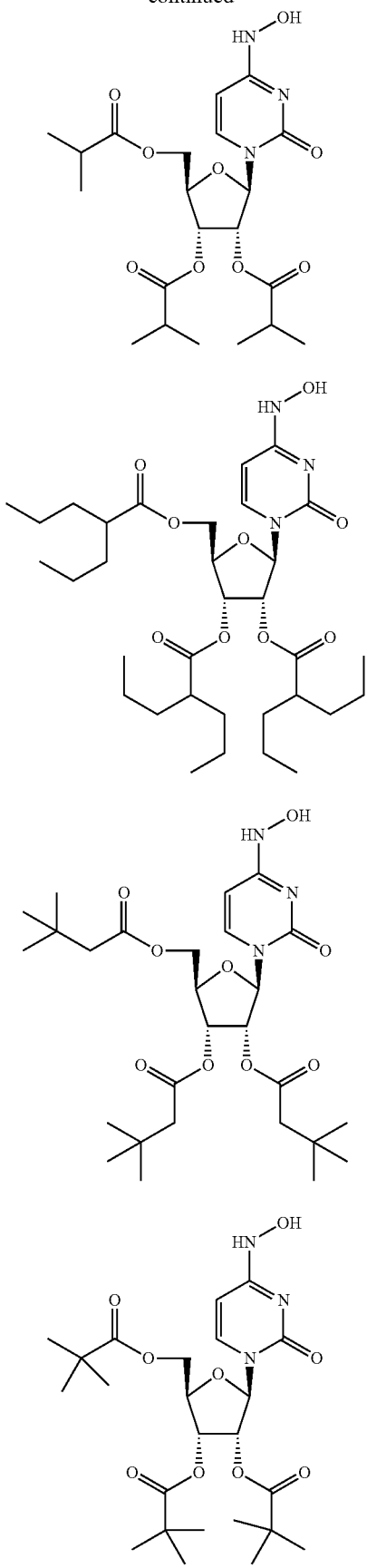
140
-continued
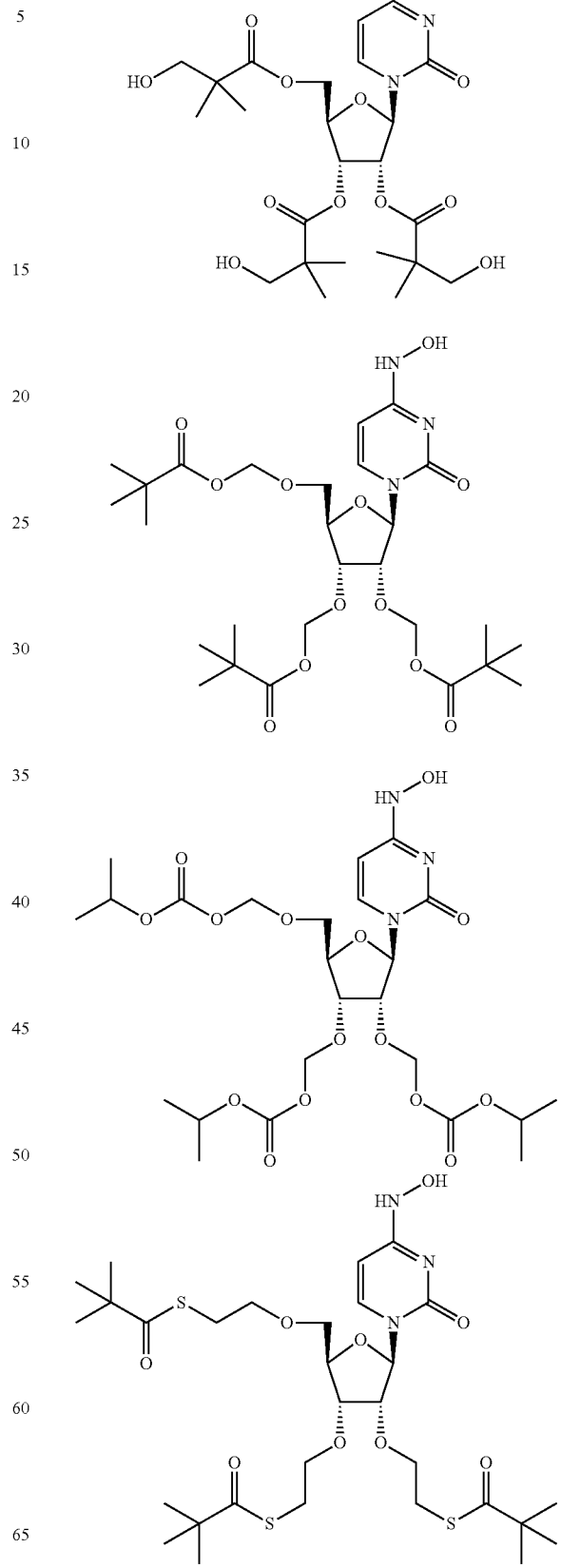

-continued
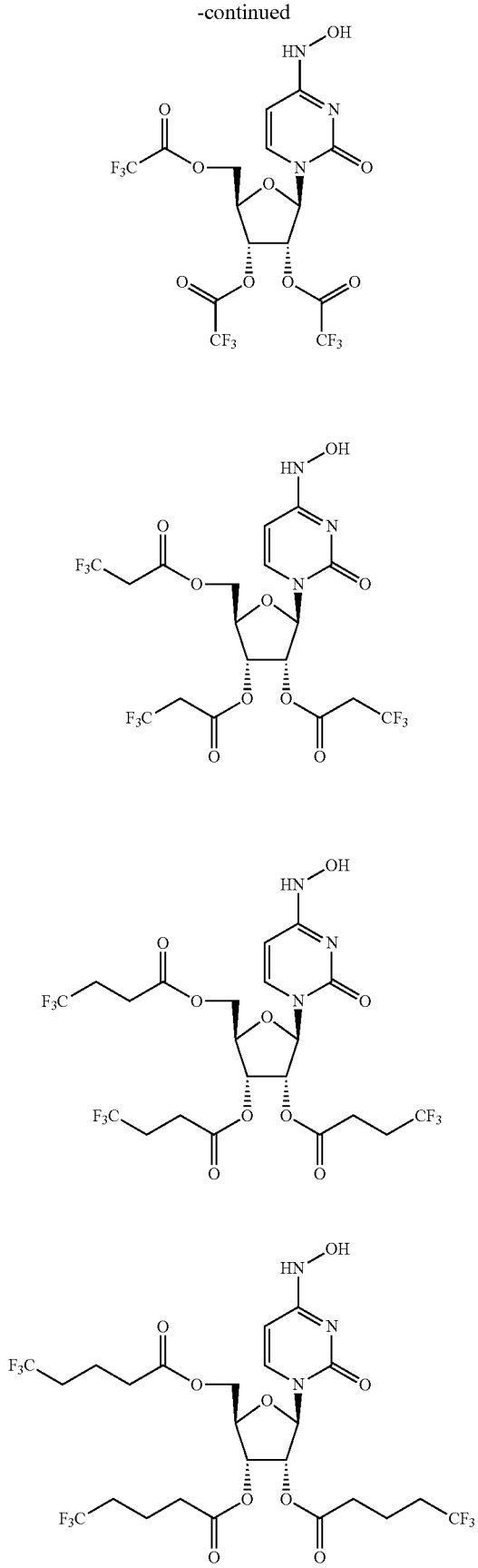
In exemplary embodiments, the compound is selected from:
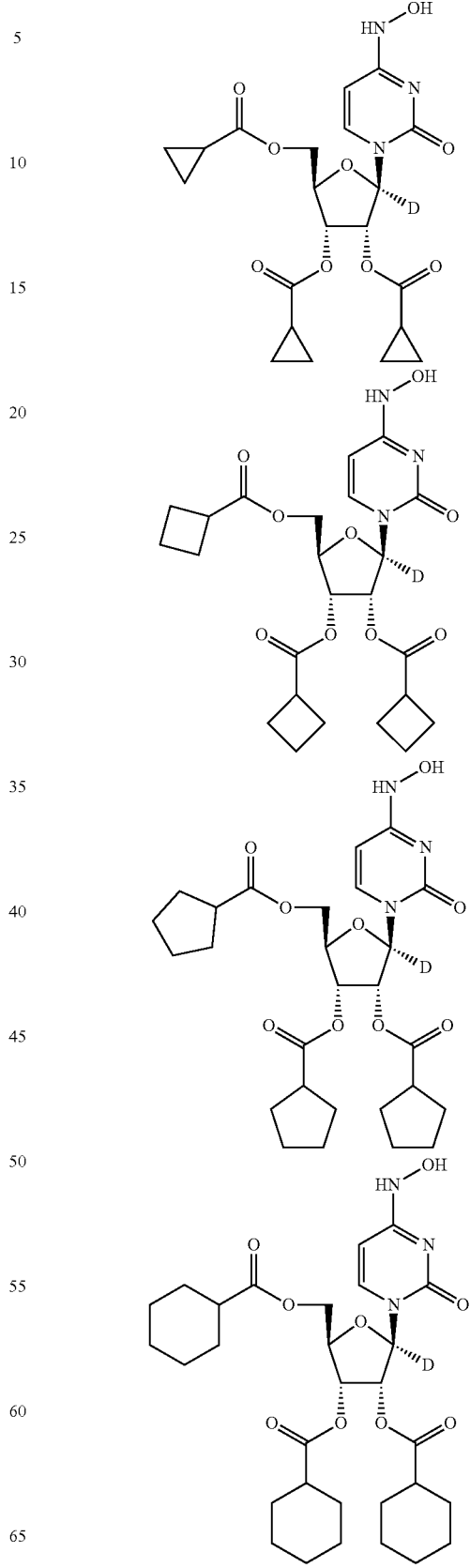

143
-continued
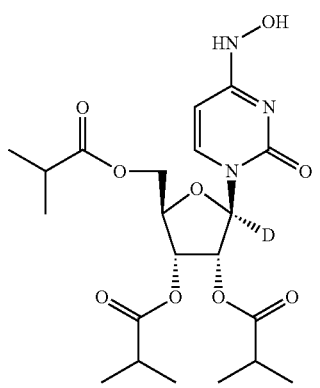
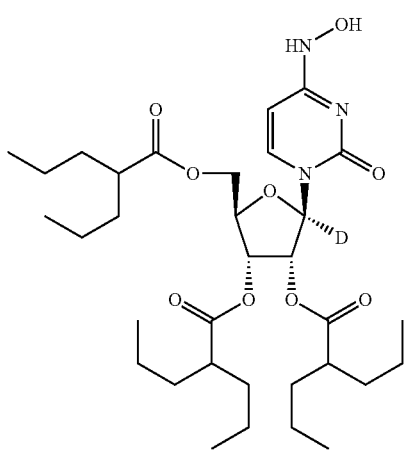
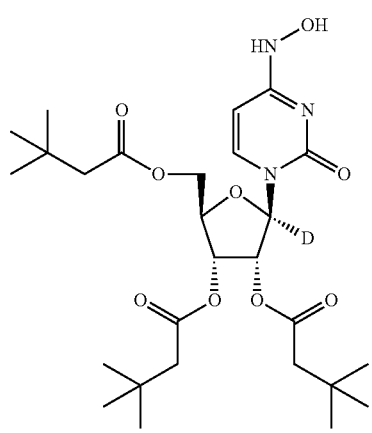
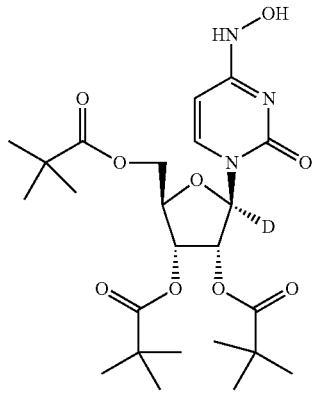
144
-continued
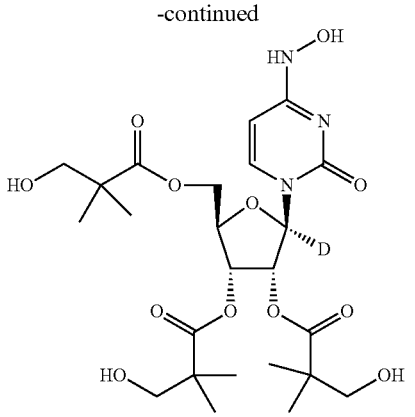
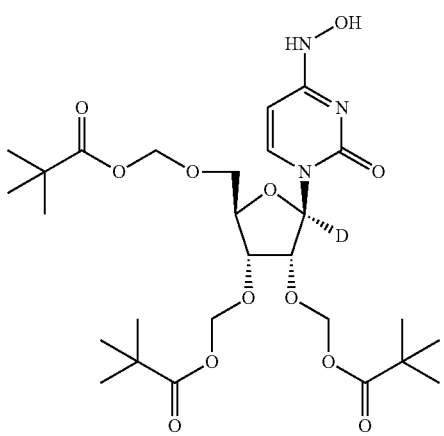
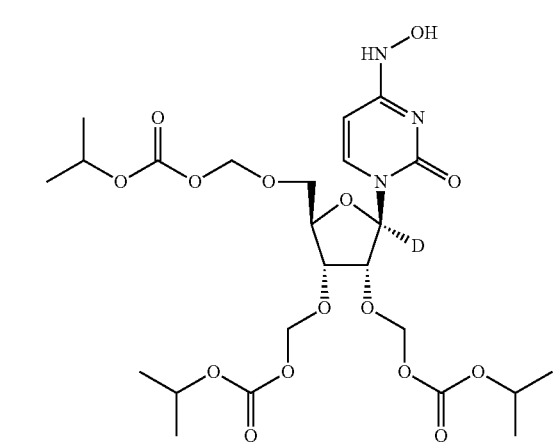
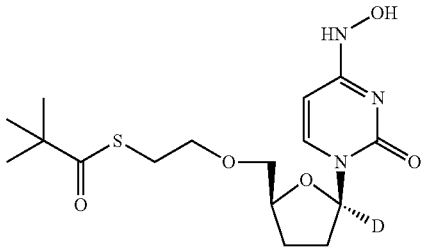
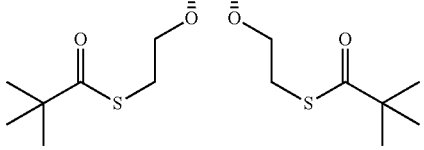

-continued
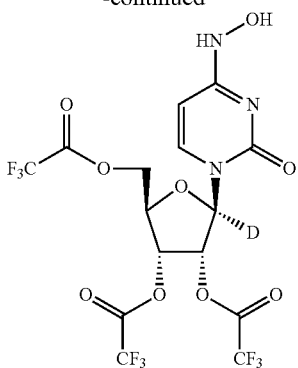
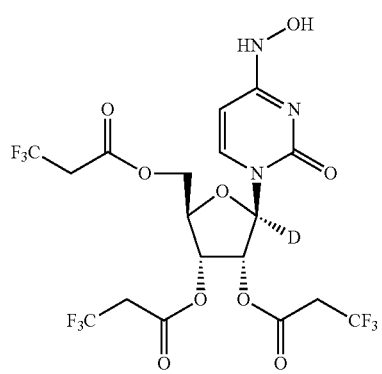
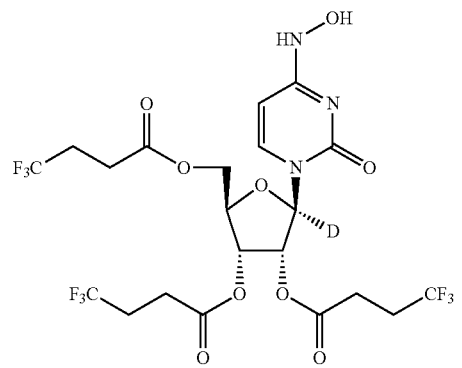
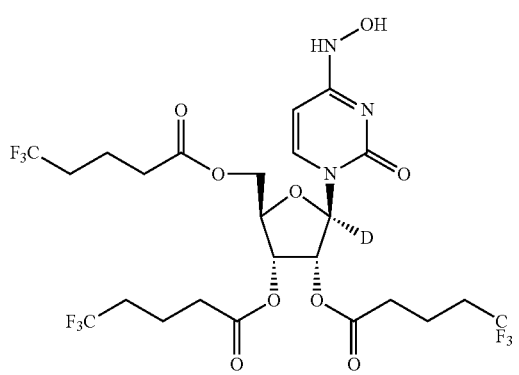
In exemplary embodiments, the compound is selected from:
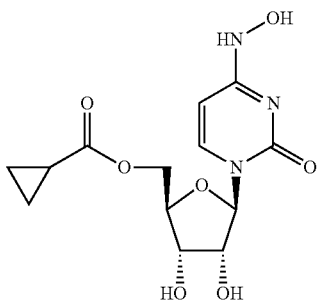
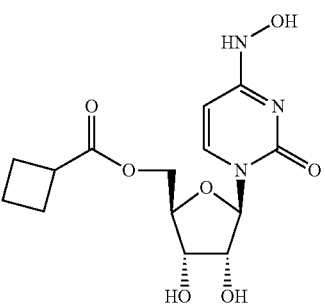
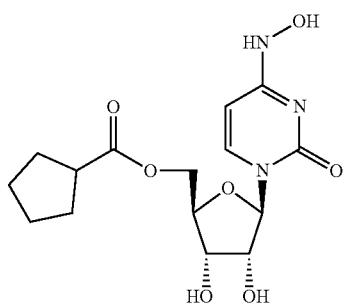
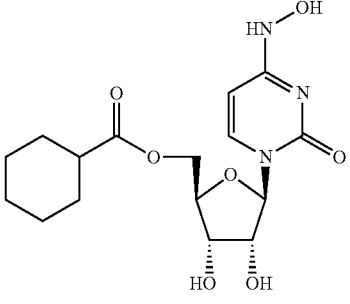
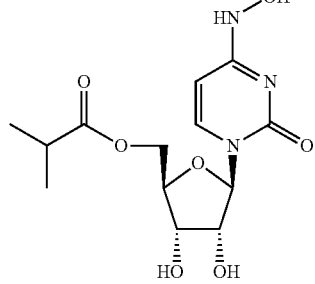

147
-continued
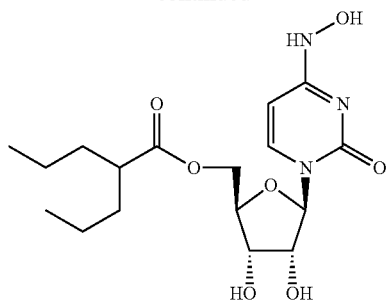
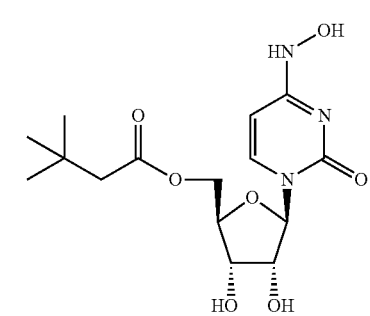
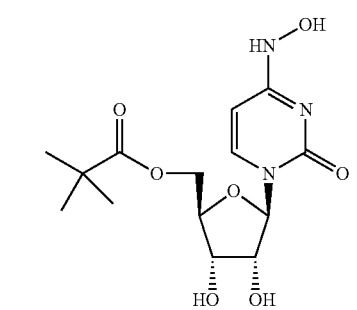
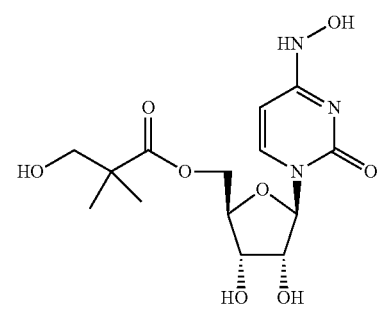
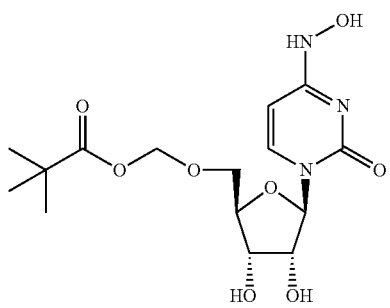
148
-continued
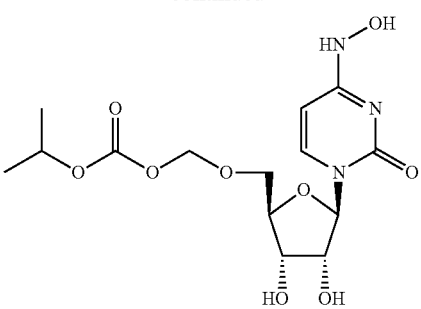
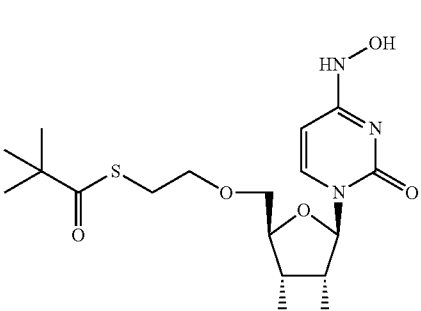
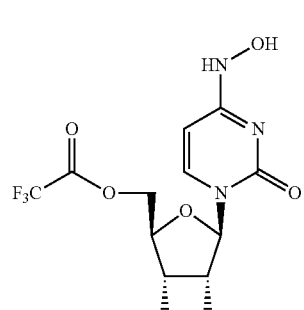
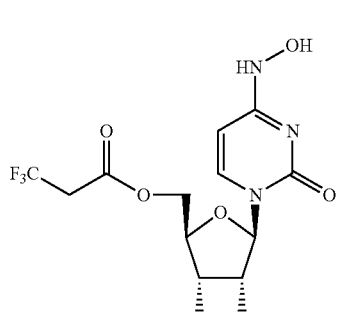
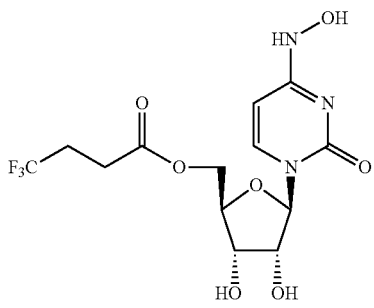

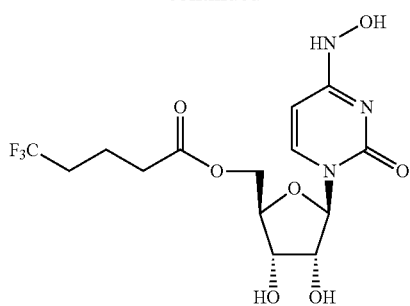 [SMILES: O=C(CCCC(F)(F)F)OC[C@H]1O[C@@H](n2ccc(NO)nc2=O)[C@H](O)[C@@H]1O]
In exemplary embodiments, the compound is selected from:
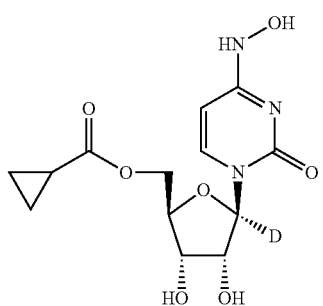
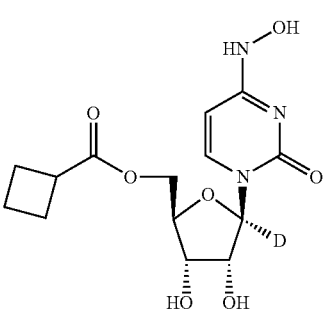
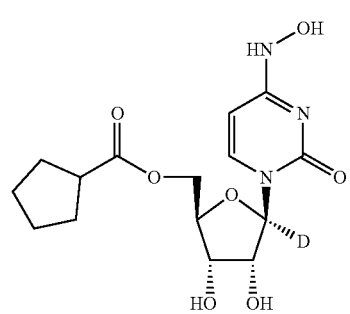
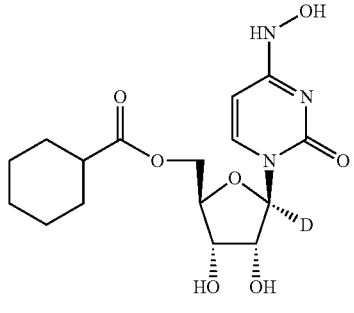
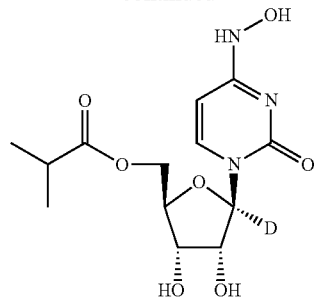
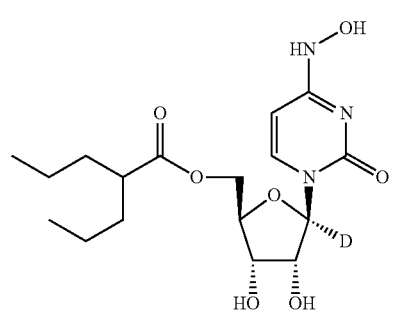
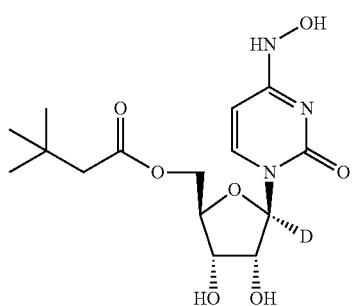
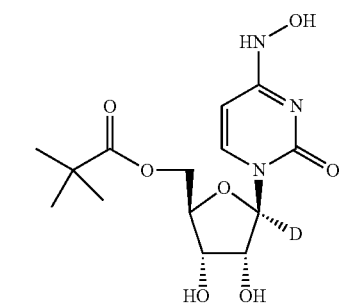
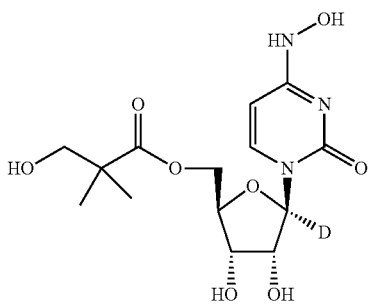

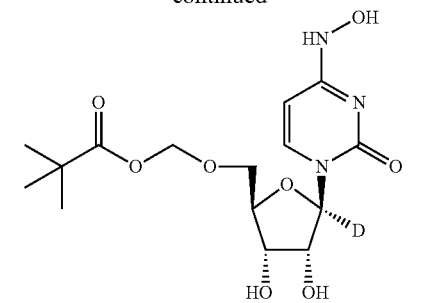
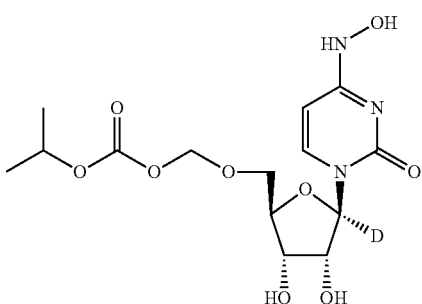
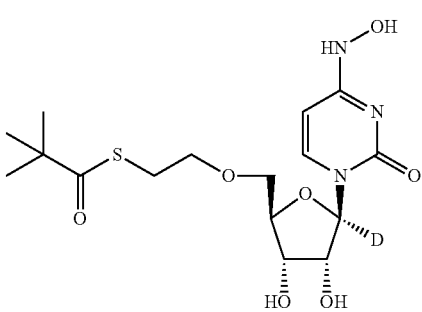
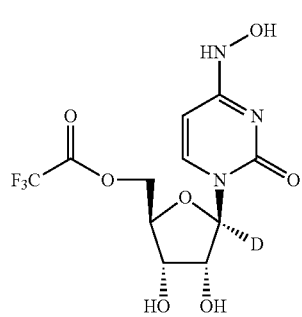
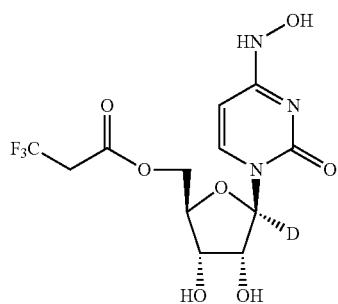
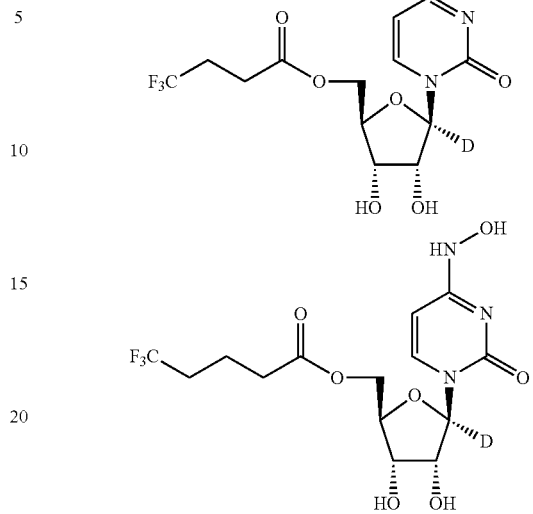

Methods of Use

In certain embodiments, the disclosure relates to methods of treating or preventing a viral infection comprising administering an effective amount of a compound or pharmaceutical composition disclosed herein to a subject in need thereof. In certain exemplary embodiments, a method of treating or preventing a Zika virus infection is provided, the method comprising administering an effective amount of a compound or pharmaceutical composition disclosed herein to a subject in need thereof.

In certain embodiments, the viral infection is, or is caused by, an alphavirus, flavivirus or coronaviruses orthomyxoviridae or paramyxoviridae, or RSV, influenza, Powassan virus or filoviridae or ebola.

In certain embodiments, the viral infection is, or is caused by, a virus selected from MERS coronavirus, Eastern equine encephalitis virus, Western equine encephalitis virus, Venezuelan equine encephalitis virus, Ross River virus, Barmah Forest virus, Powassan virus, Zika virus, and Chikungunya virus. In certain exemplary embodiments, the viral infection is, or is caused by, a Zika virus.

In certain embodiments, the compound is administered by inhalation through the lungs.

In some embodiments, the subject is at risk of, exhibiting symptoms of, or diagnosed with influenza A virus including subtype H1N1, H3N2, H7N9, or H5N1, influenza B virus, influenza C virus, rotavirus A, rotavirus B, rotavirus C, rotavirus D, rotavirus E, human coronavirus, SARS coronavirus, MERS coronavirus, human adenovirus types (HAdV-1 to 55), human papillomavirus (HPV) Types 16, 18, 31, 33, 35, 39, 45, 51, 52, 56, 58, and 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), Dengue virus, Zika virus, chikungunya, Eastern equine encephalitis virus (EEEV), Western equine encephalitis virus (WEEV), Venezuelan equine encephalitis virus (VEEV), Ross River virus, Barmah Forest virus, yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, or Kaposi's sarcoma-associated herpesvirus, hepatitis A, hepatitis B, hepatitis C, hepatitis D, hepatitis E or human immunodeficiency virus (HIV), The Human T-lymphotropic virus Type I (HTLV-1), Friend spleen focus-forming virus (SFFV) or Xenotropic MuLV-Related Virus (XMRV). In some embodiments, the subject is at risk of, exhibiting symptoms of, or diagnosed with a Zika virus infection.

In certain embodiments, the subject is diagnosed with influenza A virus including subtypes H1N1, H3N2, H7N9, H5N1 (low path), and H5N1 (high path) influenza B virus, influenza C virus, rotavirus A, rotavirus B, rotavirus C, rotavirus D, rotavirus E, SARS coronavirus, MERS-CoV, human adenovirus types (HAdV-1 to 55), human papillomavirus (HPV) Types 16, 18, 31, 33, 35, 39, 45, 51, 52, 56, 58, and 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, parainfluenza viruses 1 and 3, rinderpest virus, chikungunya, eastern equine encephalitis virus (EEEV), Venezuelan equine encephalitis virus (VEEV), western equine encephalitis virus (WEEV), California encephalitis virus, Japanese encephalitis virus, Rift Valley fever virus (RVFV), hantavirus, Dengue virus serotypes 1, 2, 3 and 4, Zika virus, West Nile virus, Tacaribe virus, Junin, rabies virus, ebola virus, marburg virus, adenovirus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, or Kaposi's sarcoma-associated herpesvirus, hepatitis A, hepatitis B, hepatitis C, hepatitis D, hepatitis E or human immunodeficiency virus (HIV). In certain embodiments, the subject is diagnosed with a Zika virus infection.

In certain embodiments, the subject is diagnosed with gastroenteritis, acute respiratory disease, severe acute respiratory syndrome, post-viral fatigue syndrome, viral hemorrhagic fevers, acquired immunodeficiency syndrome or hepatitis.

Formulations

In exemplary embodiments, a pharmaceutical composition comprises a pharmaceutically acceptable excipient, such as a pharmaceutically acceptable carrier, and an exemplary compound described herein.

In certain exemplary embodiments, the pharmaceutical composition comprises, or is in the form of, a pharmaceutically acceptable salt, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the exemplary compounds contain an acidic group as well as a basic group, the compounds can form internal salts, which can also be used in the compositions and methods described herein. When an exemplary compound contains a hydrogen-donating heteroatom (e.g., NH), salts are contemplated to cover isomers formed by transfer of said hydrogen atom to a basic group or atom within the molecule.

Pharmaceutically acceptable salts of the exemplary compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases can also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

Physiologically acceptable salts of the exemplary compounds are those that are formed internally in a subject administered compound for the treatment or prevention of disease. Suitable salts include those of lithium, sodium, potassium, magnesium, calcium, manganese, bile salts.

The exemplary compounds can be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

In exemplary embodiments, the pharmaceutical composition comprises an effective amount of an exemplary compound and a pharmaceutically acceptable carrier. Generally, for pharmaceutical use, the compounds can be formulated as a pharmaceutical preparation comprising at least one compound and at least one pharmaceutically acceptable carrier, diluent or excipient and/or adjuvant, and optionally one or more further pharmaceutically active compounds. The preparations can be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences. The disclosed pharmaceutical compositions can be in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain from 1 and 1000 mg, and usually from 5 and 500 mg, of the at least one compound of the disclosure, e.g., about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be from 0.01 to 1000 mg per kilogram body weight of the patient per day, more often from 0.1 and 500 mg, such as from 1 and 250 mg, for example about 5, 10, 20, 50, 100, 150, 200 or 250 mg, per kilogram body weight of the patient per day, which can be administered as a single daily dose, divided over one or more daily doses. The amount(s) to be administered, the route of administration and the further treatment regimen can be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Depending upon the manner of introduction, the compounds described herein can be formulated in a variety of ways. Formulations containing one or more compounds can be prepared in various pharmaceutical forms, such as granules, tablets, capsules, suppositories, powders, controlled release formulations, suspensions, emulsions, creams, gels, ointments, salves, lotions, or aerosols and the like. In certain embodiments, the formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein can be prepared using a pharmaceutically acceptable carrier composed of materials that are considered safe and effective and can be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition, which can include plasticizers, pigments, colorants, stabilizing agents, and glidants. Delayed release, extended release, and/or pulsatile release dosage formulations can be prepared as described in standard references such as "Pharmaceutical dosage form tablets", eds. Liberman et al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT™ (Roth Pharma, Westerstadt, Germany), zein, shellac, and polysaccharides.

Additionally, the coating material can contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants can be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, POLOXAMER™ 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

If desired, the tablets, beads, granules, or particles can also contain minor amount of nontoxic auxiliary substances such as wetting or emulsifying agents, dyes, pH buffering agents, or preservatives.

The concentration of the exemplary compound to pharmaceutically acceptable carrier, excipient and/or other substances can vary from about 0.5 to about 100 wt. % (weight percent). For oral use, the pharmaceutical composition can generally contain from about 5 to about 100% by weight of the active material. For other uses, the pharmaceutical composition can generally have from about 0.5 to about 50 wt. % of the active material.

The compositions described herein can be formulated for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, MD, 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkyl-celluloses such as hydroxypropyl-cellulose, hydroxypropylmethylcellulose, sodium carboxymethylcellulose, and CARBOPOL™ 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the trade name EUDRAGIT. In further preferred embodiments, the acrylic polymer comprises a mixture of two acrylic resin lacquers commercially available from Rohm Pharma under the trade names EUDRAGIT RL30D and EUDRAGIT RS30D, respectively. EUDRAGIT RL30D and EUDRAGIT RS30D are copolymers of acrylic and methacrylic esters with a low content of quaternary ammonium groups, the molar ratio of ammonium groups to the remaining neutral (meth)acrylic esters being 1:20 in EUDRAGIT RL30D and 1:40 in EUDRAGIT RS30D. The mean molecular weight is about 150,000. EUDRAGIT S-100 and EUDRAGIT L-100 are also preferred. The code designations RL (high permeability) and RS (low permeability) refer to the permeability properties of these agents. EUDRAGIT RL/RS mixtures are insoluble in water and in digestive fluids. However, multiparticulate systems formed to include the same are swellable and permeable in aqueous solutions and digestive fluids.

The polymers described above such as EUDRAGIT RL/RS can be mixed together in any desired ratio in order to ultimately obtain a sustained-release formulation having a desirable dissolution profile. Desirable sustained-release multiparticulate systems can be obtained, for instance, from 100% EUDRAGIT RL, 50% EUDRAGIT RL and 50% EUDRAGIT RS, and 10% EUDRAGIT RL and 90% EUDRAGITRS. One skilled in the art will recognize that other acrylic polymers can also be used, such as, for example, EUDRAGIT L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition can be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and can be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the trade name EUDRAGIT™ (Rohm Pharma; Westerstadt, Germany), including EUDRAGIT™ L30D-55 and L100-55 (soluble at pH 5.5 and above), EUDRAGIT™ L-100 (soluble at pH 6.0 and above), EUDRAGIT™ S (soluble at pH 7.0 and above, as a result of a higher degree of esterification), and EUDRAGIT™ NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials can also be used. Multi-layer coatings using different polymers can also be applied.

The preferred coating weights for particular coating materials can be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition can include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates can also be used. Pigments such as titanium dioxide can also be used. Small quantities of an anti-foaming agent, such as a silicone (e.g., simethicone), can also be added to the coating composition.

The formulation can provide pulsatile delivery of the one or more compounds. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses can be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit can comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule can comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that can or can not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles can be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., compound, in a liquid vehicle that is rendered semisolid by the action of a thickening agent or polymeric material dissolved or suspended in the liquid vehicle. The liquid can include a lipophilic component, an aqueous component or both. Some emulsions can be gels or otherwise include a gel component. Some gels, however, are not emulsions because they do not contain a homogenized blend of immiscible components. Methods for preparing lotions, creams, ointments, and gels are well known in the art.

Combination Therapies

The compound described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics, anti-narcoleptics, and antiviral agents. In a particular embodiment, the antiviral agent is a non-CNS targeting antiviral compound. "Adjunctive administration", as used herein, means the compound can be administered in the same dosage form or in separate dosage forms with one or more other active agents. The additional active agent(s) can be formulated for immediate release, controlled release, or combinations thereof.

Specific examples of compounds that can be adjunctively administered with the compounds include, but are not limited to, aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproxex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methyl salicylate, methysergid(e), metoclopramide, mianserin, mifepristone, milnacipran, minaprine, mirtazapine, moclobemide, modafinil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

In certain embodiments, the exemplary compounds and pharmaceutical compositions can be administered in combination with another antiviral agent(s) such as abacavir, acyclovir, acyclovir, adefovir, amantadine, amprenavir, ampligen, arbidol, atazanavir, atripla, balapiravir, BCX4430, boceprevir, cidofovir, combivir, daclatasvir, darunavir, dasabuvir, delavirdine, didanosine, docosanol, edoxudine, efavirenz, emtricitabine, enfuvirtide, entecavir, famciclovir, favipiravir, fomivirsen, fosamprenavir, foscarnet, fosfonet, ganciclovir, GS-5734, ibacitabine, imunovir, idoxuridine, imiquimod, indinavir, inosine, interferon type III, interferon type II, interferon type I, lamivudine, ledipasvir, lopinavir, loviride, maraviroc, moroxydine, methisazone, nelfinavir, nevirapine, nexavir, NITD008, ombitasvir, oseltamivir, paritaprevir, peginterferon alfa-2a, penciclovir, peramivir, pleconaril, podophyllotoxin, raltegravir, ribavirin, rimantadine, ritonavir, pyramidine, saquinavir, simeprevir, sofosbuvir, stavudine, telaprevir, telbivudine, tenofovir, tenofovir disoproxil, Tenofovir Exalidex, tipranavir, trifluridine, trizivir, tromantadine, truvada, valaciclovir, valganciclovir, vicriviroc, vidarabine, viramidine zalcitabine, zanamivir, or zidovudine and combinations thereof.

In certain embodiments, the exemplary compounds and pharmaceutical compositions disclosed herein can be administered in combination with any of the compounds disclosed in: WO2003090690A2, WO2003090690A3, WO2003090691A2, WO2003090691A3, WO2004005286A2, WO2004005286A3, WO2004006843A2, WO2004006843A3, WO2004031224A2, WO2004031224A3, WO2004035576A2, WO2004035576A3, WO2004035577A2, WO2004035577A3, WO2004050613A2, WO2004050613A3, WO2004064845A1, WO2004064846A1, WO2004096286A2, WO2004096286A3, WO2004096287A2, WO2004096287A3, WO2004096818A2, WO2004096818A3, WO2004100960A2, WO2005002626A2, WO2005002626A3, WO2005012324A2, WO2005012324A3, WO2005028478A1, WO2005039552A2, WO2005039552A3, WO2005042772A1, WO2005042773A1, WO2005047898A2, WO2005047898A3, WO2005063744A2, WO2005063744A3, WO2005063751A1, WO2005064008A1, WO2005064008A9, WO2005066189A1, WO2005070901A2, WO2005070901A3, WO2005072748A1, WO2005117904A2, WO2005117904A3, WO2006015261A2, WO2006015261A3, WO2006017044A2, WO2006017044A3, WO2006020276A2, WO2006020276A3, WO2006033703A1, WO2006047661A2, WO2006047661A3, WO2006069193A2, WO2006069193A3, WO2006091905A1, WO2006110157A2, WO2006110157A3, WO2006110157A9, WO2006125048A2, WO2006125048A3, WO2007009109A2, WO2007009109A3, WO2007011658A1, WO2007014174A2, WO2007014174A3, WO2007014352A2, WO2007014352A3, WO2007079260A1, WO2007079260A9, WO2007126812A2, WO2007126812A3, WO2008003149A2, WO2008003149A3, WO2008005519A2, WO2008005519A3, WO2008005542A2, WO2008005542A3, WO2008005555A1, WO2008009076A2, WO2008009076A3, WO2008009077A2, WO2008009077A3, WO2008009078A2, WO2008009078A3, WO2008009079A2, WO2008009079A3, WO2008010921A2, WO2008010921A3, WO2008011116A2, WO2008011116A3, WO2008011117A2, WO2008011117A3, WO2008013834A1, WO2008016522A2, WO2008016522A3, WO2008077649A1, WO2008077650A1, WO2008077651A1, WO2008100447A2, WO2008100447A3, WO2008103949A1, WO2008133669A2, WO2008133669A3, WO2009005674A2, WO2009005674A3, WO2009005676A2, WO2009005676A3, WO2009005677A2, WO2009005677A3, WO2009005687A1, WO2009005690A2, WO2009005690A3, WO2009005693A1, WO2009006199A1, WO2009006203A1, WO2009009001A1, WO2009009001A9, WO2009088719A1, WO2009105513A2, WO2009105513A3, WO2009132123A1, WO2009132135A1, WO2010002998A1, WO2010005986A1, WO2010011959A1, WO2010075127A1, WO2010077613A1, WO2010080389A1, WO2010093608A1, WO2010132601A1, WO2010151472A1, WO2010151487A1, WO2010151488A1, WO2011005842A1, WO2011011303A1, WO2011031669A1, WO2011031965A1, WO2011035231A1, WO2011049825A1, WO2011079016A1, WO2011088303A1, WO2011088345A1, WO2011106445A1, WO2011143105A1, WO2011143106A1, WO2011146817A1, WO2011150288A1, WO2011156416A1, WO2011156610A2, WO2011156610A3, WO2011156757A1, WO2011163518A1, WO2012003497A1, WO2012003498A1, WO2012012465A1, WO2012012776A1, WO2012037038A1, WO2012039787A1, WO2012039791A1, WO2012068234A2, WO2012068234A3, WO2012068535A1, WO2012078915A1, WO2012087596A1, WO2012088153A1, WO2012088156A1, WO2012088178A1, WO2012138669A1, WO2012138670A1, WO2012142523A2, WO2012142523A3, WO2012145728A1, WO2012151165A1, WO2013006721A1, WO2013006722A1, WO2013006738A1, WO2013010112A1, WO2013025788A1, WO2013040492A2, WO2013040492A3, WO2013066748A1, WO2013075029A1, WO2013082003A1, WO2013090840A1, WO2013090929A1, WO2013096512A1, WO2013096681A1, WO2013103724A1, WO2013103738A1, WO2013106732A1, WO2013115916A1, WO2013116720A1, WO2013116730A1, WO2013138236A1, WO2013158776A1, WO2013159064A1, WO2013173488A1, WO2013173492A1, WO2013185090A1, WO2013185093A1, WO2013185103A1, WO2014008285A1, WO2014028343A1, WO2014055618A1, WO2014070939A1, WO2014074620A1, WO2014100323A1, WO2014100500A1, WO2014110296A1, WO2014110297A1, WO2014110298A1, WO2014134566A2, WO2014134566A3, WO2014145095A1, WO2015023893A1, WO2015069939A1, WO2015084741A2, WO2015084741A3, WO2015099989A1, WO2015100144A1, WO2015108780A1, WO2015120057A1, WO2015130964A1, WO2015130966A1, WO2015179448A1, WO2015191526A2, WO2015191526A3, WO2015191726A1, WO2015191743A1, WO2015191745A1, WO2015191752A1, WO2015196137A1, WO2015191754A2, WO2015191754A3, WO2016007765A1, WO2016028866A1, WO2016033243A1, WO2016033243A9, WO2016036759A1, WO2016096116A1, WO2016096116A1, WO2016105532A1, WO2016105534A1, WO2016105564A1, WO2016106237A1, WO2016141092A1, WO2016161382A1, WO2016168349A1, WO2016186967A1, WO2016205141A1, WO2017004012A1, WO2017004244A1, WO2017035230A1, WO2017048727A1, WO2017049060A1, WO2017059120A1, WO2017059224A2, WO2017059224A3, WO2017083304A1, WO2017106346A2, WO2017106346A3, WO2017106556A1, WO2017184668A1, WO2017184670A2, WO2017184670A3, WO2017205078A1, WO2017205115A1, WO2017223268A1, WO9015065A1, WO9209705A1, WO9307157A1, WO9310820A1, WO9403467A2, WO9403467A3, WO9424144A2, WO9424144A3, WO9507919A1, WO9507920A1, WO9626933A1, WO9817647A1.

In exemplified embodiments, the exemplary compounds and pharmaceutical compositions can be administered in combination with

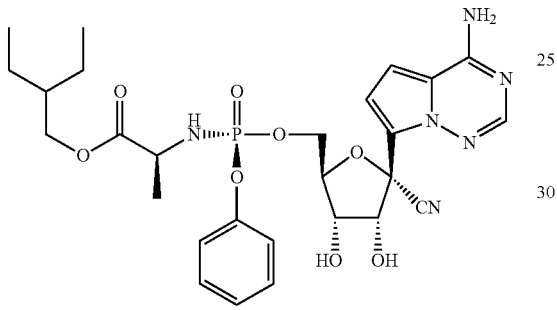

and derivatives and prodrugs thereof.

In exemplified embodiments,

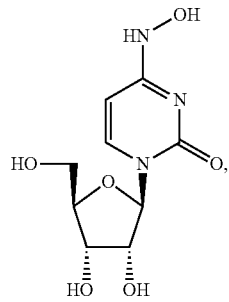 [SMILES: O=c1nc(NO)ccn1[C@@H]1O[C@H](CO)[C@@H](O)[C@H]1O]

and derivatives and prodrugs thereof, can be administered in combination with

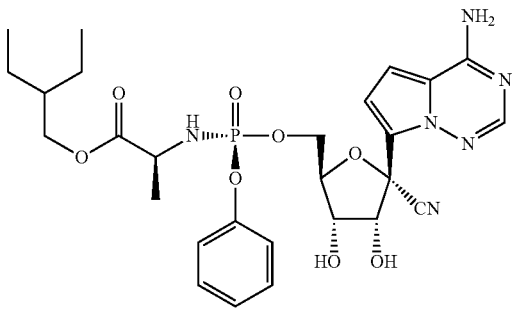 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

and derivatives and prodrugs thereof.

In exemplified embodiments,

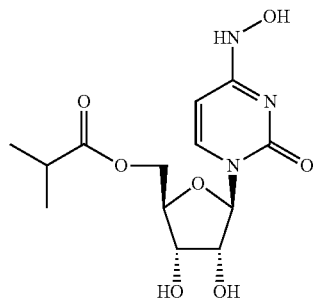 [SMILES: CC(C)C(=O)OC[C@H]1O[C@@H](n2ccc(NO)nc2=O)[C@H](O)[C@@H]1O]

can be administered in combination with

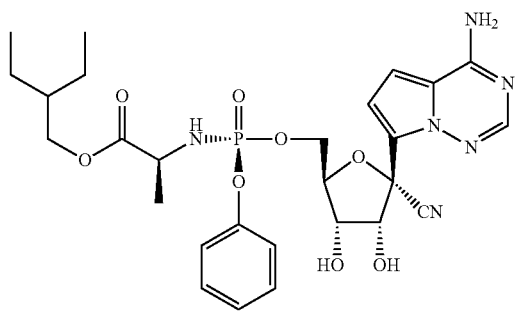 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

and derivatives and prodrugs thereof.

In exemplified embodiments,

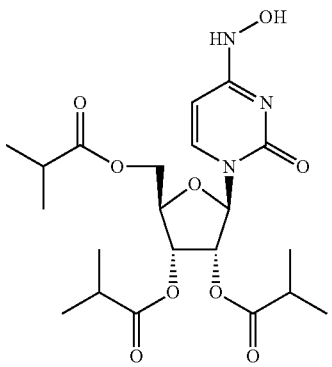 [SMILES: CC(C)C(=O)OC[C@H]1O[C@@H](n2ccc(NO)nc2=O)[C@H](OC(=O)C(C)C)[C@@H]1OC(=O)C(C)C]

can be administered in combination with

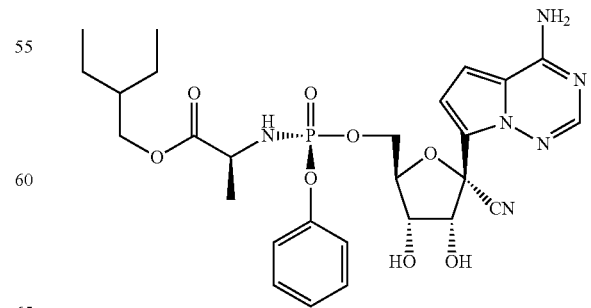

and derivatives and prodrugs thereof.

In exemplified embodiments,

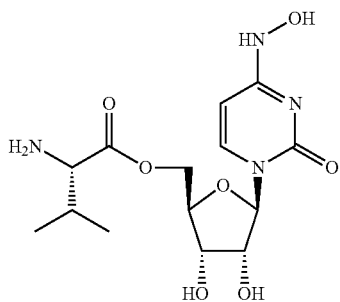 [SMILES: CC(C)[C@H](N)C(=O)OC[C@H]1O[C@@H](n2ccc(NO)nc2=O)[C@H](O)[C@@H]1O]

can be administered in combination with

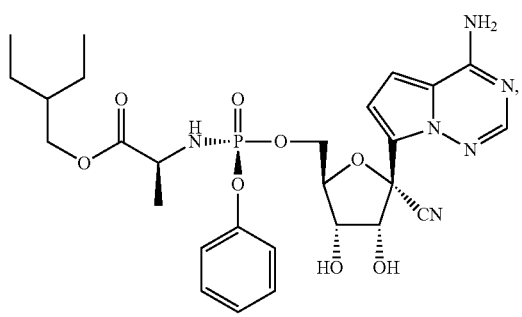 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

and depravities and prodrugs thereof.

EXAMPLES

The following examples are set forth below to illustrate the compositions, methods, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

All chemical reactions were performed in oven-dried glassware under a nitrogen atmosphere, except where noted. Chemicals and solvents were reagent-grade and purchased from commercial suppliers (typically Aldrich, Fisher, Acros, Carbosynth Limited, and Oakwood Chemical) and used as received, excepting where noted. In particular, EIDD-1910, EIDD-1993, and EIDD-2003 were purchased from Carbosynth Limited. Solvents used for reactions (tetrahydrofuran, methanol, acetonitrile, dichloromethane, toluene, pyridine, dimethylformamide) were ≥99.9% anhydrous in all cases. All reactions were followed by thin layer chromatography (TLC) to completion, unless stated otherwise. TLC analysis was performed on silica gel, using illumination with a UV lamp (254 nm) or staining with KMnO$_4$ and heating. Manual flash column chromatography was performed with 40-60 micron (60 Å particle size) RediSep Rf silica gel, purchased from Teledyne Isco, as the stationary phase. Automated gradient flash column chromatography was performed on a Teledyne Isco CombiFlash Companion; normal phase separations were performed with pre-packed RediSep Rf silica gel as the stationary phase, and reverse phase separations were performed with pre-packed RediSep Rf C18 High Performance Gold stationary phase. Triphosphate purifications were performed using ion-exchange chromatography, with DEAE (diethylaminoethyl) Sephadex A-25 as the stationary phase, and aqueous TEAB (triethylammonium bicarbonate) as the mobile phase.

$^1$H NMR spectra were measured on a Varian 400 MHz instrument, and processed using MestReNova software, version 9.0.1. Chemical shifts were measured relative to the appropriate solvent peak: CDCl$_3$ (δ7.27), DMSO-d$_6$ (δ 2.50), CD$_3$OD (δ 3.31), D$_2$O (δ 4.79). The following abbreviations were used to describe coupling: s=singlet, d=doublet, t=triplet, q=quartet, p=pentet, m=multiplet, br=broad. $^{13}$C NMR spectra were measured on a Varian instrument at 100 MHz with chemical shifts relative to the appropriate solvent peak: CDCl$_3$ (δ 77.0), DMSO-d$_6$ (δ 39.5), CD$_3$OD (δ 49.0). $^{19}$F spectra were measured on a Varian instrument at 376 MHz, and $^{31}$P spectra were measured on a Varian instrument at 162 MHz. Chemical shifts for $^{19}$F spectra, $^{31}$P spectra, and $^{13}$C spectra (in D$_2$O only) were calibrated by MestReNova software using an absolute reference function to the corresponding $^1$H NMR spectrum in the same solvent.

Nominal (low resolution) liquid chromatography/mass spectrometry was performed using an Agilent 1200 series LC (UV absorption detector at 254 nm), using a Zorbax Eclipse XDB C$_{18}$ 4.6×50 mm, 3.5 micron column, eluting with a MeOH/water mixture (typically 95/5 isocratic) and an Agilent 6120 LCMS quadrupole instrument. High resolution mass spectrometry was performed by the Emory University Mass Spectrometry Center with a Thermo LTQ-FTMS using either APCI or ESI.

Example 1

Synthesis of N4-hydroxycytidine or 1-(3,4-dihydroxy-5-(hydroxymethyl) tetrahydrofuran-2-yl)-4-(hydroxyamino)pyrimidin-2-one (EIDD-1931)

Protection of uridine by persilylation is followed by activation of the 4-position of the nucleobase by a hindered arylsulfonyl group (see FIG. 1). Displacement of this group with hydroxylamine installs the N-4-hydroxy moiety. Global deprotection using one of any number of fluoride sources available gives the desired product.

The compound can be made in one step from cytidine by heating in a pH-adjusted solution of hydroxylamine. Despite being shorter, this route tends to give lower yields and requires purification by reverse phase flash column chromatography, limiting its use to producing smaller quantities.

Another synthetic route is as shown below.

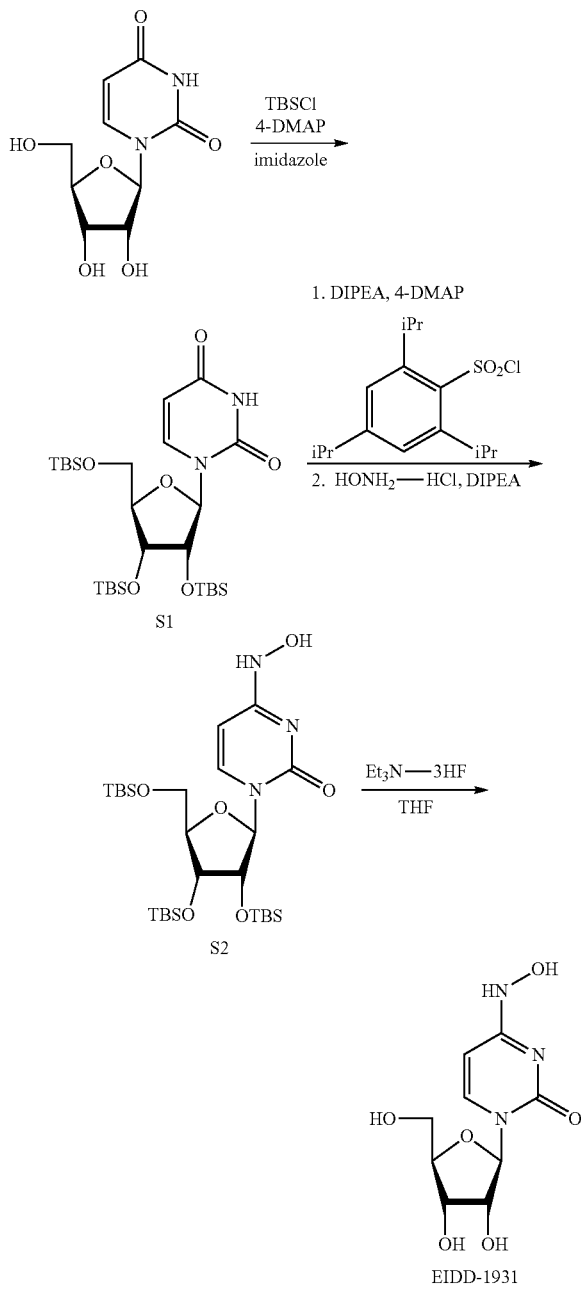

dried in vacuo: $^1$H NMR (400 MHz, CDCl$_3$) δ 8.09 (s, 1H), 8.02 (d, J=8.2 Hz, 1H), 5.87 (d, J=3.6 Hz, 1H), 5.67 (dd, J=8.1, 2.2 Hz, 1H), 4.07 (q, J=3.8, 3.3 Hz, 1H), 3.98 (dd, J=11.7, 1.7 Hz, 1H), 3.75 (dd, J=11.7, 1.1 Hz, 1H), 0.94 (s, 9H), 0.90 (s, 9H), 0.88 (s, 9H), 0.13 (s, 3H), 0.12 (s, 3H), 0.08 (s, 3H), 0.07 (s, 3H), 0.07 (s, 3H), 0.06 (s, 3H).

A 1 L round bottom flask was charged with S1 (28 g, 47.7 mmol) and dichloromethane (700 mL). The solution was cooled to 0° C. using an ice bath; 4-DMAP (0.583 g, 4.77 mmol) and N,N-diisopropylethylamine (41.7 mL, 239 mmol) were added sequentially. 2,4,6-Triisopropylbenzene-1-sulfonyl chloride (28.9 g, 95 mmol) was slowly added to the flask, and after addition was complete, the flask was warmed to ambient temperature and stirred for 18 hrs. The dark orange solution was cooled to 0° C. with an ice bath and N,N-diisopropylethylamine (24.66 g, 191 mmol) was added via syringe, followed by solid hydroxylamine hydrochloride (13.26 g, 191 mmol) all at once. The mixture was warmed to rt and stirred for 3 hrs. The reaction was quenched with water (200 mL) and the resulting layers were separated. The aqueous layer was extracted with dichloromethane (200 mL), and the combined organics were washed with brine, dried over sodium sulfate, and concentrated under reduced pressure to yield a dark orange oil. Purification by flash chromatography (15 to 50% gradient of EtOAc in hexanes) to yield S2 (19.8 g, 69% over 2 steps) as an oil which solidified to a semi solid upon drying in vacuo: $^1$H NMR (400 MHz, CDCl$_3$) δ 8.15 (s, 1H), 6.31 (s, 1H), 5.91 (d, J=4.6 Hz, 1H), 5.56 (dd, J=8.2, 2.0 Hz, 1H), 4.07 (m, 2H), 4.02 (m, 1H), 3.91 (dd, J=11.6, 2.4 Hz, 1H), 3.73 (dd, J=11.6, 2.4 Hz, 1H), 0.95 (s, 9H), 0.92 (s, 9H), 0.89 (s, 9H), 0.12 (s, 6H), 0.098 (s, 3H), 0.083 (s, 3H), 0.063 (s, 3H), 0.057 (s, 3H); LRMS m/z 602.3 [M+H]$^+$.

A 50 mL round bottom flask was charged with S2 (23.3 g, 38.7 mmol) and THF (50 mL). Triethylamine trihydrofluoride (6.30 mL, 38.7 mmol) was added all at once, and the mixture was stirred at ambient temperature for 18 hours. The mixture was concentrated under reduced pressure, and the residue was dissolved in a minimal amount of MeOH, and this solution was slowly added to an Erlenmeyer flask containing rapidly stirred dichloromethane (500 mL) to precipitate the product; the mixture was stirred at rt for 15 minutes. The triturated solid was collected by vacuum filtration and washed with dichloromethane, then ether. The solid was dried in vacuo to yield the title compound (7.10 g, 71%) as a white solid: $^1$H NMR (400 MHz, CD$_3$OD) δ 7.16 (d, j=8.2 Hz, 1H), 5.86 (d, J=5.6 Hz, 1H), 5.59 (d, J=8.2 Hz, 1H), 4.19-4.04 (m, 2H), 3.93 (q, j=3.3 Hz, 1H), 3.77 (dd, J=12.2, 2.9 Hz, 1H), 3.68 (dd, J=12.1, 2.9 Hz, 1H); $^1$H NMR (400 MHz, DMSO-d$_6$) δ 9.95 (s, 1H), 9.46 (s, 1H), 7.02 (d, J=8.2 Hz, 1H), 5.71 (d, J=6.3 Hz, 1H), 5.54 (d, J=7.7 Hz, 1H), 5.23 (d, J=6.0 Hz, 1H), 5.02 (d, J=4.6 Hz, 1H), 4.98 (t, J=5.1 Hz, 1H), 3.95 (q, J=5.9 Hz, 1H), 3.89 (td, J=4.9 Hz, 3.0 Hz, 1H), 3.75 (q, J=3.4 Hz, 1H), 3.50 (qdd, J=11.9 Hz, 5.2 Hz, 3.5 Hz, 2H); $^{13}$C NMR (101 MHz, DMSO-d$_6$) δ 150.0, 143.9, 130.5, 98.89, 87.1, 85.0, 72.8, 70.8, 61.8. LRMS m/z 260.1 [M+H]$^+$.

A 2 L 3-neck flask equipped with an overhead stirrer and nitrogen inlet was charged with uridine (25 g, 102 mmol) and 1 L of dichloromethane. The resulting solution was cooled to 0° C. and 4-DMAP (1.251 g, 10.24 mmol) and imidazole (27.9 g, 409 mmol) were added sequentially. TBSCl (61.7 g, 409 mmol) was added over 10 minutes and the resulting mixture was warmed to ambient temperature and stirred for 18 hrs. Water (300 mL) was added to the reaction mixture and stirred at rt for 2 h, the layers were separated, and the aqueous layer was extracted with additional dichloromethane. The combined organic layers were washed with brine (1×300 mL), dried over sodium sulfate, filtered and concentrated under reduced pressure to yield 75 g of a clear colorless oil. Purification by flash chromatography (5 to 20% gradient of EtOAc in hexanes) to yield S1 (45 g, 75%) as a clear, colorless oil, which solidified when

Example 2

Synthesis of EIDD-2061

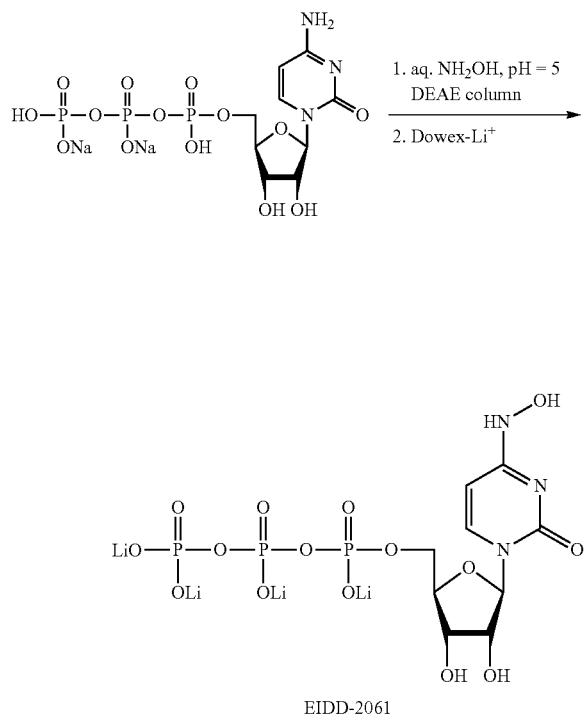

EIDD-2061

A sealable pressure tube was charged with a stir bar, cytidine triphosphate disodium salt (0.137 g, 0.260 mmol), and a 2 N aqueous hydroxylamine solution adjusted to pH=5 (2.0 mL, 4.0 mmol). After mixing the reagents, the pH of the solution was measured (pH=3) and additional drops of 10% w/w aq. NaOH solution were added to readjust the solution to pH=5. The tube was sealed and heated with stirring at 55° C. for 5 h. The mixture was cooled to rt, the sealed tube was opened, and a solution of 100 mM triethylammonium bicarbonate (TEAB) (2 mL) was added. The contents of the tube were transferred to a round bottom flask, and concentrated by rotary evaporation. The crude material was taken up in 100 mM TEAB, and chromatography on DEAE followed by lyophilization of the product gave a triethylammonium salt of the desired product.

An ion-exchange column (17 mL CV) of freshly prepared Dowex (Li$^+$ form) was rinsed with 5 CV water. The prepared triethylammonium salt was taken up in water and eluted through the ion-exchange column. Fractions containing product were combined and lyophilized to give the title compound (0.030 g, 22%) as a fluffy tan solid: $^1$H NMR (400 MHz, D$_2$O) δ 7.19 (d, J=8.3 Hz, 1H), 5.95 (d, J=6.3 Hz, 1H), 5.82 (d, J=8.3 Hz, 1H), 4.42-4.34 (m, 2H), 4.24-4.10 (m, 3H); $^{31}$P NMR (162 MHz, D$_2$O) δ −8.5 (br s), −11.2 (d, J=19.6 Hz), −22.2 (t, J=19.3 Hz); LRMS m/z 498.0 [M−H]$^−$.

Example 3

Synthesis of EIDD-2101

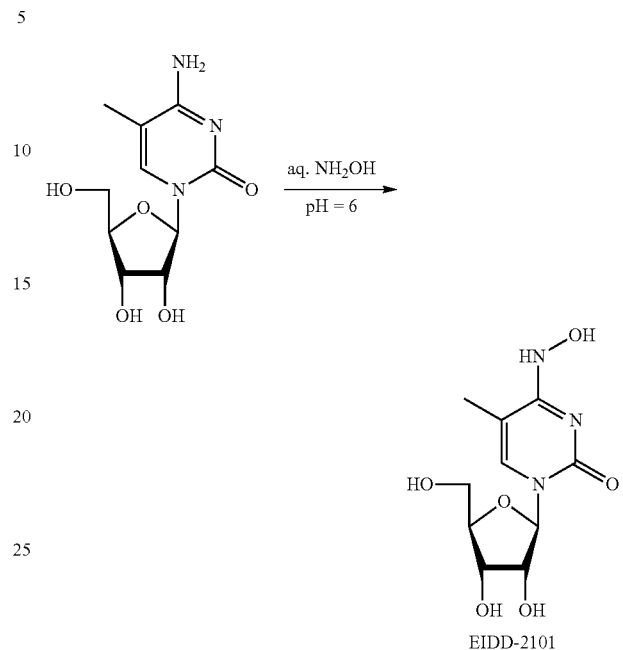

EIDD-2101

A solution of 5-methylcytidine (0.257 g, 1.00 mmol) in a 2N aq. hydroxylamine solution with pH 6 (8 mL, 16.0 mmol) was heated to 55° C. in a sealed tube with stirring for 5 hrs. The solution was cooled to rt, transferred to a round bottom flask, concentrated by rotary evaporation, and coevaporated with MeOH (2×20 mL). The crude residue was taken up in MeOH and immobilized on silica gel. Flash chromatography (2 to 10% gradient of MeOH in DCM) provided the title compound (140 mg, 51%) as a light purple solid: $^1$H NMR (400 MHz, CD$_3$OD) δ6.99 (s, 1H), 5.86 (d, J=5.7 Hz, 1H), 4.23-4.06 (m, 2H), 3.93 (q, J=3.2 Hz, 1H), 3.78 (dd, J=12.1 Hz, 2.8 Hz, 1H), 3.70 (dd, J=12.1 Hz, 3.4 Hz, 1H), 1.79 (s, 3H); $^{13}$C NMR (100 MHz, CD$_3$OD) δ152.0, 146.6, 128.4, 108.4, 89.4, 86.1, 74.4, 71.8, 62.8, 12.9; HRMS calcd. for C$_{10}$H$_{16}$O$_6$N$_3$ [M+H]$^+$: 274.10336, found: 274.10350.

Example 4

Synthesis of EIDD-2103

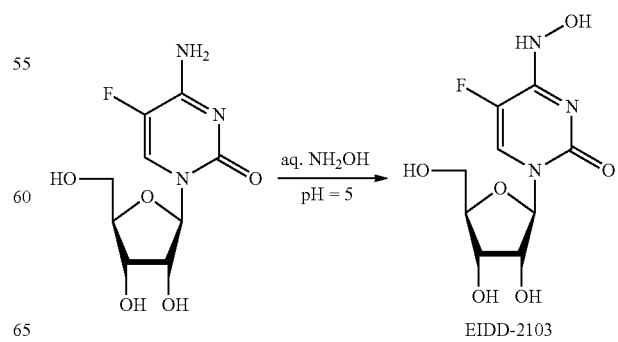

EIDD-2103

A 2 N solution of hydroxylamine hydrochloride (1.11 g, 16.0 mmol) in water (8 mL) was prepared, and adjusted to pH=5 with a small amount of aq. NaOH (10% w/w). A sealable pressure tube was charged with this solution and 5-fluorocytidine (0.261 g, 1.00 mmol), the flask was sealed, and heated with stirring at 55° C. for 16 h. The mixture was cooled to rt, transferred to a round bottom flask, and concentrated by rotary evaporation. The crude material was suspended in MeOH and immobilized on Celite. Automated flash chromatography (40 g column, 0 to 20% gradient of MeOH in DCM) gave 600 mg of a semipure pink solid. This solid was dissolved in 2 mL water, and automated reverse phase chromatography (43 g column, 5 to 100% gradient of MeOH in water) gave the desired product free from organic and inorganic impurities. The solid was dissolved in water, frozen in a dry ice/acetone bath, and lyophilized to provide the title compound (0.066 g, 0.238 mmol, 24% yield) as a white flocculent solid. $^1$H NMR (400 MHz, D$_2$O) δ7.31 (d, J=7.6 Hz, 1H), 5.87 (dd, J=5.5 Hz, 1.8 Hz, 1H), 4.26 (t, J=5.5 Hz, 1H), 4.19 (t, J=4.8 Hz, 1H), 4.07 (q, J=3.8 Hz, 1H), 3.85 (dd, J=12.8 Hz, 3.1 Hz, 1H), 3.77 (dd, J=12.7 Hz, 4.2 Hz, 1H); $^{13}$C NMR (100 MHz, D$_2$O) δ150.0, 139.7, 137.4, 115.6 (d, J=36.1 Hz), 88.0, 84.2, 72.8, 69.8, 61.0; $^{19}$F NMR (376 MHz, D$_2$O) δ−164.70 (d, J=7.6 Hz); HRMS calcd. for C$_9$H$_{13}$FN$_3$O$_6$ [M+H]$^+$: 278.07829, found: 278.07848.

Example 5

Synthesis of EIDD-2216

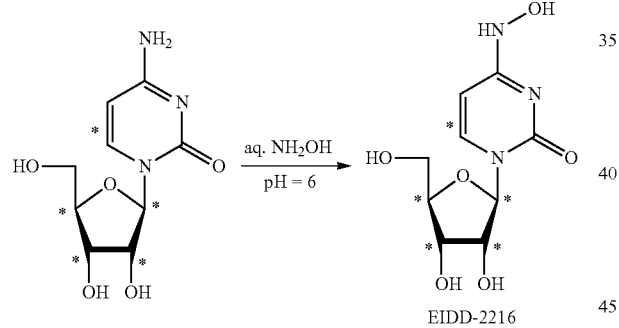

EIDD-2216

A 5 N solution of hydroxylamine hydrochloride (4.71 g, 67.8 mmol) in water (13.5 mL) was prepared, and adjusted to pH=6 with a small amount of aq. NaOH (10% w/w). A sealable pressure tube was charged with this solution and [1',2',3',4',5'-$^{13}$C$_5$]cytidine (0.661 g, 2.26 mmol), the flask was sealed, and heated with stirring at 37° C. for 16 h. The mixture was cooled to room temperature (rt), transferred to a round bottom flask, and concentrated by rotary evaporation. The crude material was taken up in water, and automated reverse phase flash chromatography (240 g C$_{18}$ column, 0 to 100% gradient of acetonitrile in water) removed bulk impurities to give 1.4 g of a wet solid. This solid was dissolved in water, and a second automated reverse phase chromatography (240 g C18 column, 0 to 100% gradient of acetonitrile in water) removed more impurities to give 400 mg semipure material. The material was dissolved in MeOH and immobilized on Celite. Automated flash chromatography (24 g column, 5 to 25% gradient of MeOH in dichloromethane) gave 200 mg of nearly pure product. The solid was dissolved in water, and a final automated reverse phase chromatography (48 g C18 column, 0 to 100% gradient of acetonitrile in water) gave the desired product free from organic and inorganic impurities. The solid was dissolved in water, frozen in a dry ice/acetone bath, and lyophilized to provide the title compound (0.119 g, 20%) as a pale purple flocculent solid, about 95% pure by NMR/LCMS analysis: $^1$HNMR (400 MHz, D$_2$O) δ 7.03 (dd, J=8.2 Hz, 2.2 Hz, 1H), 5.82 (ddd, J=167.5 Hz, 5.3 Hz, 2.9 Hz, 1H), 5.70 (d, J=8.2 Hz, 1H), 4.47-4.30 (br m, 1H), 4.23-4.03 (br m, 1H), 4.00-3.80 (br m, 2H), 3.65-3.50 (br m, 1H); $^{13}$C NMR (100 MHz, D$_2$O) δ151.3, 146.6, 131.3, 98.7, 87.9 (dd, j=43.1 Hz, 4.0 Hz), 84.0 (dd, j=41.5 Hz, 38.0 Hz), 72.5 (dd, J=43.3 Hz, 37.8 Hz), 69.8 (td, J=37.9 Hz, 3.9 Hz), 61.1 (d, J=41.5 Hz); LRMS m/z 265.1 [M+H]$^+$.

Example 6

Synthesis of EIDD-2261

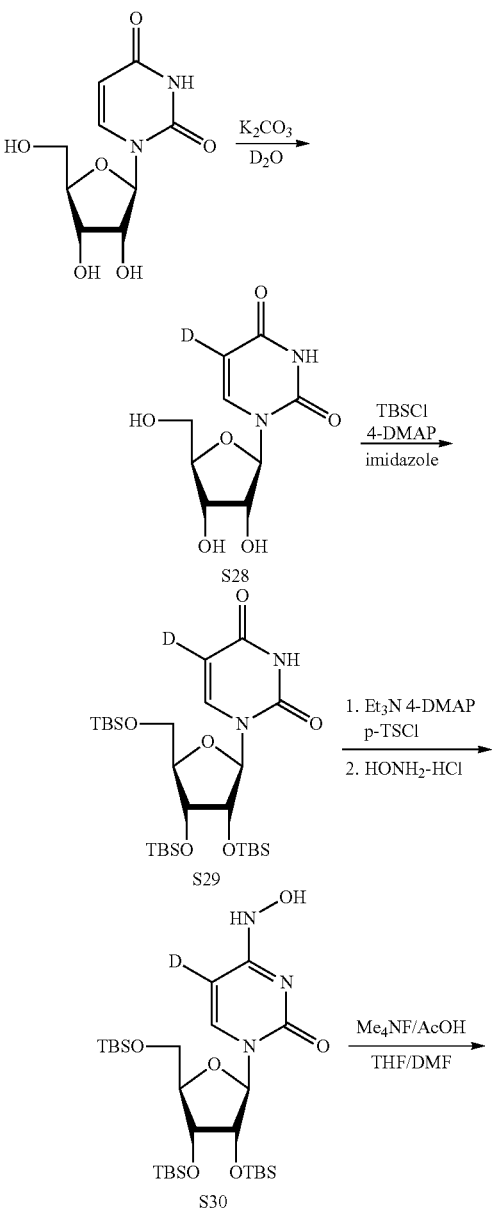

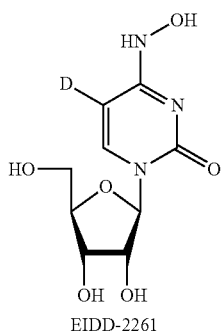

EIDD-2261

A sealable pressure tube was charged with uridine (1.00 g, 4.09 mmol), K$_2$CO$_3$ (0.679 g, 4.91 mmol), and deuterium oxide (8.2 mL). The mixture was purged with nitrogen for 15 minutes, the tubed was sealed, and the contents were heated with stirring at 95° C. for 16 h. The mixture was cooled to rt, the tube was unsealed, and the mixture was transferred to a round-bottom flask and concentrated by rotary evaporation. The resulting crude was coevaporated with MeOH (× 3) to remove water. NMR analysis showed >95% deuterium incorporation at the 5-position on the nucleobase. The light brown solid S28 (1.00 g, 100%) was used in the next step without further purification: $^1$H NMR (400 MHz, CD$_3$OD) δ 7.76 (s, 1H), 5.88 (d, J=4.2 Hz, 1H), 4.17-4.12 (m, 2H), 4.00-3.96 (m, 1H), 3.84 (dd, J=12.3 Hz, 2.8 Hz, 1H), 3.72 (dd, J=12.3 Hz, 3.5 Hz, 1H); $^{13}$C NMR (100 MHz, CD$_3$OD) δ 185.6, 177.4, 160.4, 141.1, 91.8, 85.8, 75.9, 71.2, 62.4.

A round bottom flask was charged with S28 (1.00 g, 4.09 mmol) and dichloromethane (8 mL) under nitrogen. The resulting mixture was cooled to 0° C. and 4-DMAP (0.050 g, 0.408 mmol) and imidazole (1.11 g, 16.3 mmol) were added all at once. TBSCl (2.15 g, 14.3 mmol) was added all at once as a solid, the mixture was warmed to ambient temperature, and stirred for 16 hours. Water (25 mL) was added to the reaction mixture, the layers were separated, and the aqueous layer was extracted with dichloromethane (2×25 mL). The combined organic layers were washed with brine (1×25 mL), dried over Na$_2$SO$_4$, filtered, and concentrated by rotary evaporation. Automated flash chromatography (40 g column, 0 to 35% gradient of EtOAc in hexanes) gave S29 (2.52 g, 84%) as an off-white foam: $^1$H NMR (400 MHz, CDCl$_3$) δ 8.08 (br s, 1H), 8.03 (s, 1H), 5.89 (d, J=3.6 Hz, 1H), 4.12-4.06 (m, 3H), 3.99 (dd, J=11.5 Hz, 1.8 Hz, 1H), 3.76 (d, J=12.0 Hz, 1H), 0.96 (s, 9H), 0.92 (s, 9H), 0.90 (s, 9H), 0.14 (s, 3H), 0.13 (s, 3H), 0.10 (s, 3H), 0.09 (s, 3H), 0.08 (s, 3H), 0.07 (s, 3H); $^{13}$C NMR (100 MHz, CDCl$_3$) δ 163.7, 150.3, 140.3, 89.0, 84.3, 76.1, 70.5, 61.6, 26.0 (3C), 25.8 (3C), 25.7 (3C), 18.4, 18.3, 17.9, −4.2, −4.6, −4.8, −4.9, −5.4, −5.6; HRMS calcd. for C$_{27}$H$_{54}$DN$_2$NaO$_6$Si [M+Na]$^+$: 610.32446, found: 610.32482.

To a stirred solution of S29 (0.840 g, 1.43 mmol) in acetonitrile (14.3 mL) at 0° C. under nitrogen, were added sequentially p-toluenesulfonyl chloride (0.545 g, 2.86 mmol), 4-DMAP (0.175 g, 1.43 mmol), and triethylamine (0.80 mL, 5.71 mmol). The mixture was stirred at 0° C. for 2.5 h, at which time hydroxylamine hydrochloride (0.993 g, 14.3 mmol) was added all at once as a solid. The mixture was heated at 50° C. for 3 days, then cooled to rt. The reaction mixture was diluted with EtOAc (100 mL), then washed with water (2×100 mL) and brine (1×100 mL), dried over Na$_2$SO$_4$, filtered, and concentrated by rotary evaporation. Automated flash chromatography (40 g column, 5 to 35% gradient of EtOAc in hexanes) produced a mixture of starting material and desired product. A second automated flash chromatography (24 g column, 10 to 40% gradient of EtOAc in hexanes), gave S30 (0.332 g, 39%) as an off-white foam: $^1$H NMR (400 MHz, CDCl$_3$) δ 8.37 (br s, 1H), 5.92 (d, J=4.6 Hz, 1H), 4.10-4.05 (m, 2H), 4.04-4.00 (m, 1H), 3.91 (dd, J=11.6 Hz, 2.4 Hz, 1H), 3.73 (dd, J=11.6 Hz, 1.8 Hz, 1H), 0.95 (s, 9H), 0.92 (s, 9H), 0.89 (s, 9H), 0.12 (s, 6H), 0.10 (s, 3H), 0.08 (s, 3H), 0.06 (s, 3H), 0.05 (s, 3H).

A round bottom flask was charged with S30 (0.332 g, 0.551 mmol), tetramethylammonium fluoride (0.196 g, 2.64 mmol), THF (8.25 mL), and DMF (2.75 mL) under nitrogen at 0° C. Acetic acid (0.157 mL, 2.75 mmol) was added all at once via syringe. The mixture was warmed to 45° C. and heated with stirring for 4 days, then concentrated by rotary evaporation. Automated flash chromatography (40 g column, 0 to 20% gradient of MeOH in DCM) gave the title compound (0.106 g, 74%) as a white solid. Final NMR analysis showed >95% deuterium incorporation at the 5-position of the nucleobase: $^1$HNMR (400 MHz, D$_2$O) δ 7.16 (s, 1H), 5.85 (d, J=5.6 Hz, 1H), 4.14 (t, J=5.5 Hz, 1H), 4.10 (dd, J=5.6 Hz, 3.8 Hz, 1H), 3.93 (q, J=3.4 Hz, 1H), 3.77 (dd, J=12.2 Hz, 2.9 Hz, 1H), 3.68 (dd, J=12.2 Hz, 3.4 Hz, 1H); $^{13}$C NMR (100 MHz, CD$_3$OD) δ 151.8, 146.3, 132.1, 89.7, 86.1, 74.6, 71.8, 62.8; HRMS calcd. for C$_9$H$_{13}$DN$_3$O$_6$[M+H]$^+$: 261.09399, found: 261.09371.

Example 7

Synthesis of EIDD-2345

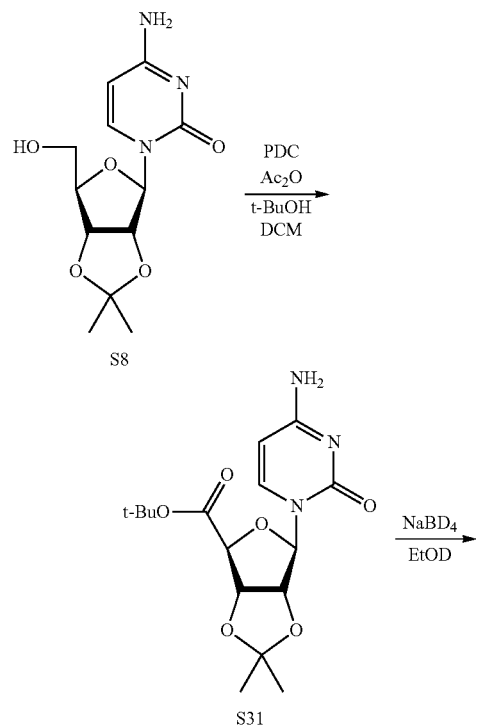

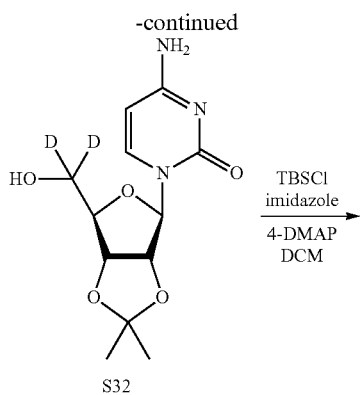

S32

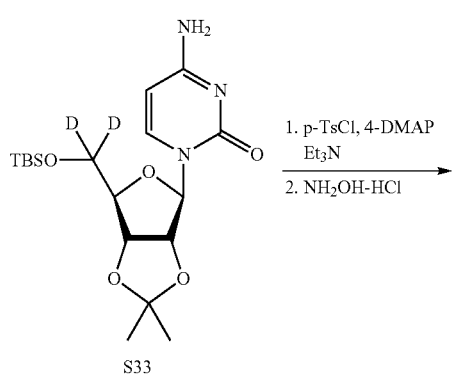

S33

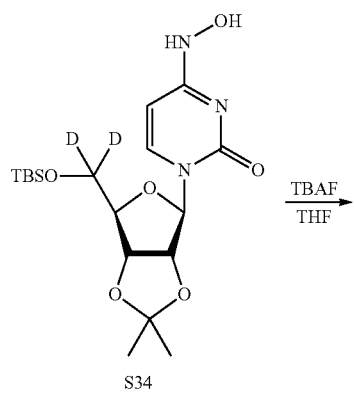

S34

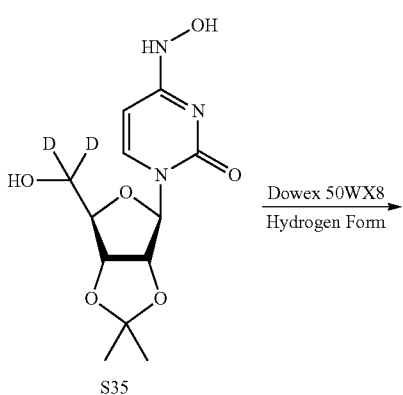

S35

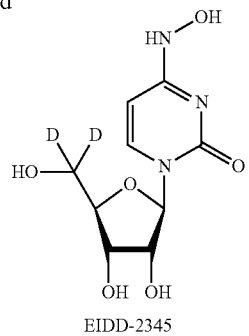

EIDD-2345

A round bottom flask was charged with S8 (3.13 g, 11.0 mmol) and dichloromethane (75 mL) under nitrogen at rt. To this stirred mixture was added sequentially pyridinium dichromate (8.28 g, 22.0 mmol), acetic anhydride (10.4 mL, 110 mmol) and t-butanol (21.1 mL, 220 mmol) at rt. The mixture was stirred for 22 hours at rt, then washed with water (1×75 mL). The aqueous layer was extracted with dichloromethane (2×75 mL) and the combined organic layers were washed with brine (1×100 mL), dried over $Na_2SO_4$, filtered, and concentrated by rotary evaporation. The obtained residue was taken up in EtOAc and filtered through a Celite plug, followed by washing with EtOAc. The filtrate was concentrated by rotary evaporation, and automated flash chromatography (120 g column, 40 to 80% gradient of EtOAc in hexanes) gave S31 (3.10 g, 72%) as an off-white foam: $^1$H NMR (400 MHz, $CDCl_3$) δ8.36 (br s, 1H), 7.42 (d, J=8.0 Hz, 1H), 5.76 (dd, J=8.0 Hz, 2.3 Hz, 1H), 5.59 (s, 1H), 5.27 (dd, J=6.0 Hz, 1.8 Hz, 1H), 5.19 (d, J=6.0 Hz, 1H), 4.62 (d, J=1.8 Hz, 1H), 1.56 (s, 3H), 1.48 (s, 9H), 1.39 (s, 3H).

To a stirred solution of S31 (2.61 g, 7.37 mmol) in EtOD (75 mL) at rt under nitrogen, was added NaBD4 (1.234 g, 29.5 mmol) in one portion. The mixture was stirred at rt for 1 hour, heated to 55° C. for 6 hours, then overnight at rt. The mixture was cooled to 0° C. and excess reagent was quenched with AcOD. The mixture was concentrated by rotary evaporation to give crude S32 (2.57 g) which was taken directly on to the next step without further purification.

To a stirred suspension of crude S32 (2.00 g impure material, 5.74 mmol) in dichloromethane (70 mL) at 0° C., was added solid imidazole (1.90 g, 27.9 mmol) and 4-DMAP (0.171 g, 1.40 mmol). Solid t-butyldimethylsilyl chloride (2.11 g, 14.0 mmol) was added, and the mixture was warmed to rt and stirred for 4 days. The mixture was washed sequentially with water and brine (1×70 mL each), dried over $Na_2SO_4$, filtered, and concentrated by rotary evaporation. Automated flash chromatography (120 g column, 0 to 35% gradient of EtOAc in hexanes) gave S33 (1.42 g, 66% over 2 steps) as a white solid: $^1$H NMR (400 MHz, $CDCl_3$) δ 8.30 (br s, 1H), 7.72 (m, 1H), 5.99 (d, J=2.8 Hz, 1H), 5.69 (dd, J=8.2 Hz, 2.3 Hz, 1H), 4.77 (dd, J=6.1 Hz, 2.9 Hz, 1H), 4.69 (dd, J=6.2 Hz, 2.8 Hz, 1H), 4.33 (d, J=3.0 Hz, 1H), 1.60 (s, 3H), 1.37 (s, 3H), 0.91 (s, 9H), 0.11 (s, 3), 0.10 (s, 3H); $^{13}$C NMR (100 MHz, $CDCl_3$) δ162.7, 149.9, 140.5, 114.1, 102.1, 91.9, 86.5, 85.4, 80.3, 27.4, 25.9 (3C), 25.4, 18.4, −5.4, −5.5; HRMS calcd. for $C_{18}H_{29}D_2N_2O_6Si$ [M+H]$^+$: 401.20714, found: 401.20663.

To a stirred solution of S33 (1.42 g, 3.55 mmol) in acetonitrile (35 mL) at 0° C. under nitrogen, was added sequentially p-toluenesulfonyl chloride (1.35 g, 7.09 mmol), 4-DMAP (0.433 g, 3.55 mmol), and triethylamine (9.88 mL, 70.9 mmol). The resulting mixture was stirred at 0° C. for 2.5 hours. Hydroxylamine hydrochloride (2.46 g, 35.5 mmol) was added, and the mixture was heated with stirring at 50° C. for 2 days. The mixture was recooled to rt and diluted with EtOAc (100 mL), then washed with water (2×50 mL) and brine (1×50 mL), dried over $Na_2SO_4$, filtered, and concentrated by rotary evaporation. Automated flash chromatography (120 g column, 1 to 3.5% gradient of methanol in dichloromethane) gave S34 (0.416 g, 28%) as an off-white solid: $^1$H NMR (400 MHz, $CDCl_3$) δ8.36 (br s, 1H), 7.00 (m, 1H), 5.97 (d, J=3.1 Hz, 1H), 5.58 (d, J=8.2 Hz, 1H), 4.77 (dd, J=6.2 Hz, 3.2 Hz, 1H), 4.68 (dd, J=6.3 Hz, 3.2 Hz, 1H), 4.22 (d, J=3.2 Hz, 1H), 1.59 (s, 3H), 1.36 (s, 3H), 0.92 (s, 9H), 0.11 (s, 3H), 0.10 (s, 3H); $^{13}$C NMR (100 MHz, $CDCl_3$) δ149.0, 145.4, 131.4, 114.1, 98.3, 90.8, 85.5, 84.5, 80.2, 27.4, 25.9 (3C), 25.5, 18.4, −5.4, −5.5; HRMS calcd. for $C_{18}H_{29}D_2N_3O_6Si$ [M+H]$^+$: 416.21804, found: 416.21827.

To a stirred solution of S34 (0.416 g, 1.00 mmol) in THF (5 mL) at 0° C. under nitrogen, was added a 1.0 M THF solution of TBAF (1.50 mL, 1.5 mmol), and the resulting mixture was kept at 0° C. for 24 hours. The reaction mixture was concentrated by rotary evaporation, and automated flash chromatography (40 g column, 0 to 8% gradient of methanol in dichloromethane) gave S35 (0.257 g, 85%) as a white solid: $^1$H NMR (400 MHz, $CD_3OD$) δ 7.02 (m, 1H), 5.81 (d, J=3.2 Hz, 1H), 5.58 (d, J=8.2 Hz, 1H), 4.86 (dd, J=6.4 Hz, 3.2 Hz, 1H), 4.79 (dd, J=6.5 Hz, 3.6 Hz, 1H), 4.09 (d, J=3.7 Hz, 1H), 1.54 (s, 3H), 1.34 (s, 3H); $^{13}$C NMR (100 MHz, $CD_3OD$) δ 151.3, 146.2, 133.4, 115.2, 99.4, 92.9, 87.2, 84.9, 82.1, 27.6, 25.6; HRMS calcd. for $C_{12}H_{16}D_2N_3O_6$ [M+H]$^+$: 302.13157, found: 302.13130.

To a stirred solution of S35 (0.140 g, 0.465 mmol) in methanol (8.4 mL) and water (0.93 mL) at rt, was added Dowex 50WX8 hydrogen form (0.30 g), and the mixture was stirred at rt for 24 hours. The reaction mixture was filtered, and the filtrate was concentrated by rotary evaporation. Automated flash chromatography (40 g column, 5 to 20% gradient of methanol in dichloromethane) gave the title compound (0.050 g, 41%) as an off-white solid: $^1$H NMR (400 MHz, $CD_3OD$) δ 7.17 (m, 1H), 5.86 (d, J=5.6 Hz, 1H), 5.60 (d, J=8.2 Hz, 1H), 4.15 (t, J=5.5 Hz, 1H), 4.11 (dd, J=5.6 Hz, 3.5 Hz, 1H), 3.94 (d, J=3.8 Hz, 1H); $^{13}$C NMR (100 MHz, $CD_3OD$) δ151.8, 146.3, 132.2, 99.3, 89.7, 86.0, 74.6, 71.7, HRMS calcd. for $C_9H_{10}D_2N_3O_6$ [M+H]+: 260.08571, found: 260.08578.

Example 8

Synthesis of EIDD-2898

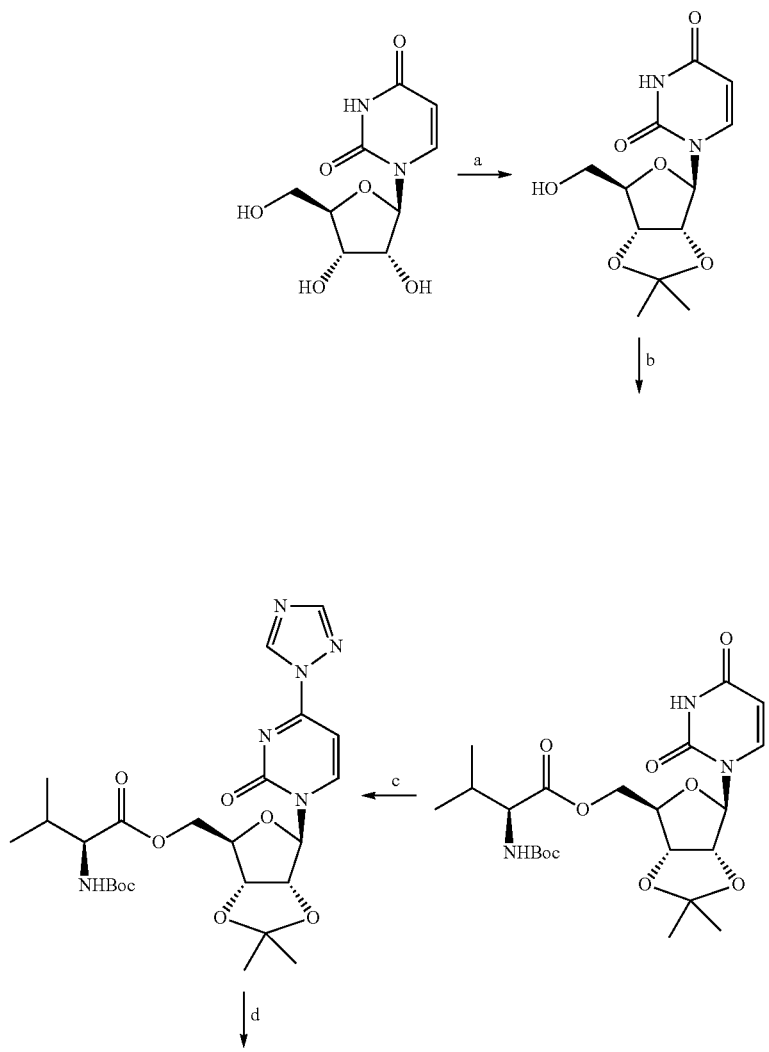

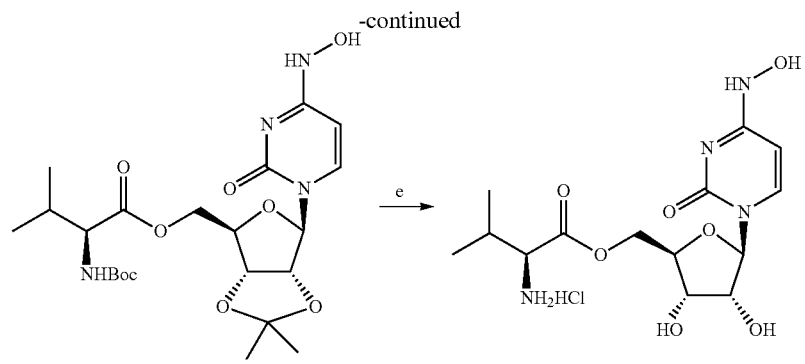

Reagents and conditions;
a) Acetone, H2SO4, 2,2-DMP, RT, 12 hr, 80-85%:
b) Boc-L-Val-OH, DCC, DMAP, DCM, RT 5-6-hr,
c) 1,2,4-triazole, POCl3, triethylamine, MeCN;
d) 50% NH2OH in water, MeCN;
e) conc•HCl, MeOH, RT, 24 hr A 2 L 3-neck RBF was charged with 1-[(3R,4S,5R)-3,4-dihydroxy-5-(hydroxymethyl)tetrahydrofuran-2-yl]pyrimidine-2,4-dione (61.4 g, 251.43 mmol) and acetone (1400 mL). The resulting slurry was stirred at RT and sulfuric acid (2 mL was added. Stirring was continued overnite. The clear colorless solution was quenched/adjusted to basic pH with 100 mL of trimethylamine. The crude solution was concentrated under reduced pressure to yield a pale yellow oil. The residue was dissolved in 600 mL of EtOAc and washed with water ×2, bicarb ×2, water, brine ×2 and dried over sodium sulfate. The colorless solution was concentrated under reduced pressure to yield 1-[(3aR,6R,6aR)-6-(hydroxymethyl)-2,2-dimethyl-3a,4,6,6a-tetrahydrofuro[3,4-d][1,3]dioxol-4-yl]pyrimidine-2,4-dione (45 g) as a white solid.

A 200 mL RBF was charged with 1-[(3aR,6R,6aR)-6-(hydroxymethyl)-2,2-dimethyl-3a,4,6,6a-tetrahydrofuro[3,4-d][1,3]dioxol-4-yl]pyrimidine-2,4-dione (2.36 g, 8.3 mmol) and DCM (50 mL). The reaction was stirred until a solution was formed. Next, (2S)-2-(tert-butoxycarbonylamino)-3-methyl-butanoic acid (2.16 g, 9.96 mmol) and N,N-dimethylpyridin-4-amine (0.1 g, 0.8300 mmol) were added. The reaction was cooled to 0° C. with an ice bath. A DCM solution of N,N'-dicyclohexylcarbodiimide (2.06 g, 9.96 mmol) was added slowly. The reaction mixture was allowed to warm to rt. Monitored by TLC (EtOAc).

A precipitate (DCU) formed after about 1 hr and no starting material was detected after 3 hrs. The solids were filtered off and rinsed with EtOAc. The filtrate was washed with water, brine, dried over sodium sulfate and concentrated under reduced pressure to yield white, gooey solid. The gummy solid was triturated with ether and filtered to remove the solid. The filtrate was concentrated under reduced pressure to yield about 8 g of thick viscous oil. The product was purified by SGC, pooled fractions 6-25 and concentrated under reduced pressure to yield [(3aR,6R,6aR)-4-(2,4-dioxopyrimidin-1-yl)-2,2-dimethyl-3a,4,6,6a-tetrahydrofuro[3,4-d][1,3]dioxol-6-yl]methyl (2S)-2-(tert-butoxycarbonylamino)-3-methyl-butanoate (3.8 g,7.8592 mmol, 94.667% yield) as a foamy white solid after drying in vacuo.

1,2,4-triazole was taken in anhydrous acetonitrile and stirred at RT after 30 min, the reaction mixture was cooled to 0° C. and POCl3 was added dropwise and continued stirring for 2 hr. After 2 hr triethylamine was added dropwise and continue stirring for 1 hr, the reaction mixture was slowly brought to RT, and the uridine derived substrate from the above reaction was added as solution in acetonitrile. The reaction mixture stirred at RT overnight. After completion of the reaction, the solvent was removed under reduced pressure and taken in DCM and extracted with water. The organic layer was dried over anhydrous sodium sulphate and concentrated under reduced pressure. The crude product was purified by flash column chromatography.

To a solution of the substrate in acetonitrile (10 mL/gm), 50% hydroxylamine in water was added dropwise and stirred at rt for 2-3 hrs. After completion of the reaction, solvent was removed under reduced pressure and the crude product was purified by flash column chromatography using hexane and EtOAc as eluent.

1 g of substrate was taken in 20 mL of methanol and treated with 2 mL of conc.HCl (36%) and after 3-4 hr 30% completion was observed. Another 5 mL of conc.HCl was added and stirred overnight. After completion of the reaction, solvent was removed and the crude product was taken in minimum methanol and added dropwise to excess diethylether with stirring, product was crashed out of solution and allowed to settle, ether was decanted and fresh ether was added, stirred, settled and decanted, the same process was repeated two times. After ether was decanted, solid was dried over a rotavap and high vacuum to get free flowing white solid. Ether was trapped in the solid and was difficult to remove. The solid was dissolved in methanol, evaporated and dried to get colorless foam, which still holds methanol. The foam was taken in water and a purple solution was observed. The purple solution was purified by reverse phase ISCO column chromatography using water and acetonitrile. The fractions containing product were evaporated under reduced pressure and lyophilized to get colorless solid.

Example 9

Synthesis of EIDD-2800

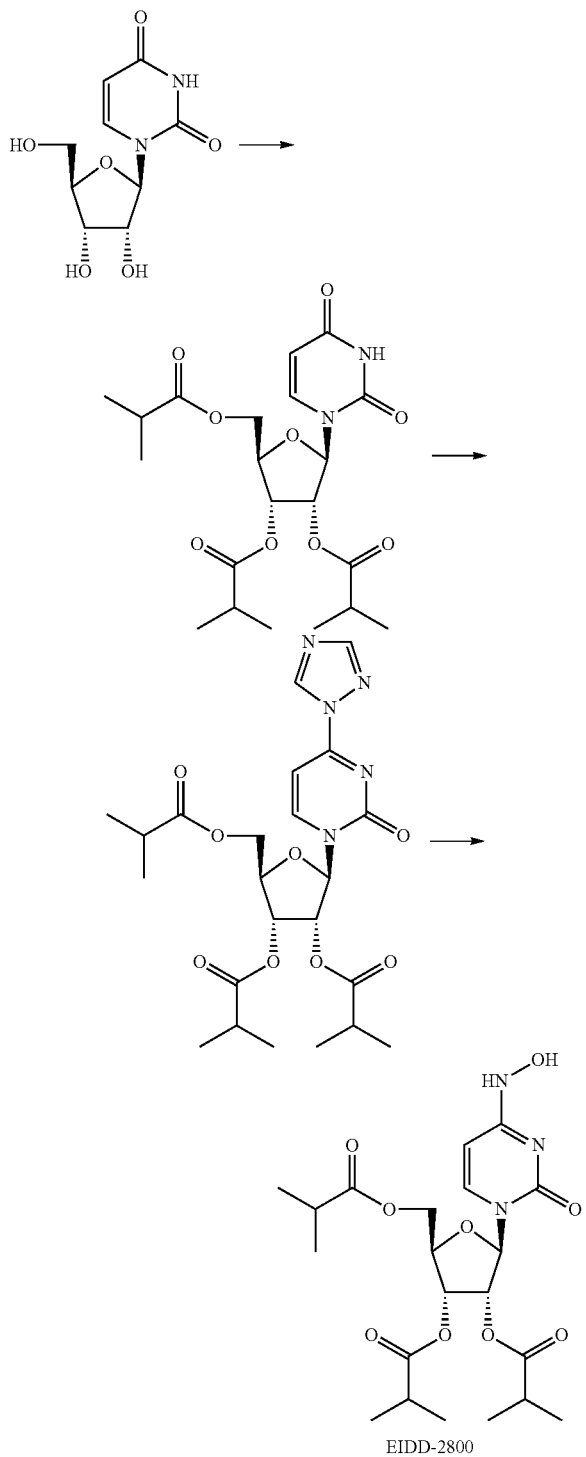

EIDD-2800

A 3-neck 1 L round bottom flask equipped with an overhead stirrer, temperature probe and addition funnel was charged with uridine (25 g, 102.38 mmol) and ethyl acetate (500 mL). The white slurry was stirred at ambient temperature while triethylamine (71.39 mL, 511.88 mmol) and DMAP (0.63 g, 5.12 mmol) were added to the mixture. The slurry was cooled in an ice bath and isobutyric anhydride (56.02 mL, 337.84 mmol) was slowly added to the reaction mixture over a 5 minute period. The temperature rose 25° C. during the addition. The resulting slurry was stirred at ambient temperature and monitored by TLC. After 1 hour, a clear colorless solution had formed and TLC showed no starting material. The reaction was quenched with 200 mL of water, stirred at rt for 20 minutes. The layers were separated, and the organics were washed with water (2×100 mL), saturated aqueous bicarbonate solution (100 mL×2), 100 mL of water, brine (100 mL×2), and then dried over sodium sulfate. The organics were filtered and the filtrate was concentrated under reduced pressure at 45° C. to yield a yellow oil. The oil was used in the next step without any further purification.

A 2 L 3-neck flask equipped with an argon inlet, overhead stirrer and temperature probe was charged with 1H-1,2,4-triazole (50.88 g, 736.68 mmol), triethylamine (114.17 mL, 818.54 mmol) and MeCN (350 mL). The reaction mixture was stirred at rt for 20 minutes. An ethyl acetate (350 mL) solution of [(2R,3R,4R)-5-(2,4-dioxopyrimidin-1-yl)-3,4-bis(2-methylpropanoyloxy)tetrahydrofuran-2-yl]methyl 2-methylpropanoate (46.5 g, 102.32 mmol) was added and the mixture was cooled to <5° C. using an ice bath. Stirring continued for 20 minutes. Next, phosphorous(V)oxychloride (14.35 mL, 153.48 mmol) was added slowly under argon at less than 20° C. over 15 minutes. The reaction was monitored by TLC (100% EtOAc), starting material (Rf=0.89) consumed in less than 2 hours and a new spot due to product (Rf=0.78) present. The reaction was quenched with 500 mL of water and 400 mL of EtOAc. The quenched reaction was allowed to stir at rt for 15 minutes. The layers were separated and the organic layer was washed with water (2×100 mL), 200 mL of 0.5N HCl, and brine (2×100 mL). The organics were dried over sodium sulfate, filtered and concentrated under reduced pressure to yield [(2R,3R,4R)-3,4-bis(2-methylpropanoyloxy)-5-[2oxo-4-(1,2,4-triazol-1-yl)pyrimidin-1-yl]tetrahydrofuran-2-yl]methyl 2-methylpropanoate (49 g, 96.93 mmol, 94.735% yield) as a yellow oil. The crude material was used in the next step without further purification.

A 500 mL round bottom flask was charged with [(2R,3R,4R)-3,4-bis(2-methylpropanoyloxy)-5-[2-oxo-4-(1,2,4-triazol-1-yl)pyrimidin-1-yl]tetrahydrofuran-2-yl]methyl 2-methylpropanoate (48.9 g, 96.73 mmol), ethyl acetate (400 mL), and isopropyl alcohol (100 mL). The reaction mixture was stirred at rt until all of the starting material was dissolved. The orange solution was treated with hydroxylamine (6.52 mL, 106.41 mmol), and the resulting pale yellow solution was stirred at rt and monitored by TLC (EtOAc). No starting material was observed after 1 hour. The reaction was quenched with 500 mL of water, and the layers were separated. The organics were washed with 100 mL of water, 100 mL×2 of brine, and then dried over sodium sulfate. The organics were filtered and concentrated under reduced pressure to yield the crude product. The crude product was dissolved in 180 mL of hot MTBE and allowed to cool to rt. Seed crystals were added, and the flask was placed in the freezer. The white solid that formed was collected by filtration, washed with a minimal amount of MTBE and dried in vacuo to yield the desired product.

Example 10

Synthesis of EIDD-2801

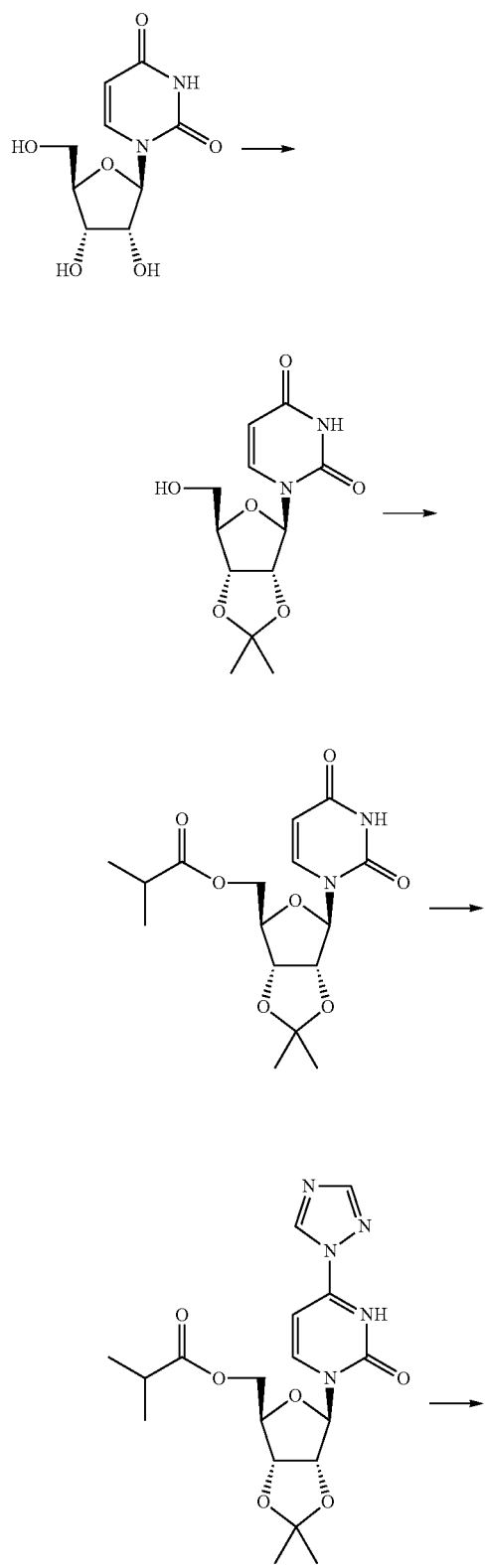

A 1 L round bottom flask was charged with uridine (25 g, 102.38 mmol) and acetone (700 mL). The reaction mixture was allowed to stir at rt. The slurry was then treated with sulfuric acid (0.27 mL, 5.12 mmol). Stirring was allowed to continue at rt for 18 hours. The reaction was quenched with 100 mL of trimethylamine and was used in the next step without further purification.

A 1 L round bottom flask was charged with the reaction mixture from the previous reaction. Triethylamine (71.09 mL, 510.08 mmol) and 4-dimethylaminopyridine (0.62 g, 5.1 mmol) were then added. The flask was cooled using an ice bath and then 2-methylpropanoyl 2-methylpropanoate (17.75 g, 112.22 mmol) was slowly added. The reaction mixture was allowed to stir at rt until the reaction was complete. The reaction mixture was concentrated under reduced pressure, and the residue was dissolved in 600 mL ethyl acetate and washed with saturated aqueous bicarbonate solution ×2, water ×2 and brine ×2. The organics were dried over sodium sulfate and concentrated under reduced pressure to yield a clear colorless oil. The crude product was used in the next step without further purification.

A 1 L round bottom flask was charged with the crude product from above (36 g, 101.59 mmol) and MeCN (406.37 mL). The reaction mixture was allowed to stir until all the starting material was dissolved. Next, 1,2,4-triazole (50.52 g, 731.46 mmol) was added followed by the addition of N,N-diethylethanamine (113.28 mL, 812.73 mmol). The reaction mixture was allowed to stir at rt until all solids dissolved. The reaction was then cooled to 0° C. using an ice bath. Phosphorous oxychloride (24.44 mL, 152.39 mmol) was added slowly. The slurry that formed was allowed to stir under argon while slowly warming to rt. The reaction was then allowed to stir until complete by TLC (EtOAc). The reaction was then quenched by the addition of 100 mL of water. The slurry then became a dark colored solution, which was then concentrated under reduced pressure. The residue was dissolved in DCM and washed with water and brine. The organics were then dried over sodium sulfate, filtered, and concentrated under reduced pressure. The product was purified by silica gel chromatography (2×330 g columns). All fractions containing product were collected and concentrated under reduced pressure.

A 500 mL round bottom flask was charged with the product from the previous step (11.8 g, 29.11 mmol) and isopropyl alcohol (150 mL). The reaction mixture was allowed to stir at rt until all solids dissolved. Next, hydroxylamine (1.34 mL, 43.66 mmol) was added and stirring continued at ambient temperature. When the reaction was complete (HPLC) some solvent was removed under high vacuum at ambient temperature. The remaining solvent was removed under reduced pressure at 45° C. The resulting residue was dissolved in EtOAc and was washed with water and brine. The organics were dried over sodium sulfate, filtered, and concentrated under reduced pressure to yield oil. Crystals formed upon standing at rt. The crystals were collected by filtration, washed with ether ×3, and dried in vacuo to provide the product as a white solid.

A 200 mL round bottom flask was charged with the product from the previous step (6.5 g, 17.6 mmol) and formic acid (100 mL, 2085.6 mmol). The reaction mixture was allowed to stir at rt overnight. The progress of the reaction was monitored by HPLC. The reaction mixture was concentrated under reduced pressure at 42° C. to yield a clear, pale pink oil. Next, 30 mL of ethanol was added. Solvent was then removed under reduced pressure. MTBE (50 mL) was added to the solid and heated. Next, isopropyl alcohol was added and heating was continued until all solid material dissolved (5 mL). The solution was then allowed to cool and stand at rt. A solid started to form after about 1 hr. The solids were collected by filtration, washed with MTBE, and dried in vacuo to yield the EIDD-2801 as a white solid. The filtrate was concentrated under reduced pressure to yield a sticky solid, which was dissolved in a small amount of isopropyl alcohol with heating. The solution was allowed to stand at rt overnight. A solid formed in the flask, which was collected by filtration, rinsed with isopropyl alcohol and MTBE, and dried in vacuo to an additional crop of desired product.

EIDD-2801 (25 g) was dissolved in 250 mL of isopropyl alcohol by heating to 70° C. to give a clear solution. The warm solution was polish filtered and filtrate transferred to 2 L three neck flask with overhead stirrer. It was warmed back to 70° C. and MTBE (250 mL) was slowly added into the flask. The clear solution was seeded and allowed to cool slowly to rt with stirring for 18 hrs. The EIDD-2801 solid that formed was filtered and washed with MTBE and dried at 50° C. under vacuum for 18 hours. The filtrate was concentrated, redissolved in 50 mL isopropyl alcohol and 40 mL MTBE by warming to give clear solution and allowed to stand at rt to give a second crop of EIDD-2801.

Example 11

General Synthesis for Deuteration

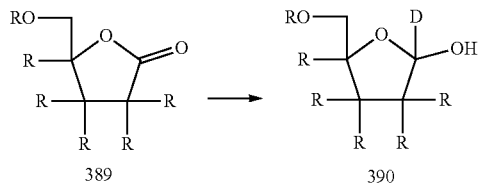

The lactone 389 (0.0325 mol) was added to a dry flask under an argon atmosphere and was then dissolved in dry THF (250 mL). The solution as then cooled to −78° C. and a DIBAL-D solution in toluene (0.065 mol) was dropwise. The reaction was allowed to stir at −78° C. for 3-4 hours. The reaction was then quenched with the slow addition of water (3 mL). The reaction was then allowed to stir while warming to rt. The mixture was then diluted with two volumes of diethyl ether and was then poured into an equal volume of saturated sodium potassium tartrate solution. The organic layer was separated, dried over $MgSO_4$, filtered, and concentrated under reduced pressure. The residue was purified on silica eluting with hexanes/ethyl acetate. The resulting lactol 390 was then converted to an acetate or benzolyate and subjected to cytosine coupling conditions and then further elaborated to N-hydroxycytidine.

Example 12

Assay Protocols

Screening Assays for DENY, JEV, POWV, WNV, YFV, PTV, RVFV, CHIKV, EEEV, VEEV, WEEV, TCRV, PCV, JUNV, MPRLV Primary Cytopathic Effect (CPE) Reduction Assay.

Four-concentration CPE inhibition assays are performed. Confluent or near-confluent cell culture monolayers in 96-well disposable microplates are prepared. Cells are maintained in MEM or DMEM supplemented with FBS as required for each cell line. For antiviral assays the same medium is used but with FBS reduced to 2% or less and supplemented with 50 μg/mL gentamicin. The test compound is prepared at four $\log_{10}$ final concentrations, usually 0.1, 1.0, 10, and 100 μg/mL or μM. The virus control and cell control wells are on every microplate. In parallel, a known active drug is tested as a positive control drug using the same method as is applied for test compounds. The positive control is tested with each test run. The assay is set up by first removing growth media from the 96-well plates of cells. Then the test compound is applied in 0.1 mL volume to wells at 2× concentration. Virus, normally at <100 50% cell culture infectious doses ($CCID_{50}$) in 0.1 mL volume, is placed in those wells designated for virus infection. Medium devoid of virus is placed in toxicity control wells and cell control wells. Virus control wells are treated similarly with virus. Plates are incubated at 37° C. with 5% $CO_2$ until maximum CPE is observed in virus control wells. The plates are then stained with 0.011% neutral red for approximately two hours at 37° C. in a 5% $CO_2$ incubator. The neutral red medium is removed by complete aspiration, and the cells can be rinsed 1× with phosphate buffered solution (PBS) to remove residual dye. The PBS is completely removed and the incorporated neutral red is eluted with 50% Sorensen's citrate buffer/50% ethanol (pH 4.2) for at least 30 minutes. Neutral red dye penetrates into living cells, thus, the more intense the red color, the larger the number of viable cells present in the wells. The dye content in each well is quantified using a 96-well spectrophotometer at 540 nm wavelength. The dye content in each set of wells is converted to a percentage of dye present in untreated control wells using a Microsoft Excel computer-based spreadsheet. The 50% effective ($EC_{50}$, virus-inhibitory) concentrations and 50% cytotoxic ($CC_{50}$, cell-inhibitory) concentrations are then calculated by linear regression analysis. The quotient of $CC_{50}$ divided by $EC_{50}$ gives the selectivity index (SI) value.

Secondary CPE/Virus Yield Reduction (VYR) Assay.

This assay involves similar methodology to what is described in the previous paragraphs using 96-well microplates of cells. The differences are noted in this section. Eight half-$\log_{10}$ concentrations of inhibitor are tested for antiviral activity and cytotoxicity. After sufficient virus replication occurs, a sample of supernatant is taken from each infected well (three replicate wells are pooled) and held for the VYR portion of this test, if needed. Alternately, a separate plate can be prepared and the plate can be frozen for the VYR assay. After maximum CPE is observed, the viable plates are stained with neutral red dye. The incorporated dye content is quantified as described above. The data generated from this portion of the test are neutral red $EC_{50}$, $CC_{50}$, and SI values. Compounds observed to be active above are further evaluated by VYR assay. The VYR test is a direct determination of how much the test compound inhibits virus replication. Virus that was replicated in the presence of test compound is titrated and compared to virus from untreated, infected controls. Titration of pooled viral samples (collected as described above) is performed by endpoint dilution. This is accomplished by titrating $\log_{10}$ dilutions of virus using 3 or 4 microwells per dilution on fresh monolayers of cells by endpoint dilution. Wells are scored for presence or absence of virus after distinct CPE (measured by neutral red uptake) is observed. Plotting the $\log_{10}$ of the inhibitor concentration versus $\log_{10}$ of virus produced at each concentration allows calculation of the 90% (one $\log_{10}$) effective concentration by linear regression. Dividing $EC_{90}$ by the $CC_{50}$ obtained in part 1 of the assay gives the SI value for this test.

Example 13

Screening Assays for Lassa Fever Virus (LASV)

Primary Lassa Fever Virus Assay.

Confluent or near-confluent cell culture monolayers in 12-well disposable cell culture plates are prepared. Cells are maintained in DMEM supplemented with 10% FBS. For antiviral assays the same medium is used but with FBS reduced to 2% or less and supplemented with 1% penicillin/streptomycin. The test compound is prepared at four $\log_{10}$ final concentrations, usually 0.1, 1.0, 10, and 100 μg/mL or μM. The virus control and cell control will be run in parallel with each tested compound. Further, a known active drug is tested as a positive control drug using the same experimental set-up as described for the virus and cell control. The positive control is tested with each test run. The assay is set up by first removing growth media from the 12-well plates of cells, and infecting cells with 0.01 MOI of LASV strain Josiah. Cells will be incubated for 90 min: 500 μL inoculum/M12 well, at 37° C., 5% $CO_2$ with constant gentle rocking. The inoculums will be removed and cells will be washed 2× with medium. Then the test compound is applied in 1 mL of total volume of media. Tissue culture supernatant (TCS) will be collected at appropriate time points. TCS will then be used to determine the compounds inhibitory effect on virus replication. Virus that was replicated in the presence of test compound is titrated and compared to virus from untreated, infected controls. For titration of TCS, serial ten-fold dilutions will be prepared and used to infect fresh monolayers of cells. Cells will be overlaid with 1% agarose mixed 1:1 with 2× MEM supplemented with 10% FBS and 1% penecillin, and the number of plaques determined. Plotting the $\log_{10}$ of the inhibitor concentration versus $\log_{10}$ of virus produced at each concentration allows calculation of the 90% (one $\log_{10}$) effective concentration by linear regression.

Secondary Lassa Fever Virus Assay.

The secondary assay involves similar methodology to what is described in the previous paragraphs using 12-well plates of cells. The differences are noted in this section. Cells are being infected as described above but this time overlaid with 1% agarose diluted 1:1 with 2× MEM and supplemented with 2% FBS and 1% penicillin/streptomycin and supplemented with the corresponding drug concentration. Cells will be incubated at 37oC with 5% $CO_2$ for 6 days. The overlay is then removed and plates stained with 0.05% crystal violet in 10% buffered formalin for approximately twenty minutes at rt. The plates are then washed, dried and the number of plaques counted. The number of plaques is in each set of compound dilution is converted to a percentage relative to the untreated virus control. The 50% effective ($EC_{50}$, virus-inhibitory) concentrations are then calculated by linear regression analysis.

Example 14

Screening Assays for Ebola Virus (EBOV) and Nipah Virus (NIV)

Primary Ebola/Nipah Virus Assay.

Four-concentration plaque reduction assays are performed. Confluent or near-confluent cell culture monolayers in 12-well disposable cell culture plates are prepared. Cells are maintained in DMEM supplemented with 10% FBS. For antiviral assays the same medium is used but with FBS reduced to 2% or less and supplemented with 1% penicillin/streptomycin. The test compound is prepared at four $\log_{10}$ final concentrations, usually 0.1, 1.0, 10, and 100 μg/mL or μM. The virus control and cell control will be run in parallel with each tested compound. Further, a known active drug is tested as a positive control drug using the same experimental set-up as described for the virus and cell control. The positive control is tested with each test run. The assay is set up by first removing growth media from the 12-well plates of cells. Then the test compound is applied in 0.1 mL volume to wells at 2× concentration. Virus, normally at approximately 200 plaque-forming units in 0.1 mL volume, is placed in those wells designated for virus infection. Medium devoid of virus is placed in toxicity control wells and cell control wells. Virus control wells are treated similarly with virus. Plates are incubated at 37° C. with 5% $CO_2$ for one hour. Virus-compound inoculums will be removed, cells washed and overlaid with 1.6% tragacanth diluted 1:1 with 2× MEM and supplemented with 2% FBS and 1% penicillin/streptomycin and supplemented with the corresponding drug concentration. Cells will be incubated at 37° C. with 5% $CO_2$ for 10 days. The overlay is then removed and plates stained with 0.05% crystal violet in 10% buffered formalin for approximately twenty minutes at rt. The plates are then washed, dried and the number of plaques counted. The number of plaques is in each set of compound dilution is converted to a percentage relative to the untreated virus control. The 50% effective ($EC_{50}$, virus-inhibitory) concentrations are then calculated by linear regression analysis.

Secondary Ebola/NIpah Virus Assay with VYR Component.

The secondary assay involves similar methodology to what is described in the previous paragraphs using 12-well plates of cells. The differences are noted in this section. Eight half-$\log_{10}$ concentrations of inhibitor are tested for antiviral activity. One positive control drug is tested per batch of compounds evaluated. For this assay, cells are infected with virus. Cells are being infected as described above but this time incubated with DMEM supplemented with 2% FBS and 1% penicillin/streptomycin and supplemented with the corresponding drug concentration. Cells will be incubated for 10 days at 37° C. with 5% $CO_2$, daily observed under microscope for the number of green fluorescent cells. Aliquots of supernatant from infected cells will be taken daily and the three replicate wells are pooled. The pooled supernatants are then used to determine the compounds inhibitory effect on virus replication. Virus that was replicated in the presence of test compound is titrated and compared to virus from untreated, infected controls. For titration of pooled viral samples, serial ten-fold dilutions will be prepared and used to infect fresh monolayers of cells. Cells are overlaid with tragacanth and the number of plaques determined. Plotting the $\log_{10}$ of the inhibitor concentration versus $\log_{10}$ of virus produced at each concentration allows calculation of the 90% (one $\log_{10}$) effective concentration by linear regression.

Example 15

Anti-Dengue Virus Cytoprotection Assay

Cell Preparation—BHK21 cells (Syrian golden hamster kidney cells, ATCC catalog #CCL-I 0), Vero cells (African green monkey kidney cells, ATCC catalog #CCL-81), or Huh-7 cells (human hepatocyte carcinoma) were passaged in DMEM supplemented with 10% FBS, 2 mM L-glutamine, 100 U/mL penicillin, and 100 µg/mL streptomycin in T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at $3\times10^3$ ($5\times10^5$ for Vero cells and Huh-7 cells) cells per well in tissue culture medium and added to flat bottom microtiter plates in a volume of 100 µL. The plates were incubated at 37° C./5% $CO_2$ overnight to allow for cell adherence. Monolayers were observed to be approximately 70% confluent.

Virus Preparation—The Dengue virus type 2 New Guinea C strain was obtained from ATCC (catalog #VR-1584) and was grown in LLC-MK2 (Rhesus monkey kidney cells; catalog #CCL-7.1) cells for the production of stock virus pools. An aliquot of virus pretitered in BHK21 cells was removed from the freezer (−80° C.) and allowed to thaw slowly to rt in a biological safety cabinet. Virus was resuspended and diluted into assay medium (DMEM supplemented with 2% heat-inactivated FBS, 2 mM L-glutamine, 100 U/mL penicillin, and 100 µg/mL streptomycin) such that the amount of virus added to each well in a volume of 100 µL was the amount determined to yield 85 to 95% cell killing at 6 days post-infection.

Plate Format—Each plate contains cell control wells (cells only), virus control wells (cells plus virus), triplicate drug toxicity wells per compound (cells plus drug only), as well as triplicate experimental wells (drug plus cells plus virus).

Efficacy and Toxicity XTT-Following incubation at 37° C. in a 5% $CO_2$ incubator, the test plates were stained with the tetrazolium dye XTT (2,3-bis(2-methoxy-4-nitro-5-sulfophenyl)-5-[(phenylamino)carbonyl]-2H-tetrazolium hydroxide). XTT-tetrazolium was metabolized by the mitochondrial enzymes of metabolically active cells to a soluble formazan product, allowing rapid quantitative analysis of the inhibition of virus-induced cell killing by antiviral test substances. XTT solution was prepared daily as a stock of 1 mg/mL in RPMI 1640. Phenazine methosulfate (PMS) solution was prepared at 0.15 mg/mL in PBS and stored in the dark at −20° C. XTT/PMS stock was prepared immediately before use by adding 40 µL of PMS per mL of XTT solution. Fifty microliters of XTT/PMS was added to each well of the plate and the plate was reincubated for 4 hours at 37° C. Plates were sealed with adhesive plate sealers and shaken gently or inverted several times to mix the soluble formazan product and the plate was read spectrophotometrically at 450/650 nm with a Molecular Devices Vmax plate reader.

Data Analysis—Raw data was collected from the Softmax Pro 4.6 software and imported into a Microsoft Excel spreadsheet for analysis. The percent reduction in viral cytopathic effect compared to the untreated virus controls was calculated for each compound. The percent cell control value was calculated for each compound comparing the drug treated uninfected cells to the uninfected cells in medium alone.

Example 16

Anti-RSV Cytoprotection Assay

Cell Preparation-HEp2 cells (human epithelial cells, A TCC catalog #CCL-23) were passaged in DMEM supplemented with 10% FBS, 2 mM L-glutamine, 100 U/mL penicillin, 100 µg/mL streptomycin 1 mM sodium pyruvate, and 0.1 mM NEAA, T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at $1\times10^4$ cells per well in tissue culture medium and added to flat bottom microtiter plates in a volume of 100 µL. The plates were incubated at 37° C./5% $CO_2$ overnight to allow for cell adherence. Virus Preparation —The RSV strain Long and RSV strain 9320 were obtained from ATCC (catalog #VR-26 and catalog #VR-955, respectively) and were grown in HEp2 cells for the production of stock virus pools. A pretitered aliquot of virus was removed from the freezer (−80° C.) and allowed to thaw slowly to rt in a biological safety cabinet. Virus was resuspended and diluted into assay medium (DMEM supplemented with 2% heat-inactivated FBS, 2 mM L-glutamine, 100 U/mL penicillin, 100 µg/mL streptomycin, 1 mM sodium pyruvate, and 0.1 mM NEAA) such that the amount of virus added to each well in a volume of 100 µL was the amount determined to yield 85 to 95% cell killing at 6 days post-infection. Efficacy and Toxicity XTT-Plates were stained and analyzed as previously described for the Dengue cytoprotection assay.

Example 17

Anti-Influenza Virus Cytoprotection Assay

Cell Preparation-MOCK cells (canine kidney cells, ATCC catalog #CCL-34) were passaged in DMEM supplemented with 10% FBS, 2 mM L-glutamine, 100 U/mL penicillin, 100 µg/mL streptomycin 1 mM sodium pyruvate, and 0.1 mM NEAA, T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at 1×10$^4$ cells per well in tissue culture medium and added to flat bottom microtiter plates in a volume of 100 µL. The plates were incubated at 37° C./5% CO$_2$ overnight to allow for cell adherence.

Virus Preparation—The influenza A/PR/8/34 (A TCC #VR-95), A/CA/05/09 (CDC), A/NY/18/09 (CDC) and A/NWS/33 (ATCC #VR-219) strains were obtained from ATCC or from the Center of Disease Control and were grown in MDCK cells for the production of stock virus pools. A pretitered aliquot of virus was removed from the freezer (−80° C.) and allowed to thaw slowly to rt in a biological safety cabinet. Virus was resuspended and diluted into assay medium (DMEM supplemented with 0.5% BSA, 2 mM L-glutamine, 100 U/mL penicillin, 100 µg/mL streptomycin, 1 mM sodium pyruvate, 0.1 mM NEAA, and 1 µg/mL TPCK-treated trypsin) such that the amount of virus added to each well in a volume of 100 µL was the amount determined to yield 85 to 95% cell killing at 4 days post-infection. Efficacy and Toxicity XTT-Plates were stained and analyzed as previously described for the Dengue cytoprotection assay.

Example 18

Anti-Hepatitis C Virus Assay

Cell Culture—The reporter cell line Huh-luc/neo-ET was obtained from Dr. Ralf Bartenschlager (Department of Molecular Virology, Hygiene Institute, University of Heidelberg, Germany) by ImQuest BioSciences through a specific licensing agreement. This cell line harbors the persistently replicating I$_{389}$luc-ubi-neo/NS3-3'/ET replicon containing the firefly luciferase gene-ubiquitin-neomycin phosphotransferase fusion protein and EMCV IRES driven NS3-5B HCV coding sequences containing the ET tissue culture adaptive mutations (E1202G, T12081, and K1846T). A stock culture of the Huh-luc/neo-ET was expanded by culture in DMEM supplemented with 1 0% FCS, 2 mM glutamine, penicillin (100 µU/mL)/streptomycin (100 µg/mL) and 1× nonessential amino acids plus 1 mg/mL G418. The cells were split 1:4 and cultured for two passages in the same media plus 250 µg/mL G418. The cells were treated with trypsin and enumerated by staining with trypan blue and seeded into 96-well tissue culture plates at a cell culture density 7.5×10$^3$ cells per well and incubated at 37° C./5% CO$_2$ for 24 hours. Following the 24 hour incubation, media was removed and replaced with the same media minus the G418 plus the test compounds in triplicate. Six wells in each plate received media alone as a no-treatment control. The cells were incubated an additional 72 hours at 37° C./5% CO$_2$ then anti-HCV activity was measured by luciferase endpoint. Duplicate plates were treated and incubated in parallel for assessment of cellular toxicity by XTT staining.

Cellular Viability—The cell culture monolayers from treated cells were stained with the tetrazolium dye XTT to evaluate the cellular viability of the Huh-luc/neo-ET reporter cell line in the presence of the compounds.

Measurement of Virus Replication-HCV replication from the replicon assay system was measured by luciferase activity using the britelite plus luminescence reporter gene kit according to the manufacturer's instructions (Perkin Elmer, Shelton, CT). Briefly, one vial of britelite plus lyophilized substrate was solubilized in 10 mL of britelite reconstitution buffer and mixed gently by inversion. After a 5 minute incubation at rt, the britelite plus reagent was added to the 96 well plates at 100 µL per well. The plates were sealed with adhesive film and incubated at rt for approximately 10 minutes to lyse the cells. The well contents were transferred to a white 96-well plate and luminescence was measured within 15 minutes using the Wallac 1450 Microbeta Trilux liquid scintillation counter. The data were imported into a customized Microsoft Excel 2007 spreadsheet for determination of the 50% virus inhibition concentration ($EC_{50}$).

Example 19

Anti-Parainfluenza-3 Cytoprotection Assay

Cell Preparation—HEp2 cells (human epithelial cells, ATCC catalog #CCL-23) were passaged in DMEM supplemented with 10% FBS, 2 mM L-glutamine, 100 U/mL penicillin, 100 µg/mL streptomycin 1 mM sodium pyruvate, and 0.1 mM NEAA, T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at 1×10$^4$ cells per well in tissue culture medium and added to flat bottom microtiter plates in a volume of 100 µL. The plates were incubated at 37° C./5% CO$_2$ overnight to allow for cell adherence.

Virus Preparation—The Parainfluenza virus type 3 SF4 strain was obtained from ATCC (catalog #VR-281) and was grown in HEp2 cells for the production of stock virus pools. A pretitered aliquot of virus was removed from the freezer (−80° C.) and allowed to thaw slowly to rt in a biological safety cabinet. Virus was resuspended and diluted into assay medium (DMEM supplemented with 2% heat-inactivated FBS, 2 mM L-glutamine, 100 U/mL penicillin, and 100 µg/mL streptomycin) such that the amount of virus added to each well in a volume of 100 µL was the amount determined to yield 85 to 95% cell killing at 6 days post-infection.

Plate Format—Each plate contains cell control wells (cells only), virus control wells (cells plus virus), triplicate drug toxicity wells per compound (cells plus drug only), as well a triplicate experimental wells (drug plus cells plus virus). Efficacy and Toxicity XTT—Following incubation at 37° C. in a 5% CO$_2$ incubator, the test plates were stained with the tetrazolium dye XTT (2,3-bis(2-methoxy-4-nitro-5-sulfophenyl)-5-[(phenylamino)carbonyl]-2H-tetrazol hydroxide). XTT-tetrazolium was metabolized by the mitochondrial enzymes of metabolically active cells to a soluble formazan product, allowing rapid quantitative analysis of the inhibition of virus-induced cell killing by antiviral test substances. XTT solution was prepared daily as a stock of 1 mg/mL in RPMI1640. Phenazine methosulfate (PMS) solution was prepared at 0.15 mg/mL in PBS and stored in the dark at −20° C. XTT/PMS stock was prepared immediately before use by adding 40 µL of PMS per mL of XTT solution. Fifty microliters of XTT/PMS was added to each well of the plate and the plate was reincubated for 4 hours at 37° C. Plates were sealed with adhesive plate sealers and shaken gently or inverted several times to mix the soluble fomlazan product and the plate was read spectrophotometrically at 450/650 nm with a Molecular Devices Vmax plate reader.

Data Analysis—Raw data was collected from the Softmax Pro 4.6 software and imported into a Microsoft Excel spreadsheet for analysis. The percent reduction in viral cytopathic effect compared to the untreated virus controls was calculated for each compound. The percent cell control value was calculated for each compound comparing the drug treated uninfected cells to the uninfected cells in medium alone.

Example 20

Influenza Polymerase Inhibition Assay

Virus Preparation—Purified influenza virus A/PR/8/34 (1 mL) was obtained from Advanced Biotechnologies, Inc. (Columbia, MD), thawed and dispensed into five aliquots for storage at −80° C. until use. On the day of assay set up, 20 µL of 2.5% Triton N-101 was added to 180 µL of purified virus. The disrupted virus was diluted 1:2 in a solution containing 0.25% Triton and PBS. Disruption provided the source of influenza ribonucleoprotein (RNP) containing the influenza RNA-dependent RNA polymerase and template RNA. Samples were stored on ice until use in the assay.

Polymerase reaction—Each 50 µL polymerase reaction contained the following: 5 µL of the disrupted RNP, 100 mM Tris-HCl (pH 8.0), 100 mM KCl, 5 mM $MgCl_2$. 1 mM dithiothreitol, 0.25% Triton N-101, 5 µCi of [α-$^{32}$P] GTP, 100 µM ATP, 50 µM each (CTP, UTP), 1 µM GTP, and 200 µM adenyl (3'-5') guanosine. For testing the inhibitor, the reactions contained the inhibitor and the same was done for reactions containing the positive control (2'-Deoxy-2'-fluoroguanosine-5'-triphosphate). Other controls included RNP +reaction mixture, and RNP+I % DMSO. The reaction mixture without the ApG primer and NTPs was incubated at 30° C. for 20 minutes. Once the ApG and NTPs were added to the reaction mixture, the samples were incubated at 30° C. for 1 hour then immediately followed by the transfer of the reaction onto glass-fiber filter plates and subsequent precipitation with 10% trichloroacetic acid (TCA). The plate was then washed five times with 5% TCA followed by one wash with 95% ethanol. Once the filter had dried, incorporation of [α-$^{32}$P] GTP was measured using a liquid scintillation counter (Microbeta).

Plate Format—Each test plate contained triplicate samples of the three compounds (6 concentrations) in addition to triplicate samples of RNP +reaction mixture (RNP alone), RNP+1% DMSO, and reaction mixture alone (no RNP).

Data Analysis—Raw data was collected from the Microbeta scintillation counter. The incorporation of radioactive GTP directly correlates with the levels of polymerase activity. The "percent inhibition values" were obtained by dividing the mean value of each test compound by the RNP+1% DMSO control. The mean obtained at each concentration of 2DFGTP was compared to the RNP+reaction control. The data was then imported into Microsoft Excel spreadsheet to calculate the $IC_{50}$ values by linear regression analysis.

Example 21

HCV Polymerase Inhibition Assay

Activity of compounds for inhibition of HCV polymerase was evaluated using methods previously described (Lam et al. *Antimicrob Agents Chemother* 2010, 54(8):3187-3196). HCV NS5B polymerase assays were performed in 20 µL volumes in 96 well reaction plates. Each reaction contained 40 ng/µL purified recombinant NS5BΔ22 genotype-1b polymerase, 20 ng/µL of HCV genotype-1b complimentary IRES template, 1 µM of each of the four natural ribonucleotides, 1 U/mL Optizyme RNAse inhibitor (Promega, Madison, WI), 1 mM $MgCl_2$, 0.75 mM $MnCl_2$, and 2 mM dithiothreitol (DTT) in 50 mM HEPES buffer (pH 7.5). Reaction mixtures were assembled on ice in two steps. Step 1 consisted of combining all reaction components except the natural nucleotides and labeled UTP in a polymerase reaction mixture. Ten microliters (10 µL) of the polymerase mixture was dispensed into individual wells of the 96 well reaction plate on ice. Polymerase reaction mixtures without NS5B polymerase were included as no enzyme controls. Serial half-logarithmic dilutions of test and control compounds, 2'-O-Methyl-CTP and 2'-O-Methyl-GTP (Trilink, San Diego, CA), were prepared in water and 5 of the serial diluted compounds or water alone (no compound control) were added to the wells containing the polymerase mixture. Five microliters of nucleotide mix (natural nucleotides and labeled UTP) was then added to the reaction plate wells and the plate was incubated at 27° C. for 30 minutes. The reactions were quenched with the addition of 80 µL stop solution (12.5 mM EDTA, 2.25 M NaCl, and 225 mM sodium citrate) and the RNA products were applied to a Hybond-N+ membrane (GE Healthcare, Piscataway, N.J) under vacuum pressure using a dot blot apparatus. The membrane was removed from the dot blot apparatus and washed four times with 4× SSC (0.6 M NaCl, and 60 mM sodium citrate), and then rinsed one time with water and once with 100% ethanol. The membrane was air dried and exposed to a phosphoimaging screen and the image captured using a Typhoon 8600 Phospho imager. Following capture of the image, the membrane was placed into a Microbeta cassette along with scintillation fluid and the CPM in each reaction was counted on a Microbeta 1450. CPM data were imported into a custom Excel spreadsheet for determination of compound $IC_{50}$.

Example 22

NS5B RNA-Dependent RNA Polymerase Reaction Conditions

Compounds were assayed for inhibition of NS5B-δ21 from HCV GT-1b Con-1. Reactions included purified recombinant enzyme, 1 µg/µL negative-strand HCV IRES RNA template, and 1 µM NTP substrates including either [$^{32}$P]-CTP or [$^{32}$P]-UTP. Assay plates were incubated at 27° C. for 1 hour before quench. [$^{32}$P] incorporation into macromolecular product was assessed by filter binding.

Example 23

Human DNA Polymerase Inhibition Assay

The human DNA polymerase alpha (catalog #1075), beta (catalog #1077), and gamma (catalog #1076) were purchased from CHIMERx (Madison, WI). Inhibition of beta and gamma DNA polymerase activity was assayed in microtiter plates in a 50 uL reaction mixture containing 50 mM Tris-HCl (pH 8.7), KCl (10 mM for beta and 100 mM for gamma), 10 mM $MgCl_2$, 0.4 mg/mL BSA, 1 mM DTT, 15% glycerol, 0.05 mM of dCTP, dTTP, and dATP, 10 uCi [$^{32}$P]-alpha-dGTP (800 Ci/mmol), 20 ug activated calf thymus DNA and the test compound at indicated concentrations. The alpha DNA polymerase reaction mixture was as follows in a 50 volume per sample: 20 mM Tris-HCl (pH 8), 5 mM magnesium acetate, 0.3 mg/mL BSA, 1 mM DTT, 0.1 mM spermine, 0.05 mM of dCTP, dTTP, and dATP, 10 µCi [$^{32}$P]-alpha-dGTP (800 Ci/mmol), 20 µg is activated calf thymus DNA and the test compound at the indicated concentrations. For each assay, the enzyme reactions were allowed to proceed for 30 minutes at 37° C. followed by the transfer onto glass-fiber filter plates and subsequent precipitation with 10% trichloroacetic acid (TCA). The plate was then washed with 5% TCA followed by one wash with 95% ethanol. Once the filter had dried, incorporation of radioactivity was measured using a liquid scintillation counter (Micro Beta).

Example 24

HIV Infected PBMC Assay

Fresh human peripheral blood mononuclear cells (PBMCs) were obtained from a commercial source (Biological Specialty) and were determined to be seronegative for HIV and HBV. Depending on the volume of donor blood received, the leukophoresed blood cells were washed several times with PBS. After washing, the leukophoresed blood was diluted 1:1 with Dulbecco's phosphate buffered saline (PBS) and layered over 15 mL of Ficoll-Hypaque density gradient in a 50 mL conical centrifuge tube. These tubes were centrifuged for 30 minutes at 600 g. Banded PBMCs were gently aspirated from the resulting interface and washed three times with PBS. After the final wash, cell number was determined by Trypan Blue dye exclusion and cells were re-suspended at $1 \times 10^6$ cells/mL in RPMI 1640 with 15% Fetal Bovine Serum (FBS), 2 mmol/L L-glutamine, 2 μg/mL PHA-P, 100 U/mL penicillin and 100 μg/mL streptomycin and allowed to incubate for 48-72 hours at 37° C. After incubation, PBMCs were centrifuged and resuspended in tissue culture medium. The cultures were maintained until use by half-volume culture changes with fresh IL-2 containing tissue culture medium every 3 days. Assays were initiated with PBMCs at 72 hours post PHA-P stimulation.

To minimize effects due to donor variability, PBMCs employed in the assay were a mixture of cells derived from 3 donors. Immediately prior to use, target cells were resuspended in fresh tissue culture medium at $1 \times 10^6$ cells/mL and plated in the interior wells of a 96-well round bottom microtiter plate at 50 μL/well. Then, 100 μL of 2× concentrations of compound-containing medium was transferred to the 96-well plate containing cells in 50 μL of the medium. AZT was employed as an internal assay standard.

Following addition of test compound to the wells, 50 μL of a predetermined dilution of HIV virus (prepared from 4× of final desired in-well concentration) was added, and mixed well. For infection, 50-150 $TCID_{50}$ of each virus was added per well (final MOI approximately 0.002). PBMCs were exposed in triplicate to virus and cultured in the presence or absence of the test material at varying concentrations as described above in the 96-well microtiter plates. After 7 days in culture, HIV-1 replication was quantified in the tissue culture supernatant by measurement of reverse transcriptase (RT) activity. Wells with cells and virus only served as virus controls. Separate plates were identically prepared without virus for drug cytotoxicity studies.

Reverse Transcriptase Activity Assay—Reverse transcriptase activity was measured in cell-free supernatants using a standard radioactive incorporation polymerization assay. Tritiated thymidine triphosphate (TTP; New England Nuclear) was purchased at 1 Ci/mL and 1 μL was used per enzyme reaction. A rAdT stock solution was prepared by mixing 0.5 mg/mL poly rA and 1.7 U/mL oligo dT in distilled water and was stored at –20° C. The RT reaction buffer was prepared fresh daily and consists of 125 μL of 1 mol/L EGTA, 125 μL of $dH_2O$, 125 μL of 20% Triton X-100, 50 μL of 1 mol/L Tris (pH 7.4), 50 μL of 1 mol/L DTT, and 40 μL of 1 mol/L $MgCl_2$. For each reaction, 1 μL of TTP, 4 μL of $dH_2O$, 2.5 μL of rAdT, and 2.5 μL of reaction buffer were mixed. Ten microliters of this reaction mixture was placed in a round bottom microtiter plate and 15 μL of virus-containing supernatant was added and mixed. The plate was incubated at 37° C. in a humidified incubator for 90 minutes. Following incubation, 10 μL of the reaction volume was spotted onto a DEAE filter mat in the appropriate plate format, washed 5 times (5 minutes each) in a 5% sodium phosphate buffer, 2 times (1 minute each) in distilled water, 2 times (1 minute each) in 70% ethanol, and then air dried. The dried filtermat was placed in a plastic sleeve and 4 mL of Opti-Fluor O was added to the sleeve. Incorporated radioactivity was quantified utilizing a Wallac 1450 Microbeta Trilux liquid scintillation counter.

Example 25

HBV

HepG2.2.15 cells (100 μL) in RPMI1640 medium with 10% fetal bovine serum was added to all wells of a 96-well plate at a density of $1 \times 10^4$ cells per well and the plate was incubated at 37° C. in an environment of 5% $CO_2$ for 24 hours. Following incubation, six ten-fold serial dilutions of test compound prepared in RPMI1640 medium with 10% fetal bovine serum were added to individual wells of the plate in triplicate. Six wells in the plate received medium alone as a virus only control. The plate was incubated for 6 days at 37° C. in an environment of 5% $CO_2$. The culture medium was changed on day 3 with medium containing the indicated concentration of each compound. One hundred microliters of supernatant was collected from each well for analysis of viral DNA by qPCR and cytotoxicity was evaluated by XTT staining of the cell culture monolayer on the sixth day.

Ten microliters of cell culture supernatant collected on the sixth day was diluted in qPCR dilution buffer (40 μg/mL sheared salmon sperm DNA) and boiled for 15 minutes. Quantitative real time PCR was performed in 386 well plates using an Applied Biosystems 7900HT Sequence Detection System and the supporting SDS 2.4 software. Five microliters (5 μL) of boiled DNA for each sample and serial 10-fold dilutions of a quantitative DNA standard were subjected to real time Q-PCR using Platinum Quantitative PCR SuperMix-UDG (Invitrogen) and specific DNA oligonucleotide primers (IDT, Coralville, ID) HBV-AD38-qF1 (5'-CCG TCT GTG CCT TCT CAT CTG-3') (SEQ ID NO.:1), HBV-AD38-qR1 (5'-AGT CCA AGA GTY CTC TTA TRY AAG ACC TT-3') (SEQ ID NO.:2), and HBV-AD38-qP1 (5'-FAM CCG TGT GCA/ZEN/CTT CGC TTC ACC TCT GC-3'BHQ1) (SEQ ID NO.:3) at a final concentration of 0.2 μM for each primer in a total reaction volume of 15 μL. The HBV DNA copy number in each sample was interpolated from the standard curve by the SDS.24 software and the data were imported into an Excel spreadsheet for analysis.

The 50% cytotoxic concentration for the test materials are derived by measuring the reduction of the tetrazolium dye XTT in the treated tissue culture plates. XTT is metabolized by the mitochondrial enzyme NADPH oxidase to a soluble formazan product in metabolically active cells. XTT solution was prepared daily as a stock of 1 mg/mL in PBS. Phenazine methosulfate (PMS) stock solution was prepared at 0.15 mg/mL in PBS and stored in the dark at –20° C.

XTT/PMS solution was prepared immediately before use by adding 40 μL of PMS per 1 mL of XTT solution. Fifty microliters of XTT/PMS was added to each well of the plate and the plate incubated for 2-4 hours at 37° C. The 2-4 hour incubation has been empirically determined to be within linear response range for XTT dye reduction with the indicated numbers of cells for each assay. Adhesive plate sealers were used in place of the lids, the sealed plate was inverted several times to mix the soluble formazan product and the plate was read at 450 nm (650 nm reference wavelength) with a Molecular Devices SpectraMax Plus 384 spectrophotometer. Data were collected by Softmax 4.6 software and imported into an Excel spreadsheet for analysis.

Example 26

Dengue RNA-Dependent RNA Polymerase Reaction Conditions

RNA polymerase assay was performed at 30° C. using 100 μL reaction mix in 1.5 mL tube. Final reaction conditions were 50 mM Hepes (pH 7.0), 2 mM DTT, 1 mM $MnCl_2$, 10 mM KCl, 100 nM UTR-Poly A (self-annealing primer), 10 μM UTP, 26 nM RdRp enzyme. The reaction mix with different compounds (inhibitors) was incubated at 30° C. for 1 hr. To assess amount of pyrophosphate generated during polymerase reaction, 30 μL of polymerase reaction mix was mixed with a luciferase coupled-enzyme reaction mix (70 μL). Final reaction conditions of luciferase reaction were 5 mM $MgCl_2$, 50 mM Tris-HCl (pH 7.5), 150 mM NaCl, 200 μU ATP sulfurylase, 5 μM APS, 10 nM Luciferase, 100 μM D-luciferin. White plates containing the reaction samples (100 μL) were immediately transferred to the luminometer Veritas (Turner Biosystems, CA) for detection of the light signal.

Example 27

Procedure for Cell Incubation and Analysis

Huh-7 cells were seeded at $0.5 \times 10^6$ cells/well in 1 mL of complete media in 12 well tissue culture treated plates. The cells were allowed to adhere overnight at 37°/5% $CO_2$. A 40 μM stock solution of test article was prepared in 100% DMSO. From the 40 μM stock solution, a 20 μM solution of test article in 25 mL of complete DMEM media was prepared. For compound treatment, the media was aspirated from the wells and 1 mL of the 20 μM solution was added in complete DMEM media to the appropriate wells. A separate plate of cells with "no" addition of the compound was also prepared. The plates were incubated at 37°/5% $CO_2$ for the following time points: 1, 3, 6 and 24 hours. After incubation at the desired time points, the cells were washed 2× with 1 mL of DPBS. The cells were extracted by adding 500 μL of 70% methanol/30% water spiked with the internal standard to each well treated with test article. The non-treated blank plate was extracted with 500 μL of 70% methanol/30% water per well. Samples were centrifuged at 16,000 rpm for 10 minutes at 4° C. Samples were analyzed by LC-MS/MS using an ABSCIEX 5500 QTRAP LC-MS/MS system with a Hypercarb (PGC) column.

Example 28

Procedure for Rodent Pharmacokinetic Experiment

DBA-1J mice (6-8 weeks old, female) were acclimated for ≥2 days after receipt. Mice were weighed the day before dosing to calculate dosing volumes. Mice were dosed by oral gavage with drug at 30 mg/kg, 100 mg/kg & 300 mg/kg. The mice were sampled at 8 time points: 0.5, 1, 2, 3, 4, 8 and 24 hrs (3 mice per time point for test drug). The mice were euthanized and their organs were collected (see below). In order to collected blood, mice with euthanized by $CO_2$ at the appropriate time point listed above. Blood was obtained by cardiac puncture (0.3 mL) at each time point. Following blood collection, the organs were removed from the mice (see below). The blood was processed by inverting Li-Heparin tube with blood gently 2 or 3 times to mix well. The tubes were then placed in a rack in ice water until able to centrifuge (≤1 hour). As soon as practical, the blood was centrifuged at 2000× g for 10 minutes in a refrigerated centrifuge to obtain plasma. Then, using a 200 μL pipette, the plasma was transferred to a labeled 1.5 mL Eppendorf tube in ice water. The plasma was then frozen in freezer or on dry ice. The samples were stored at −80° C. prior to analysis. Organs were collected from euthanized mice. The organs (lungs, liver, kidney, spleen and heart) were removed, placed in a tube, and immediately frozen in liquid nitrogen. The tubes were then transferred to dry ice. The samples were saved in cryogenic tissue vials. Samples were analyzed by LC-MS/MS using an ABSCIEX 5500 QTRAP LC-MS/MS system with a Hypercarb (PGC) column.

Pharmacokinetic Parameters:

$T_{max}$ after oral dosing is 0.25-0.5 hr $C_{max}$'s are 3.0, 7.7 and 11.7 ng/mL after PO dosing with 30, 100 and 300 mg/kg;

Bioavailability (versus i.p. delivery) is 65% at 30 mg/kg and 39-46% at 100 and 300 mg/kg PO dosing;

EIDD-1931 plasma $T_{1/2}$ is 2.2 hr after IV dosing and 4.1-4.7 hrs after PO dosing After 300 mg/kg P.O. dose, the 24 hr plasma levels are 0.4 μM; 0.1 μM after 100 mg/kg dose Example 29

Protocol for Mouse Model of Chikungunya Infection

C57BL-6J mice were injected with 100 pfus CHIK virus in the footpad. The test groups comprised an uninfected and untreated group, an infected and untreated group, an infected group receiving a high dose of 35 mg/kg i.p. of EIDD-01931, and an infected group receiving a low dose of 25 mg/kg i.p. of EIDD-01931. The two test groups receiving EIDD-01931 received compound 12 hours before challenge and then daily for 7 days. Footpads were evaluated for inflammation (paw thickness) daily for 7 days. CHIK virus induced arthritis (histology) was assessed in ankle joints using PCR after 7 days.

Example 30

N(4)-Hydroxycytidine for the Prophylaxis and Treatment of Alphavirus Infections

Activity testing in Vero cell cytopathic effect (CPE) models of infection have shown that the ribonucleoside analog N(4)-hydroxycytidine (EIDD-01931) has activity against the Ross River, EEE, WEE, VEE and CHIK viruses with $EC_{50}$ values of 2.45 μM, 1.08 μM, 1.36 μM, 1.00 μM and 1.28 μM, respectively. The cytotoxicity profile of the compound is acceptable, with selectivity indices ranging from a low of 8 in CEM cells to a high of 232 in Huh7 (liver) cells.

Example 31

Given that high titers of VEE virus can develop in the brain within hours of aerosol exposure, a direct-acting antiviral agent is desirable if it is able to rapidly achieve therapeutic levels of drug in the brain. A pilot pharmacokinetic study was conducted in male SD rats dosed by oral gavage with 5 and 50 mg/kg of EIDD-01931, to determine pharmacokinetic parameters and the tissue distribution profile of the compound into key organ systems, including the brain. EIDD-01931 is orally available and dose-proportional with a calculated bioavailability (% F) of 28%. Organ samples (brain, lung, spleen, kidney and liver) were collected at 2.5 and 24 hours post-dose from the 50 mg/kg dose group. EIDD-01931 was well distributed into all tissues tested; of particular note, it was readily distributed into brain tissue at therapeutic levels of drug, based on estimates from cellular data. Once in the brain, EIDD-01931 was rapidly metabolized to its active 5'-triphosphate form to give brain levels of 526 and 135 ng/g at 2.5 and 24 hours, respectively. Even after 24 hours levels of EIDD-01931 and its 5'-triphosphate in the brain are considerable, suggesting that once-daily oral dosing can be adequate for treatment.

Alternatively, drug delivery by aerosol (nasal spray) administration can immediately achieve therapeutic levels of drug in the nasal mucosa and the brain. EIDD-01931 has an acceptable toxicology profile after 6 day q.d. intraperitoneal (IP) injections in mice, with the NOEL (NO Effect Level) to be 33 mg/kg; weight loss was observed at the highest dose tested (100 mg/kg), which reversed on cessation of dosing.

Example 32

N4-Hydroxycytidine Arenaviridae Activity

| Virus | Cell Line | $EC_{50}$ (μM) | $EC_{90}$ (μM) | $CC_{50}$ (μM) |
|---|---|---|---|---|
| Tacaribe virus | Vero | 14.4 | | 136 |
| Tacaribe virus | Vero | 18.8 | | 104 |
| Pichinde virus | Vero | 18.4 | | 184 |
| Pichinde virus | Vero | 21.6 | | 128 |
| Junin virus | Vero | 18.4 | | 136 |
| Junin virus | Vero | 20.8 | | 124 |
| Lassa fever virus | Vero | 4.04 | | 30 |
| Lymphocytic choriomeningitis virus | Vero | | 25.2 | >400 |

Example 33

N4-Hydroxycytidine Togaviridae Activity

| Virus | Cell Line | $EC_{50}$ (μM) | $EC_{90}$ (μM) | $CC_{50}$ (μM) |
|---|---|---|---|---|
| VEEV | Vero76 | 1.28 | | 128 |
| VEEV | Vero76 | 1 | | 13.6 |
| VEEV | Vero76 | | 0.8 | 32.8 |
| VEEV | Vero76 | 1.92 | | 32.8 |
| EEEV | Vero76 | 0.96 | | 128 |
| EEEV | Vero76 | 1.08 | | 84 |
| EEEV | Vero76 | | 1.68 | 132 |
| EEEV | Vero76 | 8 | | 132 |
| WEEV | Vero76 | 1.28 | | >400 |
| WEEV | Vero76 | 1.36 | | 288 |
| WEEV | Vero76 | | <1.28 | 120 |
| WEEV | Vero76 | 0.76 | | 256 |
| CHIKV | Vero76 | 1.28 | | 76 |
| CHIKV | Vero76 | 1.28 | | 22.8 |
| CHIKV | Vero76 | | 0.72 | 96 |
| CHIKV | Vero76 | 1.8 | | 96 |

Example 34

N4-Hydroxycytidine Flaviviridae Activity

| Virus | Cell Line | $EC_{50}$ (μM) | $EC_{90}$ (μM) | $CC_{50}$ (μM) |
|---|---|---|---|---|
| DENV2 | Vero76 | 12.8 | | 60 |
| DENV2 | Vero76 | 14 | | 128 |
| WNV | Vero76 | >400 | | >400 |
| WNV | Vero76 | >400 | | >400 |
| YFV | Vero76 | 1.88 | | 224 |
| YFV | Vero76 | 20.4 | | 30 |
| YFV | Vero76 | | 26 | 52 |
| YFV | Vero76 | >52 | | 52 |
| JEV | Vero76 | 112 | | >400 |
| JEV | Vero76 | 268 | | >400 |
| POWV | BHK | 11.2 | | 30 |
| POWV | BHK | 8.8 | | 19.2 |
| ZIKV | Vero76 | 1.44 | | >400 |
| ZIKV | Vero76 | 6.8 | | 152 |
| ZIKV | Vero76 | | 2.36 | 80 |
| ZIKV | Vero76 | 3.12 | | 80 |
| Usutu virus | Vero 76 | 228 | | >400 |
| Usutu virus | Vero76 | 100 | | 212 |
| ZIKV | Vero76 | 1.46 | | 400 |
| ZIKV | Vero 76 | 3.04 | | 16.4 |

Example 35

N4-Hydroxycytidine Bunyaviridae Activity

| Virus | Cell Line | $EC_{50}$ (μM) | $EC_{90}$ (μM) | $CC_{50}$ (μM) |
|---|---|---|---|---|
| RVFV | Vero76 | 1.48 | | 60 |
| RVFV | Vero76 | 1.44 | | 48 |
| RVFV | Vero76 | 6.8 | | 96 |
| RVFV | Vero76 | 7.6 | | 96 |
| RVFV | Vero | | 1 | 20.4 |
| RVFV | Vero | 1.68 | | 20.4 |
| Punta Toro virus | Vero76 | 20.4 | | 184 |
| Punta Toro virus | Vero76 | 20 | | 160 |
| La Crosse virus | Vero76 | 25.2 | | 268 |
| La Crosse virus | Vero76 | 15.2 | | 188 |
| La Crosse virus | Vero76 | | 1 | 112 |
| La Crosse virus | Vero76 | 1.96 | | 112 |
| Maporal virus | Vero76 | 84 | | 140 |
| Maporal virus | Vero76 | >124 | | 124 |
| Heartland virus | Vero | | 7.84 | >400 |
| Lymphocytic choriomeningitis virus | Vero | | 25.2 | >400 |
| Severe fever thrombocytopenia syndrome virus | Vero | | 4.96 | >400 |

Example 36

N4-Hydroxycytidine Coronaviridae Activity

| Virus | Cell Line | $EC_{50}$ (μM) | $EC_{90}$ (μM) | $CC_{50}$ (μM) |
|---|---|---|---|---|
| MERS | Vero E6 | <0.80 | <0.80 | 20 |
| SARS | Vero76 | <0.4 | | 252 |
| SARS | Vero76 | <0.4 | | 144 |
| SARS | Vero76 | | 0.56 | 76 |
| SARS | Vero76 | 2.2 | | 76 |
| SARS | Vero E6 | <0.80 | <0.80 | 20 |
| HCoV | HEL | 1.28 | | 100 |
| HCoV | HEL | 5.6 | | 36 |
| HCoV | HEL | | <0.128 | 192 |
| HCoV | HEL | 0.228 | | 192 |
| HCoV | Vero76 | <0.4 | | 400 |
| HCoV | Vero E6 | <0.4 | | 400 |
| HCoV | HEL | 1.28 | | 100 |
| HCoV | HEL | 4 | | 60 |
| HCoV | HEL | | 0.4 | 232 |
| HCoV | HEL | 0.212 | | 232 |
| HCov | Vero76 | 12.8 | | 400 |
| HCoV | Vero76 | | 0.32 | 44 |
| HCov | Vero76 | 0.44 | | 44 |

Example 37

N4-Hydroxycytidine Influenza Activity

| Virus | Cell Line | $EC_{50}$ (μM) | $EC_{90}$ (μM) | $CC_{50}$ (μM) |
|---|---|---|---|---|
| Influenza A H1N1 | MDCK | 1.28 | | 168 |
| Influenza A H1N1 | MDCK | 1.16 | | 136 |
| Flu A H7N9 (High Path) | MDCK | >48 | | 48 |
| Flu A H7N9 (High Path) | MDCK | >44 | | 44 |
| Flu A H5N1 (High Path) | MDCK | >96 | | 96 |
| Flu A H5N1 (High Path) | MDCK | >88 | | 88 |
| Flu A H1N1 | MDCK | 1.44 | | 76 |
| Flu A H1N1 | MDCK | 1.24 | | 68 |
| Flu A H3N2 | MDCK | 0.96 | | 60 |
| Flu A H3N2 | MDCK | 0.88 | | 52 |
| Flu A H5N1 (Low Path) | MDCK | 1.28 | | 48 |
| Flu A H5N1 (Low Path) | MDCK | 1.28 | | 27.6 |
| Flu B | MDCK | <0.4 | | 48 |
| Flu B | MDCK | <0.4 | | 30.4 |
| Flu B | MDCK | <0.4 | | 48 |
| Flu B | MDCK | <0.4 | | 76 |

Example 38

N4-Hydroxycytidine Ebola Activity

| Virus | Cell Line | $EC_{50}$ (μM) | $EC_{90}$ (μM) | $CC_{50}$ (μM) |
|---|---|---|---|---|
| EBOV | Vero | 4.7 | | >100 |
| EBOV | Vero | | 25 | >320 |

Example 39

N4-Hydroxycytidine Norovirus Activity

| Virus | Cell Line | $EC_{50}$ (μM) | $EC_{90}$ (μM) | $CC_{50}$ (μM) |
|---|---|---|---|---|
| NV | HG23 | >100 | >100 | >100 |

Example 40

N4-Hydroxycytidine Picornaviridae Activity

| Virus | Cell Line | $EC_{50}$ (μM) | $EC_{90}$ (μM) | $CC_{50}$ (μM) |
|---|---|---|---|---|
| Enterovirus-71 | Vero76 | 3.44 | | >400 |
| Enterovirus-71 | Vero76 | 3.36 | | 256 |
| Enterovirus-68 | RD | 1.28 | | >400 |
| Enterovirus-68 | RD | 1.16 | | 25.6 |
| Poliovirus -1 | Vero76 | 12.8 | | 128 |
| Poliovirus -1 | Vero76 | 10.4 | | 76 |
| Coxsackie virus B3 | Vero 76 | 1.44 | | 184 |
| Coxsackie virus B3 | Vero 76 | 1.4 | | 76 |
| HRV-14 | HeLa-Ohio | 1.28 | | >40 |
| HRV-14 | HeLa-Ohio | 1.36 | | >40 |
| Coxsackie virus B3 | Vero 76 | | 2.24 | 56 |
| Coxsackie virus B3 | Vero 76 | 2.12 | | 56 |
| Enterovirus-71 | Vero76 | | 0.76 | 48 |
| Enterovirus-71 | Vero76 | 2.32 | | 48 |
| Enterovirus-68 | RD | | 0.92 | 52 |
| Enterovirus-68 | RD | 2.28 | | 52 |

Example 41

N4-Hydroxycytidine Parainfluenza and RSV Activity

| Virus | Cell Line | $EC_{50}$ (μM) | $EC_{90}$ (μM) | $CC_{50}$ (μM) |
|---|---|---|---|---|
| Parainfluenza virus 3 | MA-104 | 212 | | 272 |
| Parainfluenza virus 3 | MA-104 | 248 | | 264 |
| RSV | MA-104 | 14 | | >400 |
| RSV | MA-104 | 27.6 | | >400 |

Example 42

Methods for Pharmacokinetic Studies in Cynomolgus Macaques

Eight cynomolgus macaques (4 males/4 females) were dosed by oral gavage with a single dose of EIDD-1931 or a prodrug conjugate as shown in Table 1. One week washout periods were allowed between doses. Blood samples were collected after each dosing event at predose, and 0.25, 0.5, 1, 2, 3, 4, 6, 8, 12, 18 and 24 hrs post dose.

TABLE 1

Study design for pharmacokinetic evaluation of EIDD-1931 and 4 prodrug conjugates

| Grp # | Compound | # Animals (M/F) | Dose level mmol/kg | Dose level (mg/Kg) | Feeding State |
|---|---|---|---|---|---|
| 1 | EIDD-1931 | 4/4 | 0.4 | 100 | Fasted |
| 2 | EIDD-1931 | 4/4 | 0.4 | 100 | Fed |
| 3 | EIDD-2800 | 4/4 | 0.4 | 180 | Fed |
| 4 | EIDD-2801 | 4/4 | 0.4 | 130 | Fed |
| 5 | EIDD-2776 | 4/4 | 0.4 | 175 | Fed |
| 6 | EIDD-2898 | 4/4 | 0.4 | 160 | Fed |

Aliquots of Plasma were extracted with Acetonitrile that included $^{13}C_5$ EIDD-1931 as an Internal Standard. Samples were then vortexed and centrifuged in a Sorvall RT1 centrifuge (Thermo Fisher, Waltham, MA) at 3,500 RPM for 10 minutes. The supernatant was transferred to a microcentrifuge tube and centrifuged again in a Biofuge pico centrifuge (Heraeus, Hanau, Germany) for 10 minutes at 13,000 rpm. The remaining supernatant was then transferred to an HPLC vial for analysis.

LC-MS/MS conditions for EIDD-02898. HPLC separation was performed on an Agilent 1200 system (Agilent Technologies, Santa Clara, CA, USA). An Atlantis HILIC Silica column, 50×4.6 mm, 5 μm particle size (Waters Corporation, Milford, MA, USA) was used for the separation of EIDD-1931, EIDD-2898 and $^{13}C_5$ EIDD-1931 (used as internal standard) with isocratic mode (70:30) with acetonitrile in 100 mM ammonium acetate buffer, pH 5.0 at a flow rate of 1.0 mL/min over 2 minutes. Mass Spectrometry analysis was performed on a QTrap 5500 Mass Spectrometer (AB Sciex, Farmingham, MA) using Positive Mode Electrospray Ionization (ESI) in Multiple Reaction Monitoring (MRM) Mode. An eight-point standard curve prepared in blank plasma covered concentrations range of 10 to 10,000 ng/mL. Separately prepared quality-control samples of 30, 500 and 5000 ng/mL in blank plasma were analyzed at the beginning of each sample set to ensure accuracy and precision within 20%. Calibration in each matrix showed linearity with an $R^2$ value of >0.99. Data analysis was performed using Analyst Software (AB Sciex, Farmingham).

LC-MS/MS conditions for EIDD-02800 and EIDD-02801. HPLC separation was performed on an Agilent 1200 system (Agilent Technologies, Santa Clara, CA, USA). An Acclaim HILIC-1 Mixed Mode column, 150×4.6 mm, 5 μm particle size (Thermo Fisher, Waltham, MA) was used for the separation of EIDD-1931, EIDD-2800, EIDD-2801, and $^{13}C_5$ EIDD-1931 (used as internal standard) with isocratic mode (90:10) with acetonitrile in 100 mM ammonium acetate buffer, pH 5.0 at a flow rate of 1.0 mL/min over 5 minutes. Mass Spectrometry analysis was performed on a QTrap 5500 Mass Spectrometer (AB Sciex, Farmingham, MA) using Negative Mode Electrospray Ionization (ESI) in Multiple Reaction Monitoring (MRM) Mode. An eight-point standard curve prepared in blank plasma covered concentrations range of 10 to 10,000 ng/mL. Separately prepared quality-control samples of 30, 500 and 5000 ng/mL in blank plasma were analyzed at the beginning of each sample set to ensure accuracy and precision within 20%. Data analysis was performed using Analyst Software (AB Sciex, Farmingham).

Example 43

Pharmacokinetic Parameters from Cynomolgus Macaques

As can be seen from FIGS. 11 through 15, these data show that after administration by oral gavage to cynomolgus macaques, the parent ribonucleoside is unexpectedly sequestered, largely unchanged, in the enterocytes of the gut. This results in the low apparent bioavailability of the compound in cynomolgus macaques. However, when administered via i.v. injection, the compound is widely distributed. As a result of these studies, it appears that EIDD-1931 has low bioavailability in cynomolgus monkeys as a result of inefficient transit/release from intestinal and stomach linings to circulating blood.

The low bioavailability of EIDD-1931 in cynomolgus macaques can be successfully addressed by utilizing chemically and/or enzymatically cleavable prodrug moieties that facilitate the movement of EIDD-1931 across the gut wall into the circulating blood. Three prodrugs, EIDD-2800, EIDD-2801, and EIDD-2898, significantly improved the bioavailability if EIDD-1931 by 4-8 fold in cynomolgus macaques as can be seen from FIGS. 14 and 15.

Additional results are shown in Tables 2 and 3.

TABLE 2

Pharmacokinetic Parameters from Male Cynomolgus Macaques

| Compound Dosed | $t_{max}$ (h) | $C_{max}$ (nmol/mL) | $AUC_{0\to 24\,h}$ (h · nmol/mL) | CL (L/h*kg) | $t_{1/2}$ (h) | F* (%) |
|---|---|---|---|---|---|---|
| EIDD-1931 | 0.75 ± 0.28 | 3.31 ± 1.82 | 5.75 ± 1.99 | 70.1 ± 18.7 | 1.2 ± 1.2 | ~3 |
| EIDD-2800 | 0.37 ± 0.14 | 16.3 ± 13.2 | 38.9 ± 7.58 | 9.1 ± 1.3 | 5.5 ± 4.2 | ~27 |
| EIDD-2801 | 2 ± 0.81 | 8.08 ± 1.32 | 31.7 ± 7.82 | 13 ± 3.7 | 1.8 ± 0.91 | ~22 |
| EIDD-2898 | 2.3 ± 0.96 | 9.1 ± 2.7 | 26.1 ± 5.2 | 16.4 ± 3.1 | 0.53 ± 0.16 | ~18 |
| EIDD-2776 | 5 ± 1.2 | 0.58 ± 0.21 | 2.6 ± 0.65 | 142 ± 37.3 | 0.97 ± 0.21 | ~2 |

TABLE 3

Pharmacokinetic Parameters from Female Cynomolgus Macaques

| Compound Dosed | $t_{max}$ (h) | $C_{max}$ (nmol/mL) | $AUC_{0\to 24\,h}$ (h · nmol/mL) | CL (L/h*kg) | $t_{1/2}$ (h) | F (%) |
|---|---|---|---|---|---|---|
| EIDD-1931 | 0.87 ± 0.75 | 3.31 ± 1.99 | 7.21 ± 4.21 | 65.7 ± 31.6 | 0.78 ± 0.2 | ~3 |
| EIDD-2800 | 0.31 ± 0.12 | 8.10 ± 5.06 | 27.4 ± 11.5 | 15.9 ± 7.7 | 4.4 ± 1.2 | ~16 |

TABLE 3-continued

Pharmacokinetic Parameters from Female Cynomolgus Macaques

| Compound Dosed | $t_{max}$ (h) | $C_{max}$ (nmol/mL) | $AUC_{0->24\,h}$ (h · nmol/mL) | CL (L/h*kg) | $t_{1/2}$ (h) | F (%) |
|---|---|---|---|---|---|---|
| EIDD-2801 | 1.25 ± 0.5 | 12.3 ± 2.33 | 43.8 ± 17.0 | 10.3 ± 5.6 | 1.9 ± 1.3 | ~26 |
| EIDD-2898 | 1.3 ± 0.5 | 15.9 ± 8.1 | 26.9 ± 4.8 | 15.9 ± 3.2 | 0.55 ± 0.25 | ~15 |
| EIDD-2776 | 3 ± 2.4 | 0.69 ± 0.26 | 3.3 ± 2.7 | 158 ± 85.5 | 1.2 ± 0.41 | ~2 |

Example 44 Methods for Pharmacokinetic Studies in Ferrets

EIDD-2801 and vehicle control were delivered via single oral gavage (P.O.). EIDD-2801 and vehicle control were delivered via oral gavage (P.O.) twice a day (BID). The first dose was at (−3 hrs) relative to virus challenge; the second dose at 0 hrs, and then every 12 hrs thereafter for 3.5 days; total 8 doses. The vehicle used consisted of 1% Methylcellulose in water (w/v). Female 6-8 month old outbred ferrets (*Mustela putorius furo*), acquired from Triple F Farms, weighing 0.8-1.0 kg, were used for PK and efficacy studies:
  Pharmacokinetics: 8 ferrets total (2 groups, 4 ferrets/group)
  Efficacy testing: Prophylactic dosing against A/Netherlands/602/2009 (H1N1)NL/09; $5\times10^4$ $TCID_{50}$/animal intranasally—12 ferrets total (3 groups, 4 ferrets/group)
Pharmacokinetic study: EIDD-2801 was administered as a suspension by oral gavage in 3.5 mL total volume, followed by catheter flushing with MIRACLEVET solution. Blood samples were collected from the anterior vena cava. At 72 hrs pre-dose, 0.5 mL of blood was collected from each animal. After dosing, blood samples (0.3 mL) were collected at 0.25, 0.5, 1, 2, 4, 6, 8, and 24 hours in ice-cold Li Heparin tubes for plasma. Plasma was prepared within 1 hr after blood collection and was stored for up to 12 hours on ice before being transferred to −80° C. freezer. Samples were analyzed by LC/MS/MS.

Example 45

Pharmacokinetic Parameters from Ferrets

Pharmacokinetic parameters for EIDD-1931 in ferrets after single doses of EIDD-2801.

| Dose mg/kg | $C_{max}$ (nmol/mL) | $AUC_{inf}$ (h · nmol/mL) | $t_{1/2}$ (h) |
|---|---|---|---|
| 4 | 3.5 ± 1.5 | 13.2 ± 4.8 | 8.2 ± 1.7 |
| 20 | 15.4 ± 1.9 | 73 ± 32 | 4.7 ± 1.3 |
| 128 | 100 ± 22 | 322 ± 43 | 5.1 ± 0.8 |
| 512 | 209 ± 106 | 791 ± 391 | 4.2 ± 0.6 |

Example 46

Methods for Treatment with EIDD-2801 in a Ferret Model of Influenza Infection

A dose of $5\times10^4$ $TCID_{50}$/animal of NL/09 was delivered intranasally in 0.2 ml (0.1 ml to each mare). Virus stocks were diluted in phosphate buffered saline (PBS). Ferrets were anaesthetized with a mixture of ketamine/dexmedetomidin prior to infection.

Endpoints: Fever, body weight, clinical signs (nasal discharge; activity levels; respiratory distress), and virus load in nasal lavages were assessed daily. Dosing commenced 3 hrs pre-infection, followed by dosing at 1 hr post-infection and then every 12 hrs until euthanasia of animals. Ferrets were sacrificed 3.5 days post-infection 12 hours post-last treatment dose, upper and lower respiratory tract tissue harvested separately, and a blood sample taken. Blood samples (0.3 mL) were collected, worked-up, and stored as described in the PK section above and analyzed for EIDD-1931 concentration. Virus load lower respiratory tissues was determined. Dosing: EIDD-2801 was administered orally. The total gavage volume was 3.5 ml, followed by flushing of gavage catheters with 3.5 ml of MIRACLEVET.

TABLE 4

Study Design of EIDD-2801 Efficacy Finding with Influenza Challenge.

| Exp | Grp | Virus | n | Sex | Compound | Total dose/Day | Dose Level | Dose Vol. | Treatment Regimen* |
|---|---|---|---|---|---|---|---|---|---|
| 1 | 1 | IAV (H1N1) | 4 | F | EIDD-2801 | 200 mg/kg/d | 100 mg/kg BID | 3.5 ml/kg | p.o. (bid), −3 hr, +1 hr, and 6 doses every 12 hrs PD; total 8 doses |
| 1 | 2 | IAV (H1N1) | 4 | F | EIDD-2801 | 1,000 mg/kg/d | 500 mg/kg BID | 3.5 ml/kg | p.o. (bid), −3 hr, +1 hr, and 6 doses every 12 hrs PD; total 8 doses |
| 1 | 3 | mock | 4 | F | Vehicle | 0 mg/kg/d | 0 mg/kg BID | 3.5 ml/kg | p.o. (bid), −3 hr, +1 hr, and 6 doses every 12 hrs PD; total 8 doses |

Example 47

Figure 16:
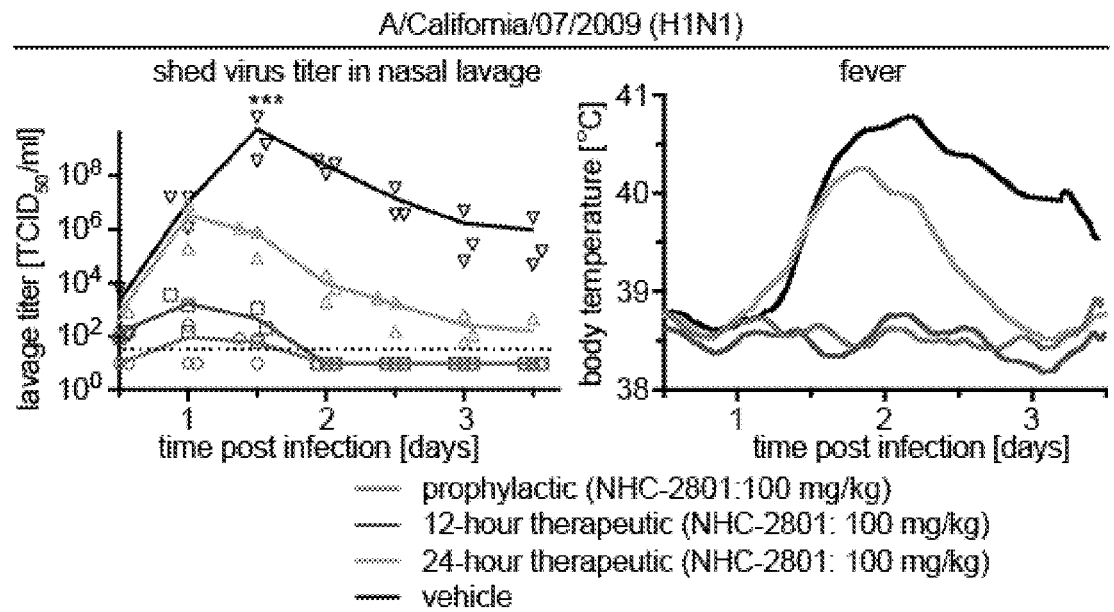
FIG. 16 shows virus titer from nasal lavage and fever in Influenza A/California/07/2009 (H1N1) infected ferrets treated orally with EIDD-2801 BID or vehicle.
Figure 17:
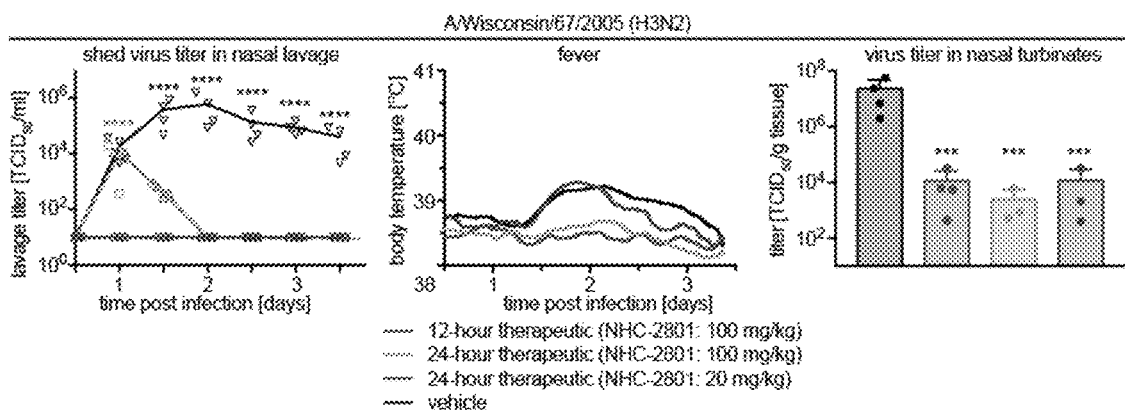
FIG. 17 shows virus titer from nasal lavage, fever, and virus titer in nasal turbinates in Influenza A/Wisconsin/67/2005 (H3N2) infected ferrets treated orally with EIDD-2801 BID or vehicle.

Results of Treatment with EIDD-2801 in a Ferret Model of Influenza Infection Results of EIDD-2801 treatment in a ferret model of influenza infection (A/California/07/2009 (H1N1)) can be found in FIG. 16. Viral titers in nasal lavage samples were greatly reduced with prophylaxis and 12 hour post infection treatment with EIDD-2801. Fever in ferrets was completely avoided with prophylaxis and 12 hour post infection treatment with EIDD-2801. Even EIDD-2801 treatment at 24 hours post infection was able to rapidly reduce viral titers in nasal lavage samples as well as fever. Results of EIDD-2801 treatment in a ferret model of influenza infection (A/Wisconsin/67/2005 (H3N2)) can be found in FIG. 17. Viral titers in nasal lavage, fever, and viral titers in turbinates was greatly reduced with EIDD-2801 (100 mg/kg) treatment initiated 12 and 24 hours post infection. Even when the dose of EIDD-2801 was reduced from 100 mg/kg to 20 mg/kg and administered 24 hours post infection viral titers in nasal lavage and turbinates was greatly reduced.

Example 48

Methods for Pharmacokinetic Studies in Mice

ICR (CD-1), 7-8 weeks old mice were acclimated for ~1 week after receipt. The mice were weighed to ±1 gram the day or morning before dosing to calculate dosing volumes. EIDD-2801 was completely dissolved in 5 mL of Solution A (PEG 400/Tween 80 (90%/10%)) with warming and vortexing and then was diluted with 5 mL of Solution B (30% Solutol/10% DMA). Mice were dosed p.o. There were 3 mice/group, to be sampled at 8 different time points: 0.25, 0.50, 1, 2, 3, 4, 8, and 24 hrs. Blood was collected at all 7 time points. Blood was obtained by retro-orbital bleeding under isoflurane anesthesia. Each mouse was sampled once (300 μL) and blood transferred immediately to Li heparin microtainers on ice water. The Li-Heparin tubes with blood were gently inverted 2 or 3 times to mix well; then placed in a rack in ice water until able to centrifuge (≤1 hour). Tubes were spun at ~2000× g for 10 min in a refrigerated centrifuge to separate plasma from RBCs. Plasma was immediately transferred to Eppendorf tubes which were then placed in ice water. All samples were frozen on dry ice within ~1 hr. Samples were stored at −80° C. prior to analysis by LC/MS/MS.

Example 49

Methods for Pharmacokinetic Studies in Rats

Male Sprague Dawley (SD) rats, between 225-249 g in weight, were acclimated for at least two days before the experiment. The day before the experiment, the rats were weighed to determine average dosing volume of EIDD-2801. For dosing by oral gavage, EIDD-2801 was dissolved in 10% PEG 400, 2.5% Cremophor RH40 in water at 64 mg/mL and dosed at 5 mL/kg. Three rats were euthanized at each time by asphyxiation with carbon dioxide. Tissues and plasmas were collected 1, 2, 4, 6, 8, and 24 hours post-dose. One rat was dosed with the vehicle and euthanized by asphyxiation 6 hours post-dose. Plasma was collected from each animal by snipping the aorta to collect approximately 0.3 mL of whole blood into a lithium heparin tube. Blood was centrifuged at 2000× g for 10 min at 5° C. Plasma was then transferred to a 1.5 mL micro-centrifuge tube and stored at −80° C. until analysis. The Brain, Spleen, Lung, Kidney, Liver, and Heart were collected from each rat. Tissues were snap frozen in liquid nitrogen and stored at −80° C. 30-70 mg pieces of frozen animal tissue were weighed in 2 mL reinforced tubes and the weights were recorded. Samples were homogenized in 70% Acetonitrile in water that included $^{13}C_5$-labelled-EIDD-1931 and $^{13}C_5$-labelled-EIDD-1931-TP as internal standards at 4° C. using an Omni bead-ruptor (Omni International, Inc., Kennesaw, GA). Homogenates were transferred to 2 mL micro-centrifuge tubes and centrifuged for 5 minutes at 15,000 rpm in an Eppendorf 5415D centrifuge (Eppendorf, Hamburg, Germany) to remove large solids. The supernatant was then transferred to a new 2 mL micro-centrifuge tube and centrifuged again in an Eppendorf 5415D centrifuge for 10 minutes at 15,000 rpm to remove any remaining solids. The remaining supernatant was transferred to a LCMS vial and analyzed via LCMS-MS. Aliquots of rat plasma were extracted with acetonitrile that included $^{13}C_5$-labeled-EIDD-1931 as an Internal Standard. Samples were clarified by centrifugation in an Eppendorf 5415D centrifuge for 10 minutes at 15,000 rpm. The clarified supernatants were transferred to HPLC vials for analysis using qualified method BAM-106.

Samples were maintained at 4° C. in a Leap Pal Autosampler (CTC Analytics AG, Zwingen, Switzerland). HPLC separation was performed on an Agilent 1200 system (Agilent Technologies, Santa Clara, CA, USA) equipped with a column oven, UV lamp, and binary pump. For tissue samples, a SeQuant ZIC-pHILIC (100×4.6 mm, 5 μm) column (Merck Millipore, Burlington, MA, USA) was used for the separation of EIDD-1931, EIDD-2781, EIDD-2061, ATP, $^{13}C_5$-labelled-EIDD-1931, and $^{13}C_5$-labelled-EIDD-1931-TP. Mobile Phase A consisted of 25 mM ammonium bicarbonate buffer in HPLC grade water pH 9.8 and Mobile phase B consisted of pure Acetonitrile. An 8.5-minute isocratic HPLC method at 35% mobile phase A was performed to separate the analytes. Mass Spectrometry analysis was performed on a QTRAP 5500 Mass Spectrometer (AB Sciex, Framingham, MA, USA) using negative mode Electrospray Ionization (ESI) in Multiple Reaction Monitoring (MRM) Mode. An Acclaim Polar Advantage II (3.0×50 mm, 3 μm particle size) column (Thermo Fisher Scientific, Waltham, MA) was used for the analysis of EIDD-2801. Mobile phase A consisted of 100 mM Ammonium Formate buffer in HPLC grade water and mobile phase B consisted of pure acetonitrile. A gradient method was employed from 5-100% mobile phase B over 3 minutes. Mass Spectrometry analysis was performed on an QTRAP 5500 Mass Spectrometer (AB Sciex, Framingham, MA, USA) using positive mode Electrospray Ionization (ESI) in Multiple Reaction Monitoring (MRM) Mode. For plasma samples, a SeQuant ZIC-pHILIC (100×4.6 mm, 5 μm) column (Merck Millipore, Burlington, MA, USA) was used for the separation of EIDD-1931, EIDD-2801, and $^{13}C_5$-labelled-1931. Mobile Phase A consisted of 25 mM ammonium bicarbonate buffer in HPLC grade water pH 9.8 and Mobile phase B consisted of pure Acetonitrile. An 4.5-minute isocratic HPLC method at 35% mobile phase A was performed to separate the analytes. Mass Spectrometry analysis was performed on a QTRAP 5500 Mass Spectrometer (AB Sciex, Framingham, Mass, USA) using negative mode Electrospray Ionization (ESI) in Multiple Reaction Monitoring (MRM) Mode. Data analysis was performed using Analyst Software (AB Sciex, Framingham, Mass, USA).

Example 50

Methods for Pharmacokinetic Studies in Dogs

Experimentally non-naïve dogs (from Marshall Biosciences) between the ages of 6.5 to 6.8 months, weighing between 7.1 to 7.95 kg were acclimated to their environment for at least three days prior to the first dosing event. Subsequent dosing events were executed after a 7-day washout period. Dogs were weighed at least once before each dose event to determine the dosing volume. EIDD-1931 was dissolved in sterile saline at 8 mg/mL for I.V. dosing. For oral dosing, EIDD-2801 was resuspended in 1% (v/v) methylcellulose in water at 6, 20, and 60 mg/mL. For I.V. dosing, dogs were dosed with a 1 mL/kg dose volume, and dogs dosed P.O. were dosed with a 5 mL/kg dose volume. Blood samples collected from dogs dosed by oral gavage were collected pre-dose, 0.25, 0.50, 1, 2, 3, 4, 8, 12, 18, and 24 hours post-dose. Blood samples collected from dogs dosed intravenously were collected pre-dose, 0.083, 0.25, 0.50, 1, 2, 4, 6, 8, 12, and 24 hours post-dose. Blood samples were collected from the jugular and/or cephalic vein into lithium-heparin microtainer tubes, centrifuged at 2000× g for 10 min at 5° C., and the plasmas were transferred into fresh tubes and stored at −80° C. before processing for quantitation by LC-MS/MS. 50 µL aliquots of dog plasma were extracted with 950 µL of acetonitrile that included $^{13}C_5$-labeled-EIDD-1931 as an Internal Standard. Samples were clarified by centrifugation at 20,000× g at 4° C. for 5 min. The clarified supernatants were transferred to HPLC vials for analysis. Samples were maintained at 4° C. in a Leap Pal Autosampler (CTC Analytics AG, Zwingen, Switzerland). HPLC separation was performed on an Agilent 1200 system (Agilent Technologies, Santa Clara, CA, USA) equipped with a column oven, UV lamp, and binary pump. A SeQuant ZIC-pHILIC (100×4.6 mm, 5 µm) column (Merck Millipore, Burlington, MA, USA) was used for the separation of EIDD-1931, EIDD-2801, and $^{13}C_5$-labeled-EIDD-1931. Mobile Phase A consisted of 25 mM Ammonium Bicarbonate buffer in HPLC grade Water pH 9.8 and Mobile phase B consisted of pure Acetonitrile. A 4-minute isocratic HPLC method at 35% mobile phase A was performed to separate the analytes. Mass Spectrometry analysis was performed on an QTRAP 5500 Mass Spectrometer (AB Sciex, Farmingham, MA, USA) using Negative Mode Electrospray Ionization (ESI) in Multiple Reaction Monitoring (MRM) Mode. Data analysis was performed using Analyst Software (AB Sciex, Farmingham, MA, USA). PK parameters are calculated using the Phoenix WinNonLin 6.4 (Build 6.4.0.768) Non-compartmental analysis tool (Certara, Princeton, NJ, USA). Bioavailability of EIDD-2801 is calculated by comparing the exposure (AUC-inf) of EIDD-1931 after EIDD-2801 oral dosing with the exposure of EIDD-1931 after intravenous dosing with EIDD-1931 using the formula below.

$$\text{Oral Bioavailability} = \frac{\text{Dose}_{I.V.}}{\text{Dose}_{P.O.}} \times \frac{AUC_{P.O.}}{AUC_{I.V.}}$$

Example 51

Plasma and Liver Microsome Stability for EIDD-2800, 2801, and 2898

| Substrate | Species | Plasma t1/2 (min) | Liver Microsomes t1/2 (min) |
|---|---|---|---|
| EIDD-2800 | Mouse | 1 | <1 |
| | Monkey | 2 | 2 |
| | Human | 1 | 1 |
| EIDD-2801 | Mouse | 1 | 2 |
| | Rat | 1 | 5 |
| | Dog | 192 | 1 |
| | Monkey | 24 | 1 |
| | Human | 63 | 73 |
| EIDD-2898 | Mouse | 144 | 6 |
| | Monkey | 138 | 13 |
| | Human | 198 | 14 |

Example 52

Pharmacokinetic Parameters from Mice

Plasma pharmacokinetic parameters for EIDD-1931 and EIDD-2898 in mice after single doses of EIDD-2898.

| EIDD-2989 Dose mg/kg | Analyte | $t_{max}$ (h) | $C_{max}$ (nmol/mL) | $AUC_{inf}$ (h · nmol/mL) | $t_{1/2}$ (h) |
|---|---|---|---|---|---|
| 15 | 1931 | 0.25 | 11 | 10.2 | 2.9 |
| | 2898 | 0.08 | 23.1 | 8.23 | 0.34 |
| 225 | 1931 | 0.5 | 69.3 | 83.4 | 4.2 |
| | 2989 | 0.5 | 7.61 | 9.57 | 3.1 |
| 750 | 1931 | 0.5 | 71.3 | 228.9 | 5.2 |
| | 2989 | 0.25 | 7.3 | 21.9 | 6.7 |

Example 53

Pharmacokinetic Parameters from Mice

Tissue pharmacokinetic parameters for EIDD-1931 and EIDD-2061 (EIDD-1931-5'-triphosphate) in mice after single doses of EIDD-2898.

| EIDD-2898 | | Spleen | | Brain | | Lung | |
|---|---|---|---|---|---|---|---|
| Dose mg/kg | Analyte | $AUC_{0 \to t}$ (h · nmol/g) | $C_{max}$ (nmol/g) | $AUC_{0 \to t}$ (h · nmol/g) | $C_{max}$ (nmol/g) | $AUC_{0 \to t}$ (h · nmol/g) | $C_{max}$ (nmol/g) |
| 225 | 1931 | 536.4 | 285.1 | 202.4 | 12.6 | 113.4 | 76.7 |
| | 2061 | 110.8 | 9.9 | 63.1 | 3.5 | 35.0 | 2.5 |
| 750 | 1931 | 1420.8 | 373.1 | 107.9 | 18.8 | 386.9 | 82.4 |
| | 2061 | 257.0 | 24.7 | 64.1 | 5.5 | 120.2 | 10.9 |

Example 54

Pharmacokinetic Parameters from Mice

Plasma pharmacokinetic parameters for EIDD-1931 in mice after a single dose of EIDD-2800 (180 mg/kg). No EIDD-2800 (parent) was observed at any time point.

| Analyte | $t_{max}$ (h) | $C_{max}$ (nmol/mL) | $AUC_{inf}$ (h · nmol/mL) | $t_{1/2}$ (h) |
|---|---|---|---|---|
| EIDD-1931 | 0.5 | 11.4 | 42.5 | 1.86 |

Example 55

Pharmacokinetic Parameters from Dogs

Plasma pharmacokinetic parameters for EIDD-1931 in dogs after a single dose of EIDD-2800 (140 mg/kg). No EIDD-2800 (parent) was observed at any time point.

| Analyte | $t_{max}$ (h) | $C_{max}$ (nmol/mL) | $AUC_{inf}$ (h · nmol/mL) | $t_{1/2}$ (h) |
|---|---|---|---|---|
| EIDD-1931 | 1.4 ± 0.5 | 112.8 ± 21.1 | 497.7 ± 40.4 | 4.8 ± 1 |

Example 56

Protocol for Evaluating EIDD-2801 in a Mouse Model of Intranasal VEEV Infection CD-1 female mice 7-8 weeks old were used for this study. The Trinidad donkey strain of VEEV was originally obtained from Centers for Disease Control and was additionally passaged once on Vero cells to expand the virus and was titrated by a plaque assay. The residual inoculum used for the experiment was back titrated after the challenge to confirm the dose delivered. Mice were randomly assigned to groups of 10 animals. Virus challenge consisted of intranasal application of ~100 pfu of virus, corresponding to ~100 $LD_{50}$, in 25 µl volume of PBS split into two nostrils and delivered under ketamine-xylazine anesthesia. EIDD-2801 was administered PO by gavage feeding, twice a day for 6 days. The first treatment was administered 6 h post virus challenge and a follow-up treatment was then given every 12 hours (BID) starting 12 hours post infection (total 13 doses, 6 days of treatment). The inoculation virus was back-titrated after the challenge to confirm the dose.

Animals were dosed by gavage using a sterilized gavage needle. The virus titers in serum and brain were assayed using a standard double-overlay plaque assay where 0.1 ml volumes of serial dilutions of serum or brain homogenate were inoculated onto Vero cells cultured in 6-well plates. Plaques were counted ~48 hours after inoculation and titers calculated on the basis of mL of serum or gram of brain. The limit of detection of this assay was 100 plaques per mL or per gram. Animal survival were analyzed using a Log-rank (Mantel-Cox) test, a Logrank test for trend and Gehan-Breslow-Wilcox test for groups comparisons (all part of Prism 6, GraphPad Software, Inc.).

Example 57

Results of Dosing EIDD-2801 in a Mouse Model of Intranasal VEEV Infection

Figure 18:
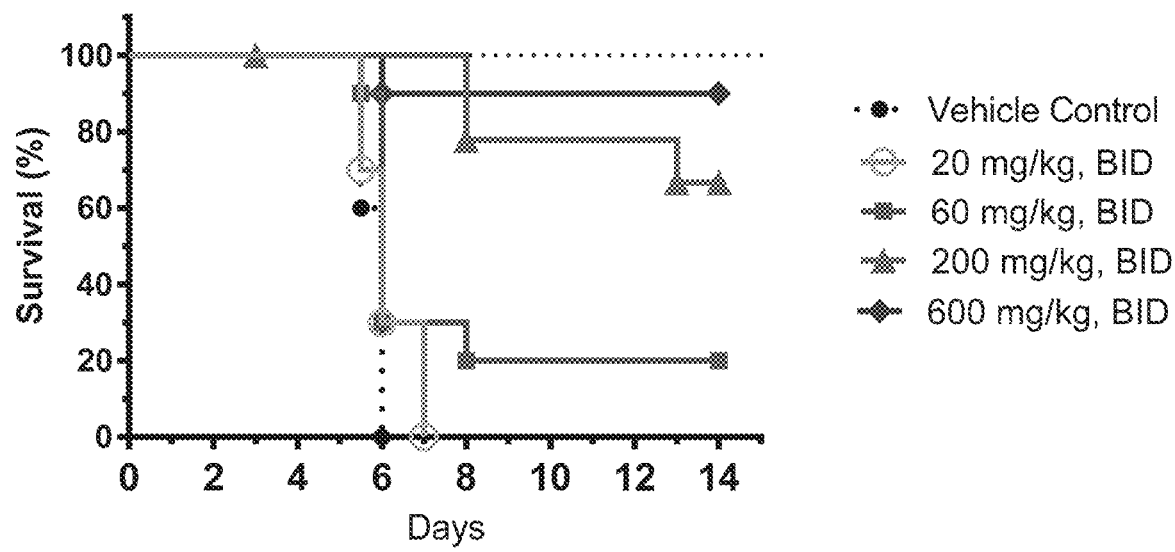
FIG. 18 shows the effect of EIDD-2801 treatment on survival of intranasal VEEV infected mice.

Mice infected with intranasal VEEV were treated with four different dose levels of EIDD-2801. Effect of treatment on survival can be found in FIG. 18.

Example 58

Protocol for Evaluating Time of Treatment of EIDD-2801 in a Mouse Model of Intranasal VEEV Infection ICR female mice 7-8 weeks old were used for this study. The Trinidad donkey strain of VEEV was passaged once on Vero cells to expand the virus and was titrated by a plaque assay. The residual inoculum used for the experiment was back titrated after the challenge to confirm the dose delivered. Mice were randomly assigned to groups of 10 animals. Virus challenge consisted of intranasal application of ~100 pfu of virus, corresponding to ~100 $LD_{50}$, in 25 µl volume of PBS split into two nostrils and delivered under ketamine-xylazine anesthesia. EIDD-2801 was administered PO by gavage feeding. The treatments were initiated either at 6, 24, 48 or 72 hrs post-infection, and were continued twice a day (every 12 hours; BID) for 6 days regardless of the start time. The vehicle control group (Group 6) was treated the same way with the vehicle only (10% PEG-400, 2.5% Cremophor RH 40 in water). The virus titers in serum and brain were assayed using a standard double-overlay plaque assay where 0.1 ml volumes of serial dilutions of serum or brain homogenate were inoculated onto Vero cells cultured in 6-well plates. Plaques were counted ~48 hours after inoculation and titers calculated on the basis of mL of serum or gram of brain. The limit of detection of this assay was 100 plaques per mL or per gram. Animal survival were analyzed using a Log-rank (Mantel-Cox) test for groups' comparison (Prism 6, GraphPad Software, Inc.).

Example 59

Figure 19:
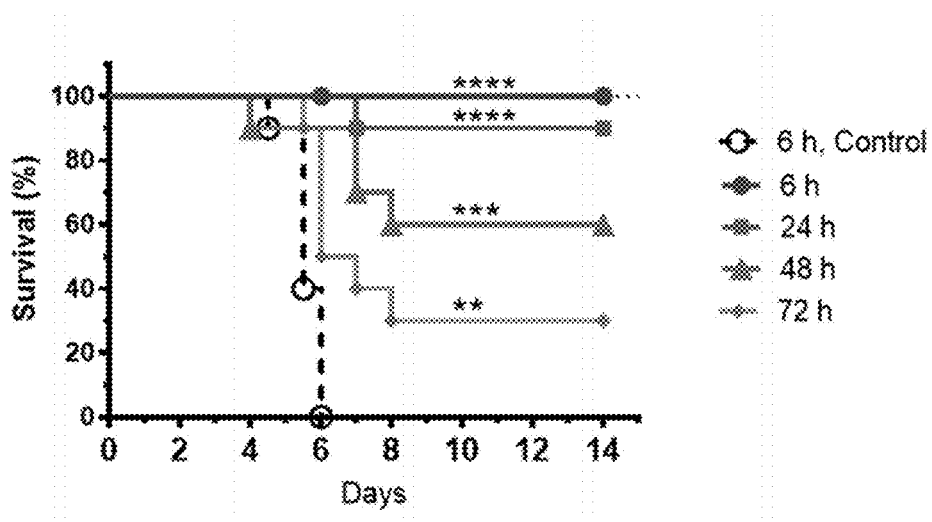
FIG. 19 shows the effect of EIDD-2801 time of treatment initiation on survival of intranasal VEEV infected mice.

Results of Time of Treatment Dosing with EIDD-2801 in a Mouse Model of Intranasal VEEV Infection Mice infected with intranasal VEEV were treated with EIDD-2801 (600 mg/kg). Effect of delay in treatment initiation on survival can be found in FIG. 19.

Example 60

Protocol for Evaluating EIDD-2801 Prophylactic Treatment in a Mouse Model of SARS Infection Female and male 20 week old C57BL/6J mice were used after a five day or greater acclimation period in BSL3. For each sex, animals were randomly assigned to treatment groups and individually marked with ear punches. The virus stock utilized for these studies was derived from the infectious clone of the mouse adapted SARS-CoV MA15 (MA15) strain. After electroporation of Vero E6 cells with viral genomic RNA from SARS MA15, supernatant was harvested when the monolayer exhibited >80% CPE. The resultant stock was passaged twice on Vero E6 cells to generate a working stock with a titer of $6.3 \times 10^7$ pfu/ml.

The large left lung lobe of each mouse was harvested into a 2 ml screw cap tube containing glass beads and 1 ml PBS. This sample was frozen at −80° C. until the plaque assay was performed. 24 hr prior to performing the plaque assay, 6-well plates of Vero E6 cells were seeded at 500,000 cells/well/2 ml. Cells were incubated at 37° C. in 5% $CO_2$ for 24 hr. On the day of the assay, lungs were homogenized using a Roche Magnalyzer, lung homogenates were clarified via centrifugation at >10,000× g, serially diluted in PBS, added to monolayers of Vero E6 cells, and incubated at 37° C. with 5% $CO_2$ for 1 hr after which cells were overlayed with medium containing 0.8% agarose. Two days later, monolayers were stained with neutral red viability stain to aid in plaque visualization. The numbers of plaques per virus diluted were enumerated to generate the plaque forming units per lung lobe (pfu/lobe).

Equivalent numbers of male and female 20-25 week old SPF C57BL/6J (Stock 000664 Jackson Labs) were used for these studies. Mice were randomly assigned to each treatment group. Groups to be infected with SARS-CoV were comprised of 10 mice (5 male/5 female). To control for potential effects associated with oral dosing on animal weight or pulmonary function, as well as the effect of the tested compound, two smaller "sham" infected groups will also be included (n=6, 3 males and 3 females each). EIDD-2801 or vehicle control was delivered via oral gavage (P.O.) twice a day (BID). The first dose was initiated at −2 hr relative to virus challenge; the second dose was at 12 hpi, and then every 12 hrs thereafter for 5 days; total 10 doses. Mice were anaesthetized with a mixture of ketamine/xylazine prior to intranasal infection with a dose of $1 \times 10^4$ plaque forming units (PFU) of SARS-CoV MA15 strain in 0.05 ml diluted in PBS at time 0hpi. All mice were weighed daily, and a subset of mice were assayed by whole body plethysmography (4 mice 2 males and 2 females per treatment group) to determine pulmonary function daily for 5 days post infection. Following sacrifice at Day 5 post infection, lungs were assessed for lung hemorrhage score. Tissue was then removed for virus lung titer and pathology. The large left lobe was harvested for virus lung titer and the lower right lobe was harvested for pathology. Whole body plethysmography: Pulmonary function was monitored once daily via whole-body plethysmography (Buxco Respiratory Solutions, DSI Inc.). Mice destined for this analysis were chosen prior to infection. Briefly, after a 30-minute acclimation time in the plethysmograph, data for 11 parameters was recorded every 2 seconds for 5 minutes.

Statistical analysis: All statistical data analysis was performed in Graphpad Prism 7. Statistical significance for each endpoint was determined with specific statistical tests. For each test, a p-value <0.05 was considered significant. For percent starting weight and whole body plethysmography, we performed a two-way ANOVA and Dunnet's multiple comparison test. For lung hemorrhage and virus lung titer, we performed a one-way ANOVA with a Kruskall-Wallace multiple comparison test.

Example 61

Figure 20:
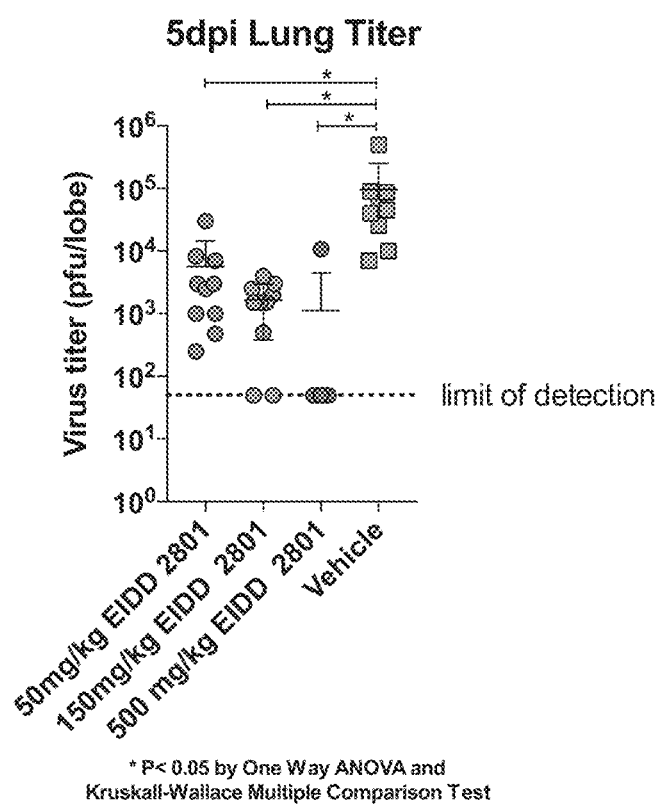
FIG. 20 shows the effect of EIDD-2801 prophylactic treatment on lung viral titers of SARS infected mice.

Results of Prophylactic Dosing with EIDD-2801 in a Mouse Model of SARS Infection Mice infected with SARS were treated prophylactically with EIDD-2801. Effect of treatment on lung viral titers can be found in FIG. 20.

Example 62

Protocol for Evaluating EIDD-2801 Time of Treatment in a Mouse Model of SARS Infection Female and male 25-29 week old C57BL/6J mice were used after a five day or greater acclimation period in BSL3. For each sex, animals were randomly assigned to treatment groups and individually marked with ear punches. The virus stock utilized for these studies was derived from the infectious clone of the mouse adapted SARS-CoV MA15 (MA15) strain that was generated in the Baric laboratory. After electroporation of Vero E6 cells with viral genomic RNA from SARS MA15, supernatant was harvest when the monolayer exhibited >80% CPE. The resultant stock was passaged twice on Vero E6 cells to generate a working stock with a titer of $6.3 \times 10^7$ pfu/ml. The lower right lung lobe of each mouse was harvested into a 2 ml screw cap tube containing glass beads and 1 ml PBS. This sample was frozen at −80° C. until the plaque assay was performed. 24 hr prior to performing the plaque assay, 6-well plates of Vero E6 cells were seeded at 500,000 cells/well/2 ml. Cells were incubated at 37° C. in 5% $CO_2$ for 24 hr. On the day of the assay, lungs were homogenized using a Roche Magnalyzer, lung homogenates were clarified via centrifugation at >10,000× g, serially diluted in PBS, added to monolayers of Vero E6 cells, and incubated at 37° C. with 5% $CO_2$ for 1 hr after which cells were overlayed with medium containing 0.8% agarose. Two days later, monolayers were stained with neutral red viability stain to aid in plaque visualization. The numbers of plaques per virus diluted were enumerated to generate the plaque forming units per lung lobe (pfu/lobe). Equivalent numbers of male and female 25-29 week old SPF C57BL/6J were used for these studies. Mice were randomly assigned to each treatment group. Groups to be infected with SARS-CoV were comprised of 10 mice (5 male/5 female). EIDD-2801 or vehicle control was delivered via oral gavage (P.O.) twice a day (BID). We initiated dosing at −2 hr, +12 hr, +24 hr or +48 hr relative to virus challenge. Mice were anaesthetized with a mixture of ketamine/xylazine prior to intranasal infection with a dose of $1 \times 10^4$ plaque forming units (PFU) of SARS-CoV MA15 strain in 0.05 ml diluted in PBS at time 0hpi. All mice were weighed daily, and a subset of mice were assayed by whole body plethysmography (4 females per treatment group) daily to determine pulmonary function. Following sacrifice at 5 dpi, lungs were assessed for lung hemorrhage score. Tissue was then removed for virus lung titer and pathology. The large left lobe was harvested for pathology and the lower left lobe was harvested for virus titer. Pulmonary function was monitored once daily via whole-body plethysmography (Buxco Respiratory Solutions, DSI Inc.). Mice destined for this analysis were chosen prior to infection. Briefly, after a 30-minute acclimation time in the plethysmograph, data for 11 parameters was recorded every 2 seconds for 5 minutes. All statistical data analysis was performed in Graphpad Prism 7. Statistical significance for each endpoint was determined with specific statistical tests. For each test, a p-value <0.05 was considered significant. For percent starting weight and whole body plethysmography, we performed a two-way ANOVA and Dunnet's multiple comparison test. For lung hemorrhage and virus lung titer, we performed a one-way ANOVA with a Kruskall-Wallace multiple comparison test.

Example 63

Results of Therapeutic Dosing with EIDD-2801 in a Mouse Model of SARS Infection Mice infected with SARS were treated with EIDD-2801. Effect of treatment on lung hemorrhage scores and lung viral titers can be found in FIGS. 21 and 22, respectively.

Example 64

Protocol for Evaluating EIDD-2801 Therapeutic Treatment in a Mouse Model of MERS Infection Female and male 10-11 week old C57BL/6J 288/330 DPP4 mice created and bred by the Baric Laboratory were used after a five day or greater acclimation period in BSL3. For each sex, animals were randomly assigned to treatment groups and individually marked with ear punches. The virus stock utilized for these studies was derived from a plaque purified isolate of the mouse adapted MERS-CoV p35C4 (MERS) strain that was generated in the Baric laboratory. After plaque purification, virus was passaged twice on Vero CC81 cells. The resultant stock titer was of $1.1 \times 10^8$ pfu/ml. The lower right lung lobe of each mouse was harvested into a 2 ml screw cap tube containing glass beads and 1 ml PBS. This sample was frozen at $-80°$ C. until the plaque assay was performed. 24 hr prior to performing the plaque assay, 6-well plates of Vero CC81 cells were seeded at 500,000 cells/well/2 ml. Cells were incubated at 37° C. in 5% $CO_2$ for 24 hr. On the day of the assay, lungs were homogenized using a Roche Magnalyzer, lung homogenates were clarified via centrifugation at >10,000× g, serially diluted in PBS, added to monolayers of Vero CC81 cells, and incubated at 37° C. with 5% $CO_2$ for 1 hr after which cells were overlayed with medium containing 0.8% agarose. Three days later, monolayers were stained with neutral red viability stain to aid in plaque visualization. The number of plaques per virus diluted were enumerated to generate the plaque forming units per lung lobe (pfu/lobe). Equivalent numbers of 10-11 week old C57BL/6J 288/330 DPP4 mice were randomly assigned to each treatment group for these studies. Each group was comprised of 10 mice (5 male/5 female). EIDD-2801 or vehicle control was delivered via oral gavage (P.O.) twice a day (BID) beginning at $-2$ hr and then every 12 hr thereafter. Mice were anaesthetized with a mixture of ketamine/xylazine prior to intranasal infection with a dose of $5 \times 10^4$ plaque forming units (PFU) of MERS strain in 0.05 ml diluted in PBS at time 0hpi. All mice were weighed daily, and a subset of mice were assayed by whole body plethysmography (4 females per treatment group) daily to determine pulmonary function. Following sacrifice at 5 dpi, lungs were assessed for lung hemorrhage score. Tissue was then removed for virus lung titer and pathology. The large left lobe was harvested for pathology and the lower left lobe was harvested for virus titer. Pulmonary function was monitored once daily via whole-body plethysmography (Buxco Respiratory Solutions, DSI Inc.). Mice destined for this analysis were chosen prior to infection. Briefly, after a 30-minute acclimation time in the plethysmograph, data for 11 parameters was recorded every 2 seconds for 5 minutes.

All statistical data analysis was performed in Graphpad Prism 7. Statistical significance for each endpoint was determined with specific statistical tests. For each test, a p-value <0.05 was considered significant. For percent starting weight and whole-body plethysmography, we performed a two-way ANOVA and Dunnet's multiple comparison test. For lung hemorrhage, we performed a one-way ANOVA with a Kruskall-Wallace multiple comparison test.

Example 65

Figure 23:
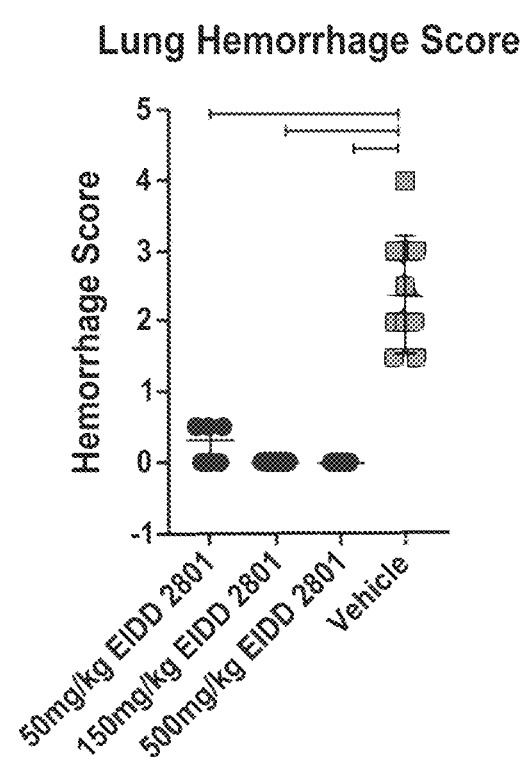
FIG. 23 shows the effect of EIDD-2801 treatment on lung hemorrhage scores of MERS infected mice.

Results of Therapeutic Dosing with EIDD-2801 in a Mouse Model of MERS Infection Mice infected with MERS were treated with EIDD-2801. Effect of treatment on lung hemorrhage scores can be found in FIGS. 23.

Example 66

Method for Evaluating Cell Uptake and Metabolism of EIDD-2801 in Vero Cells

Three 24-well plates were plated with primary vero cells at a seeding density of $0.350 \times 10^6$/mL viable cells per well. The plates were incubated at 37°/5% $CO_2$ overnight to allow the cells to attach. A 40 mM solution of EIDD-2801 in 100% DMSO was prepared. From the 40 mM stock solution, a 20 μM solution of EIDD-2801 was prepared in 25 ml of complete DMEM media. For compound treatment plates, the media was aspirated and 1.0 mL of 20 μM EIDD-2801 in complete DMEM media was added to the appropriate wells. A separate plate of cells was prepared with no compound added. The plates were then incubated at 37°/5% $CO_2$ for the following time points: 1, 2, 3, 4, 6, 16 and 24 hours. The non-treated plate was sampled at 0 hrs. After incubation at the desired time points, cells were washed 2× with 1.0 mL of DPBS. Cells were extracted by adding 500 ul of 70% Acetonitrile/30% water spiked with the internal standard to each well treated with EIDD-2801. The non-treated blank plate was extracted with 500 ul of 70% Acetonitrile/30% water per well. The samples were pipetted up and down several times. The samples were transferred to labeled microcentrifuge tubes. The samples were centrifuged at 16,000× g for 10 minutes at 4° C. 300 ul of supernatant was transferred to labeled HPLC vials, and the samples were stored at $-80°$ C. or submitted to the BCDMPK group for LC-MS/MS analysis.

Example 67

Results for the Cell Uptake and Metabolism of EIDD-2801 in Vero Cells

| Analyte | $C_{max}$ (pmol/M Cells) | $t_{max}$ (h) | $AUC_{0 \to t}$ (pmol · h/M cells) |
|---|---|---|---|
| EIDD-1931 (Nuc) | 13.5 | 24 | 228.6 |
| EIDD-2061 (TP) | 872.0 | 16 | 13850 |
| EIDD-2801 (Parent) | 121.2 | 3 | 1724 |

Example 68

Method for Evaluating Cell Uptake and Metabolism of EIDD-2801 in Huh-7 Cells Four 24-well plates were plated with Huh-7 cells at a seeding density of $0.35 \times 10^6$/mL viable cells per well. The plates were incubated at 37°/5% $CO_2$ overnight to allow the cells to attach. A 40 mM stock solution of EIDD-2801 was prepared in 100% DMSO. From the 40 mM solution, a 20

μM solution of EIDD-2801 in 25 ml of complete DMEM media was prepared by pipetting 12.5 μL of EIDD-2801 into the media. For compound treatment plates, the media was aspirated and 1.0 mL of 20 μM EIDD-2801 solution in complete DMEM media was added to the appropriate wells. A separate plate of cells had no compound added and was aspirated and replaced with media without compound. The plates were incubated at 37°/5% $CO_2$ for the following time points: 1, 2, 3, 4, 6, 16 and 24 hours. A non-treated plate was 0 hrs sample. After incubation at the desired time points, cells were washed 2× with 1.0 mL of DPBS. Cells were extracted by adding 500 ul of 70% acetonitrile/30% water spiked with the internal standard to each well treated with EIDD-2801. The non-treated blank plate was extracted with 500 ul of 70% acetonitrile/30% water per well without an internal standard. The samples were pipetted up and down several times. The samples were transferred to labeled microcentrifuge tubes. The samples were centrifuged at 16,000× g for 10 minutes at 4° C. 350 ul of supernatant was transferred to labeled 5 mL tubes or if samples were not being dried down put in labeled HPLC vials. Samples were stored at −80° C. or submitted to the BCDMPK group for LC-MS/MS analysis.

Example 69

Results for the Cell Uptake and Metabolism of EIDD-2801 in Huh-7 Cells

| Analyte | $C_{max}$ (pmol/M Cells) | $t_{max}$ (h) | $AUC_{0\to t}$ (pmol · h/M cells) |
| --- | --- | --- | --- |
| EIDD-1931 (Nuc) | 29.0 | 24 | 449.2 |
| EIDD-2061 (TP) | 1113.3 | 24 | 14640 |
| EIDD-2801 (Parent) | 77.5 | 2 | 1025 |

Example 70

Method for Evaluating Cell Uptake and Metabolism of EIDD-2801 in HepG2 Cells

Three 24-well plates were plated with primary vero cells at a seeding density of 0.350×10⁶/mL viable cells per well. The plates were incubated at 37°/5% $CO_2$ overnight to allow the cells to attach. A 40 mM stock solution of EIDD-2801 in 100% DMSO was prepared. From the 40 mM solution, a 20 μM solution of EIDD-2801 was prepared in 25 ml of complete RPMI media. For compound treatment plates, the media was aspirated and 1.0 mL of 20 μM EIDD-2801 in complete RPMI media was added to the appropriate wells. A separate plate of cells was prepared with no compound added. The plates were then incubated at 37°/5% $CO_2$ for the following time points: 1, 2, 3, 4, 6, 16 and 24 hours. The non-treated plate was sampled at 0 hrs. After incubation at the desired time points, cells were washed 2× with 1.0 mL of DPBS. Cells were extracted by adding 500 ul of 70% Acetonitrile/30% water spiked with the internal standard to each well treated with EIDD-2801. The non-treated blank plate was extracted with 500 ul of 70% Acetonitrile/30% water per well. The samples were pipetted up and down several times. The samples were transferred to labeled microcentrifuge tubes. The samples were centrifuged at 16,000×g for 10 minutes at 4° C. 300 ul of supernatant was transferred to labeled HPLC vials, and the samples were stored at −80° C. or submitted to the BCDMPK group for LC-MS/MS analysis.

Example 71

Results for the Cell Uptake and Metabolism of EIDD-2801 in HepG2 Cells

| Analyte | $C_{max}$ (pmol/M Cells) | $t_{max}$ (h) | $AUC_{0\to t}$ (pmol · h/M cells) |
| --- | --- | --- | --- |
| EIDD-1931 (Nuc) | 13.4 | 16 | 249.8 |
| EIDD-2061 (TP) | 470.3 | 16 | 299.8 |
| EIDD-2801 (Parent) | 18.9 | 3 | 360.3 |

Example 72

Method for Evaluating Cell Uptake and Metabolism of EIDD-2801 in CEM Cells

Three 24-well plates were plated with primary vero cells at a seeding density of 2×10⁶/mL viable cells per well. The plates were incubated at 37°/5% $CO_2$ overnight to allow the cells to attach. A 40 mM stock solution of EIDD-2801 in 100% DMSO was prepared. From the 40 mM solution, a 40 μM solution of EIDD-2801 was prepared in 25 ml of complete RPMI media. For compound treatment plates, the media was aspirated and 1.0 mL of 40 μM EIDD-2801 in complete RPMI media was added to the appropriate wells. A separate plate of cells was prepared with no compound added. The plates were then incubated at 37°/5% $CO_2$ for the following time points: 1, 2, 3, 4, 6, 16 and 24 hours. The non-treated plate was sampled at 0 hrs. After incubation at the desired time points, cells were washed 2× with 1.0 mL of DPBS. Cells were extracted by adding 500 ul of 70% Acetonitrile/30% water spiked with the internal standard to each well treated with EIDD-2801. The non-treated blank plate was extracted with 500 ul of 70% Acetonitrile/30% water per well. The samples were pipetted up and down several times. The samples were transferred to labeled microcentrifuge tubes. The samples were centrifuged at 16,000× g for 10 minutes at 4° C. 300 ul of supernatant was transferred to labeled HPLC vials, and the samples were stored at −80° C. or submitted to the BCDMPK group for LC-MS/MS analysis.

Example 73

Results for the Cell Uptake and Metabolism of EIDD-2801 in CEM Cells

| Analyte | $C_{max}$ (pmol/M Cells) | $t_{max}$ (h) | $AUC_{0\to t}$ (pmol · h/M cells) |
| --- | --- | --- | --- |
| EIDD-1931 (Nuc) | 0.3 | 3 | 5.8 |
| EIDD-2061 (TP) | 171.3 | 24 | 2355 |
| EIDD-2801 (Parent) | 5.4 | 4 | 85.3 |

It will be apparent to those skilled in the art that various modifications and variations can be made in the present invention without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A process for producing a compound, comprising
   a) reacting uridine having hydroxyl groups at positions 2', 3', and 5' with a compound to protect or esterify the hydroxyl groups at positions 2' and 3' of uridine thereby forming a first intermediate;
   b) simultaneously or subsequent to step a), esterifying the hydroxyl group at position 5' of the first intermediate to form a carboxylic acid ester as a second intermediate;
   c) reacting the second intermediate with a 1,2, 4-triazole compound followed by reaction with a hydroxylamine moiety at position 4, thereby forming a third intermediate; and
   d) optionally deprotecting the third intermediate.

2. The process of claim 1, wherein the uridine having hydroxyl groups at positions 2', 3', and 5' is reacted with acetone to protect the hydroxyl groups a positions 2' and 3' of uridine.

3. The process of claim 1, wherein the hydroxyl group at position 5' of the first intermediate is esterified to form an isobutyrate ester as the second intermediate.

4. The process of claim 3, wherein the hydroxyl group at position 5' of the first intermediate is esterified with 2-methylpropanoyl 2-methylpropanoate.

5. The process of claim 1, wherein the third intermediate is deprotected.

6. A compound obtained by the process of claim 5.

7. A pharmaceutical composition comprising a pharmaceutically acceptable excipient and a compound as claimed in claim 6.

8. A product produced by the process of claim 1.

* * * * *